US012466837B2

(12) United States Patent
Lee et al.

(10) Patent No.: US 12,466,837 B2
(45) Date of Patent: Nov. 11, 2025

(54) COMPOUND FOR ORGANIC ELECTRIC DEVICE, ORGANIC ELECTRIC DEVICE USING THE SAME, AND ELECTRONIC DEVICE THEREOF

(71) Applicant: Duksan Neolux Co., LTD, Cheonan-si (KR)

(72) Inventors: Je Woo Lee, Cheonan-si (KR); Dae Sic Kim, Cheonan-si (KR); Hyun Ji Oh, Cheonan-si (KR); Won Sam Kim, Cheonan-si (KR); Jung Geun Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 862 days.

(21) Appl. No.: 17/597,873

(22) PCT Filed: Jul. 29, 2020

(86) PCT No.: PCT/KR2020/009974
§ 371 (c)(1),
(2) Date: Jan. 27, 2022

(87) PCT Pub. No.: WO2021/020873
PCT Pub. Date: Feb. 4, 2021

(65) Prior Publication Data

US 2022/0251063 A1 Aug. 11, 2022

(30) Foreign Application Priority Data

Jul. 31, 2019 (KR) ........................ 10-2019-0092820
Jun. 18, 2020 (KR) ........................ 10-2020-0074494

(51) Int. Cl.
*C07D 495/04* (2006.01)
*C07D 401/04* (2006.01)
(Continued)

(52) U.S. Cl.
CPC ......... *C07D 495/04* (2013.01); *C07D 401/04* (2013.01); *C07D 401/14* (2013.01); *C07D 405/14* (2013.01); *C07D 407/14* (2013.01); *C07D 409/14* (2013.01); *C07D 487/04* (2013.01); *C07D 487/14* (2013.01); *C07D 491/048* (2013.01); *C07D 491/147* (2013.01);
(Continued)

(58) Field of Classification Search
CPC .. H10K 85/631; H10K 85/633; H10K 85/636; H10K 85/654
See application file for complete search history.

(56) References Cited

FOREIGN PATENT DOCUMENTS

WO WO-2010104047 A1 * 9/2010 ................ C07F 5/00

OTHER PUBLICATIONS

Machine-generated English-language translation of WO-2010104047-A1.*

* cited by examiner

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound for an organic electric device, an organic electric device using the same, and an electronic device including the organic electric device. According to the presently claimed subject matter, an organic electric device with high luminous efficiency, low driving voltage, and high heat resistance can be provided, and the color purity and lifetime of the organic electric device can be improved.

17 Claims, 3 Drawing Sheets

(51) Int. Cl.

| | |
|---|---|
| ***C07D 401/14*** | (2006.01) |
| ***C07D 405/14*** | (2006.01) |
| ***C07D 407/14*** | (2006.01) |
| ***C07D 409/14*** | (2006.01) |
| ***C07D 487/04*** | (2006.01) |
| ***C07D 487/14*** | (2006.01) |
| ***C07D 491/048*** | (2006.01) |
| ***C07D 491/147*** | (2006.01) |
| ***C07D 519/00*** | (2006.01) |
| ***H10K 50/13*** | (2023.01) |
| ***H10K 50/15*** | (2023.01) |
| ***H10K 50/16*** | (2023.01) |
| ***H10K 50/844*** | (2023.01) |
| ***H10K 59/80*** | (2023.01) |
| ***H10K 85/60*** | (2023.01) |

(52) U.S. Cl.

CPC ......... *C07D 519/00* (2013.01); *H10K 85/622* (2023.02); *H10K 85/626* (2023.02); *H10K 85/654* (2023.02); *H10K 85/6572* (2023.02); *H10K 85/6574* (2023.02); *H10K 85/6576* (2023.02); *C07B 2200/13* (2013.01); *H10K 50/13* (2023.02); *H10K 50/15* (2023.02); *H10K 50/16* (2023.02); *H10K 50/844* (2023.02); *H10K 59/873* (2023.02)

【Fig. 1】
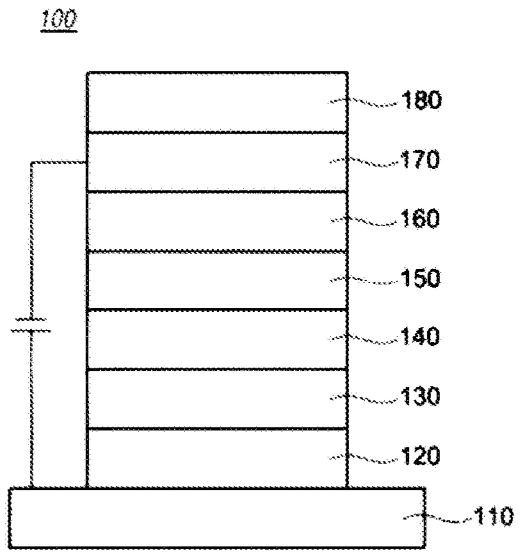

【Fig. 2】
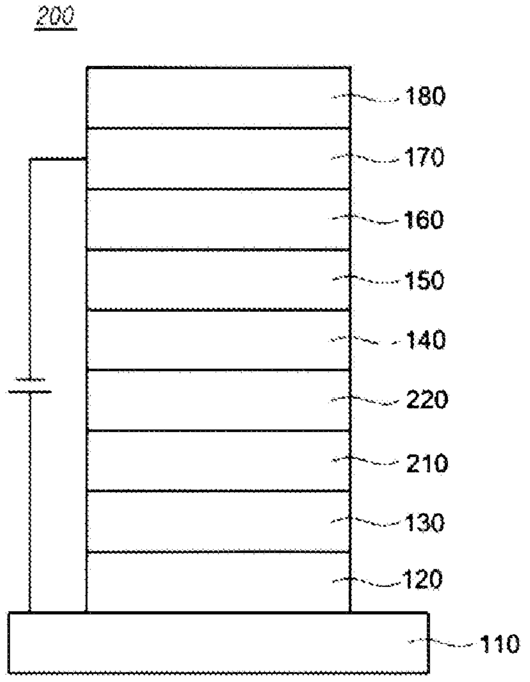

【Fig. 3】
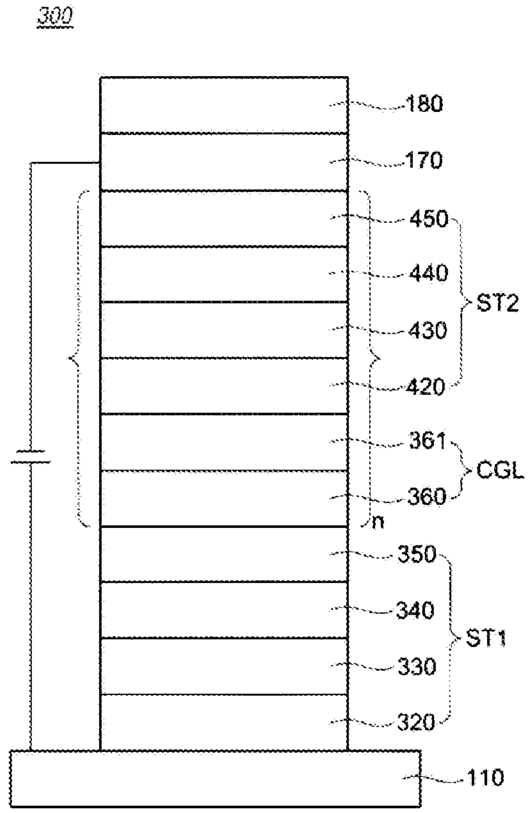
【Fig. 4】
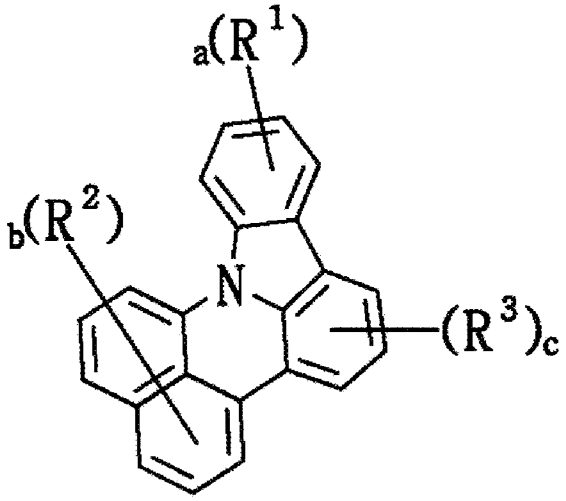

COMPOUND FOR ORGANIC ELECTRIC DEVICE, ORGANIC ELECTRIC DEVICE USING THE SAME, AND ELECTRONIC DEVICE THEREOF

BACKGROUND OF THE DISCLOSURE

Field of the Disclosure

The present disclosure relates to a compound for an organic electric device, an organic electric device using the same, and an electronic device thereof.

Related Art

In general, the organic light emission phenomenon refers to a phenomenon in which electrical energy is converted into light energy using an organic material. An organic electric device using the organic light emission phenomenon has a structure including an organic material layer disposed between an anode and a cathode. In particular, the organic material layer is often made of a multi-layered structure consisting of different materials so as to increase the efficiency and stability of the organic electric device, and may consisting of, for example, a hole injection layer, a hole transport layer, a light emitting layer, an electron transport layer, an electron injection layer, etc.

Materials used as an organic material layer in the organic electric device can be classified into light emitting materials and charge transport materials (e.g, hole injection materials, hole transport materials, electron transport materials, electron injection materials, etc.) according to their functions. In addition, the light emitting materials can be classified into a high molecular type and a low molecular type according to their molecular weight, and into a fluorescent material derived from a singlet excited state of electrons and a phosphorescent material derived from a triplet excited state of electrons according to their light emitting mechanism. Further, the light emitting materials may be divided into blue, green, and red light emitting materials according to the colors being emitted, and yellow and orange light emitting materials necessary for realizing better natural colors.

Meanwhile, when only one material is used as the light emitting material, there are problems in that the maximum light emission wavelength is shifted to a longer wavelength due to an intermolecular interaction and the color purity decreases or the efficiency of the device decreases due to the attenuation of luminescence, a host/dopant system may be used as a light emitting material so as to increase color purity and luminous efficiency through energy transfer. The principle is that when a small amount of a dopant having a smaller energy band gap, instead of the host forming a light emitting layer, is mixed with a light emitting layer, excitons generated from the light emitting layer are transported to the dopant to emit light with high efficiency. At this time, since the wavelength of the host moves to the wavelength band of the dopant, the light with a desired wavelength can be obtained according to the type of the dopant being used.

Currently, the portable display market is a large-area display, and the size thereof is increasing, and thus, greater power consumption than the power consumption required by the existing portable display is required. Therefore, power consumption has become an important factor for portable display that has a limited power supply (i.e., a battery), and life and efficiency are also important issues that must be resolved.

Life and efficiency are the most problematic issues in organic electronic devices, and as displays become larger, these efficiency and lifetime issues must be resolved.

Efficiency, lifespan, and driving voltage are mutually associated. There is a tendency that when the efficiency is increased, the driving voltage decreases relatively, and as the driving voltage decreases, the crystallization of organic materials caused by Jouleheating during the decrease of driving, resulting in an increase of lifespan. However, a mere improvement of the organic material layer cannot guarantee the maximization of efficiency. This is because when the energy level and T1 value between each organic material layer and the intrinsic properties of the material (mobility, interfacial properties, etc.) are optimally combined, long life and high efficiency can be achieved at the same time.

In general, electrons are transferred from the electron transport layer to the light emitting layer, and holes are transferred from the hole transport layer to the light emitting layer, and excitons are thereby generated by recombination.

However, in the case of the materials used for a hole transport layer, most of them have a low T1 value because they should have a low HOMO value. As a result, excitons generated in the light emitting layer are transferred to the electron transport layer, thereby causing a light emission at the interface of the hole transport layer or charge imbalance in the light emitting layer, thereby emitting a light at the interface of the electron transport layer.

When a light is emitted at the interface of the hole transport layer, there is a problem in that the color purity and efficiency of the organic electric device are deteriorated and the lifetime is shortened. Thus, the material must have a HOMO level between the HOMO energy level of the hole transport layer and the HOMO energy level of the light emitting layer. Accordingly, there is an urgent need for the development of an auxiliary light emitting layer having a high T1 value and a hole mobility within an appropriate range (within the range of driving voltage of the blue device of a full device).

However, this cannot be achieved merely with the structural characteristics for the core of an auxiliary light emitting layer material, and a device with high efficiency and long lifetime can be realized when the characteristics of the core and sub-substituents of the auxiliary light emitting layer material, and an appropriate balance between the auxiliary light emitting layer and the hole transport layer and between the auxiliary light emitting layer and the light emitting layer are achieved.

Meanwhile, with regard to the Joule heating generated during the driving of the device, there is also a need for the development of materials for a light emitting layer and an auxiliary light emitting layer with stable characteristics (i.e., a high glass transition temperature). It has been reported that the low glass transition temperature of the materials for the light emitting layer and the auxiliary light emitting layer material can reduce the uniformity level of the surface of the thin film when the device is driven, and the materials may be deformed due to the heat generated while the device is driven, which have a significant effect on the lifetime of the device.

Therefore, there is also a need for the development of materials that can tolerate for a long period of time during deposition, that is, materials with strong heat resistance. For full exhibition of excellent characteristics of an organic electric device, it is essential that the materials forming an organic material layer within the device (e.g., hole injection materials, hole transport materials, light emitting materials, electron transport materials, electron injection materials, auxiliary light emitting layer materials, etc.) be supported in advance by stable and efficient raw materials, and in particular, there is an urgent need for the development of materials used for the auxiliary light emitting layer, light emitting layer, hole transport layer, etc.

SUMMARY

An object of the present disclosure is to provide a compound which has high heat resistance, is capable of lowering the driving voltage of a device, and is capable of improving the luminous efficiency, color purity, and lifetime of the device; an organic electric device using the compound, and an electronic device including the organic electronic device.

In an aspect, the present disclosure provides a compound represented by the following Formula.

<Formula 1>

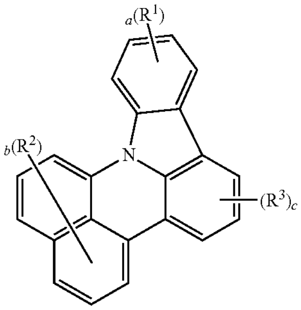

In another aspect, the present disclosure provides an organic electric device using the compound represented by Formula above and an electronic device thereof.

Advantageous Effects

By using the compound according to the present disclosure, it is possible to achieve high luminous efficiency, low driving voltage, and high heat resistance of the device, and it also provides the effects of improving the color purity and lifespan of the device.

BRIEF DESCRIPTION OF THE DRAWINGS

FIGS. 1 to 3 schematically illustrate organic electric devices according to embodiments of the present disclosure.

FIG. 4 illustrates the formula of the compound according to the present disclosure.

BEST MODE FOR CARRYING OUT THE INVENTION

The present disclosure provides the compound represented by the following Formula 1.

<Formula 1>

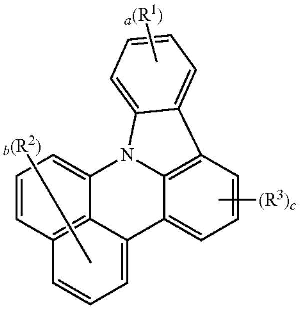

In another aspect, the present disclosure provides an organic electric device using the compound represented by the Formula above and an electronic device thereof.

DESCRIPTION OF EXEMPLARY EMBODIMENTS

Hereinafter, preferred embodiments of the present disclosure will be described with reference to the accompanying drawings.

In order to describe the present embodiments, it should be noted that in adding reference numerals to components of each drawing, the same components are given the same reference numerals as much as possible even though they are indicated on different drawings. In addition, when it is determined that a detailed description of a related known constitution or function may obscure the gist of the present disclosure in describing the present disclosure, the detailed description thereof will be omitted. In the drawings referenced below, no scale ratio applies.

In describing the components of the present disclosure, terms such as first, second, A, B, (a), (b), etc. may be used. These terms are only for distinguishing the elements from other elements, and the essence, order, or order of the elements are not limited by the terms.

When a component is described as "linked", "bound" or "connected" to another component, the component may be directly linked or connected to the another component, but it should be understood that another component may be "linked", "bound" or "connected" between each component.

In addition, when a component (e.g., a layer, film, region, plate, etc.) is described to be "on top" or "on" of another component, it should be understood that this may include a case in which another component is "immediately on top of" as well as a case in which another component in disposed therebetween. In contrast, it should be understood that when a component is described to be "immediately on top of" another component, it means that there is no other component disposed therebetween.

The terms used in this specification and the appended claims are as described below, unless otherwise stated, without departing from the spirit of the present disclosure.

As used herein, the term "halo" or "halogen" includes fluorine (F), chlorine (Cl), bromine (Br), and iodine (I), unless otherwise specified.

As used herein, the term "alkyl" or "alkyl group" has 1 to 60 carbons linked by a single bond unless otherwise specified, and refers to a radical of a saturated aliphatic functional group, including a linear chain alkyl group, a branched chain alkyl group, a cycloalkyl (alicyclic) group, an alkyl-substituted cycloalkyl group, and a cycloalkyl-substituted alkyl group.

As used herein, the term "haloalkyl group" or "halogenalkyl group" refers to an alkyl group in which halogen is substituted, unless otherwise specified.

As used herein, the term "alkenyl" or "alkynyl" has a double bond or a triple bond, respectively, includes a linear or branched chain group, and has 2 to 60 carbon atoms, unless otherwise specified, but is not limited thereto.

As used herein, the term "cycloalkyl" refers to an alkyl which forms a ring having 3 to 60 carbon atoms unless otherwise specified, but is not limited thereto.

As used herein, the term "an alkoxy group" or "alkyloxy group" refers to an alkyl group to which an oxygen radical is bound, and has 1 to 60 carbon atoms unless otherwise specified, but is not limited thereto.

As used herein, the term "alkenoxyl group", "alkenoxy group", "alkenyloxyl group", or "alkenyloxy group" refers to an alkenyl group to which an oxygen radical is attached, and has 2 to 60 carbon atoms unless otherwise specified, but is not limited thereto.

As used herein, the terms "aryl group" and "arylene group" each have 6 to 60 carbon atoms unless otherwise specified, but are not limited thereto. As used herein, the aryl group or arylene group includes a single ring type, a ring assembly, a fused multiple ring compound, etc. For example, the aryl group may include a phenyl group, a monovalent functional group of biphenyl, a monovalent functional group of naphthalene, a fluorenyl group, and a substituted fluorenyl group, and the arylene group may include a fluorenylene group and a substituted fluorenylene group.

As used herein, the terms "a ring assembly" means that two or more ring systems (monocyclic or fused ring systems) are directly connected to each other through a single bond or double bond, in which the number of direct links between such rings is one less than the total number of ring systems in the compound. In the ring assembly, the same or different ring systems may be directly connected to each other through a single bond or double bond.

As used herein, since the aryl group includes a ring aggregate, the aryl group includes biphenyl and terphenyl in which a benzene ring, which is a single aromatic ring, is connected by a single bond. In addition, since the aryl group also includes a compound in which an aromatic ring system fused to an aromatic single ring is connected by a single bond, it also includes, for example, a compound in which a benzene ring (which is an aromatic single ring) and fluorine (which is a fused aromatic ring system) are linked by a single bond.

As used herein, the term "fused multiple ring system" refers to a fused ring form in which at least two atoms are shared, and it includes a form in which ring systems of two or more hydrocarbons are fused, a form in which at least one heterocyclic systems including at least one heteroatom is fused, etc. Such a fused multiple ring system may be an aromatic ring, a heteroaromatic ring, an aliphatic ring, or a combination of these rings.

As used herein, the term "a spiro compound" has a spiro union, and the spiro union refers to a linkage in which two rings share only one atom. In particular, the atom shared by the two rings is called a "spiro atom", and they are each called "monospiro-", "dispiro-", and "trispiro-" compounds depending on the number of spiro atoms included in a compound.

As used herein, the terms "fluorenyl group", "fluorenylene group", and "fluorenetriyl group" refer to a monovalent, divalent, or trivalent functional group in which R, R', R" and R" are all hydrogen in the following structures, respectively, unless otherwise specified; "substituted fluorenyl group", "substituted fluorenylene group", or "substituted fluorenetriyl group" means that at least one of the substituents R, R', R", and R" is a substituent other than hydrogen, and include cases where R and R' are bound to each other to form a spiro compound together with the carbon to which they are attached. As used herein, all of a fluorenyl group, a fluorenylene group, and a fluorenetriyl group may also be referred to as fluorene groups regardless of valences such as monovalent, divalent, trivalent, etc.

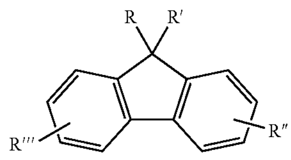

In addition, the R, R', R", and R''' may each independently be an alkyl group having 1 to 20 carbon atoms, an alkenyl group having 1 to 20 carbon atoms, an aryl group having 6 to 30 carbon atoms, and a heterocyclic group having 3 to 30 carbon atoms and, for example, the aryl group may be phenyl, biphenyl, naphthalene, anthracene, or phenanthrene, and the heterocyclic group may be pyrrole, furan, thiophene, pyrazole, imidazole, triazole, pyridine, pyrimidine, pyridazine, pyrazine, triazine, indole, benzofuran, quinazoline, or quinoxaline. For example, the substituted fluorenyl group and the fluorenylene group may each be a monovalent functional group or divalent functional group of 9,9-dimethylfluorene, 9,9-diphenylfluorene and 9,9'-spirobi[9H-fluorene].

As used herein, the term "heterocyclic group" includes not only aromatic rings (e.g., "heteroaryl group" and "heteroarylene group"), but also non-aromatic rings, and may refer to a ring having 2 to 60 carbon atoms each including one or more heteroatoms unless otherwise specified, but is not limited thereto. As used herein, the term "heteroatom" refers to N, O, S, P, or Si unless otherwise specified, and a heterocyclic group refers to a monocyclic group including a heteroatom, a ring assembly, a fused multiple ring system, a spiro compound, etc.

For example, the "heterocyclic group" may include a compound including a heteroatom group (e.g., $SO_2$, P=O, etc.), such as the following compound instead of carbon that forms a ring.

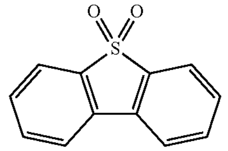 [SMILES: O=S1(=O)c2ccccc2-c2ccccc21]

As used herein, the term "ring" includes monocyclic and polycyclic rings, and includes heterocycles containing at least one heteroatom as well as hydrocarbon rings, and includes aromatic and non-aromatic rings.

As used herein, the term "polycyclic" includes ring assemblies (e.g., biphenyl, terphenyl, etc.), fused multiple ring systems, and spiro compounds; includes non-aromatic as well as aromatic, and includes heterocycles containing at least one heteroatom as well as hydrocarbon rings.

As used herein, the term "fused multiple ring system" refers to a fused ring type that shares at least two atoms. For example, in the case of an aryl group, it may be a naphthalenyl group, a phenanthrenyl group, a fluorenyl group, etc., but is not limited thereto.

As used herein, the term "alicyclic group" refers to cyclic hydrocarbons other than aromatic hydrocarbons, and they include monocyclic, ring assemblies, fused multiple ring systems, spiro compounds, etc., and refers to a ring having 3 to 60 carbon atoms unless otherwise specified, but is not limited thereto. For example, when benzene (i.e., an aromatic ring) and cyclohexane (i.e., a non-aromatic ring) are fused, it also corresponds to an aliphatic ring.

Additionally, when prefixes are named consecutively, it is meant that the substituents are listed in the order they were listed. For example, in the case of an arylalkoxy group, it means an alkoxy group substituted with an aryl group; in the case of an alkoxycarbonyl group, it means a carbonyl group substituted with an alkoxy group; additionally, in the case of an arylcarbonyl alkenyl group, it means an alkenyl group substituted with an arylcarbonyl group, in which the arylcarbonyl group is a carbonyl group substituted with an aryl group.

Additionally, unless otherwise specified, the term the "substituted" in the expression "substituted or unsubstituted" as used herein refers to a substitution with one or more substituents selected from the group consisting of a deuterium, a halogen, an amino group, a nitrile group, a nitro group, a $C_{1-20}$ alkyl group, a $C_{1-20}$ alkoxy group, a $C_{1-20}$ alkylamine group, a $C_{1-20}$ alkylthiophene group, a $C_{6-20}$ arylthiophene group, a $C_{2-20}$ alkenyl group, a $C_{2-20}$ alkynyl group, a $C_{3-20}$ cycloalkyl group, a $C_{6-20}$ aryl group, a $C_{6-20}$ aryl group substituted with a deuterium, a $C_{8-20}$ an arylalkenyl group, a silane group, a boron group, a germanium group, and a $C_{2-20}$ heterocyclic group comprising at least one heteroatom among O, N, S, Si, and P, but is not limited to these substituents.

As used herein, the "names of functional groups" corresponding to the aryl group, arylene group, heterocyclic group, etc. exemplified as examples of each symbol and a substituent thereof may be described as "a name of the functional group reflecting the valence", and may also be described as the "name of parent compound". For example, in the case of "phenanthrene", which is a type of an aryl group, the names of the groups may be described such that the monovalent group as "phenanthryl (group)", and the divalent group as "phenanthrylene (group)", etc., but may also be described as "phenanthrene", which is the name of the parent compound, regardless of the valence.

Similarly, in the case of pyrimidine, it may be described regardless of the valence, or in the case of a monovalent, it may be described as pyrimidinyl (group); in the case of a divalent, it may be described as the "name of the group" of the valence (e.g., pyrimidinylene (group)). Therefore, as used herein, when the type of the substituent is described as the name of the parent compound, it may refer to an n-valent "group" formed by detachment of a hydrogen atom bound to a carbon atom and/or hetero atom of the parent compound.

In addition, in describing the names of the compounds or the substituents in the present specification, the numbers or alphabets indicating positions may be omitted. For example, pyrido[4,3-d]pyrimidine may be described as pyridopyrimidine; benzofuro[2,3-d]pyrimidine as benzofuropyrimidine; 9,9-dimethyl-9H-fluorene as dimethylfluorene, etc. Therefore, both benzo[g]quinoxaline and benzo[f]quinoxaline may be described as benzoquinoxaline.

In addition, unless there is an explicit description, the formulas used in the present disclosure are applied in the same manner as the definition of the substituents by the exponent definition of Formula below.

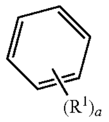

In particular, when a is an integer of 0, the substituent $R^1$ means that it does not exist, that is, when a is 0, it means that all hydrogens are bound to carbons forming the benzene ring, and in this case, the formula or compound may be described while omitting the indication of the hydrogen bound to carbon. In addition, when a is an integer of 1, one substituent $R^1$ may be bound to any one of the carbons forming the benzene ring; when a is an integer of 2 or 3, it may be bound, for example, as shown below; even when a is an integer of 4 to 6, it may be bound to the carbon of the benzene ring in a similar manner; and when a is an integer of 2 or greater, $R^1$ may be the same as or different from each other.

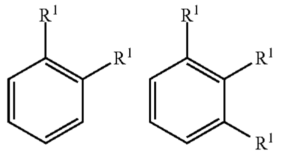

(a = 2) (a = 3)

Unless otherwise specified in the present application, forming a ring means that adjacent groups bind to one another to form a single ring or fused multiple ring, and a single ring and a formed fused multiple ring include a heterocycle containing at least one heteroatom as well as a hydrocarbon ring, and may include aromatic and non-aromatic rings.

Hereinafter, the stacked structure of an organic electric device including the compound of the present disclosure will be described with reference to FIGS. 1 to 3.

Referring to FIG. 1, an organic electric device 100 according to an embodiment of the present disclosure includes a first electrode 110, a second electrode 170, and an organic material layer including a compound according to the present disclosure disposed between the first electrode 110 and the second electrode 170 formed on a substrate (not shown).

The first electrode 110 may be an anode (a positive electrode), a second electrode 170 may be a cathode (a negative electrode), and in the case of an inverted type, the first electrode may be a cathode and the second electrode may be an anode.

The organic material layer may include a hole injection layer 120, a hole transport layer 130, a light emitting layer 140, an electron transport layer 150, and an electron injection layer 160. Specifically, the hole injection layer 120, the hole transport layer 130, the light emitting layer 140, the electron transport layer 150, and the electron injection layer 160 may be formed sequentially on the first electrode 110.

Preferably, a capping layer 180 may be formed on one surface of both surfaces of the first electrode 110 or the second electrode 170, which is not in contact with an organic material layer, and when the capping layer 180 is formed the light efficiency of the organic electric device can be improved.

For example, the capping layer 180 may be formed on the second electrode 170. In the case of a top emission organic light emitting device, it is possible to reduce optical energy loss due to surface plasmon polaritons (SPPs) in the second electrode 170 by the formation of the capping layer 180, whereas in the case of a bottom emission organic light emitting device, the capping layer 180 may act as a buffer for the second electrode 170.

Meanwhile, a buffer layer 210 or an auxiliary light emitting layer 220 may be further formed between the hole transport layer 130 and the light emitting layer 140, which will be described with reference to FIG. 2.

Referring to FIG. 2, an organic electric device 200 according to another embodiment of the present disclosure may include the hole injection layer 120, the hole transport layer 130, a buffer layer 210, an auxiliary light emitting layer 220, the light emitting layer 140, the electron transport layer 150, the electron injection layer 160, and the second electrode 170; and the capping layer 180 may be formed on the second electrode.

Although not shown in FIG. 2, an auxiliary electron transport layer may be further formed between the light emitting layer 140 and the electron transport layer 150.

In addition, according to another embodiment of the present disclosure, the organic material layer may have a form in which a plurality of stacks including a hole transport layer, a light emitting layer, and an electron transport layer are formed, which will be described with reference to FIG. 3.

Referring to FIG. 3, in an organic electric device 300 according to still another embodiment of the present disclosure, two or more sets of stacks ST1 and ST2 of an organic material layer consisting of multiple layers may be formed between the first electrode 110 and the second electrode 170, and a charge generation layer (CGL) may be formed between the stacks of the organic material layer.

Specifically, an organic electric device according to an embodiment in the present disclosure may include the first electrode 110, a first stack ST1, the charge generation layer (CGL), a second stack ST2, the second electrode 170, and the capping layer 180.

The first stack ST1, which is an organic material layer formed on the first electrode 110, may include a first a hole injection layer 320, a first a hole transport layer 330, a first light emitting layer 340, and a first electron transport layer 350.

The second stack ST2 may include a second hole injection layer 420, a second hole transport layer 430, a second light emitting layer 440, and a second electron transport layer 450.

As described above, the first stack and the second stack may be an organic material layer having the same stacked structure, but they may also be an organic material layer having a different stacked structure from each other.

A charge generation layer CGL may be formed between the first stack ST1 and the second stack ST2. The charge generation layer CGL may include a first charge generation layer 360 and a second charge generation layer 361. These charge generation layers (CGLs) may be formed between the first a light emitting layer 340 and the second a light emitting layer 440 thereby increasing the current efficiency generated by each light emitting layer and play a role in distributing the charge smoothly.

The first light emitting layer 340 may include a light emitting material including a blue fluorescent dopant in a blue host, and the second light emitting layer 440 may include a material in which a green host is doped with a greenish yellow dopant and a red dopant; however, the materials of the first light emitting layer 340 and the second light emitting layer 440 according to the embodiment of the present disclosure are not limited thereto.

In particular, the second hole transport layer 430 is achieved such that it includes the second stack ST2, in which the energy level is set higher than the triplet excitation energy level of the second light emitting layer 440.

Since the energy level of the second hole transport layer 430 is higher than that of the second light emitting layer 440, it is possible to prevent triplet excitons of the second light emitting layer 440 from passing to the second hole transport layer 430 and from decreasing luminous efficiency. That is, the second hole transport layer 430 may function as an exciton blocking layer for preventing triplet excitons from passing over while performing a function of transporting holes from the inherent second light emitting layer 440.

In addition, for the function of the exciton blocking layer, the first hole transport layer 330 may also be set to an energy level higher than the triplet excitation energy level of the first light emitting layer 340. And, it is preferable that the first electron transport layer 350 be also set to an energy level higher than the triplet excitation energy level of the first light emitting layer 340, and the second electron transport layer 450 be also set to an energy level higher than the triplet excitation energy level of the second light emitting layer 440.

In FIG. 3, n may be an integer of 1 to 5. When n is 2, the charge generation layer CGL and the third stack may additionally be stacked on the second stack ST2.

When a plurality of a light emitting layer are formed by a multi-layer stack structure method as shown in FIG. 3, not only it is possible to manufacture an organic electroluminescent device that emits white light by the mixing effect of the light emitted from each light emitting layer, but also it is possible to manufacture an organic electroluminescent device that emits light of various colors.

The compound represented by Formula 1 of the present disclosure may be used as a material for a hole injection layer (120, 320, 420), a hole transport layer (130, 330, 430), a buffer layer 210, an auxiliary light emitting layer 220, an electron transport layer (150, 350, 450), an electron injection layer 160, a light emitting layer (140, 340, 440), or a capping layer 180, and preferably, the compound represented by Formula 1 of the present disclosure may be used as a material for an auxiliary light emitting layer 220, a light emitting layer 140, 340, 440, and/or a capping layer 180.

An organic electric device according to FIGS. 1 to 3 may further include a protective layer (not shown) and an encapsulation layer (not shown). The protective layer may be disposed on the capping layer, and the encapsulation layer disposed on the capping layer, and in order to protect the first electrode, the second electrode, and the organic material layer, it may be formed to cover one or more sides among the first electrode, the second electrode, and the organic material layer.

The protective layer can provide a planarized surface so that the encapsulation layer can be uniformly formed, and it may serve to protect the first electrode, the second electrode, and the organic material layer during the process of manufacturing the encapsulation layer.

The encapsulation layer can serve to prevent the penetration of external oxygen and moisture into the organic electric device.

Meanwhile, even for the same and similar core, the band gap, electrical properties, interface properties, etc. may vary depending to which position the substituent is bound; therefore, it is necessary to study the selection of the core and the combination of sub-substituents bound thereto, and in particular, when the energy level and T1 value between each organic material layer and the intrinsic properties of the material (mobility, interfacial properties, etc.) are optimally combined, long lifetime and high efficiency can be achieved at the same time.

Accordingly, in the present disclosure, by using the compound represented by Formula 1 as a material of the auxiliary light emitting layer 220, the light emitting layer (140, 340, 440) and/or the capping layer 180, it was possible to optimize the energy level, T1 value, and material properties (mobility, interfacial properties, etc.) between each of the organic material layers, thereby simultaneously improving the lifetime and efficiency of the organic electric device.

The organic electroluminescent diode according to an embodiment of the present disclosure may be manufactured using various deposition methods. The organic electroluminescent device may be manufactured using a deposition method such as PVD or CVD, for example, it may be manufactured in such a manner that a metal or a metal oxide having conductivity or an alloy thereof is deposited on a substrate to form the cathode 110, and then an organic material layer (which includes the hole injection layer (120, 320, 420), the hole transport layer (130, 330, 430), the light emitting layer (140, 340, 440), the electron transport layer (150, 350, 450), and the electron injection layer (160)) is formed thereon, and a material that can be used as the anode 170 is deposited thereon. In addition, the auxiliary light emitting layer 220 may be further formed between the hole transport layer (130, 330, 430) and the light emitting layer (140, 340, 440), and an auxiliary electron transport layer (not shown) may be further formed between the light emitting layer 140 and the electron transport layer 150, it may be formed in a stack structure as described above.

In addition, the organic material layer may be manufactured with a smaller number of layers by a solution process or solvent process rather than a deposition method using various polymer materials, for example methods such as spin coating process, nozzle printing process, inkjet printing process, slot coating process, dip coating process, roll-to-roll process, doctor blading process, screen printing process, or thermal transfer method. Since an organic material layer according to the present disclosure can be formed in various ways, the scope of the right of the present disclosure is not limited by the formation method.

The organic electric device according to an embodiment of the present disclosure may be a top emission type, a bottom emission type, or a double side emission type according to the material used.

The organic electric device according to an embodiment of the present disclosure may include an organic electroluminescent diode, an organic solar cell, an organic photoreceptor, an organic transistor, a single color lighting device, a quantum dot display device, etc.

Another embodiment of the present disclosure may include a display device including an organic electric device of the present disclosure described above, and an electric device including a control unit for controlling the display device. In particular, the electric device may be a current or future wired/wireless communication terminal, and it includes all electric devices such as mobile communication terminals (e.g., mobile phones), PDA, electronic dictionary, PMP, remote control, navigation, game machines, various TVs, various computers, etc.

Hereinafter, the compound according to an aspect of the present disclosure will be described.

The compound according to one aspect of the present disclosure is represented by Formula 1 below.

<Formula 1>

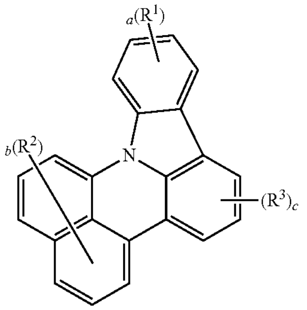

<Formula 1-1>

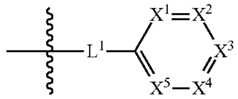

<Formula 1-2>

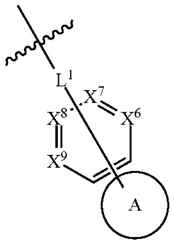

<Formula 1-3>

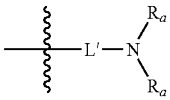

In Formula 1 above,

1) $R^1$ to $R^3$ are each independently selected from the group consisting of a hydrogen; a deuterium; a halogen; an amino group; a cyano group; a nitro group; a $C_{6-60}$ aryl group; a fluorenyl group; a $C_{2-60}$ heterocyclic group comprising at least one heteroatom among O, N, S, Si, and P; a fused ring group between a $C_{3-60}$ aliphatic ring and a $C_{6-60}$ aromatic ring; a $C_{1-50}$ alkyl group; a $C_{2-20}$ alkenyl group; a $C_{2-20}$ alkynyl group; a $C_{1-30}$ alkoxyl group; a $C_{6-30}$ aryloxy group; Formula 1-1; Formula 1-2; and Formula 1-3, or adjacent groups thereof can bind to one another to form a ring;

2) at least one of $R^1$ to $R^3$ is any one of Formula 1-1 to Formula 1-3 above;

3) L' is selected from the group consisting of a single bond; a $C_{6-60}$ arylene group; a fluorenylene group; a fused ring group between a $C_{3-60}$ aliphatic ring and a $C_{6-60}$ aromatic ring; a $C_{2-60}$ heterocyclic group comprising at least one heteroatom among O, N, S, Si, and P; and a combination thereof; and $R_a$ and $R_b$ are each independently selected from the group consisting of a $C_{6-60}$ aryl group; a fluorenyl group; a $C_{3-60}$ aliphatic ring group; a $C_{2-60}$ heterocyclic group comprising at least one heteroatom among O, N, S, Si, and P; and a combination thereof;

4) a is an integer from 0 to 4; b is an integer from 0 to 6; c is an integer from 0 to 3; and a+b+c is greater than or equal to 1;

5) when a, b, and c are 2 or greater, they are the same as or different from one another; and a plurality of $R^1$, or a plurality of $R^2$, or a plurality of $R^3$ can bind to one another to form a ring;

$X^1$ to $X^9$ are each independently N or $C(R_c)$;

7) at least one of $X^1$ to $X^5$ and at least one of $X^6$ to $X^9$ are N;

8) $L^1$ are each independently selected from the group consisting of a single bond; a $C_{6-60}$ arylene group; a fluorenylene group; a fused ring group between a $C_{3-60}$ aliphatic ring and a $C_{6-60}$ aromatic ring; a $C_{2-60}$ heterocyclic group comprising at least one heteroatom among O, N, S, Si, and P; and a combination thereof;

9) $R^c$ is selected from the group consisting of a hydrogen; a deuterium; a halogen; an amino group; a cyano group; a nitro group; a $C_{6-60}$ aryl group; a fluorenyl group; a $C_{2-60}$ heterocyclic group comprising at least one heteroatom among O, N, S, Si, and P; a fused ring group between a $C_{3-60}$ aliphatic ring and a $C_{6-60}$ aromatic ring; a $C_{1-50}$ alkyl group; a $C_{2-20}$ alkenyl group; a $C_{2-20}$ alkynyl group; a $C_{1-30}$ alkoxyl group; a $C_{6-30}$ aryloxy group; and -L'-N($R_c$)($R_d$);

10) the definition of L" is the same as that of L' above; the definitions of $R_c$ and $R_d$ are the same as those of $R_a$ and $R_b$ above;

11) the ring A of Formula 1-2 above is selected from the group consisting of Formula A-1 to Formula A-16 below, <Formula A-1>

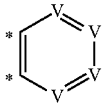

<Formula A-2>

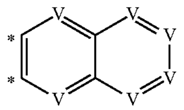

<Formula A-3>

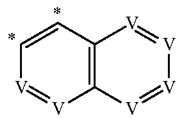

<Formula A-4>

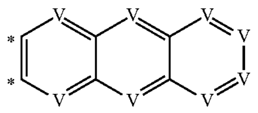

<Formula A-5>

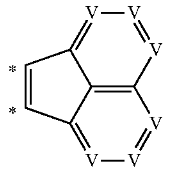

<Formula A-6>

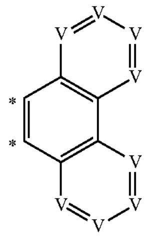

-continued

<Formula A-7>

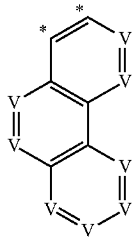

<Formula A-8>

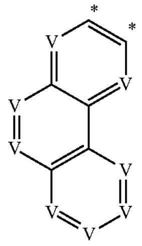

<Formula A-9>

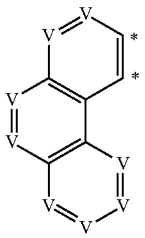

<Formula A-10>

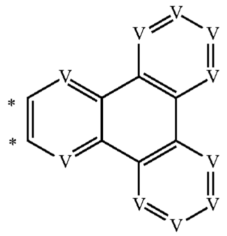

<Formula A-11>

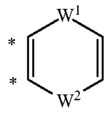

<Formula A-12>

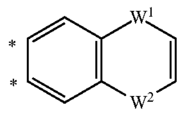

<Formula A-13>

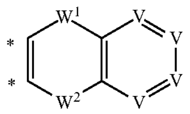

<Formula A-14>

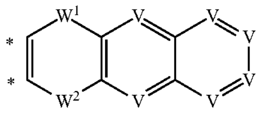

-continued

<Formula A-15>

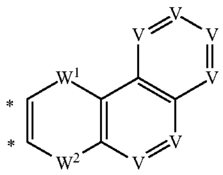

<Formula A-16>

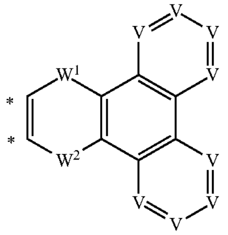

wherein in the formulas above, 11-1) * is a site to be bound to a ring comprising $X^6$ to $X^9$;

11-2) V are each independently N or $C(R^e)$;

11-3) $W^1$ and $W^2$ are each independently a single bond, —N—$L^3$-$Ar^3$, S, O, or CR'R"; with the proviso that $W^1$ and $W^2$ are not a single bond at the same time;

11-4) $L^3$ is the same as the definition of $L^1$ in Formula 1 above;

11-5) $Ar^3$ is selected from the group consisting of a $C_{6-60}$ aryl group; a fluorenyl group; a fused ring group between a $C_{3-60}$ aliphatic ring and a $C_{6-60}$ aromatic ring; a $C_{2-60}$ heterocyclic group comprising at least one heteroatom among O, N, S, Si, and P; and a combination thereof; and 11-6) $R^e$, R', and R" are each of a hydrogen; a deuterium; a halogen; an amino group; a cyano group; a nitro group; a $C_{6-60}$ aryl group; a fluorenyl group; a $C_{2-60}$ heterocyclic group comprising at least one heteroatom among O, N, S, Si, and P; a fused ring group between a $C_{3-60}$ aliphatic ring and a $C_{6-60}$ aromatic ring; a $C_{1-50}$ alkyl group; a $C_{2-20}$ alkenyl group; a $C_{2-20}$ alkynyl group; a $C_{1-30}$ alkoxyl group; a $C_{6-30}$ aryloxy group; or —L'—$N(R_c)(R_d)$; or these groups can bind to one another to form a ring; or R' and R" can bind to one another to form a spiro ring; and 12) the rings formed by $R^1$ to $R^3$, $L^1$, L', $L^3$, $Ar^3$, $R_a$ to $R_d$, $R^c$, $R^e$, R', R", and adjacent groups thereof can be each further substituted with one or more substituents selected from the group consisting of a deuterium; a halogen; a silane group substituted or unsubstituted with a $C_{1-20}$ alkyl group or a $C_{6-20}$ aryl group; a siloxane group; a boron group; a germanium group; a cyano group; an amino group; a nitro group; a $C_{1-20}$ alkylthio group; a $C_{1-20}$ alkoxy group; a $C_{6-20}$ arylalkoxy group; a $C_{1-20}$ alkyl group; a $C_{2-20}$ alkenyl group; a $C_{2-20}$ alkynyl group; a $C_{6-20}$ aryl group; a $C_{6-20}$ aryl group substituted with a deuterium; a fluorenyl group; a $C_{2-20}$ heterocyclic group comprising at least one heteroatom among O, N, S, Si, and P; a $C_{3-20}$ aliphatic ring group; a $C_{7-20}$ arylalkyl group; a $C_{8-20}$ arylalkenyl group; and a combination thereof; or adjacent groups thereof can form a ring with one another.

When the $Ar^3$, $R_a$ to $R_d$, $R^1$ to $R^3$, $R^c$, $R^e$, R', and R" are an aryl group, preferably, it may be a $C_{6-30}$ aryl group, and more preferably a $C_{6-18}$ aryl group, such as phenyl, biphenyl, naphthyl, terphenyl, etc.

When the L', L', $L^3$, $R_a$ to $R_d$, $R^1$ to $R^3$, $R^c$, $R^e$, R', and R" are a heterocyclic group, it may be a $C_{2-30}$ heterocyclic group, more preferably a $C_{2-18}$ heterocyclic group, for example, may be dibenzofuran, dibenzothiophene, naphthobenzothiophene, naphthobenzofuran, etc.

When the $Ar^3$, $R_a$ to $R_d$, $R^1$ to $R^3$, $R^c$, $R^e$, R', and R" are a fluorenyl group, preferably, it may be 9,9-dimethyl-9H-fluorene, 9,9-diphenyl-9H-fluorenyl group, 9,9'-spirobifluorene, etc.

When the $L^1$, L', and $L^3$ are an arylene group, preferably, it may be a $C_{6-30}$ arylene group, more preferably a $C_{6-18}$ arylene group, such as phenyl, biphenyl, naphthyl, terphenyl, etc.

When the $R^1$ to $R^3$, $R^c$, $R^e$, R', and R" are an alkyl group, preferably, it may be a $C_{1-10}$ alkyl group, for example, methyl, t-butyl, etc.

When the $R^1$ to $R^3$, $R^c$, $R^e$, R', and R" are an alkoxyl group, preferably, it may be a $C_{1-20}$ alkoxyl group, more preferably a $C_{1-10}$ alkoxyl group, such as methoxy, t-butoxy, etc.

The ring formed by the adjacent groups of the $L^1$, L', $L^3$, $R_a$ to $R_d$, $R^1$ to $R^3$, $R^c$, $R^e$, R', and R" may be a $C_{6-60}$ aromatic ring group; a fluorenyl group; a $C_{2-60}$ heterocyclic group comprising at least one heteroatom among O, N, S, Si, and P; or a $C_{3-60}$ aliphatic ring group, and for example, when the adjacent groups bind to one another to form an aromatic ring, preferably, a $C_{6-20}$ aromatic ring, more preferably a $C_{6-14}$ aromatic ring, such as benzene, naphthalene, phenanthrene, etc. may be formed.

More preferably, Formula 1 may be represented by any one of Formula 1-1 to Formula 1-9 below, but is not limited thereto.

<Formula 1-1>

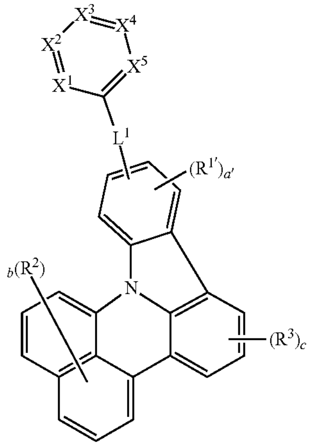

<Formula 1-2>

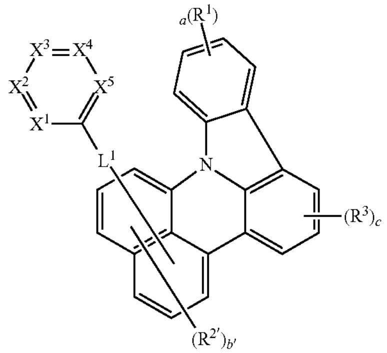

-continued

<Formula 1-3>

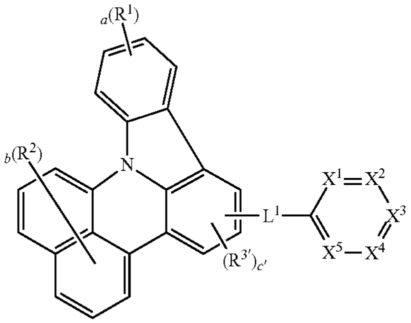

<Formula 1-4>

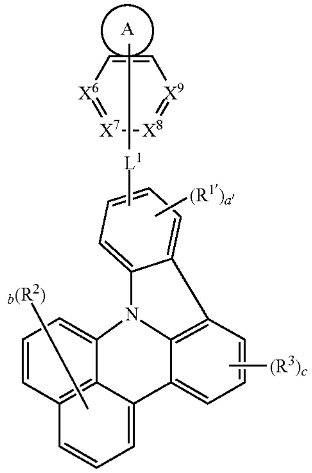

<Formula 1-5>

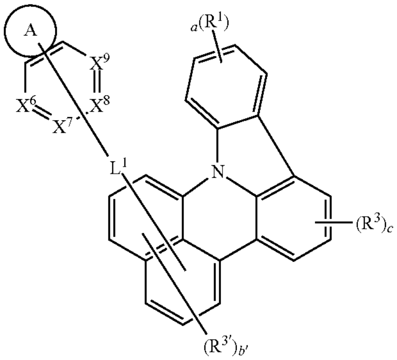

<Formula 1-6>

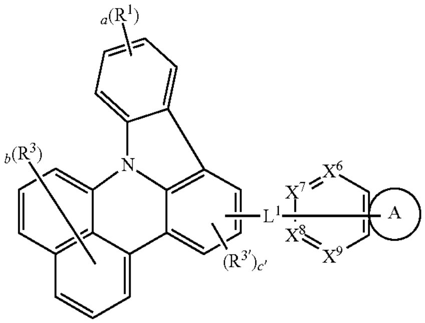

-continued

<Formula 1-7>

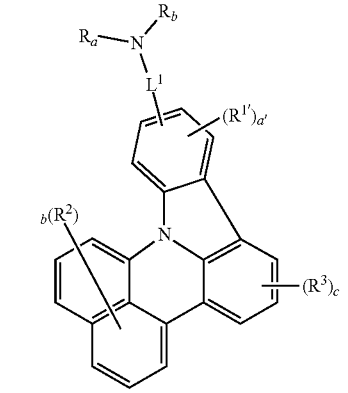

<Formula 1-8>

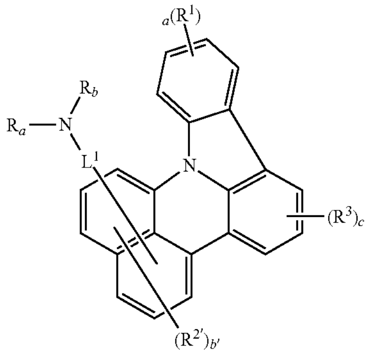

<Formula 1-9>

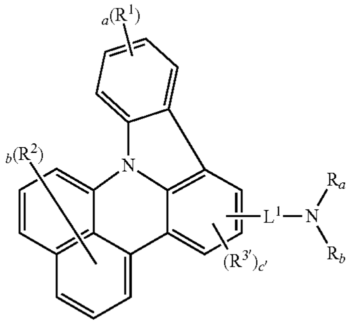

In Formula 1-1 to Formula 1-9 above,

1) $R^{1'}$ to $R^{3'}$ are the same as the definition of $R^1$ in Formula 1 above;

2) a' and c' are each independently an integer of 0 to 3; and b' is an integer from 0 to 5; and 3) $R^1$ to $R^3$, a, b, c, $L^1$, L', $R_a$, $R_b$, $X^1$ to $X^9$, and ring A are the same as defined in Formula 1 above.

More preferably, the compound represented by Formula 1-1 or Formula 1-2 is any one of Formula B-1 to Formula B-12, but is not limited thereto.

B-1

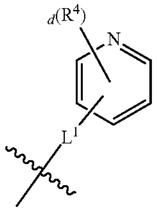

-continued

B-2

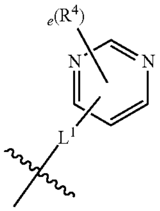

B-3

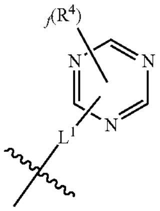

B-4

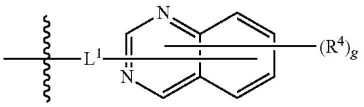

B-5

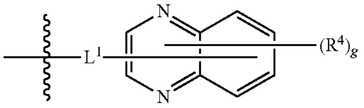

B-6

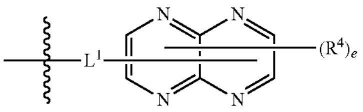

B-7

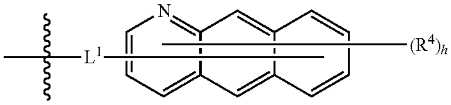

B-8

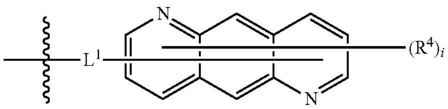

B-9

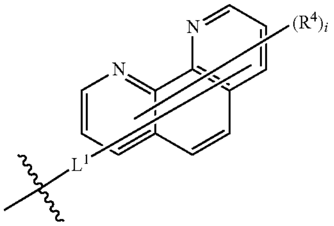

-continued

B-10

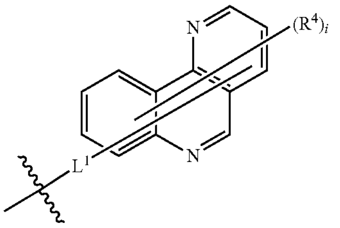

B-11

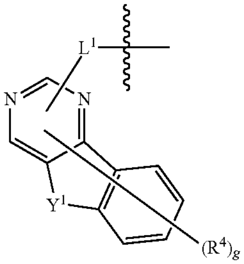

B-12

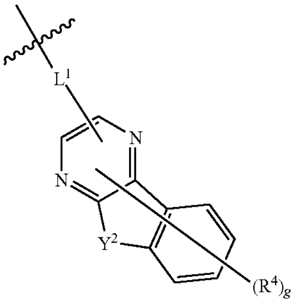

In Formula B-1 to Formula B-12 above,

1) $R^4$ is the same as the definition of $R^1$ of Formula 1 above;

2) $Y^1$ and $Y^2$ are each independently —N—$L^3$—$Ar^3$, S, O, or CR'R";

3) d is an integer from 0 to 4; e is an integer from 0 to 3; f is an integer from 0 to 2; g is an integer from 0 to 5; h is an integer from 0 to 8; and i is an integer from 0 to 7; and 4) $L^1$, $L^3$, $Ar^3$, R', and R" are the same as defined in Formula 1 above.

Meanwhile, the compound of Formula 1 above is any one of the following compounds P-1 to P-212, but is not limited thereto.

P-1
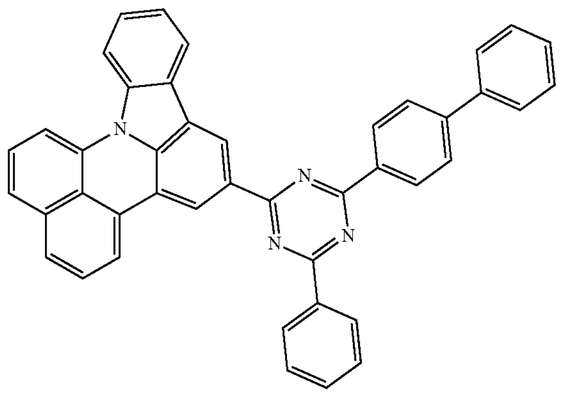
P-2
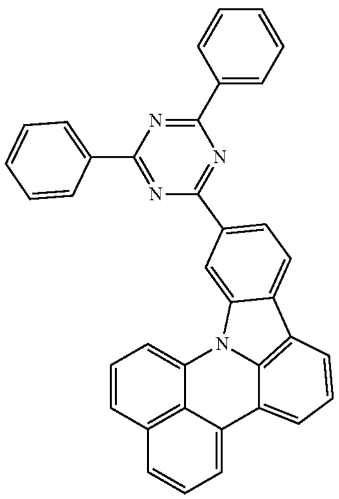
P-3
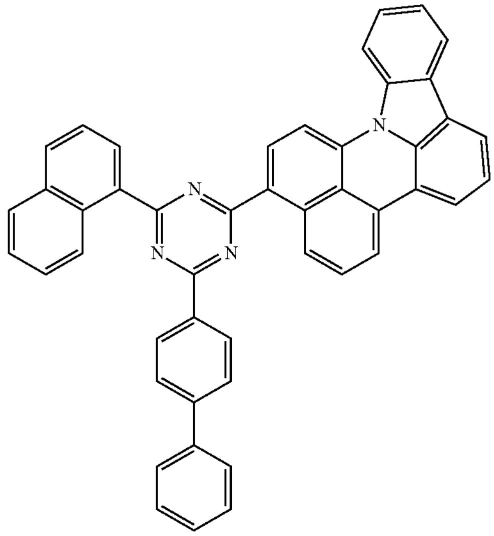
P-4
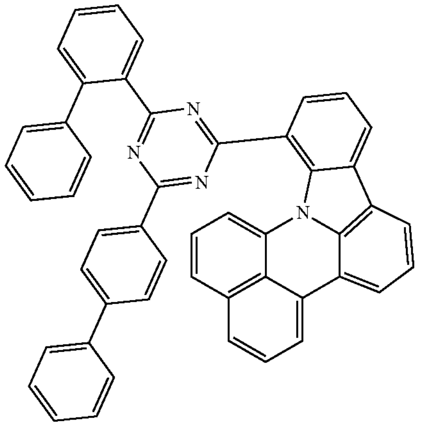
P-5
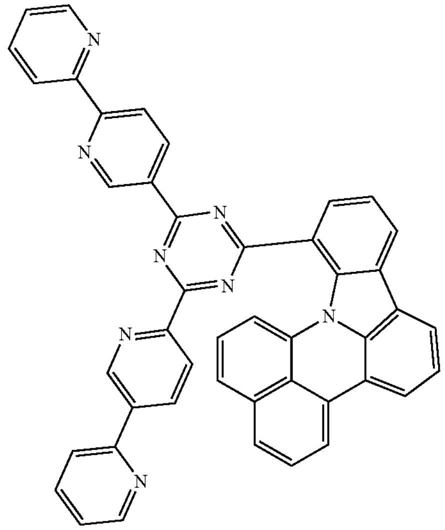
P-6
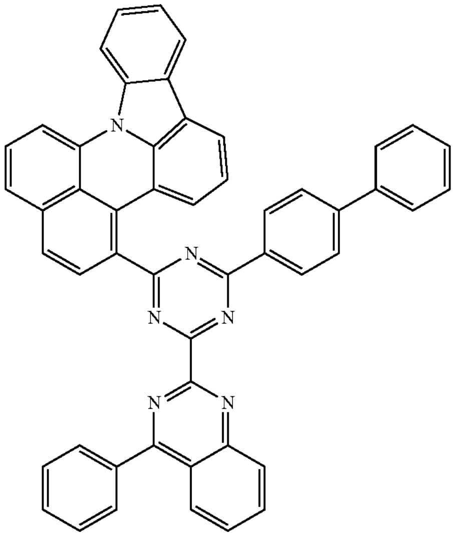

-continued
P-7
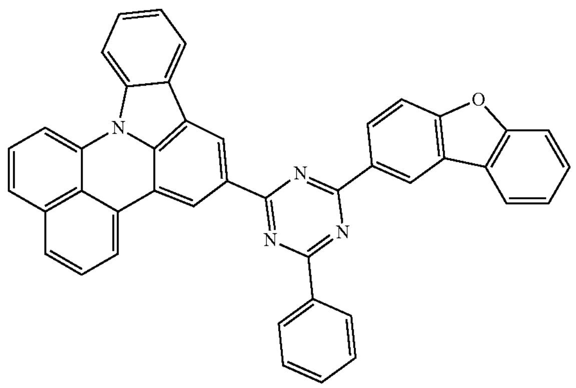
P-8
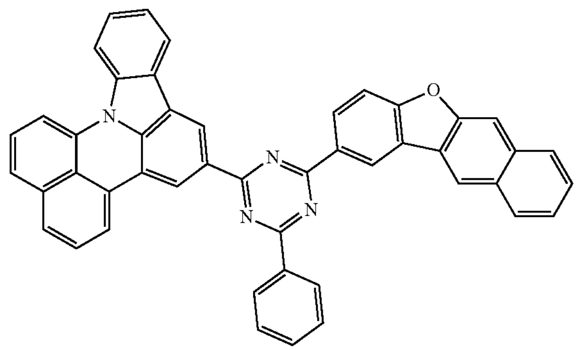
P-9
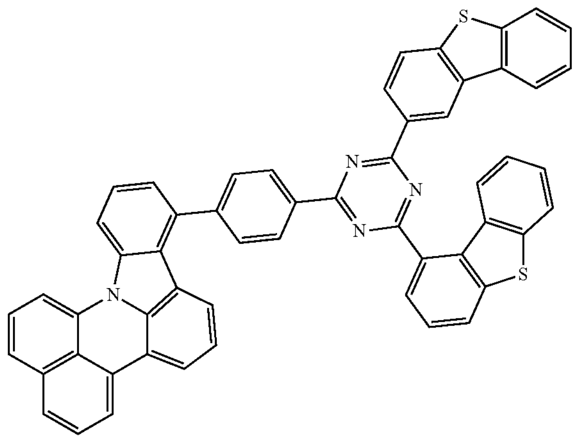
P-10
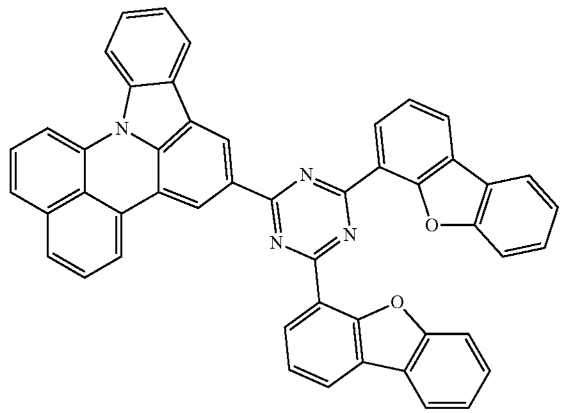
P-11
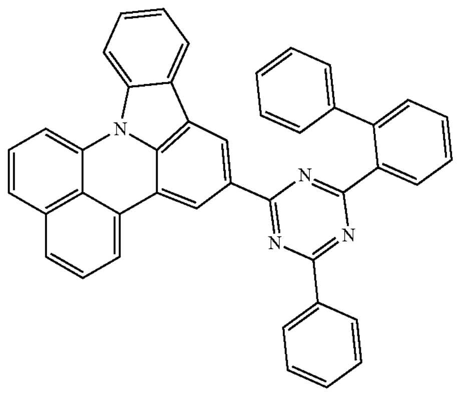
P-12
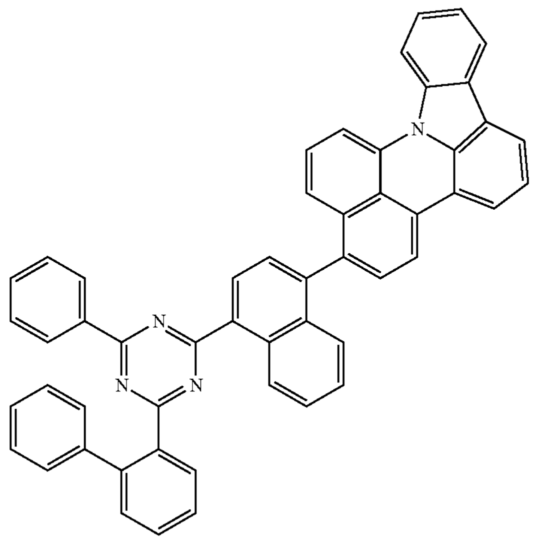

-continued
P-13
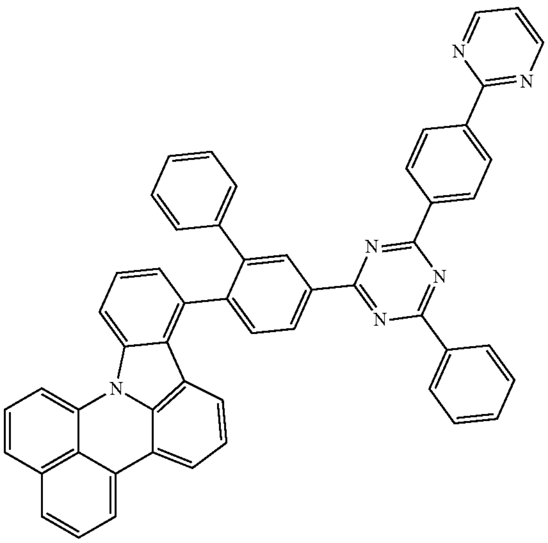
P-14
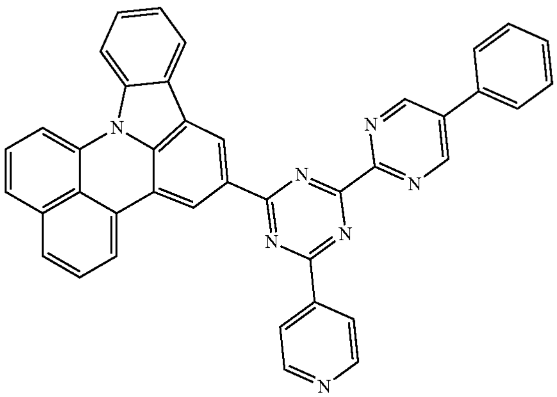
P-15
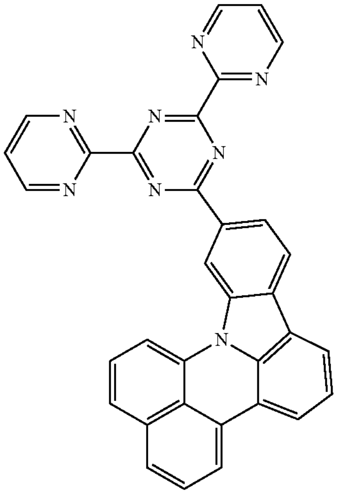
P-16
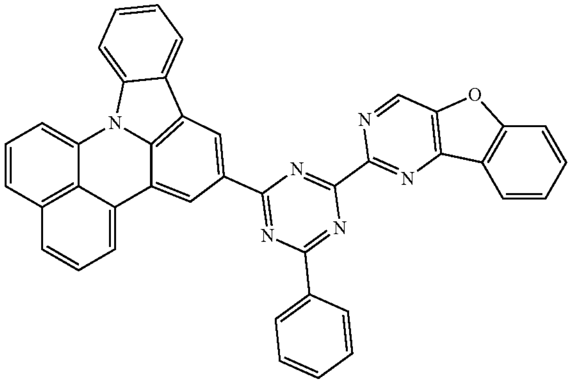
P-17
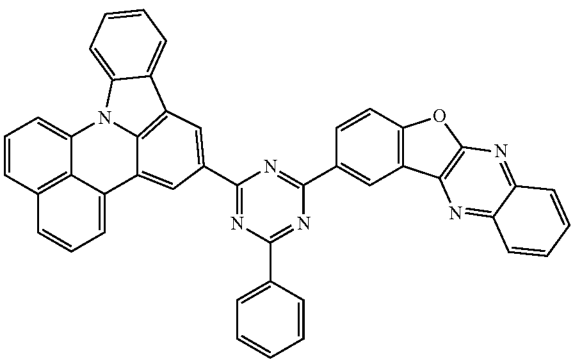
P-18
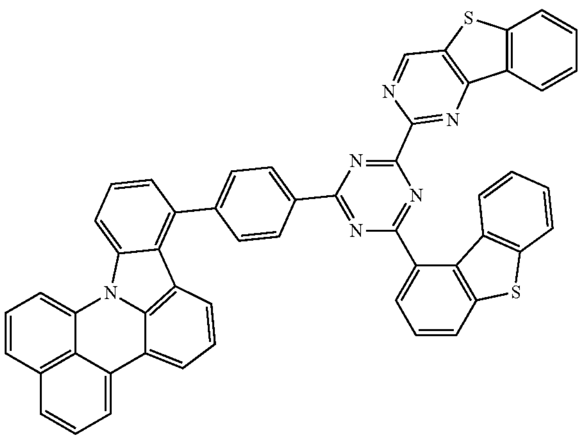

-continued
P-19
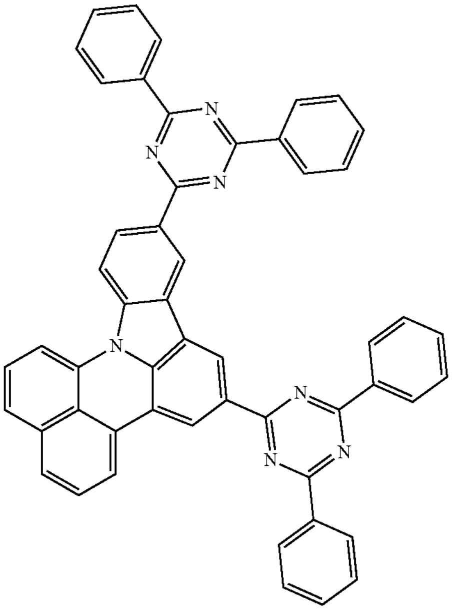
P-20
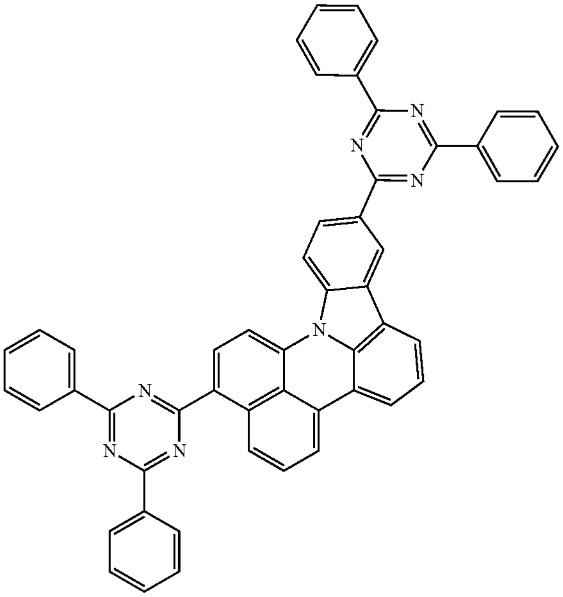
P-21
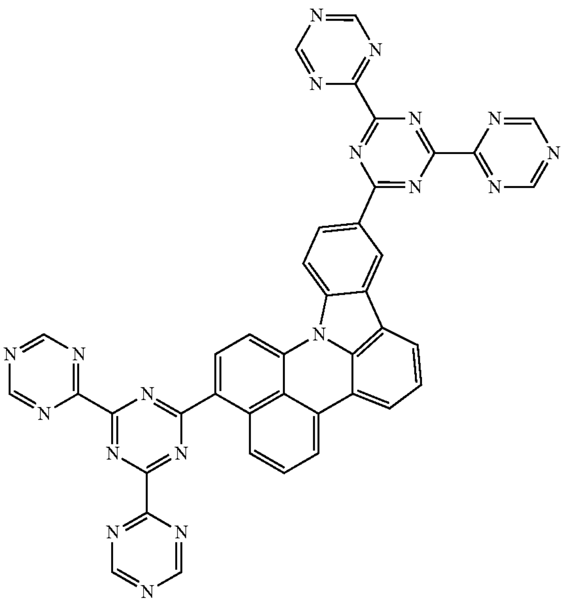
P-22
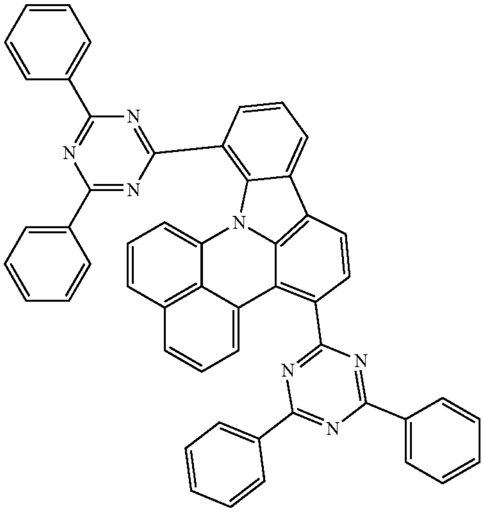

-continued
P-23
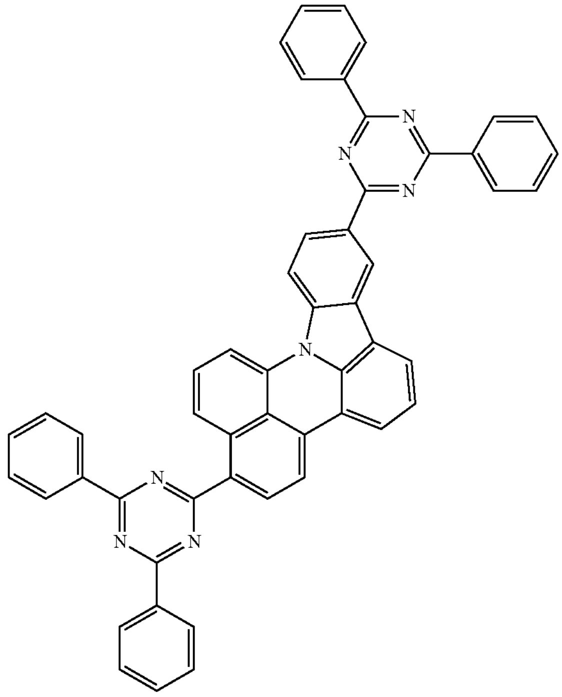
P-24
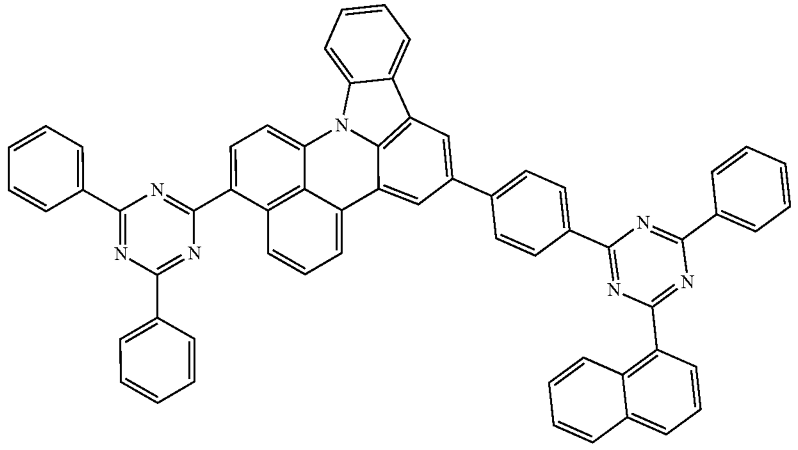

-continued
P-25
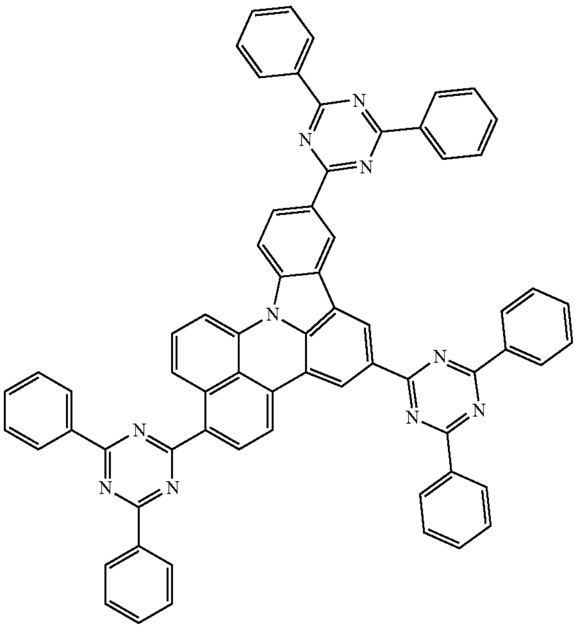
P-26
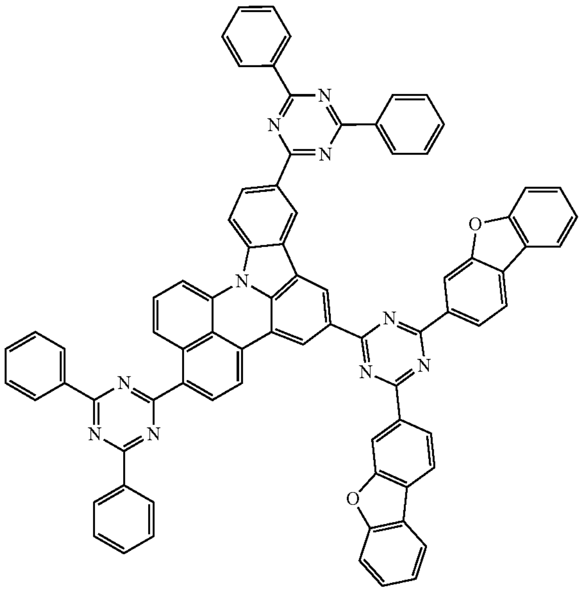
P-27
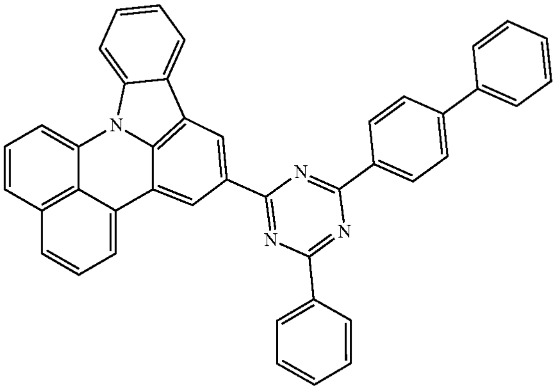
P-28
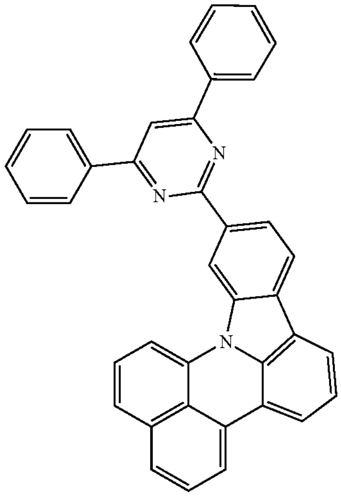

-continued
P-29
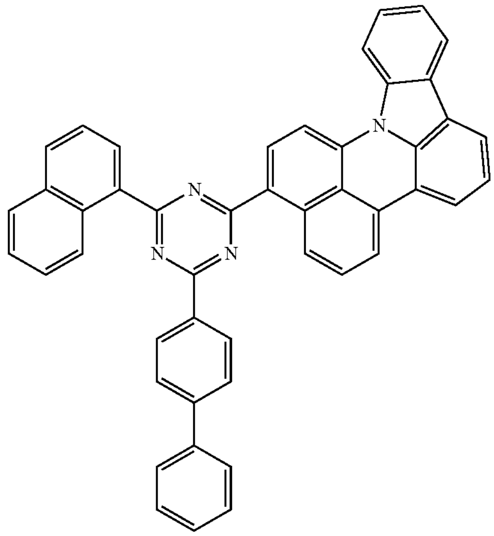
P-30
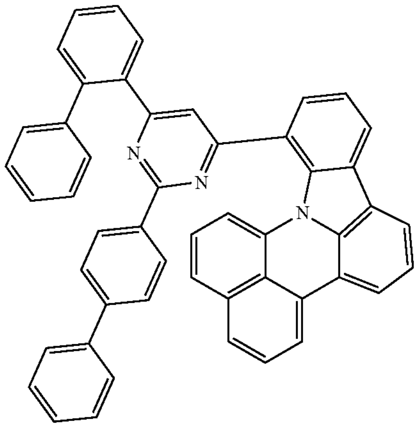
P-31
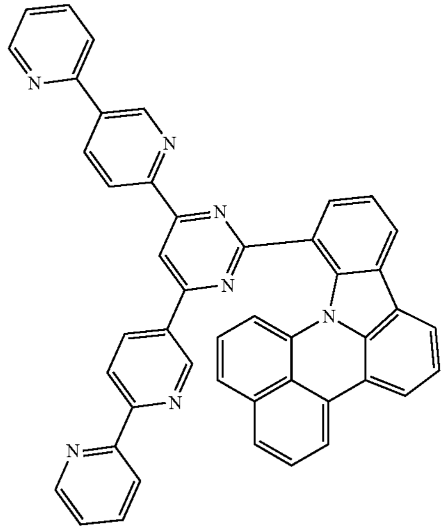
P-32
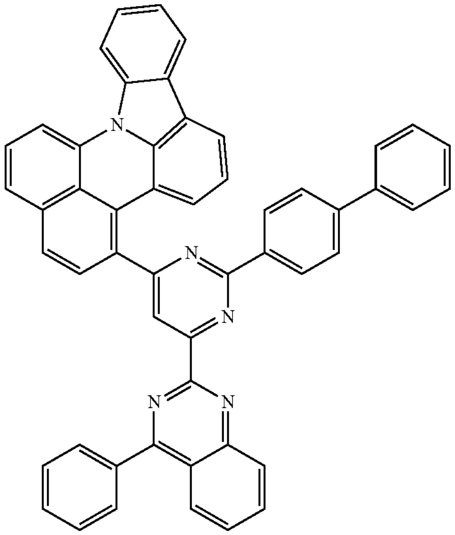
P-33
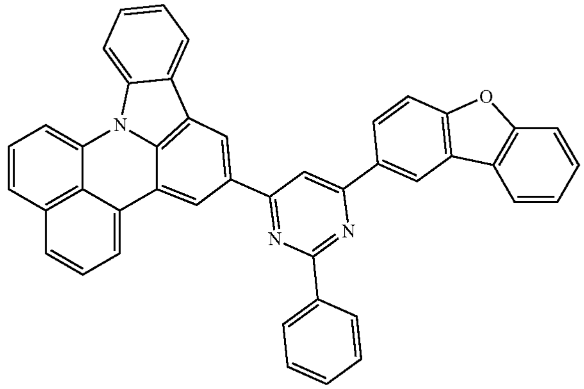
P-34
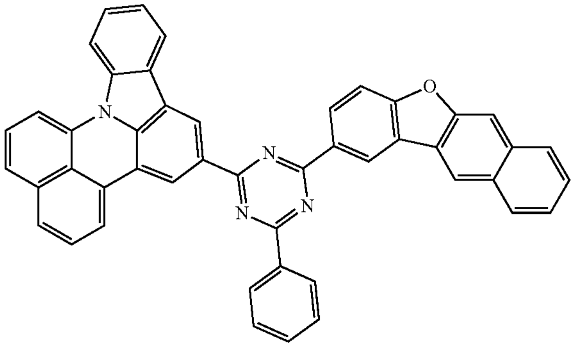

-continued
P-35
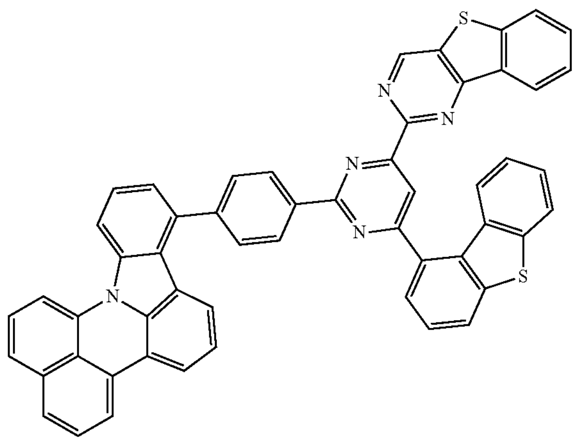
P-36
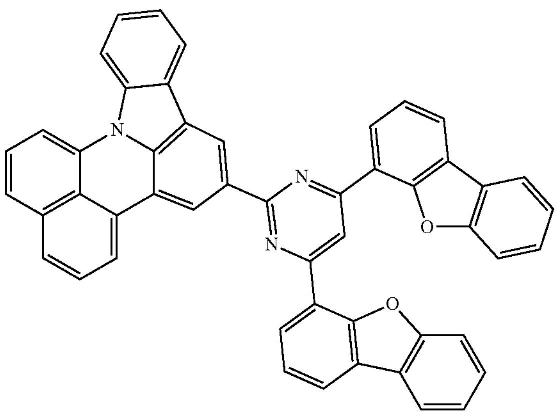
P-37
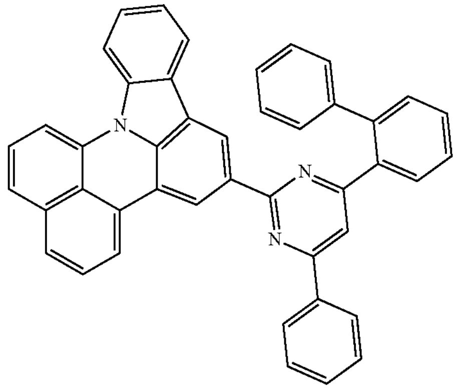
P-38
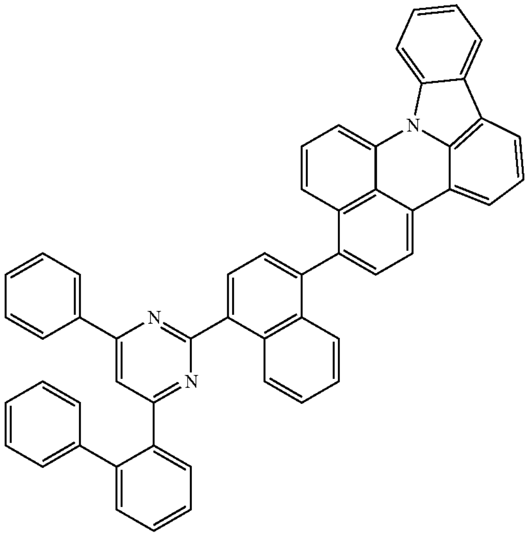
P-39
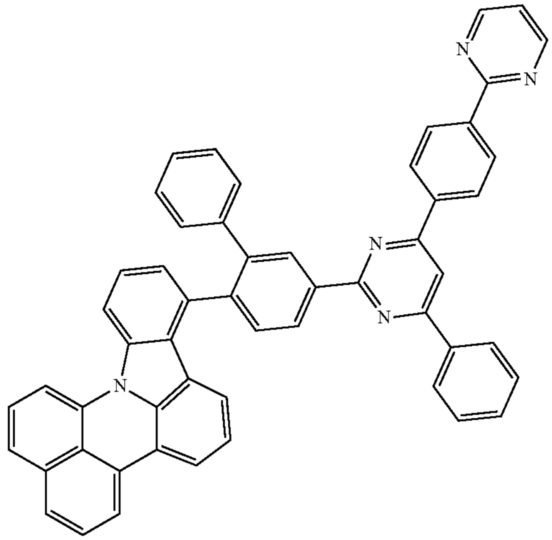
P-40
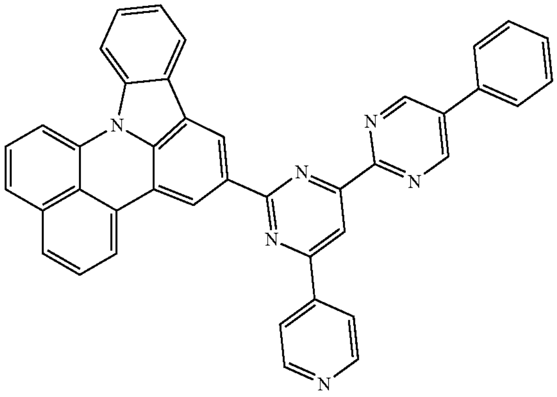

-continued
P-41
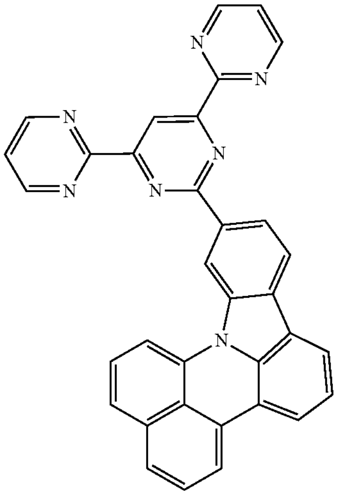
P-42
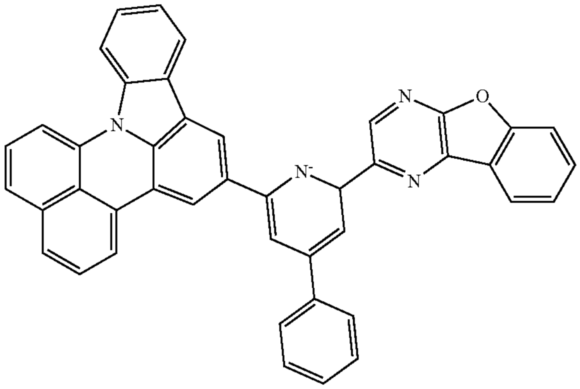
P-43
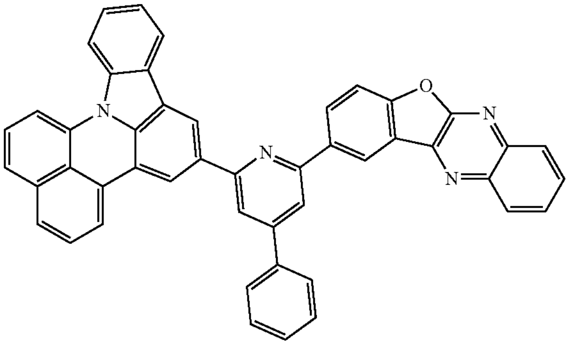
P-44
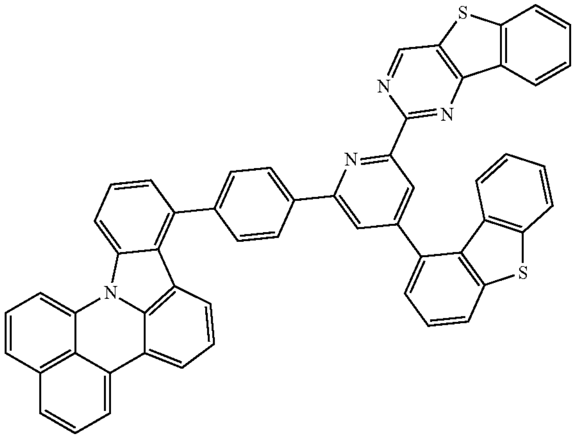

-continued
P-45
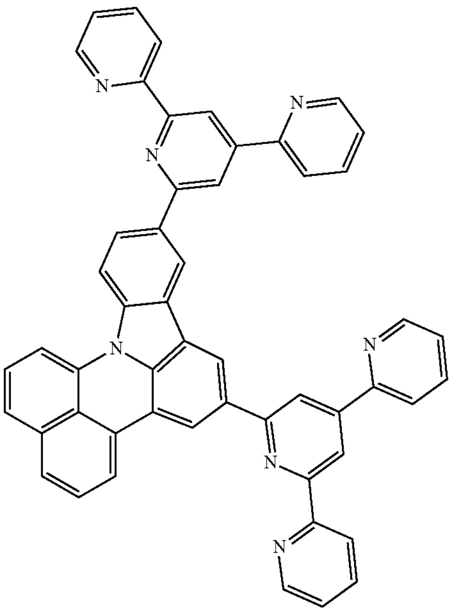
P-46
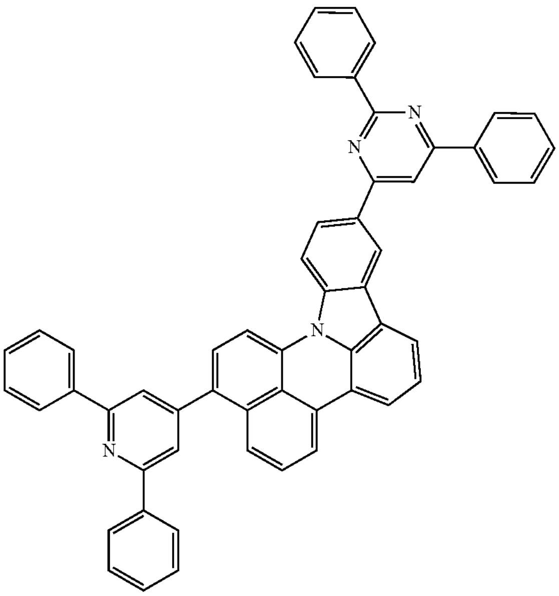
P-47
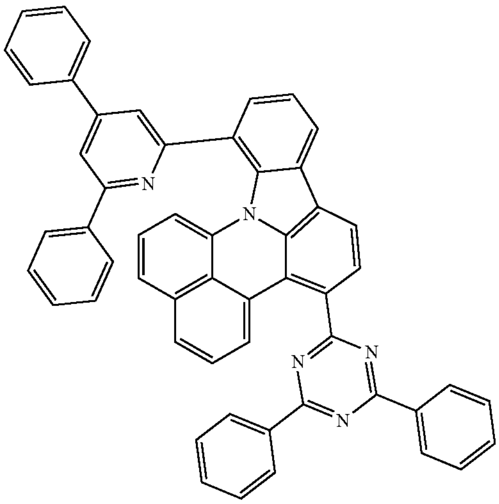
P-48
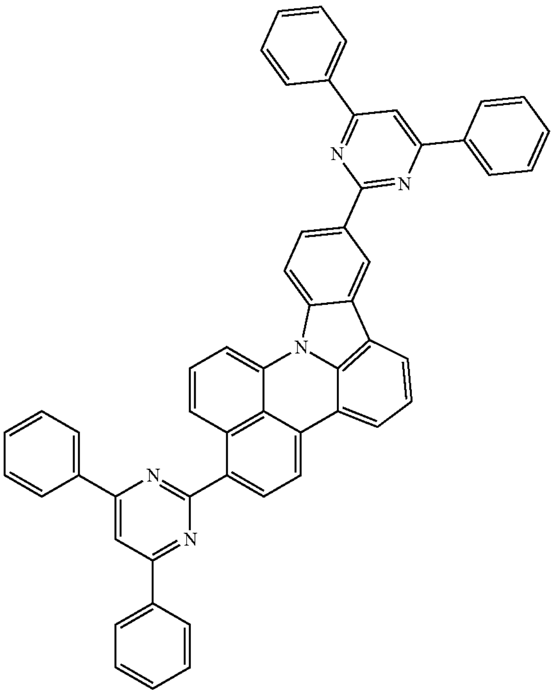

P-49
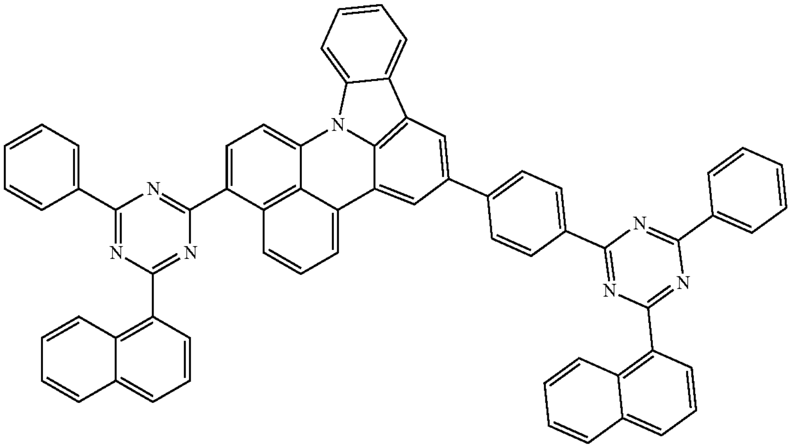
P-50
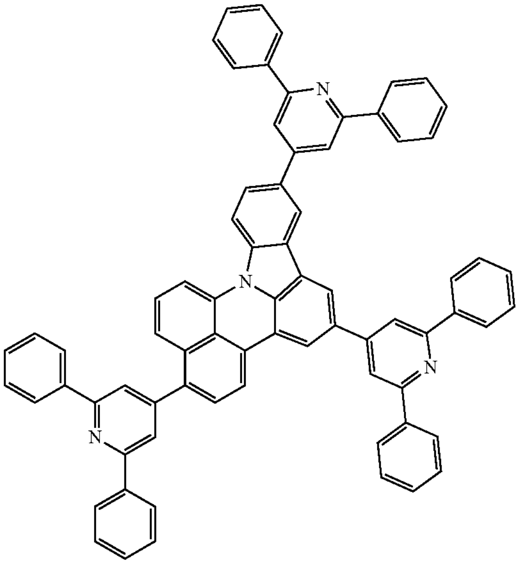
P-51
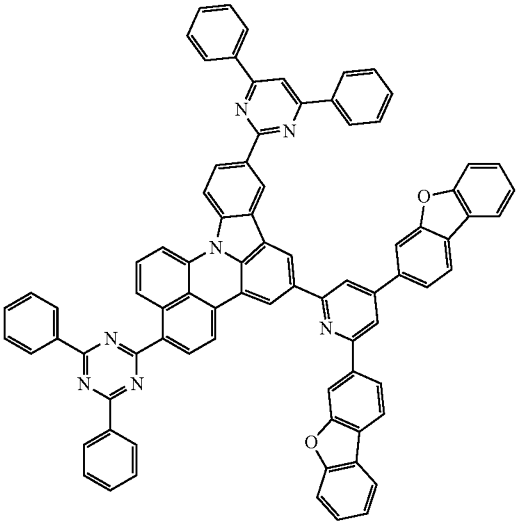
P-52
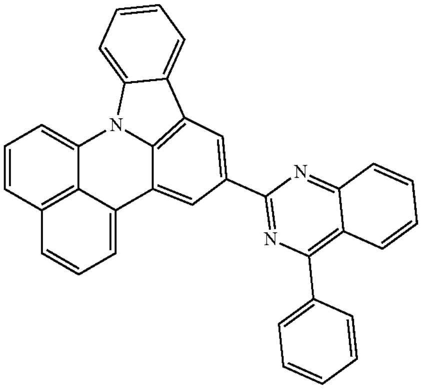
P-53
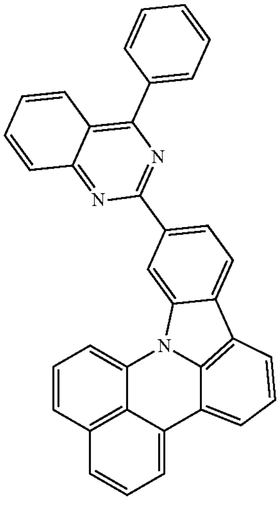

-continued
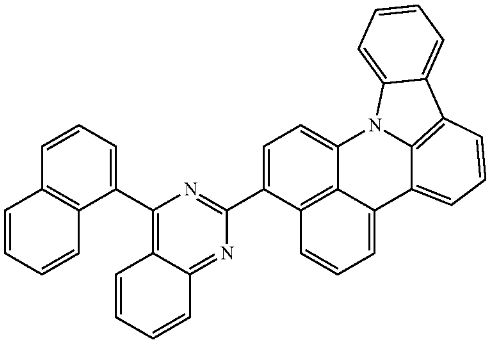
P-54
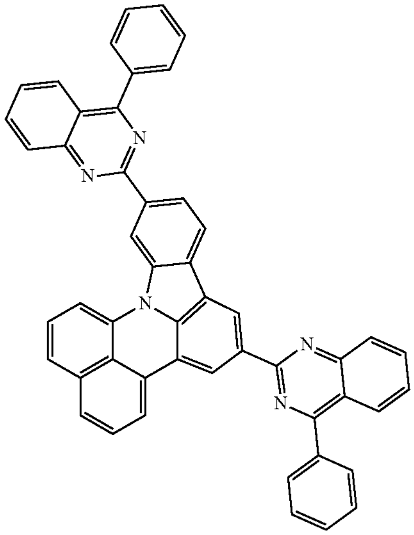
P-55
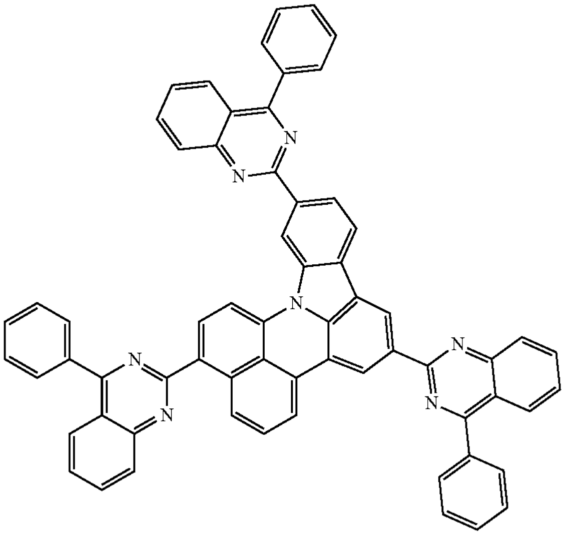
P-56
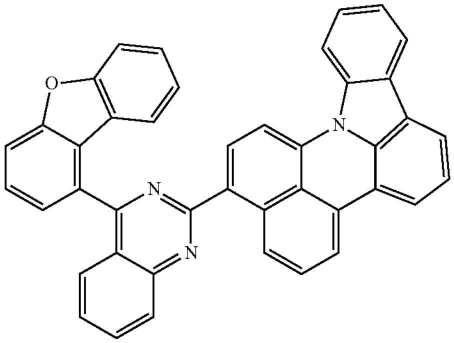
P-57
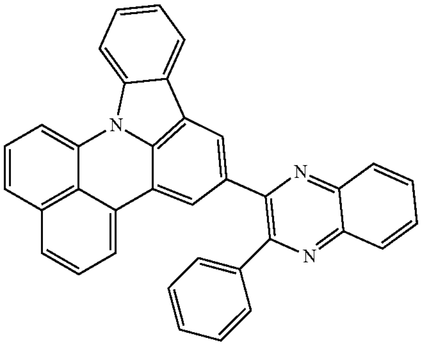
P-58
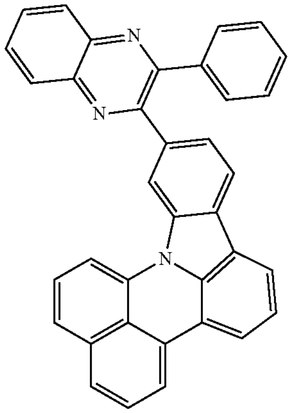
P-59

-continued
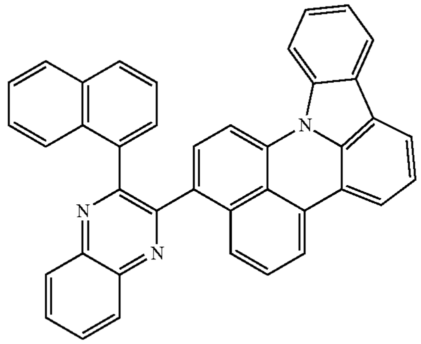
P-60
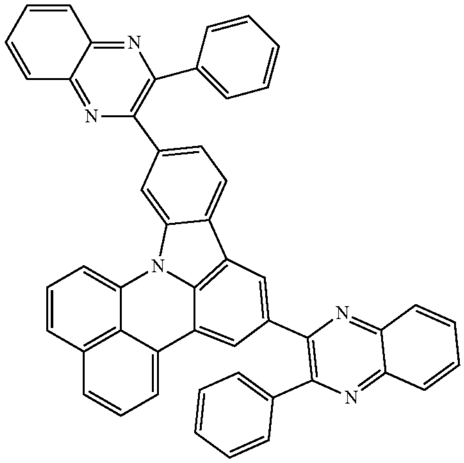
P-61
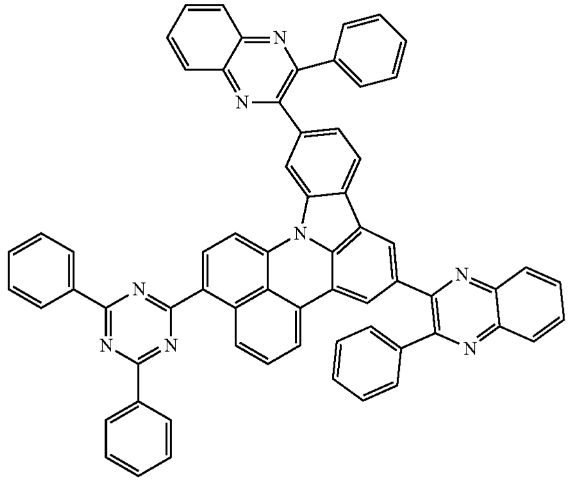
P-62
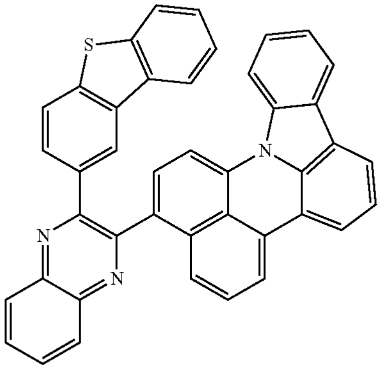
P-63
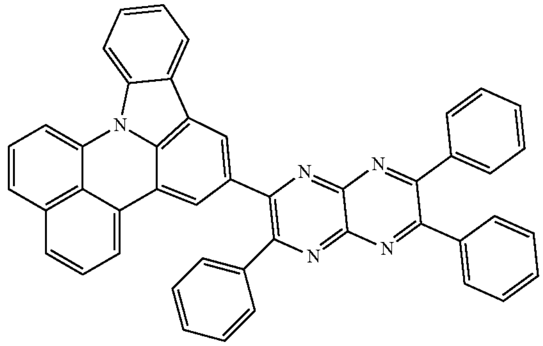
P-64
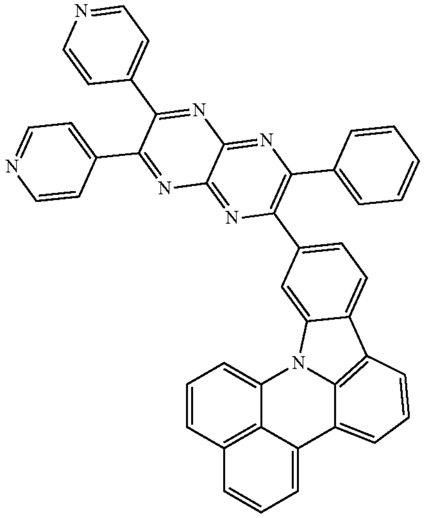
P-65

-continued
P-66
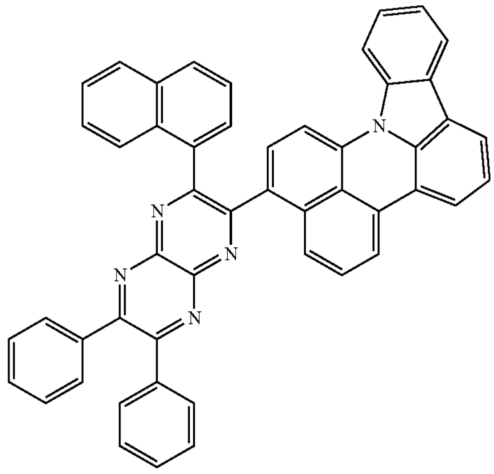
P-67
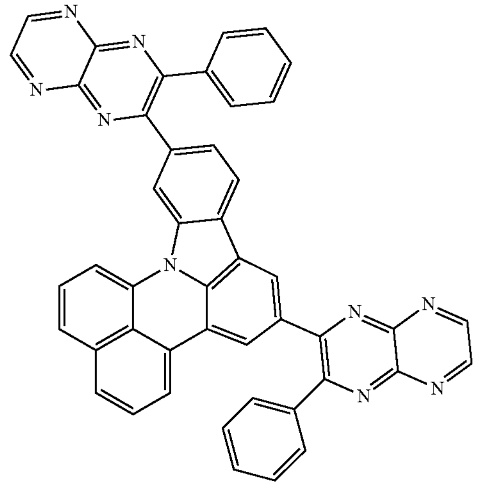
P-68
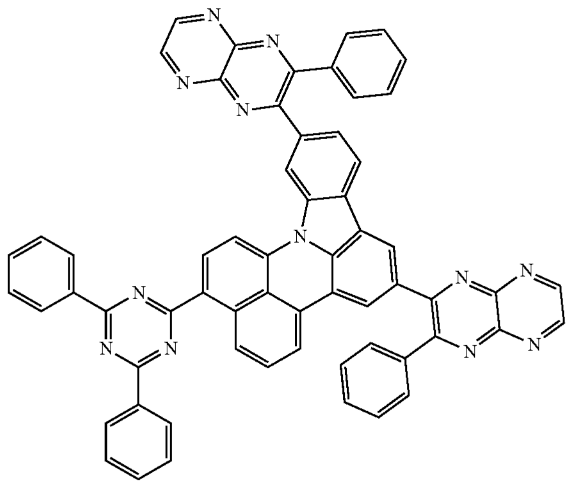
P-69
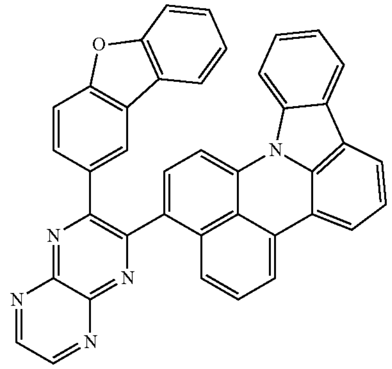
P-70
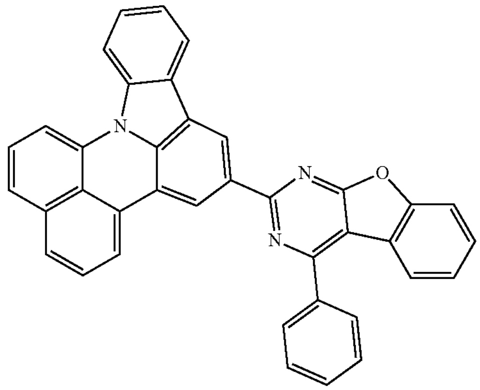
P-71
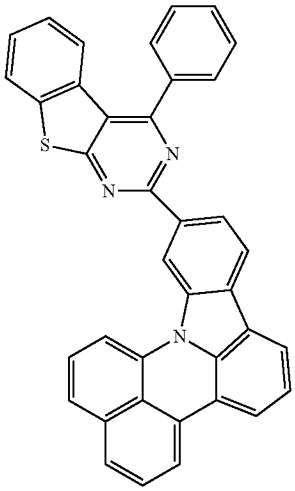

-continued
P-72
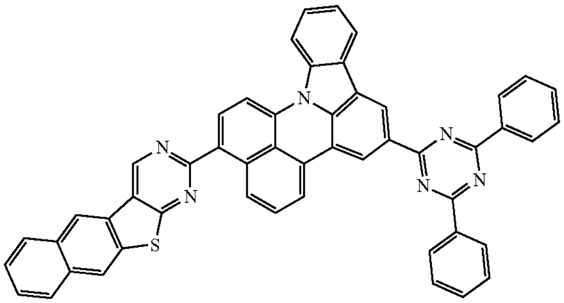
P-73
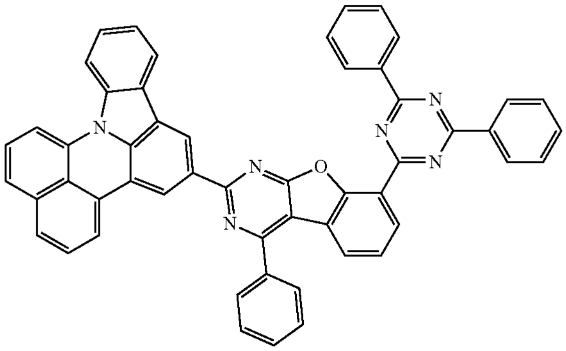
P-74
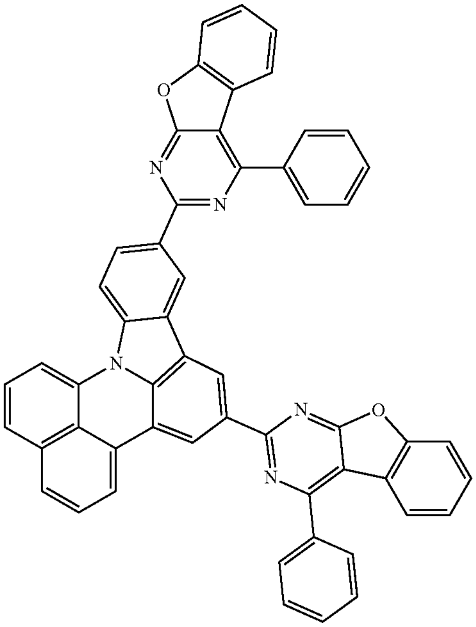
P-75
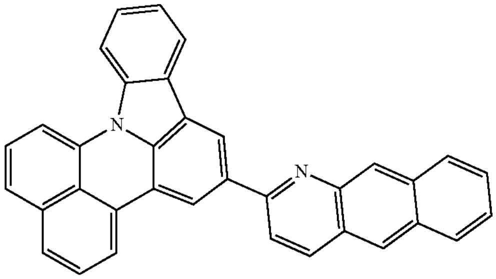
P-76
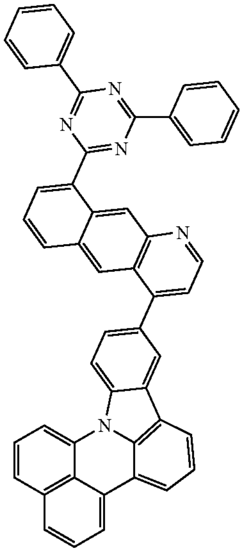
P-77
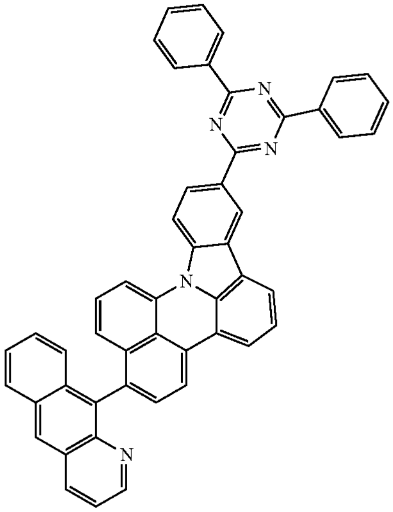

-continued
P-78
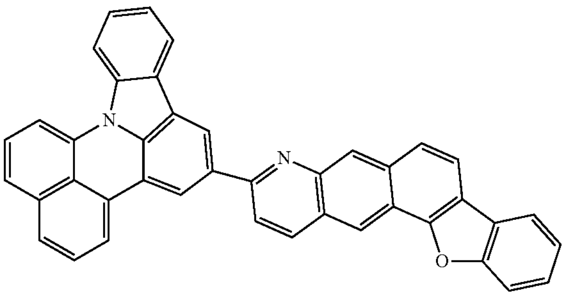
P-79
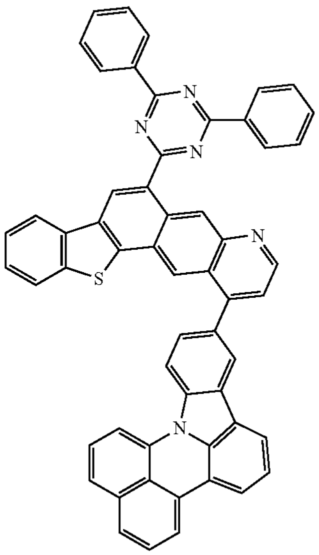
P-80
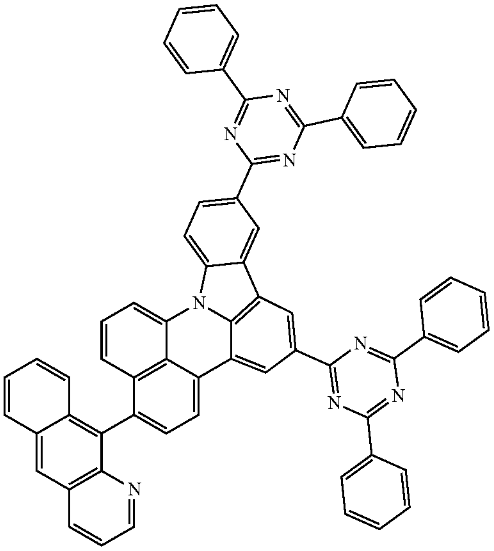
P-81
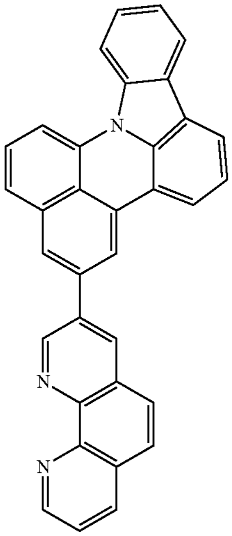
P-82
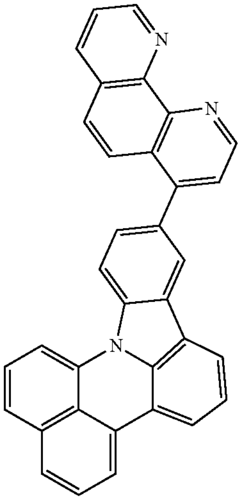
P-83
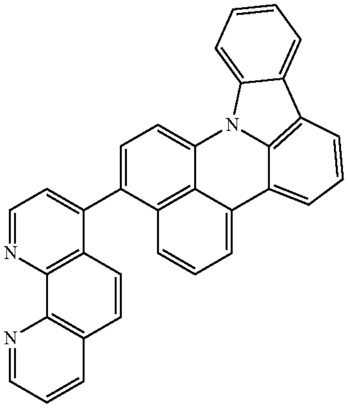

-continued
P-84
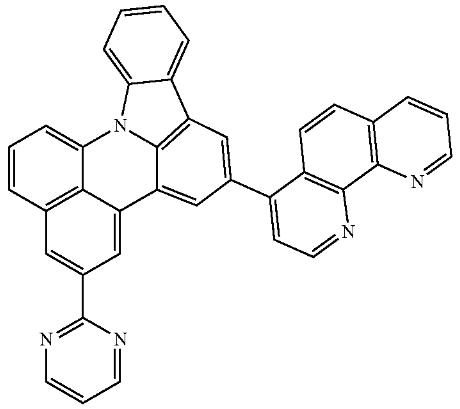
P-85
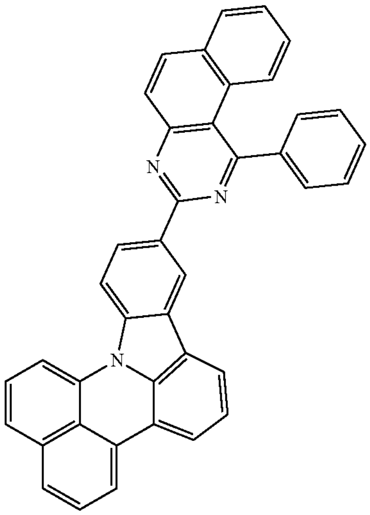
P-86
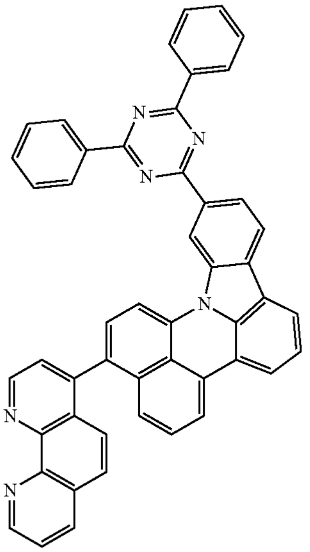
P-87
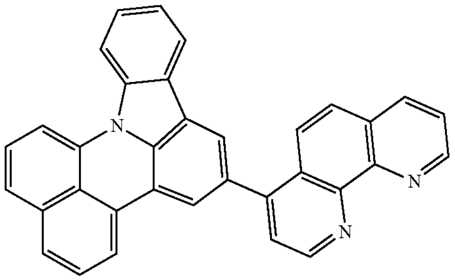
P-88
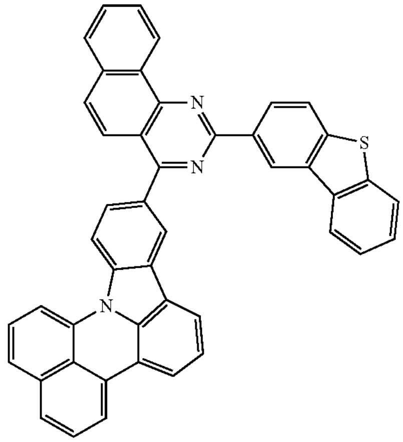
P-89
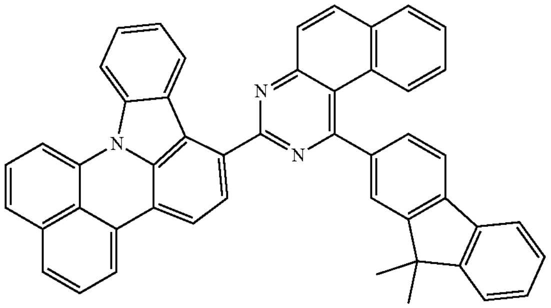

-continued
P-90
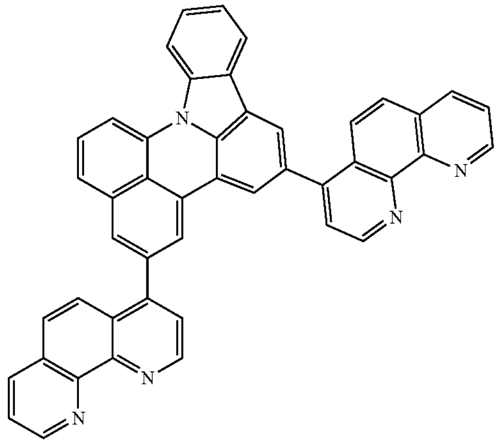
P-91
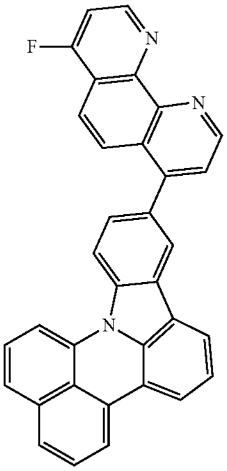
P-92
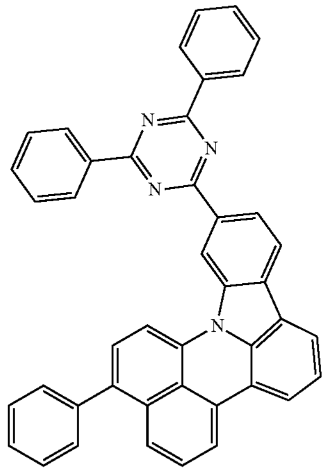
P-93
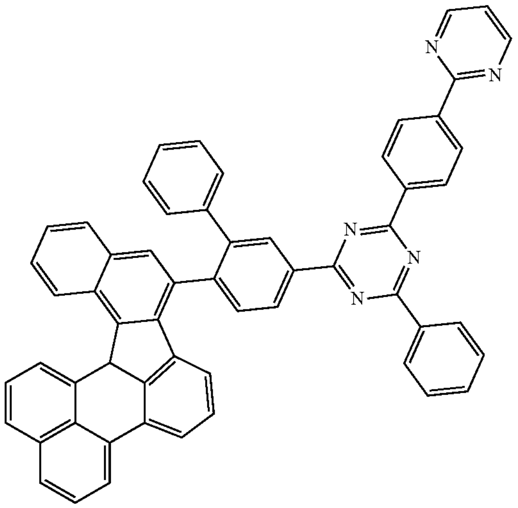
P-94
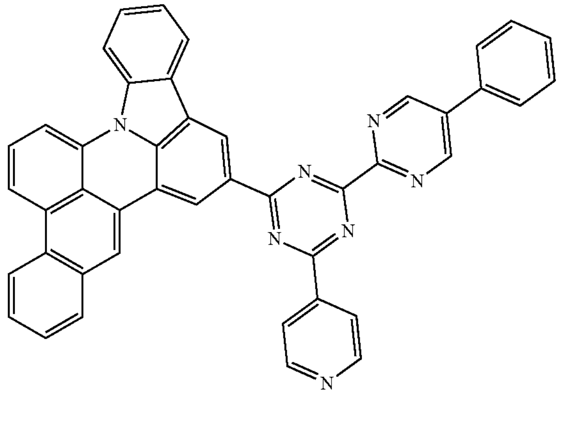
P-95
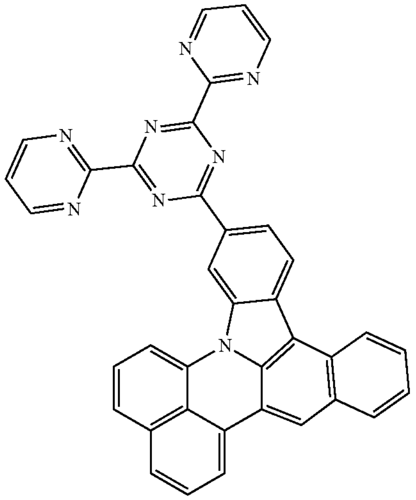

-continued
P-96
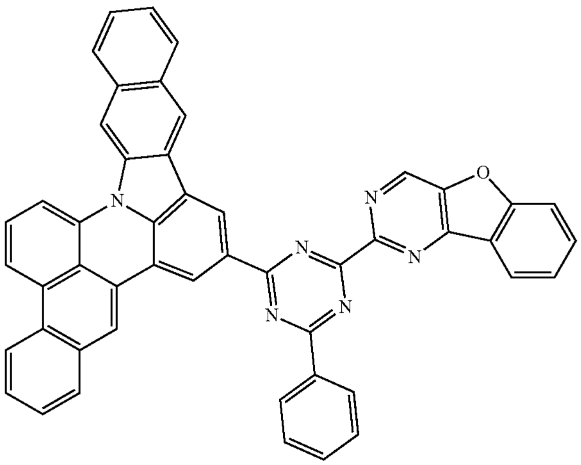
P-97
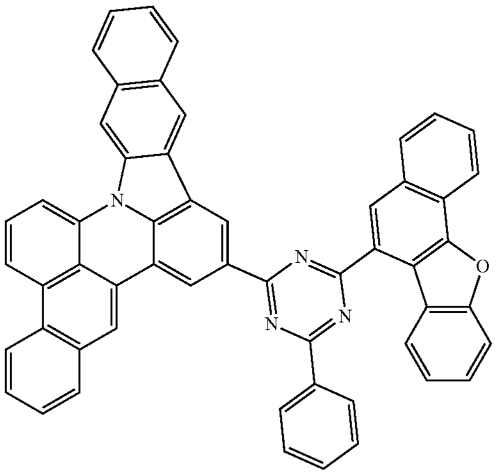
P-98
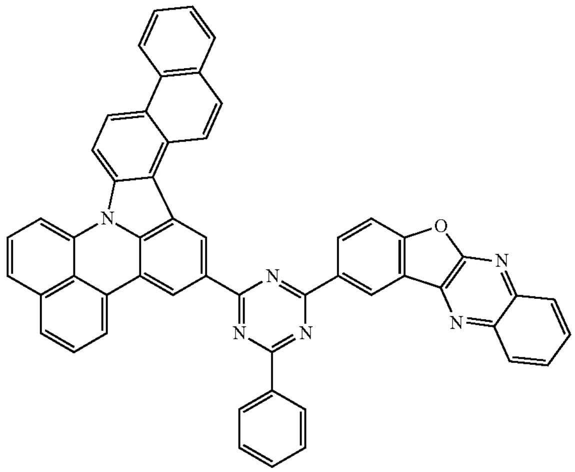
P-99
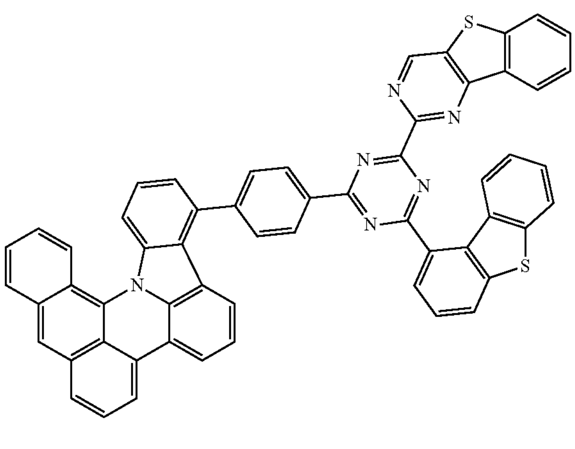
P-100
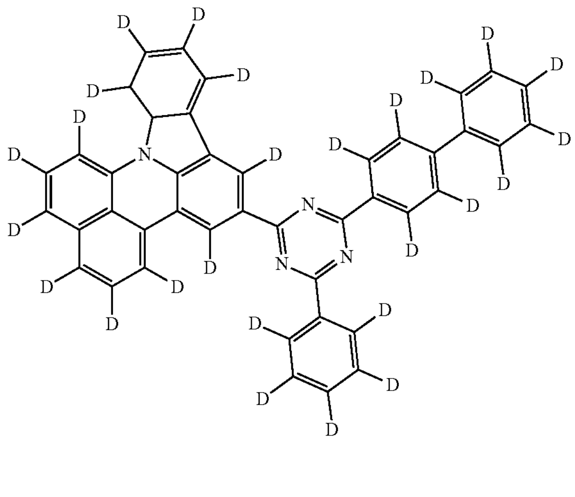

-continued
P-101
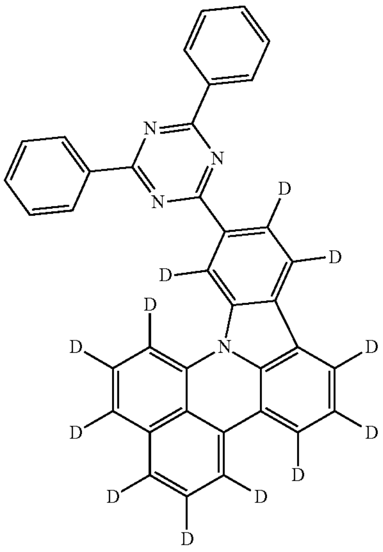
P-102
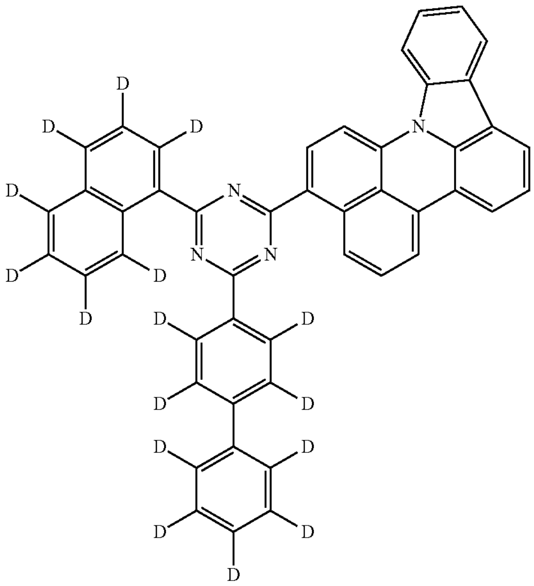
P-103
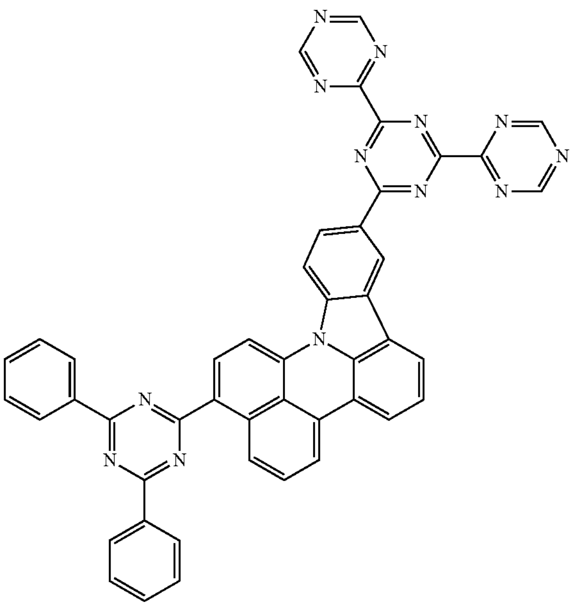
P-104
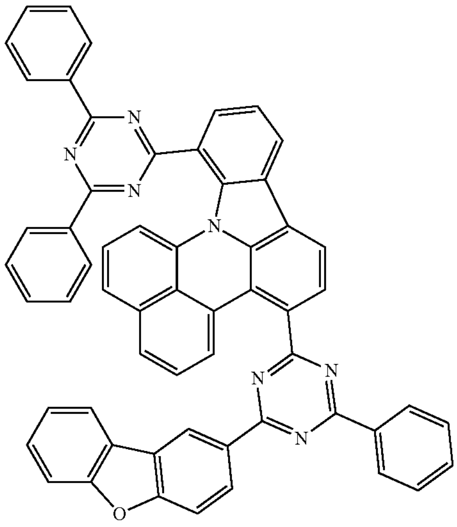

-continued
P-105
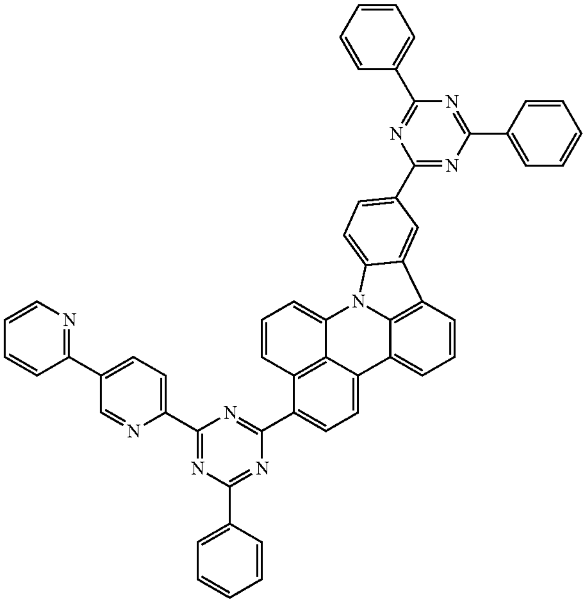
P-106
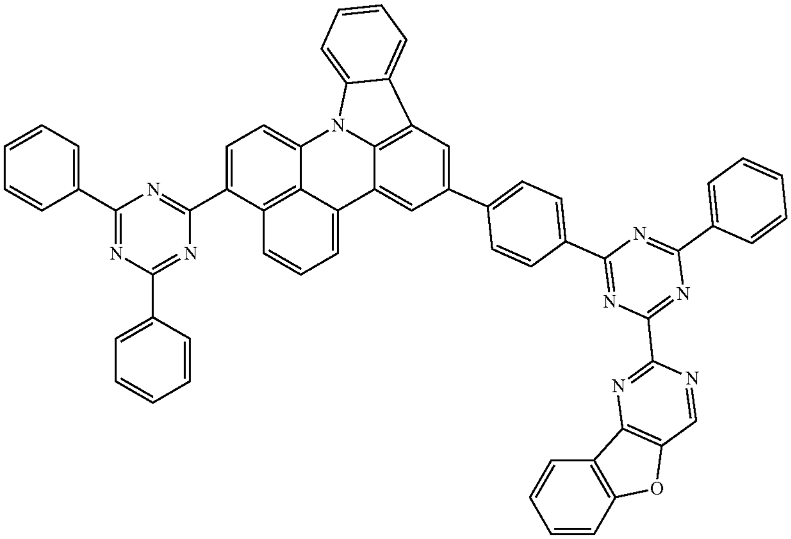
P-107
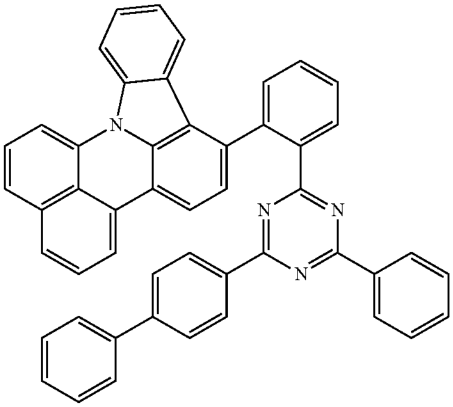
P-108
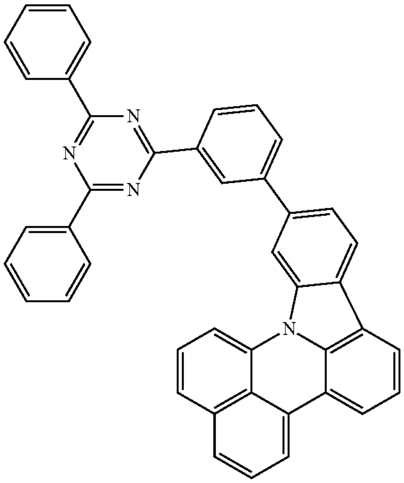

-continued
P-109
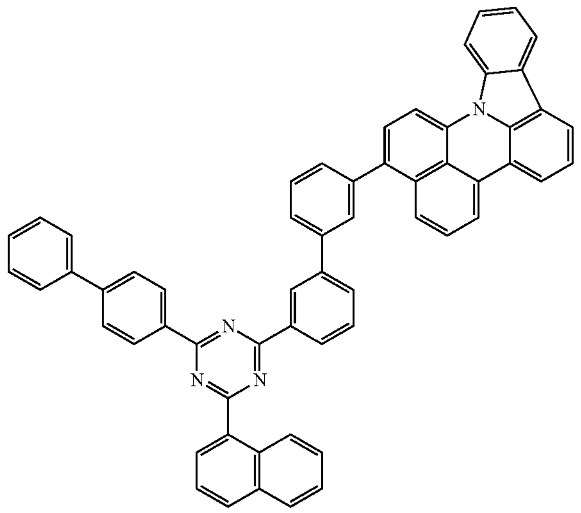
P-110
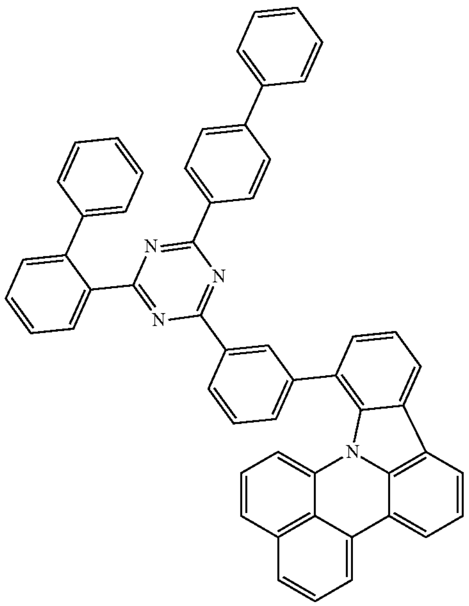
P-111
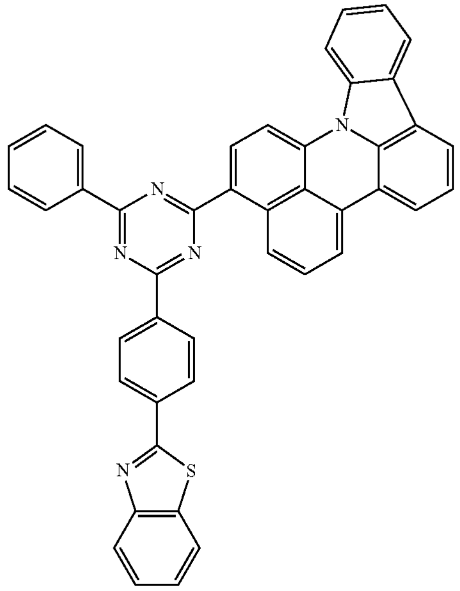
P-112
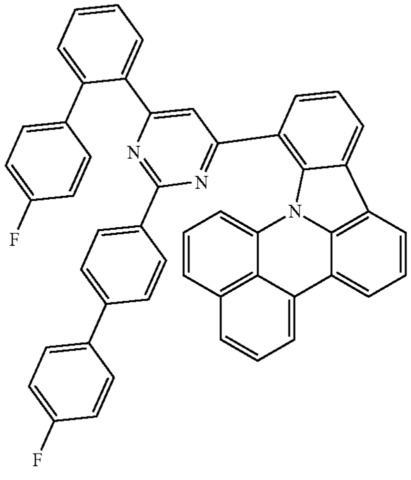

-continued
P-113
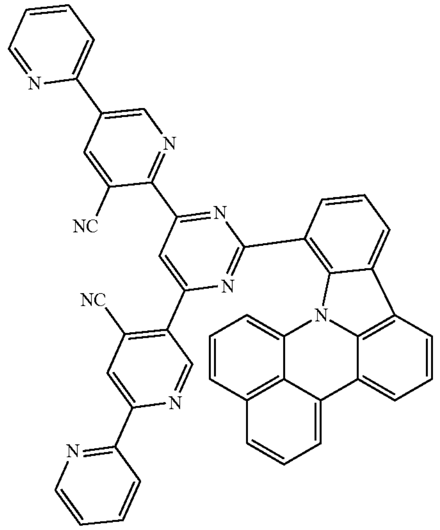
P-114
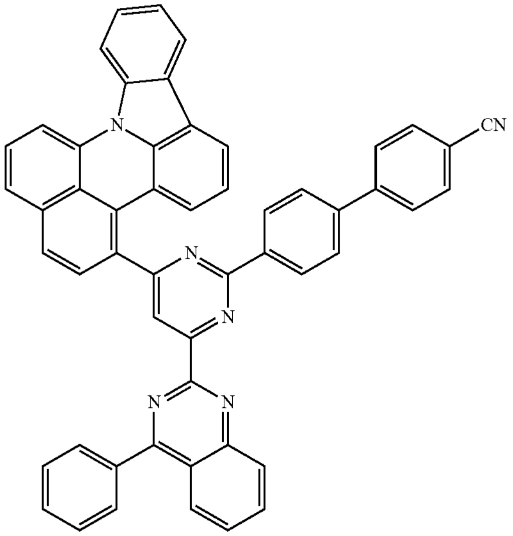
P-115
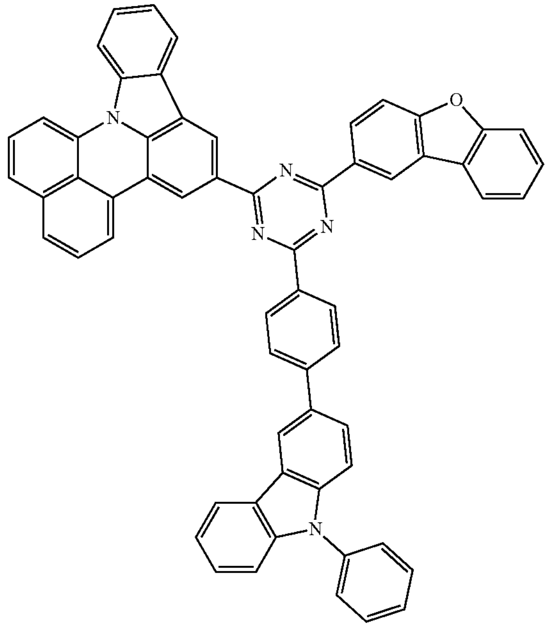
P-116
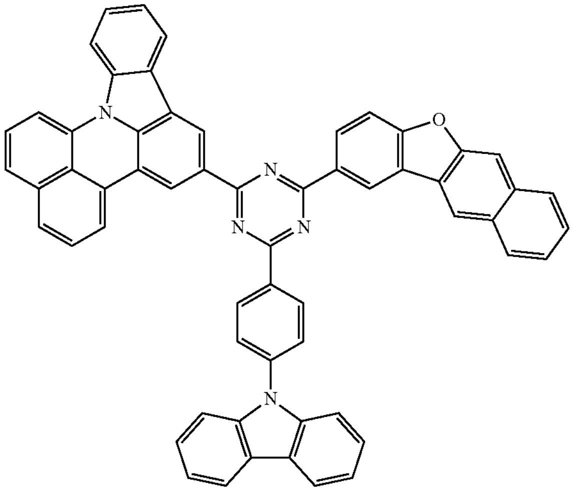

-continued
P-117
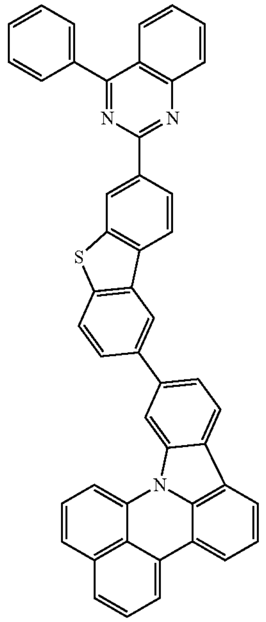
P-118
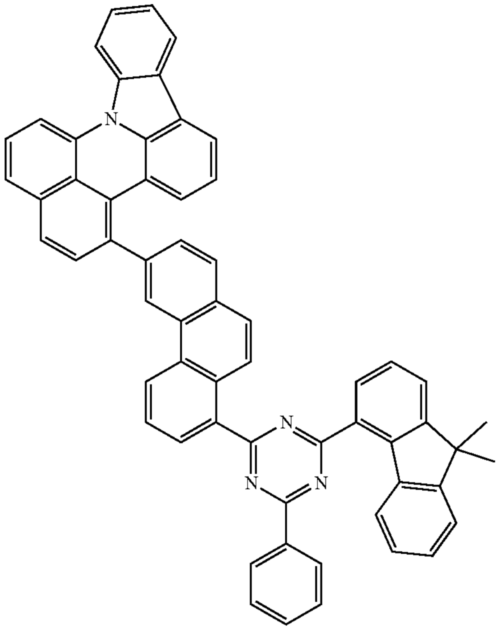
P-119
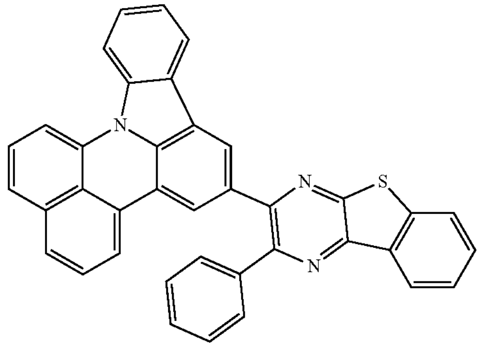
P-120
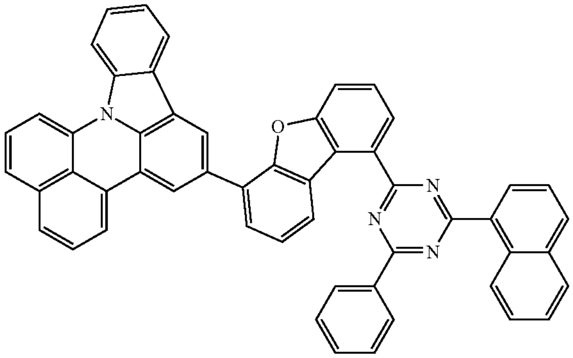
P-121
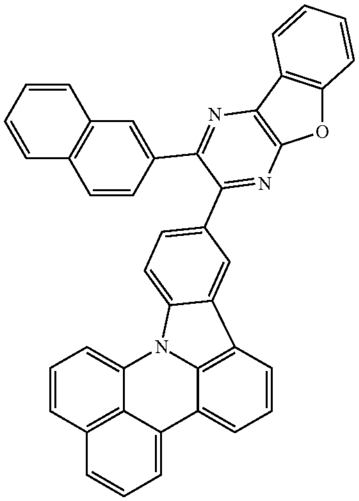
P-122
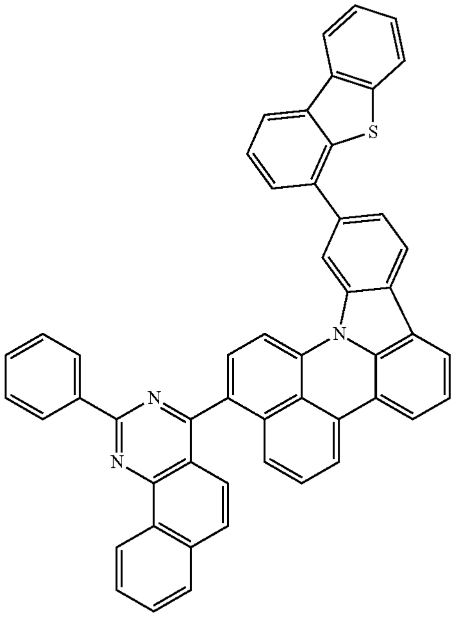

-continued
P-123
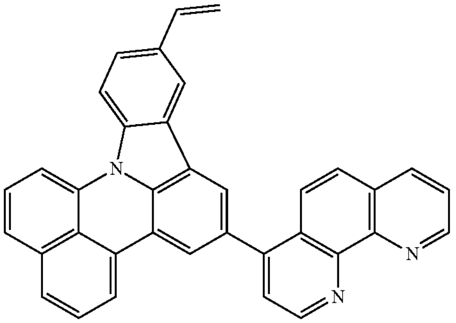
P-124
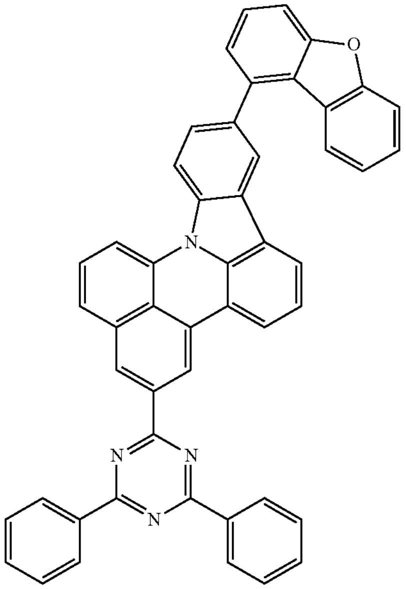
P-125
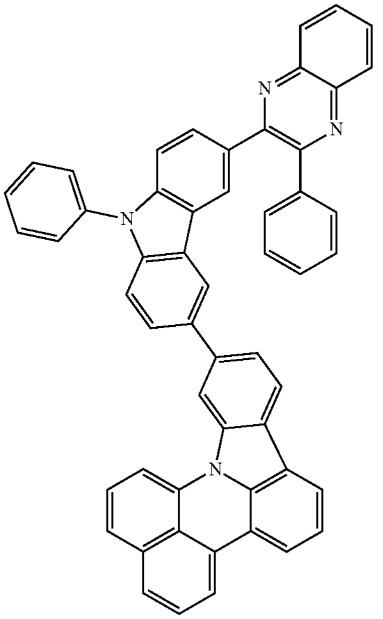
P-126
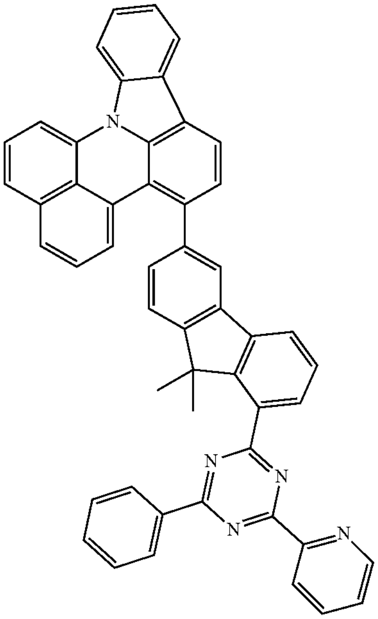

-continued
P-127
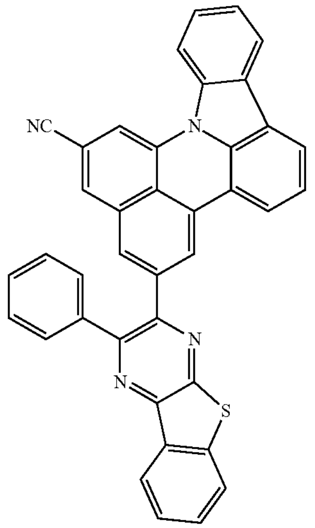
P-128
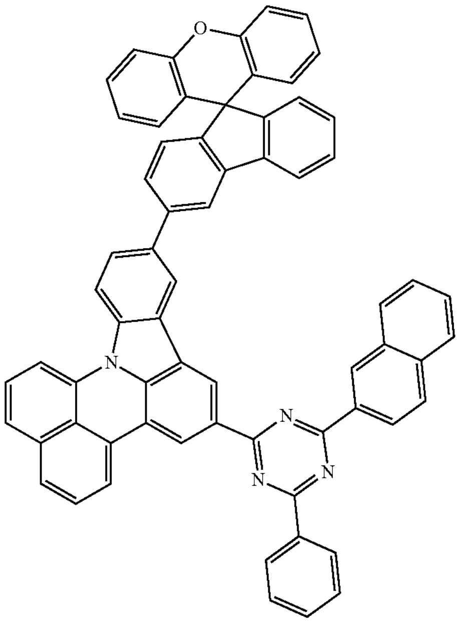
P-129
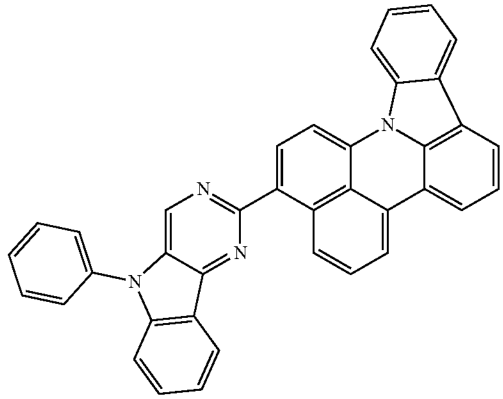
P-130
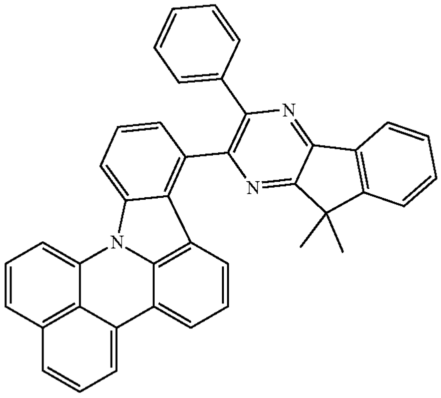
P-131
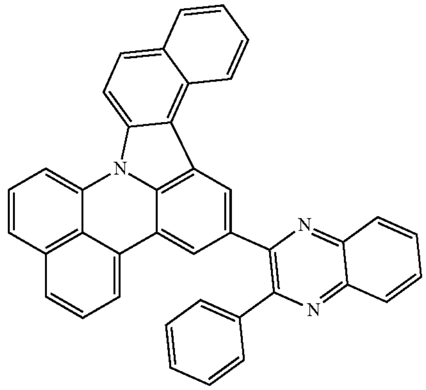
P-132
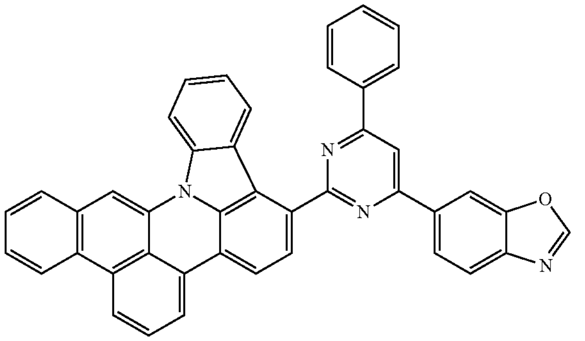

-continued
P-133
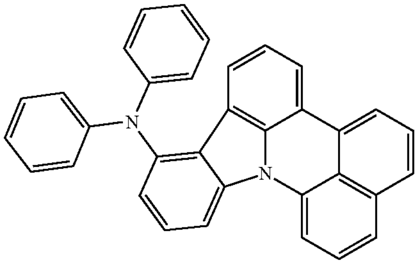
P-134
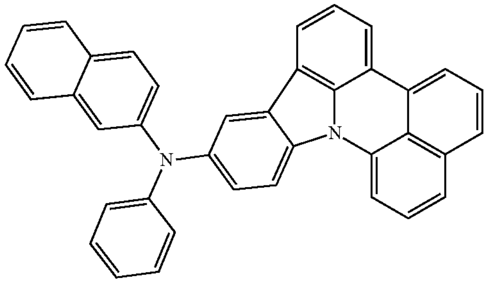
P-135
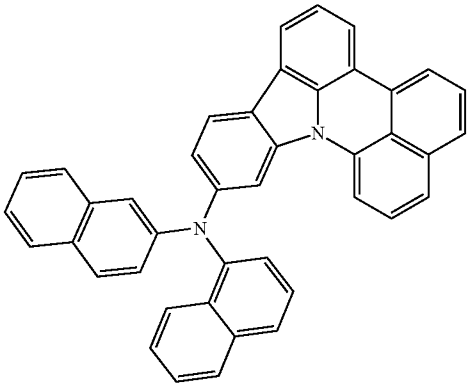
P-136
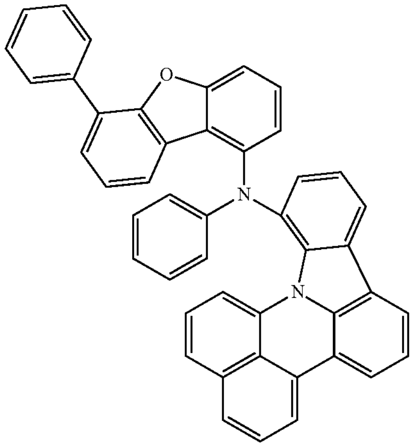
P-137
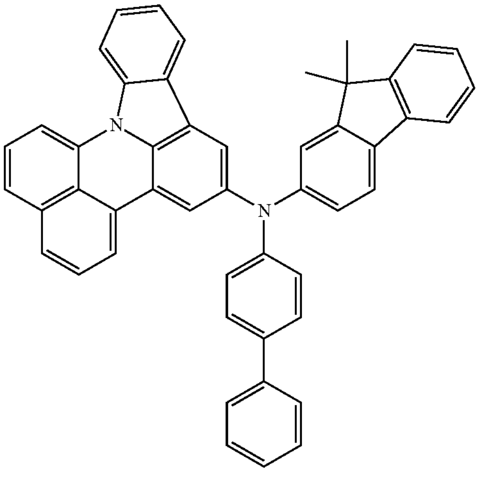
P-138
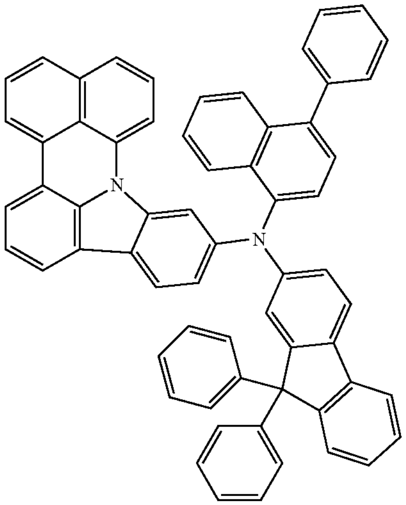

-continued
P-139
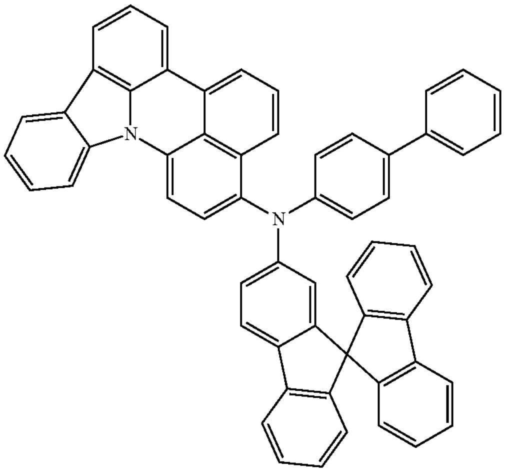
P-140
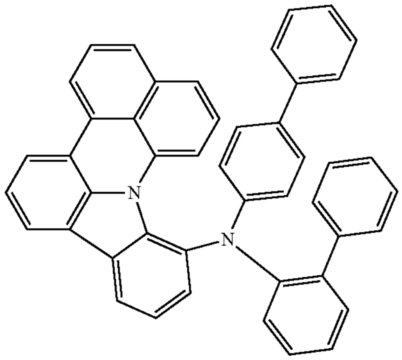
P-141
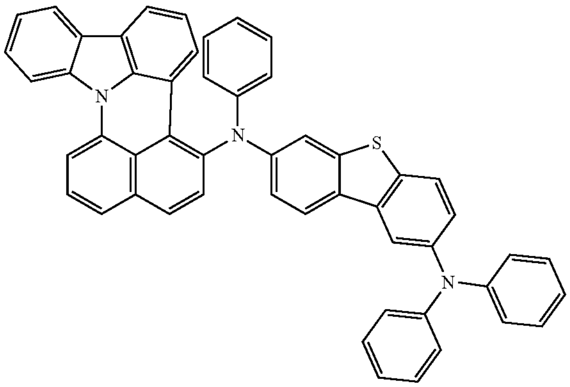
P-142
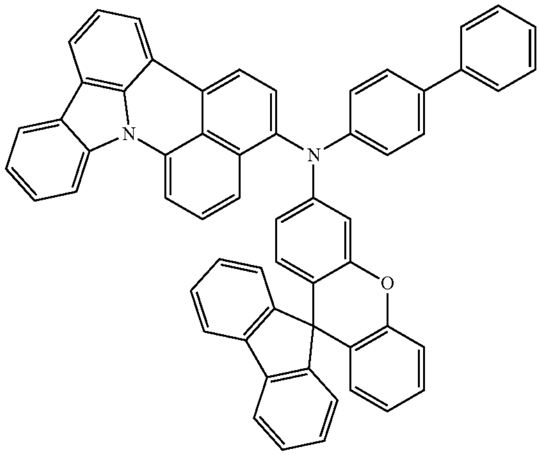
-continued
P-143
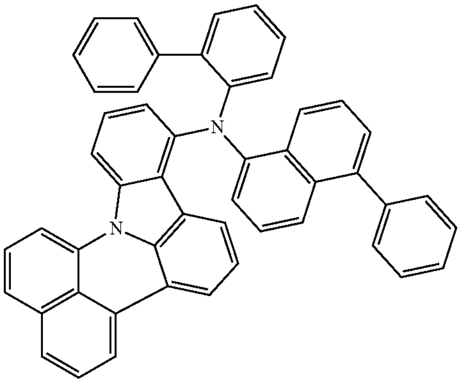
P-144
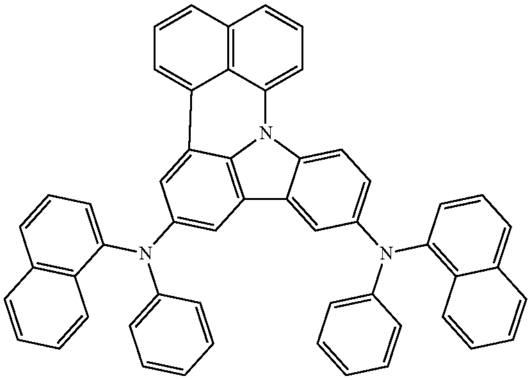

-continued
P-145
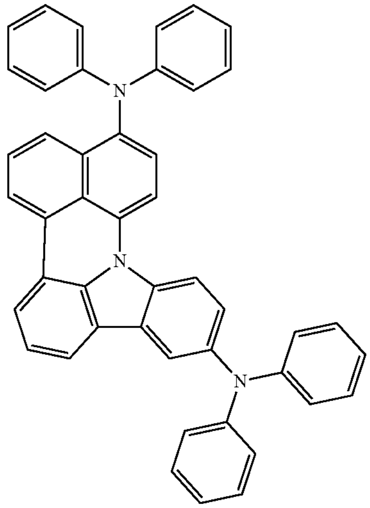
P-146
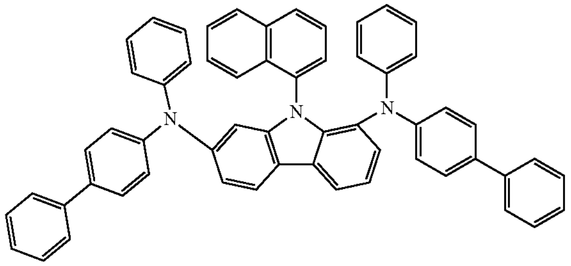
P-147
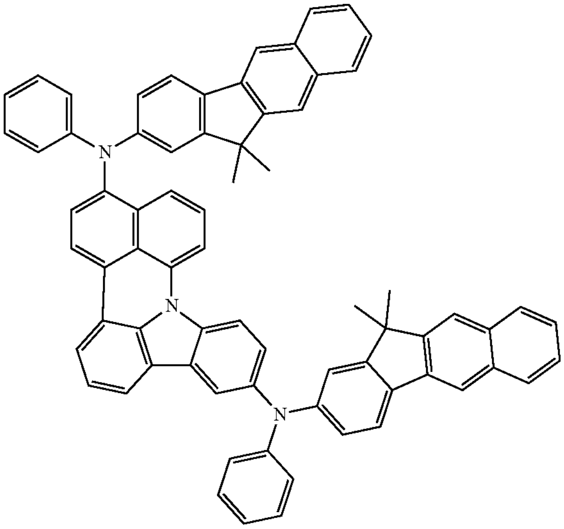
-continued
P-148
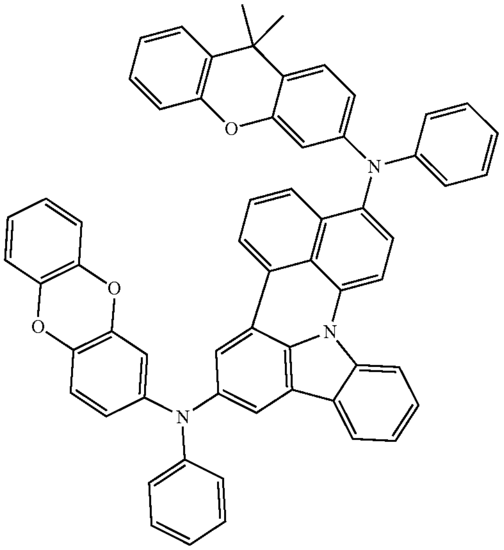
P-149
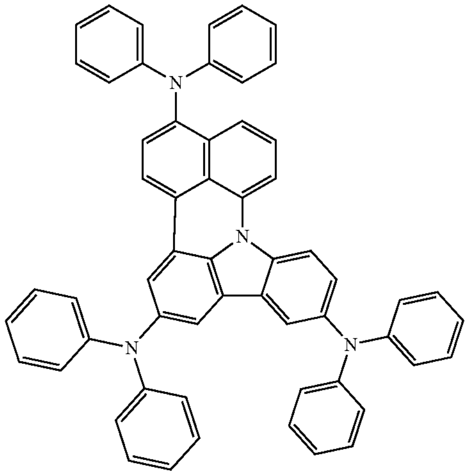
P-150
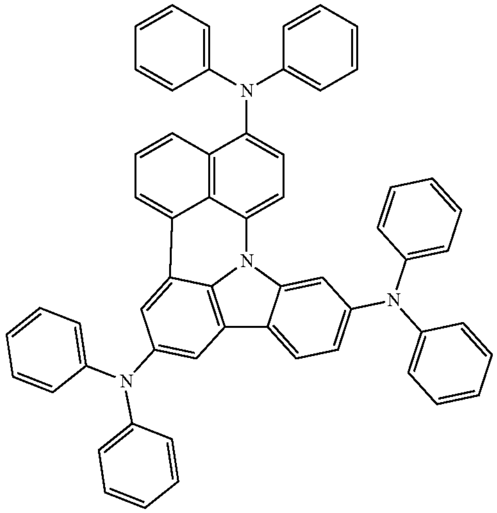

-continued
P-151
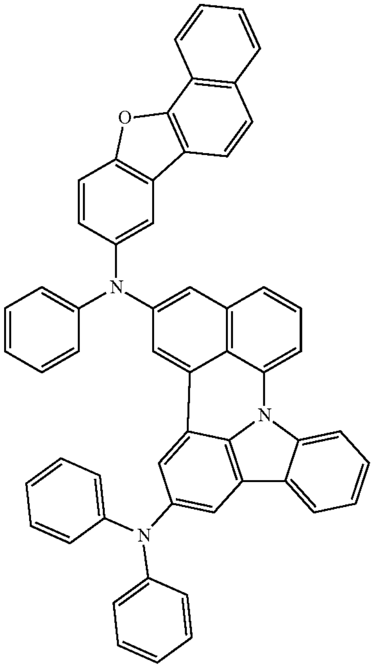
P-152
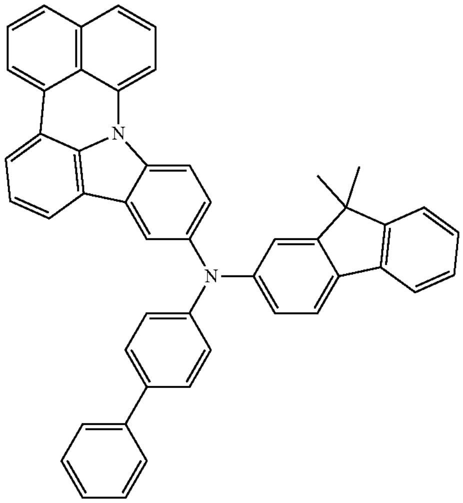
-continued
P-153
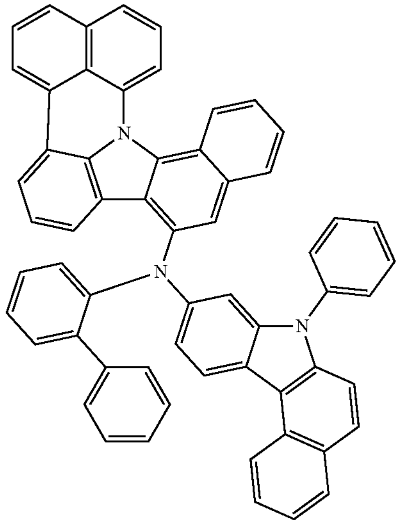
P-154
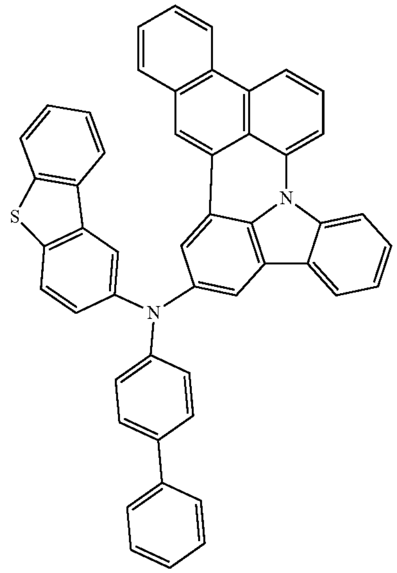
P-155
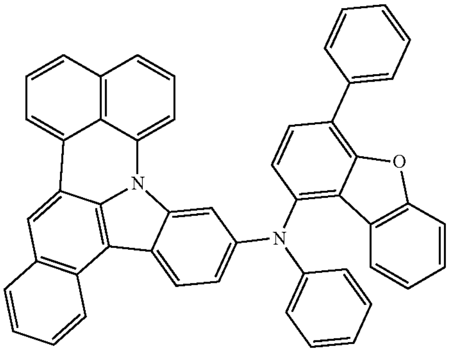

-continued
P-156
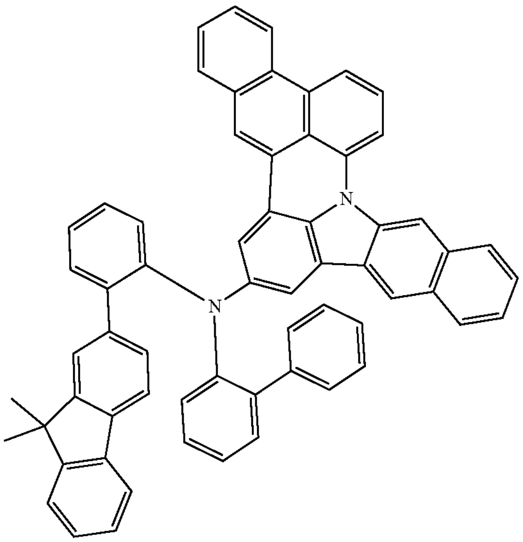
P-157
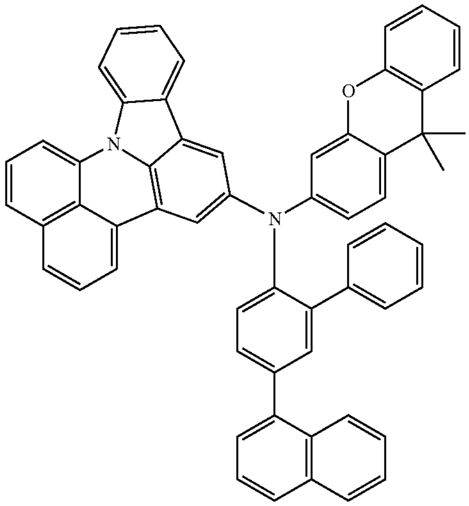
P-158
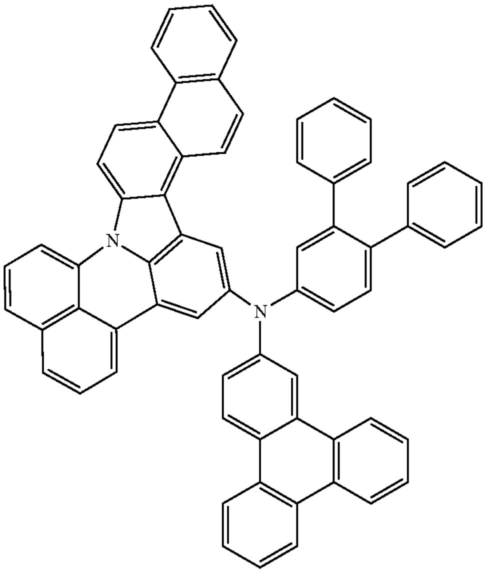
-continued
P-159
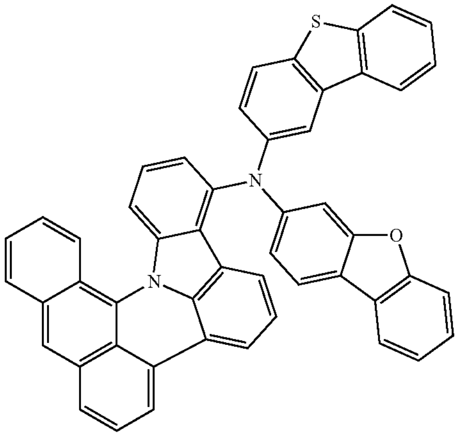
P-160
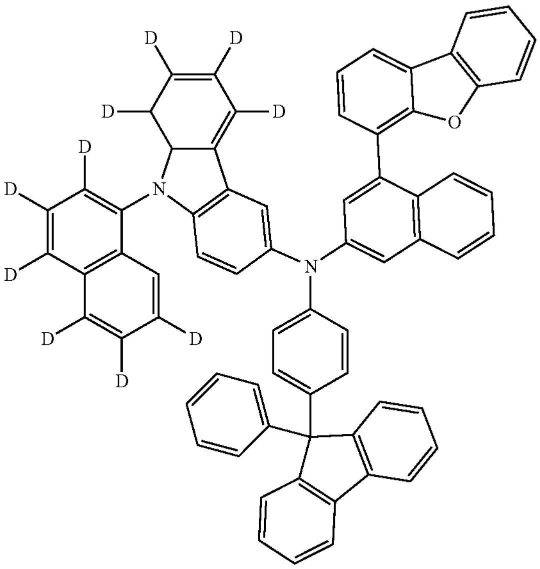

-continued
P-161
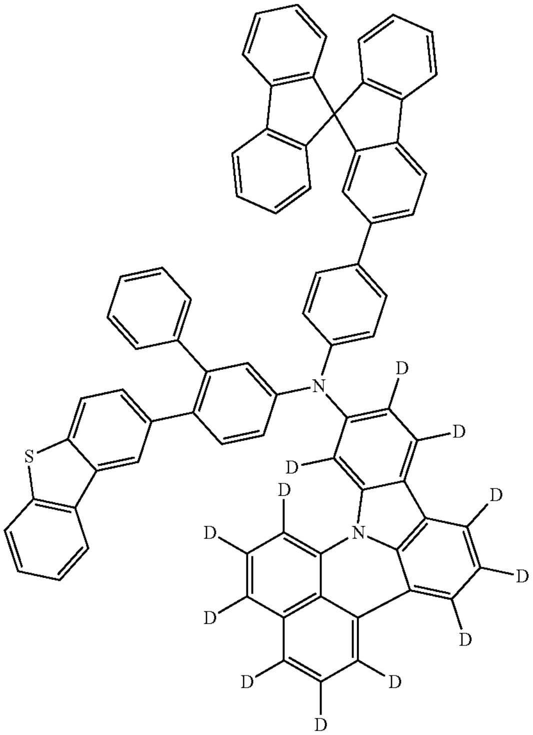
P-162
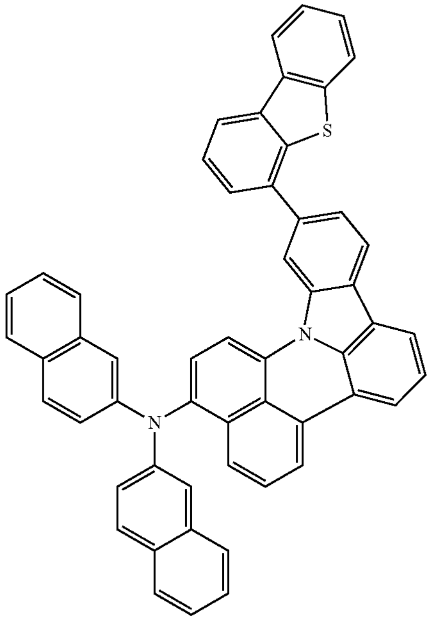
-continued
P-163
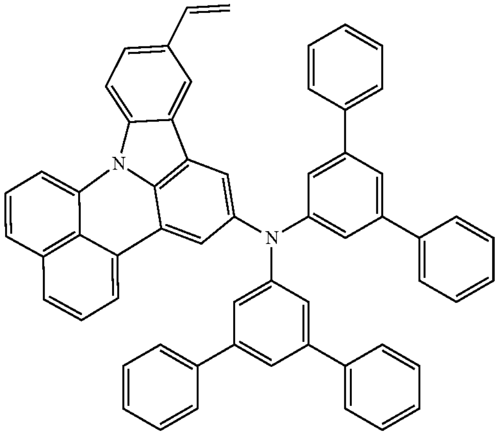
P-164
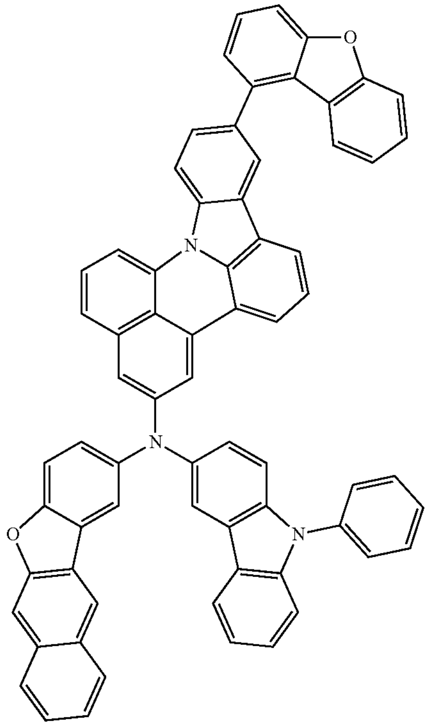
P-165
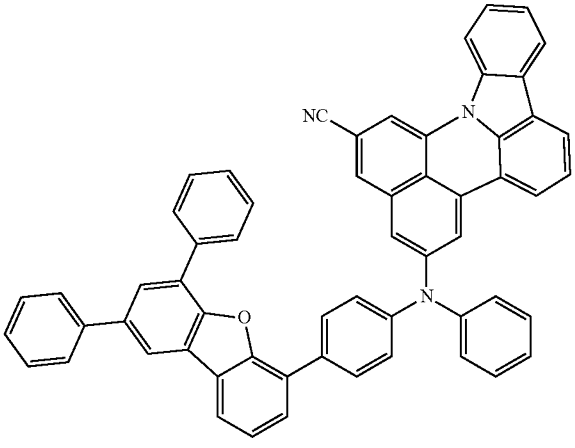

-continued
P-166
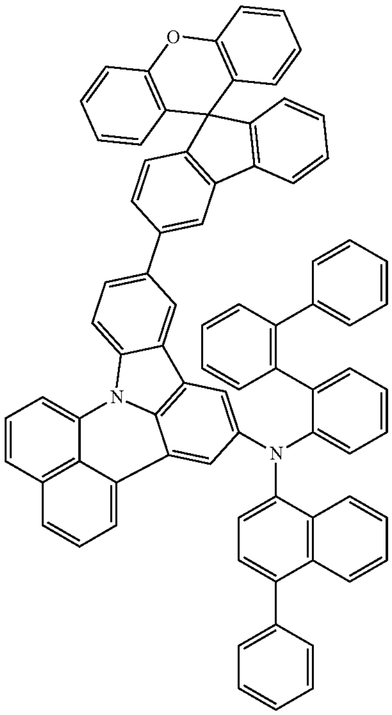
P-167
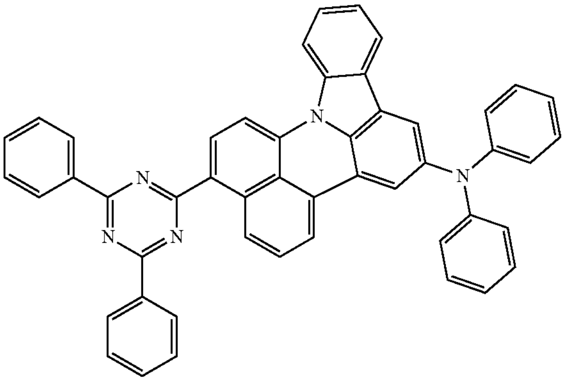
-continued
P-168
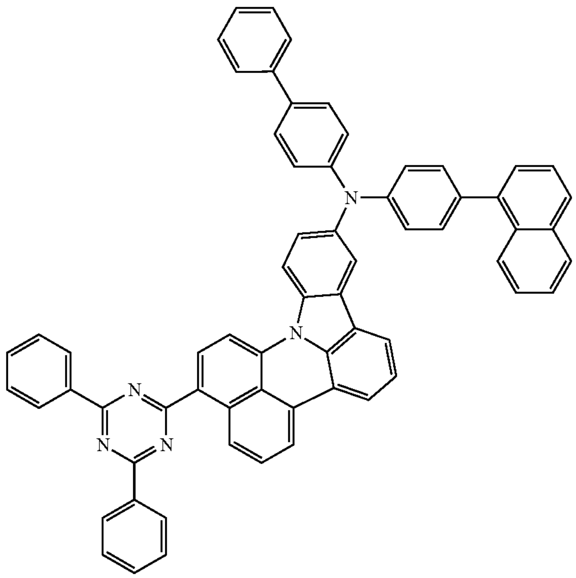
P-169
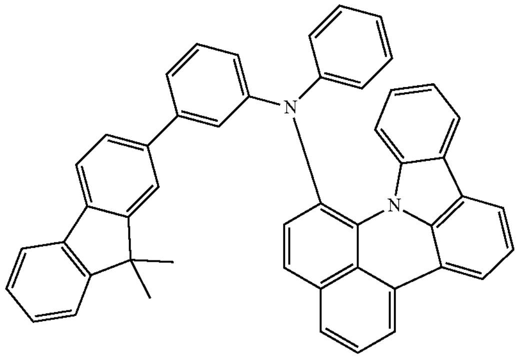
P-170
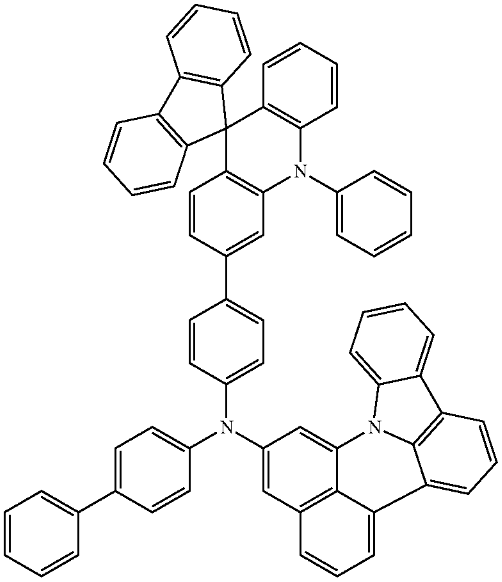

-continued
P-171
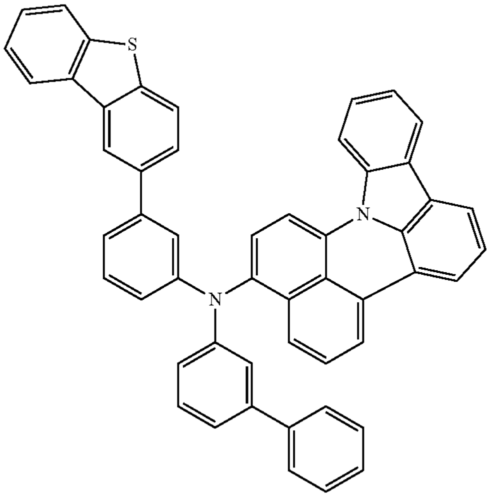
P-172
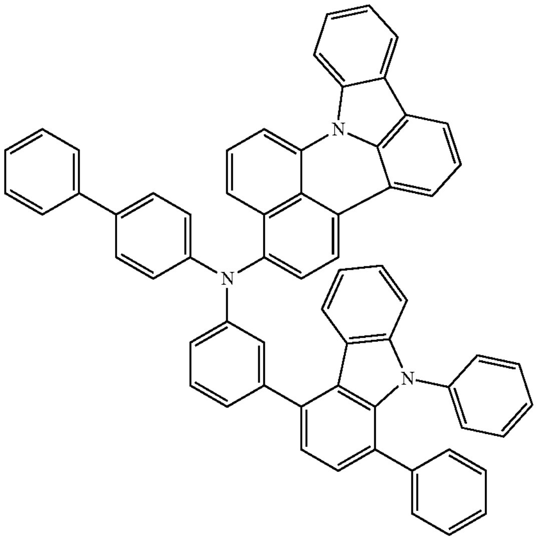
P-173
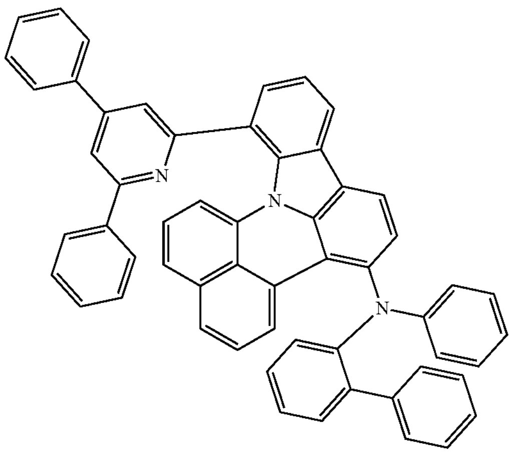
-continued
P-174
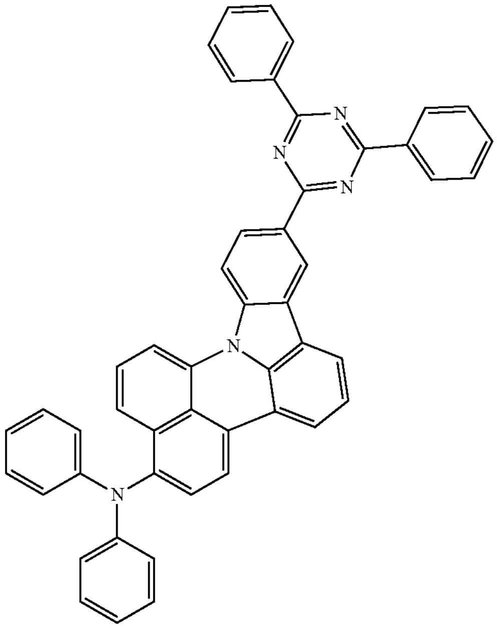
P-175
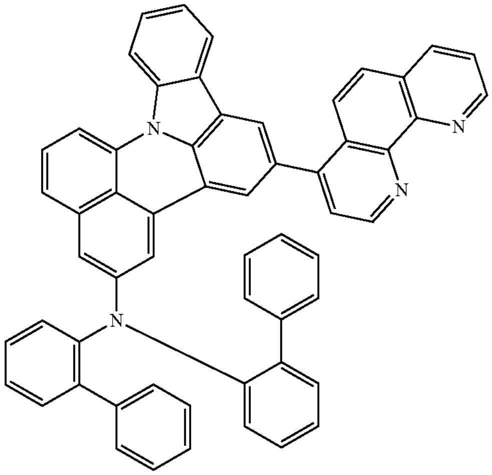

-continued
P-176
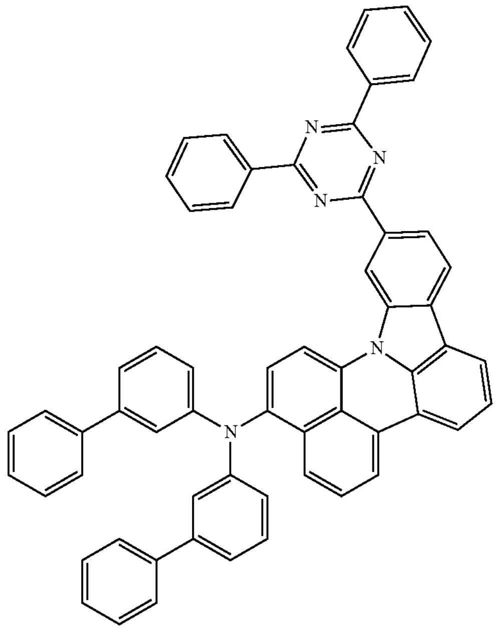
P-177
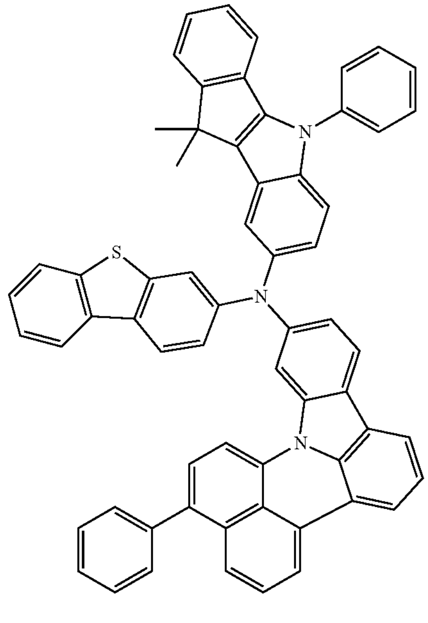
-continued
P-178
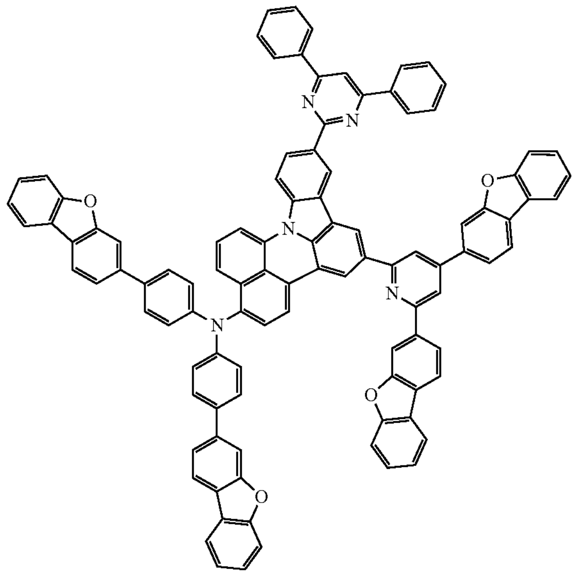
P-179
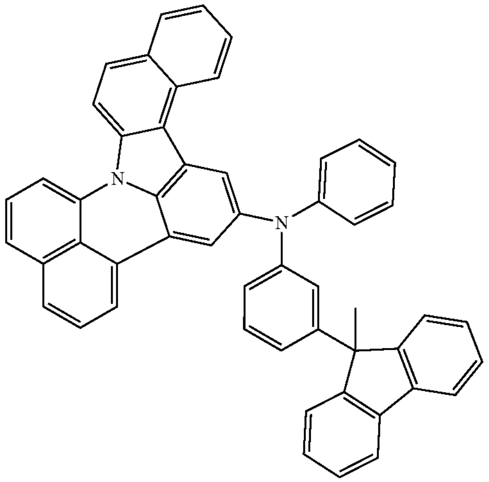
P-180
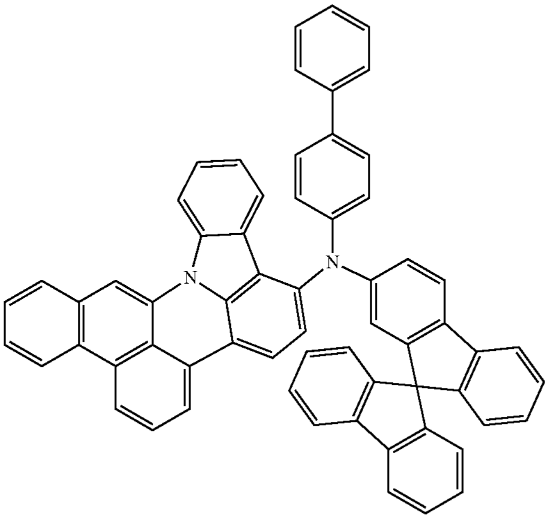

-continued
P-181
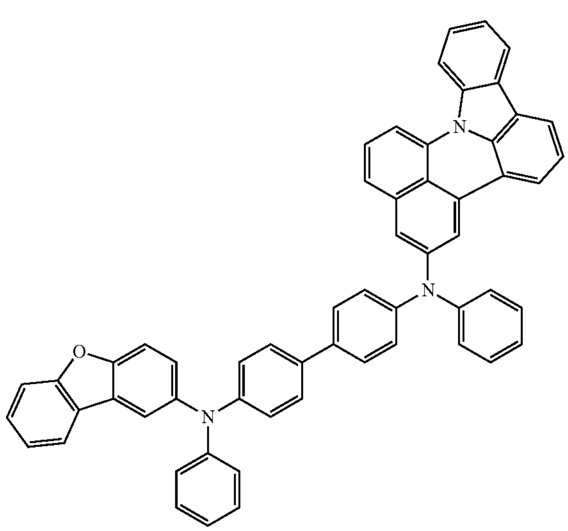
P-182
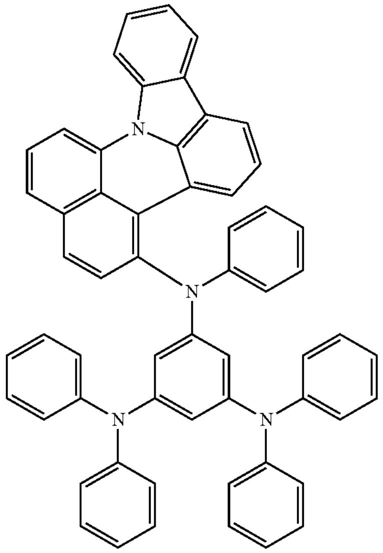
P-183
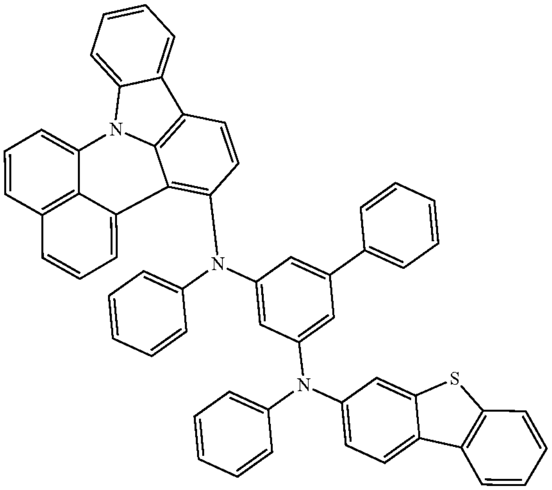
-continued
P-184
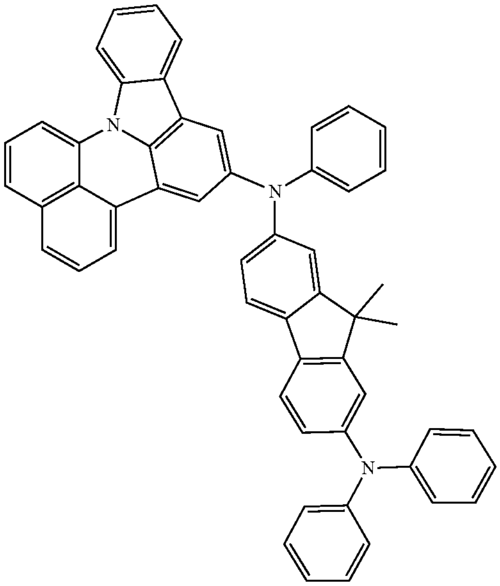
P-185
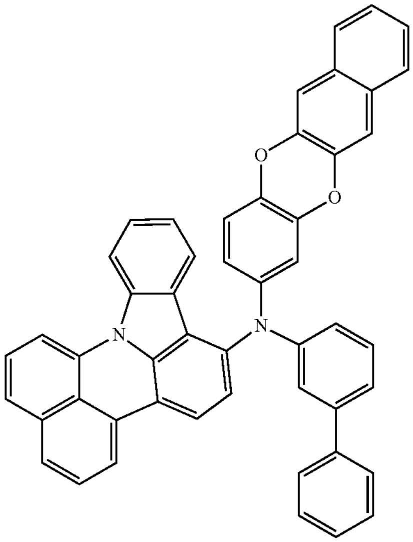
P-186
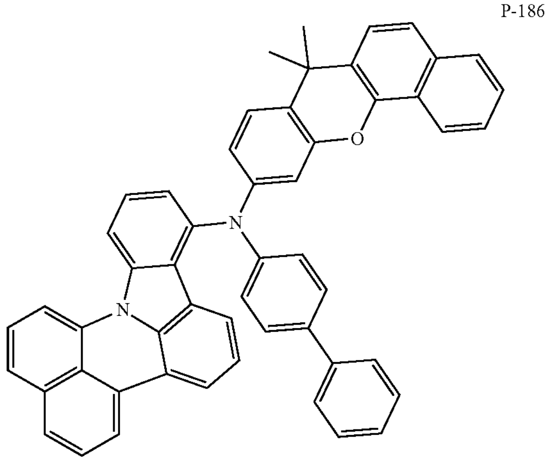

-continued
P-187
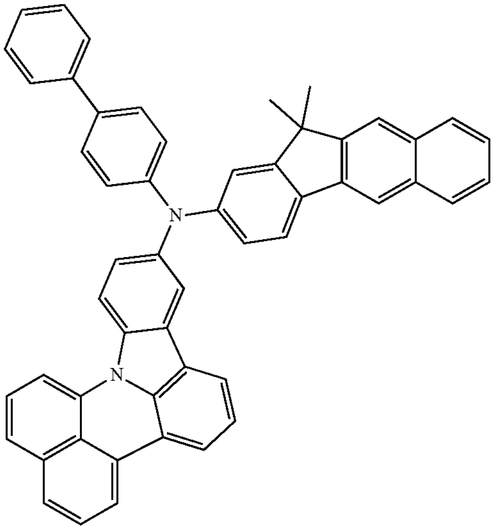
P-188
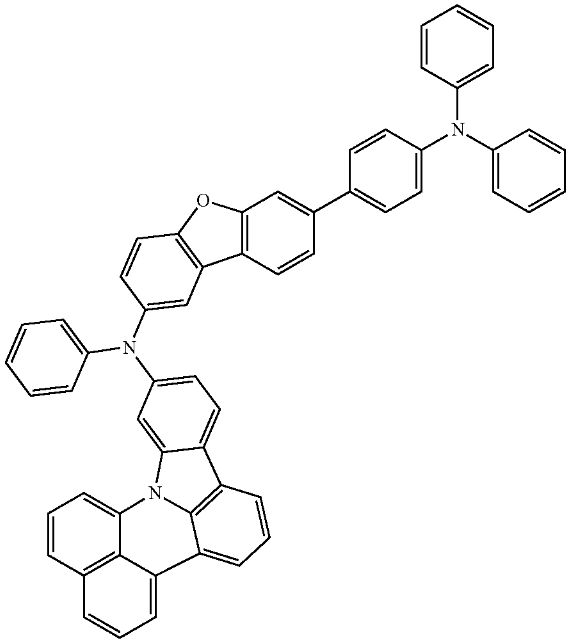
P-189
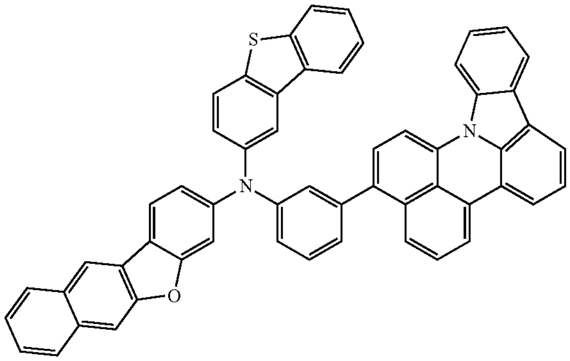
-continued
P-190
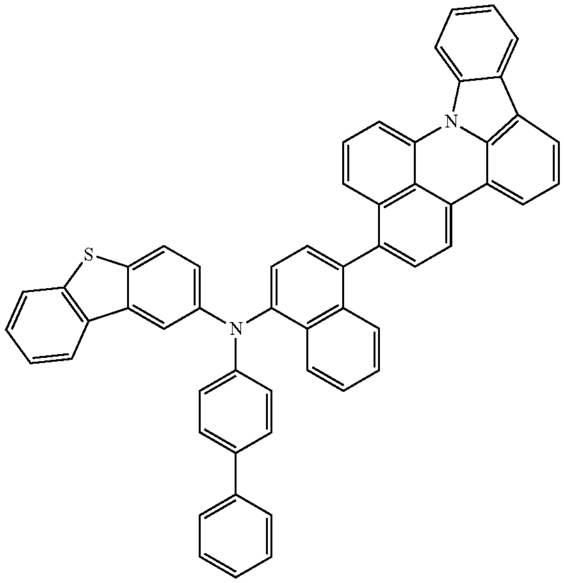
P-191
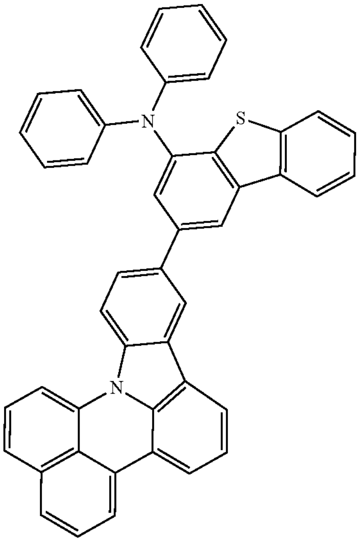
P-192
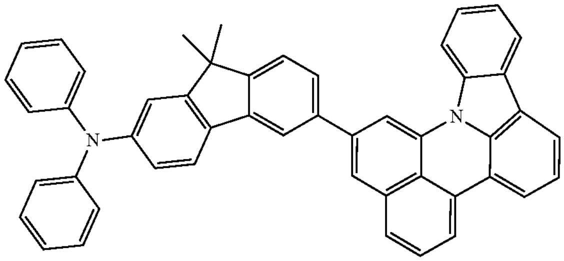

-continued
P-193
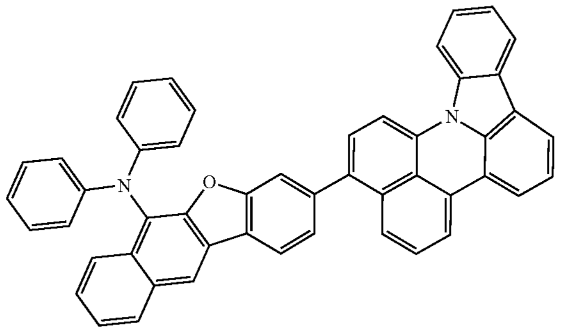
P-194
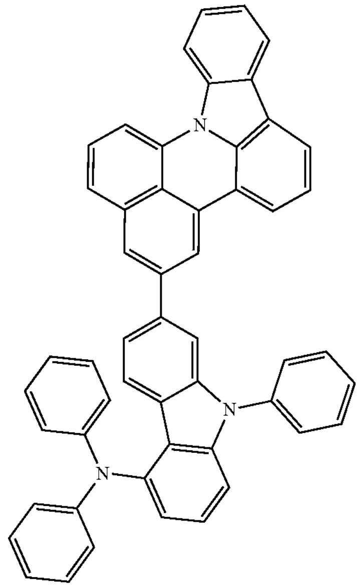
P-195
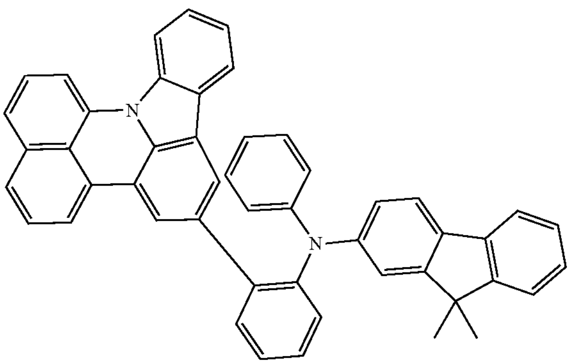
-continued
P-196
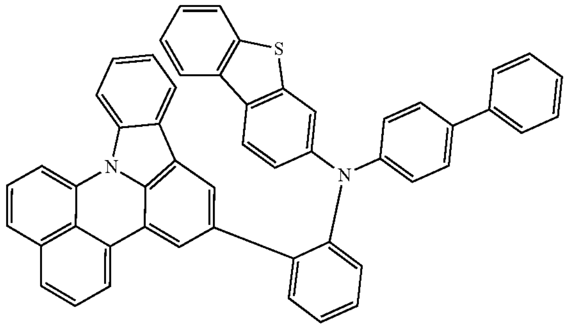
P-197
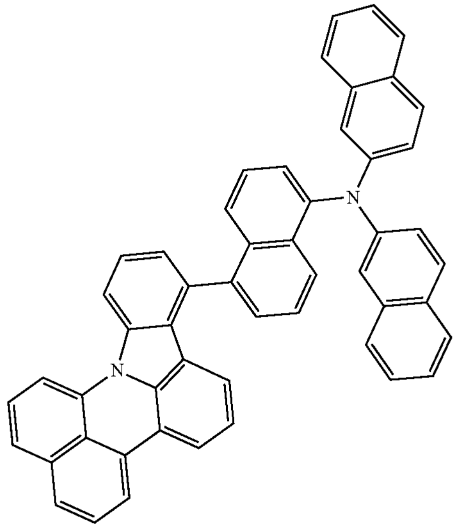
P-198
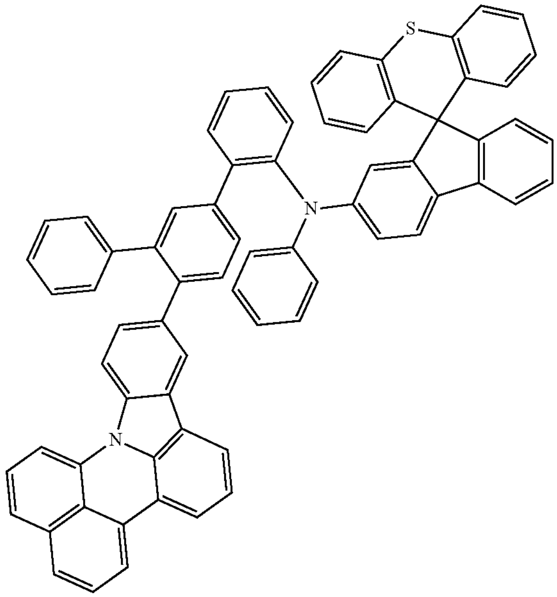

-continued
P-199
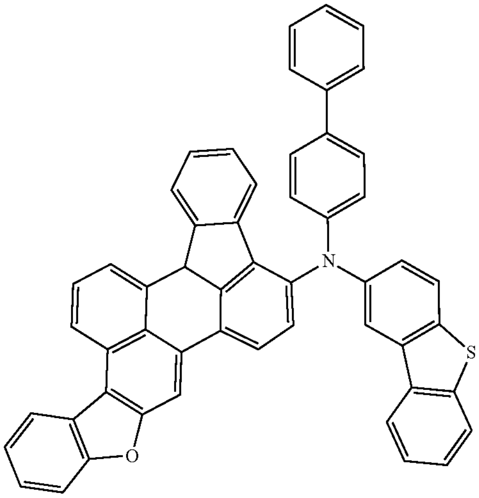
P-200
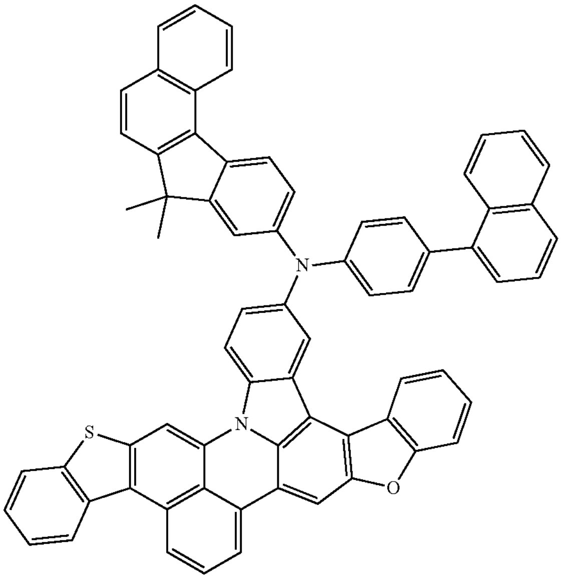
P-201
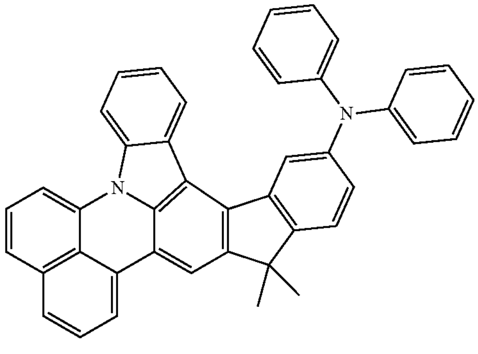
-continued
P-202
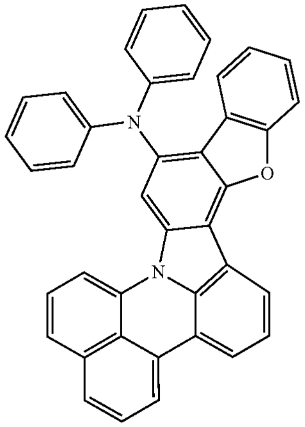
P-203
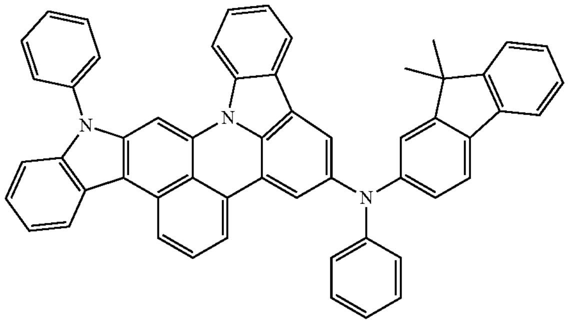
P-204
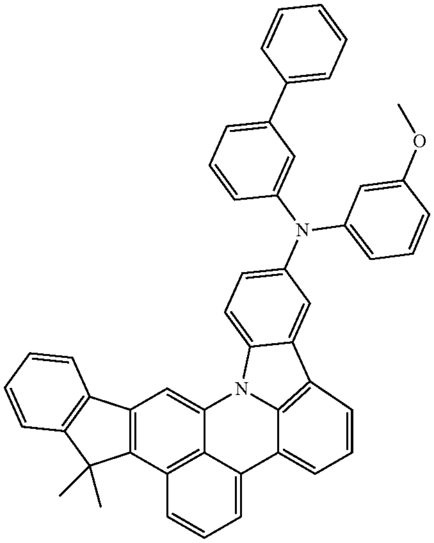

-continued
P-205
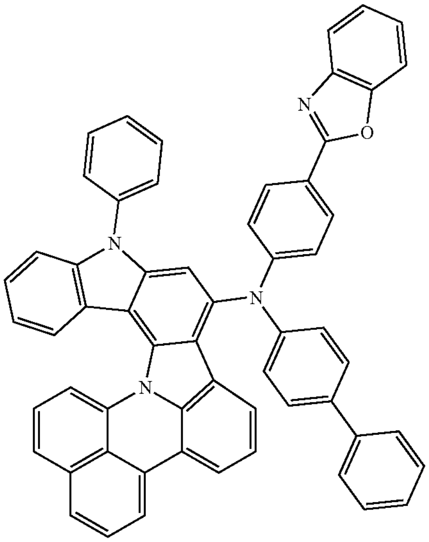
P-206
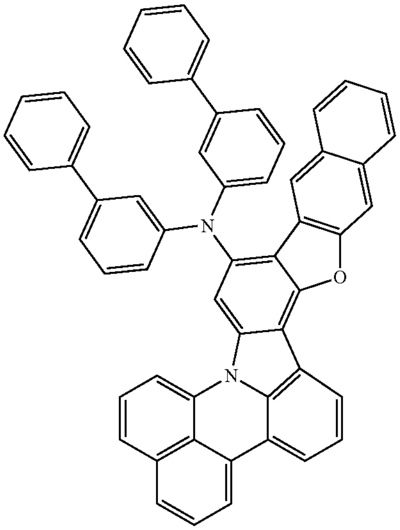
P-207
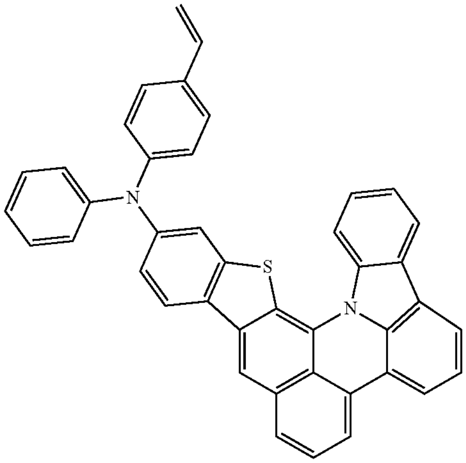
-continued
P-208
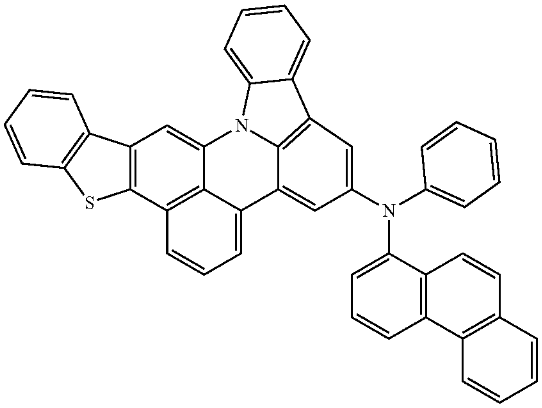
P-209
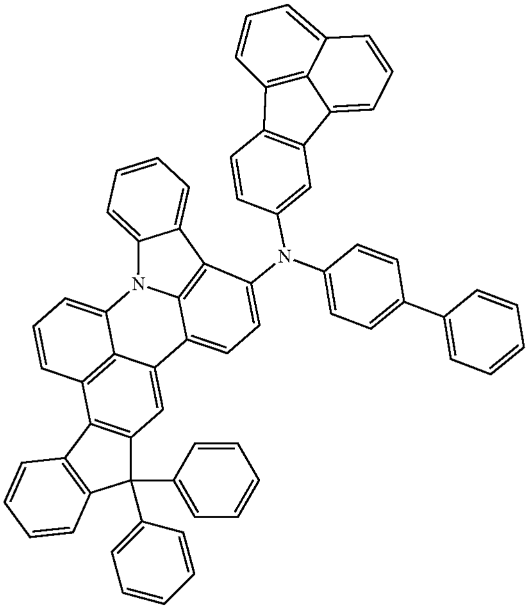
P-210
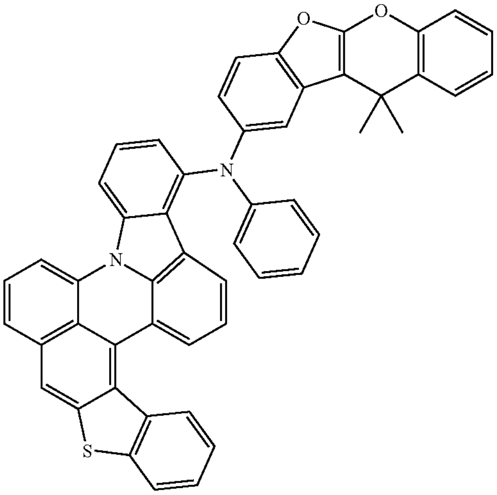

-continued

P-211

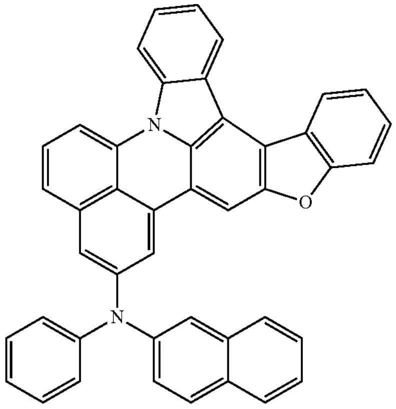

P-212

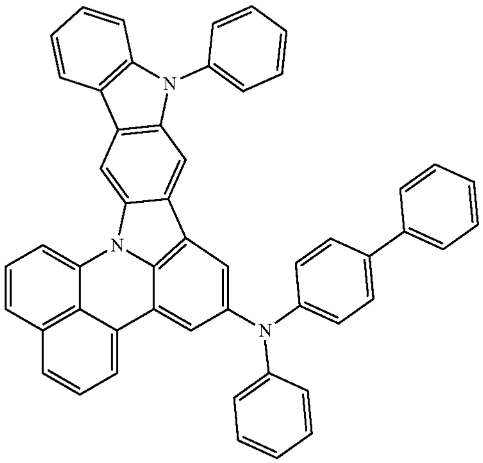

In another embodiment of the present disclosure, the present disclosure provides an organic electronic device which includes a first electrode; a second electrode; and an organic material layer formed between the first electrode and the second electrode, in which the organic material layer includes the compound represented by Formula 1 alone or in combination.

In still another embodiment of the present disclosure, the present disclosure provides an organic electronic device which includes a first electrode; a second electrode; an organic material layer formed between the first electrode and the second electrode; and a capping layer, the capping layer is formed on one surface that is not in contact with the organic material layer between the two electrodes of the first electrode and the second electrode; and in which the organic material layer or capping layer includes the compound represented by Formula 1 alone or in combination.

The organic material layer includes at least one among a hole injection layer, a hole transport layer, an auxiliary light emitting layer, a light emitting layer, an auxiliary electron transport layer, an electron transport layer, and an electron injection layer. That is, at least one layer among the hole injection layer, the hole transport layer, the auxiliary light emitting layer, the light emitting layer, the auxiliary electron transport layer, the electron transport layer, and the electron injection layer, which are included in the organic material layer, may include a compound represented by Formula 1.

Preferably, the organic material layer includes at least one of the hole transport layer, the light emitting layer, and the auxiliary light emitting layer. That is, the compound may be included in at least one of the hole transport layer, the light emitting layer, and the auxiliary light emitting layer.

The organic material layer includes two or more stacks including the hole transport layer, the light emitting layer, and the electron transport layer sequentially formed between the two electrodes.

Preferably, the organic material layer further includes a charge generation layer formed between the two or more stacks.

In still another embodiment of the present disclosure, the present disclosure provides an electronic device, which includes a display device including a compound represented by Formula 1 above; and an electric device which includes a control unit that drives the display device.

In an embodiment of the present disclosure, the compound represented by Formula 1 above may be included alone; the compound may be included in a combination of two or more different compounds; or the compound may be included in a combination of two or more other compounds.

Hereinafter, synthesis examples of the compound represented by Formula 1 according to the present disclosure and preparation examples of the organic electric device will be described in detail with reference to examples, but the present disclosure is not limited to the following examples.

Synthesis Example

The final compound represented by Formula 1 above according to the present disclosure may be synthesized by reacting Sub A and Sub 4 or Sub 5 as shown in Reaction Scheme 1-1 or Reaction Scheme 1-2 below, but are not limited thereto.

<Reaction Scheme 1-1>

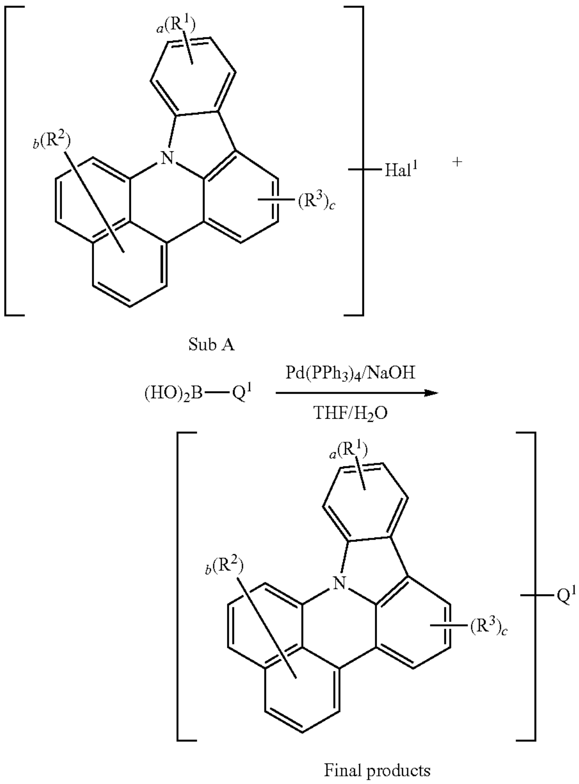

<Reaction Scheme 1-2>

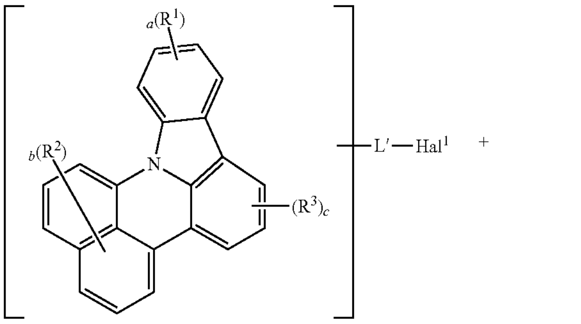

Sub A

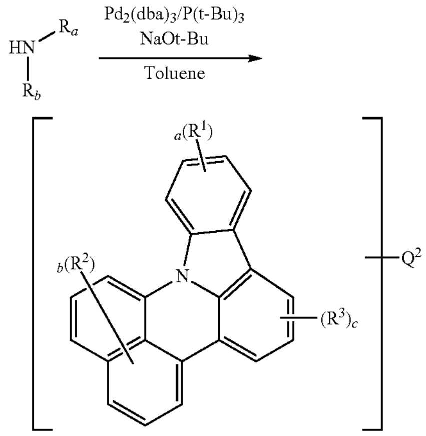

Final products

In Reaction Scheme 1-1 and Reaction Scheme 1-2 above, 1) at least one of $R^1$ to $R^3$ is substituted with a halogen (represented by $Hal^1$ above) atom;

2) $Hal^1$ is $C_1$ or Br; and

3) $Q^1$ is Formula 1-1 or Formula 1-2; and

4) $Q^2$ is Formula 1-3.

I. Synthesis of Sub A

Sub A of Reaction Scheme 1 may be synthesized by the reaction route of Reaction Scheme 2 below, but is not limited thereto.

<Reaction Scheme 2>

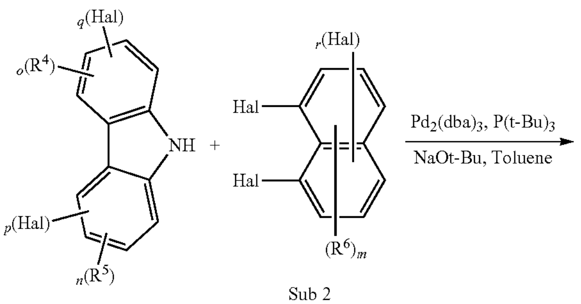

Sub 1 Sub 2

-continued

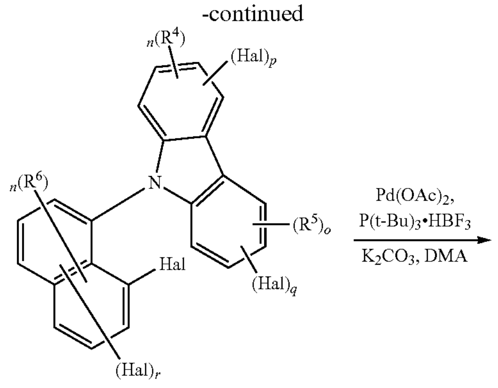

Sub 3

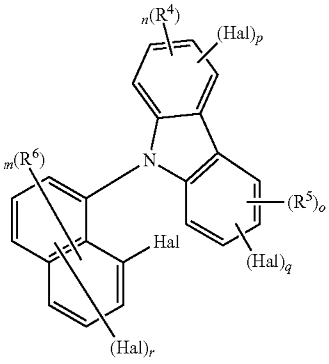

Sub 3

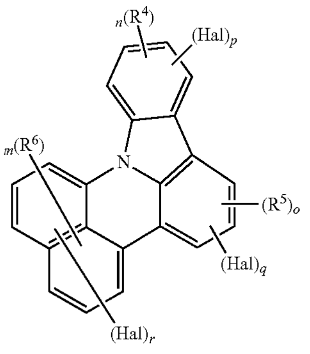

Sub A

In Reaction Scheme 2 above,

1) $R^4$ to $R^6$ are the same as the definition of $R^1$ to $R^3$ of Formula 1 above;

2) Hal is F, Cl, Br, or I;

3) n and p are each independently an integer of 0 to 4; o and q are each independently an integer from 0 to 3; m and r are each independently an integer from 0 to 6; and at least one of p, q, and r is 1.

1. Synthesis Example of Sub A-1

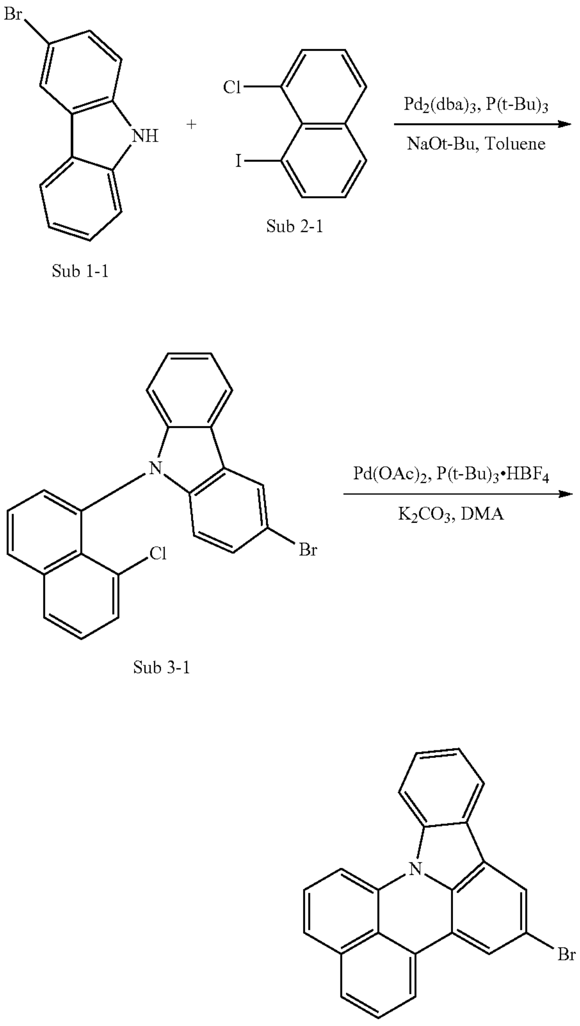

Sub 1-1

Sub 2-1

Sub 3-1

Sub A-1

(1) Synthesis of Sub 3-1

$Pd_2(dba)_3$ (18.60 g, 20.32 mmol), NaOt-Bu (117.15 g, 1218.97 mmol), $P(t-Bu)_3$ (8.22 g, 40.63 mmol), and toluene (2,000 mL) were added to Sub 2-1 (117.23 g, 406.32 mmol) and stirred at 100° C. Upon completion of the reaction, the resultant was extracted with $CH_2Cl_2$ and water, the organic layer was dried over $MgSO_4$ and concentrated, and the resulting compound was subjected to silica gel column and recrystallization to obtain 147.08 g (yield: 89%) of a product.

(1) Synthesis of Sub A-1

$Pd(OAc)_2$ (2.76 g, 12.29 mmol), $P(t-Bu)_3 \cdot HBF_4$ (7.13 g, 24.59 mmol), $K_2CO_3$ (101.79 g, 737.61 mmol), and DMA (1,200 mL) were added to Sub 3-1 (100 g, 245.87 mmol) which was obtained from the synthesis above and stirred at 100° C. Upon completion of the reaction, the resultant was extracted with $CH_2Cl_2$ and water, the organic layer was dried over $MgSO_4$ and concentrated, and the resulting compound was subjected to silica gel column and recrystallization to obtain 49.15 g (yield: 54%) of a product.

2. Synthesis Example of Sub A-2

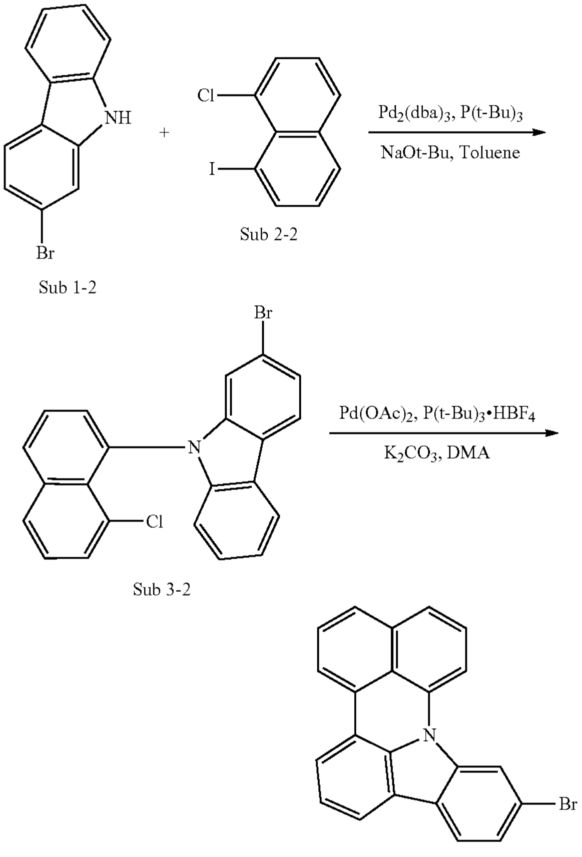

Sub 1-2

Sub 2-2

Sub 3-2

Sub A-2

(1) Synthesis of Sub 3-2

Sub 1-2 (100 g, 406.32 mmol), Sub 2-2 (117.23 g, 406.32 mmol), $Pd_2(dba)_3$ (18.60 g, 20.32 mmol), NaOt-Bu (117.15 g, 1218.97 mmol), $P(t-Bu)_3$ (8.22 g, 40.63 mmol), and toluene (2,000 mL) were added, and a product in the amount of 117.33 g (yield: 71%) was obtained using the synthesis method of Sub 3-1 above.

(2) Synthesis of Sub A-2

Sub 3-2 (100 g, 245.87 mmol), $Pd(OAc)_2$ (2.76 g, 12.29 mmol), $P(t-Bu)_3 \cdot HBF_4$ (7.13 g, 24.59 mmol), $K_2CO_3$ (101.79 g, 737.61 mmol), and DMA (1,200 mL) were added, and a product in the amount of 44.60 g (yield: 49%) was obtained using the synthesis method of Sub A-1 above.

3. Synthesis Example of Sub A-3

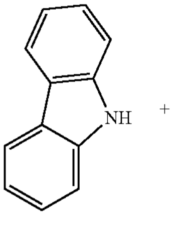

Sub 1-3

-continued

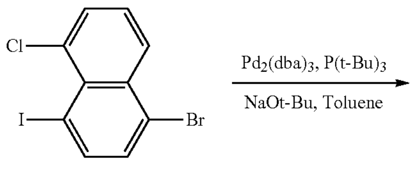

Sub 2-3

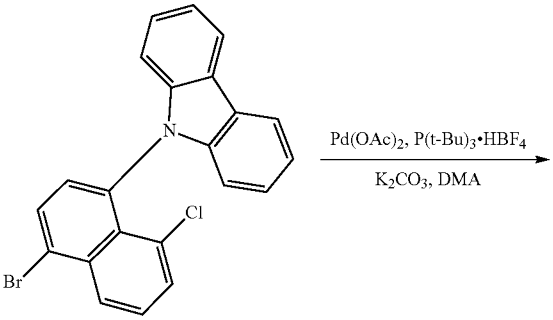

Sub 3-3

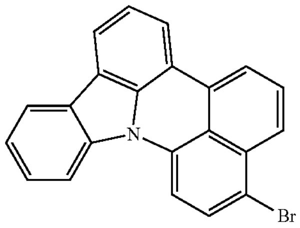

Sub A-3

(1) Synthesis of Sub 3-3

Sub 1-3 (100 g, 598.05 mmol), Sub 2-3 (219.73 g, 598.05 mmol), $Pd_2(dba)_3$ (27.38 g, 29.90 mmol), NaOt-Bu (172.44 g, 1794.15 mmol), $P(t\text{-}Bu)_3$ (12.10 g, 59.81 mmol), and toluene (3,000 mL) were added, and a product in the amount of 158.10 g (yield: 65%) was obtained using the synthesis method of Sub 3-1 above.

(2) Synthesis of Sub A-3

Sub 3-3 (100 g, 245.88 mmol), $Pd(OAc)_2$ (2.76 g, 12.29 mmol), $P(t\text{-}Bu)_3\cdot HBF_4$ (7.13 g, 24.59 mmol), $K_2CO_3$ (101.79 g, 737.61 mmol), and DMA (1,200 mL) were added, and a product in the amount of 32.77 g (yield: 36%) was obtained using the synthesis method of Sub A-1 above.

4. Synthesis Example of Sub A-5

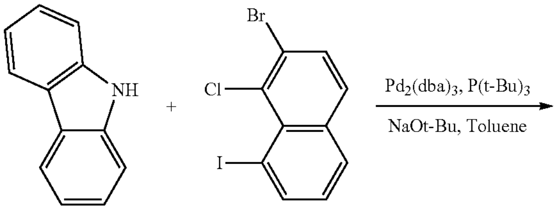

Sub 1-5

Sub 2-5

-continued

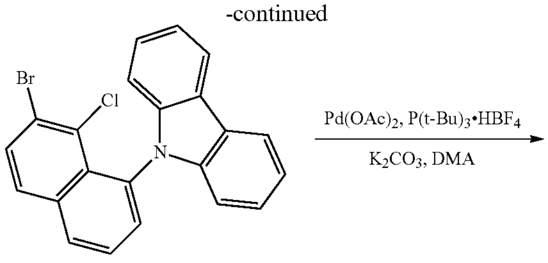

Sub 3-5

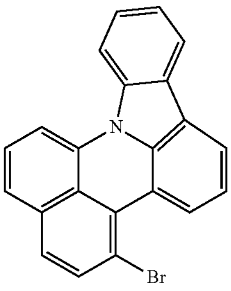

Sub A-5

(1) Synthesis of 3-5

Sub 1-5 (100 g, 598.05 mmol), Sub 2-5 (219.73 g, 598.05 mmol), $Pd_2(dba)_3$ (27.38 g, 29.90 mmol), NaOt-Bu (172.44 g, 1794.15 mmol), $P(t\text{-}Bu)_3$ (12.10 g, 59.81 mmol), and toluene (3,000 mL) were added, and a product in the amount of 223.77 g (yield: 92%) was obtained using the synthesis method of Sub 3-1 above.

(1) Synthesis of Sub A-5

Sub 3-5 (100 g, 245.87 mmol), $Pd(OAc)_2$ (2.76 g, 12.29 mmol), $P(t\text{-}Bu)_3\cdot HBF_4$ (7.13 g, 24.59 mmol), $K_2CO_3$ (101.79 g, 737.61 mmol), and DMA (1,200 mL) were added, and a product in the amount of 44.42 g (yield: 51%) was obtained using the synthesis method of Sub A-1 above.

5. Synthesis Example of Sub A-10

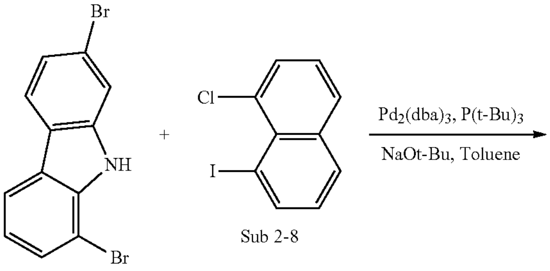

Sub 2-8

Sub 1-8

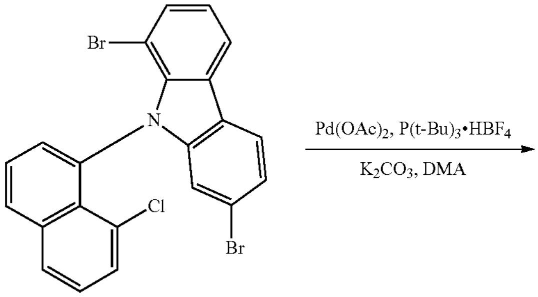

Sub 3-8

-continued

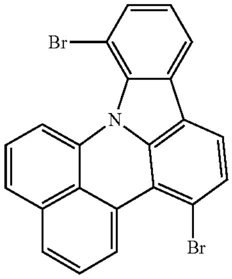

Sub A-10

(1) Synthesis of Sub 3-8

Sub 1-8 (100 g, 307.69 mmol), Sub 2-8 (88.77 g, 307.69 mmol), $Pd_2(dba)_3$ (14.09 g, 15.38 mmol), NaOt-Bu (88.72 g, 923.08 mmol), $P(t-Bu)_3$ (6.23 g, 30.77 mmol), and toluene (1,500 mL) were added, and a product in the amount of 118.03 g (yield: 79%) was obtained using the synthesis method of Sub 3-1 above.

(2) Synthesis of Sub A-10

Sub 3-8 (100 g, 205.93 mmol), $Pd(OAc)_2$ (2.31 g, 10.30 mmol), $P(t-Bu)_3 \cdot HBF_4$ (5.97 g, 20.59 mmol), $K_2CO_3$ (85.26 g, 617.79 mmol), and DMA (1,000 mL) were added, and a product in the amount of 47.17 g (yield: 51%) was obtained using the synthesis method of Sub A-1 above.

6. Synthesis Example of Sub A-11

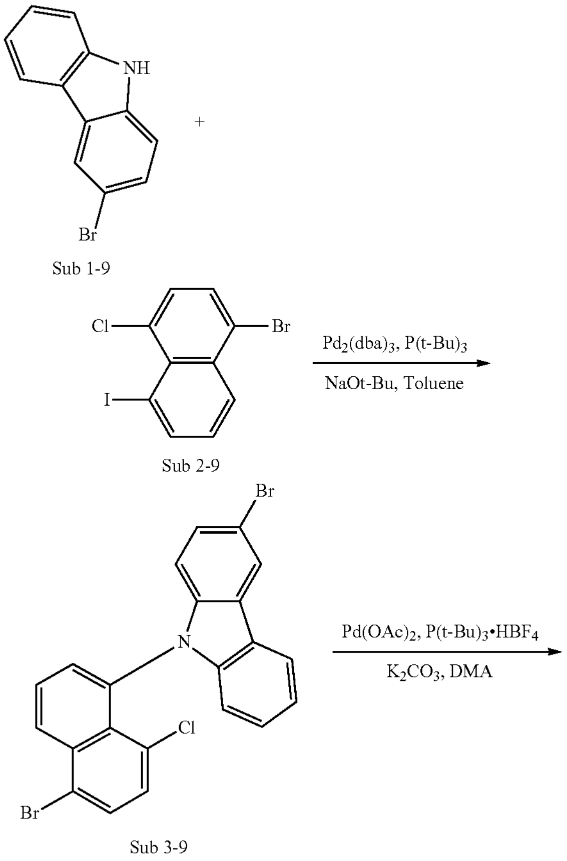

-continued

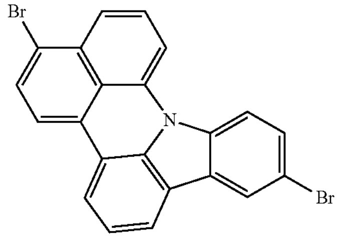

Sub A-11

(1) Synthesis of Sub 3-9

Sub 1-9 (100 g, 406.32 mmol), Sub 2-9 (149.29 g, 406.32 mmol), $Pd_2(dba)_3$ (18.60 g, 20.32 mmol), NaOt-Bu (117.15 g, 1218.97 mmol), $P(t-Bu)_3$ (8.22 g, 40.63 mmol), and toluene (2,000 mL) were added, and a product in the amount of 124.30 g (yield: 63%) was obtained using the synthesis method of Sub 3-1 above.

(2) Synthesis of Sub A-11

Sub 3-9 (100 g, 205.93 mmol), $Pd(OAc)_2$ (2.31 g, 10.30 mmol), $P(t-Bu)_3 \cdot HBF_4$ (5.97 g, 20.59 mmol), $K_2CO_3$ (85.26 g, 617.19 mmol), and DMA (1,000 mL) were added, and a product in the amount of 55.49 g (yield: 60%) was obtained using the synthesis method of Sub A-1 above.

7. Synthesis Example of Sub A-12

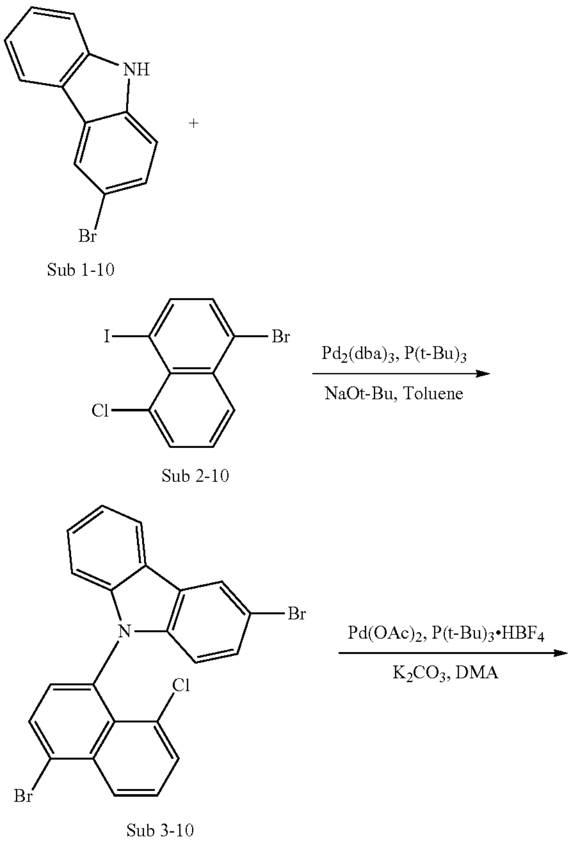

-continued

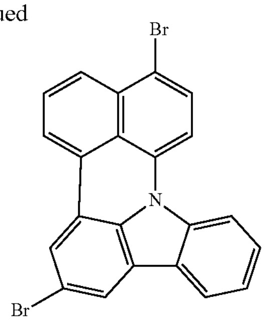

Sub A-12

(1) Synthesis of Sub 3-10

Sub 1-10 (100 g, 406.32 mmol), Sub 2-10 (149.29 g, 406.32 mmol), $Pd_2(dba)_3$ (18.60 g, 20.32 mmol), NaOt-Bu (117.15 g, 1218.97 mmol), $P(t\text{-}Bu)_3$ (8.22 g, 40.63 mmol), and toluene (2,000 mL) were added, and a product in the amount of 173.63 g (yield: 88%) was obtained using the synthesis method of Sub 3-1 above.

(2) Synthesis of Sub A-12

Sub 3-10 (100 g, 205.93 mmol), $Pd(OAc)_2$ (2.31 g, 10.30 mmol), $P(t\text{-}Bu)_3{\cdot}HBF_4$ (5.97 g, 20.59 mmol), $K_2CO_3$ (85.26 g, 617.79 mmol), and DMA (1,000 mL) were added, and a product in the amount of 36.07 g (yield: 39%) was obtained using the synthesis method of Sub A-1 above.

8. Synthesis Example of Sub A-13

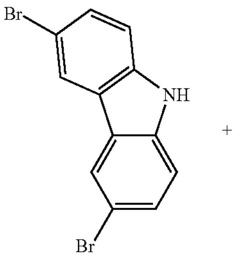

Sub 1-11

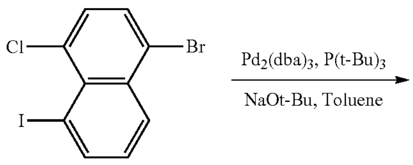

Sub 2-11

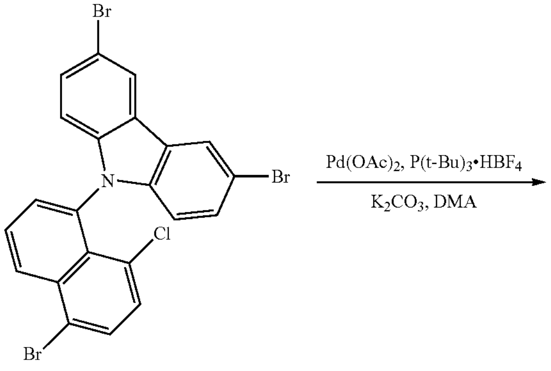

Sub 3-11

-continued

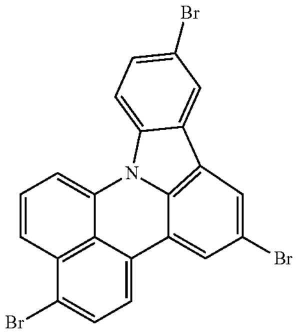

Sub A-13

(1) Synthesis of Sub 3-11

Sub 1-11 (100 g, 307.69 mmol), Sub 2-11 (113.05 g, 307.69 mmol), $Pd_2(dba)_3$ (14.09 g, 15.38 mmol), NaOt-Bu (88.72 g, 923.08 mmol), $P(t\text{-}Bu)_3$ (6.23 g, 30.77 mmol), and toluene (1,500 mL) were added, and a product in the amount of 123.32 g (yield: 71%) was obtained using the synthesis method of Sub 3-1 above.

(2) Synthesis of Sub A-13

Sub 3-11 (100 g, 177.15 mmol), $Pd(OAc)_2$ (1.99 g, 8.86 mmol), $P(t\text{-}Bu)_3{\cdot}HBF_4$ (5.14 g, 17.71 mmol), $K_2CO_3$ (73.34 g, 531.44 mmol), and DMA (880 mL) were added, and a product in the amount of 41.15 g (yield: 44%) was obtained using the synthesis method of Sub A-1 above.

9. Synthesis Example of Sub A-15

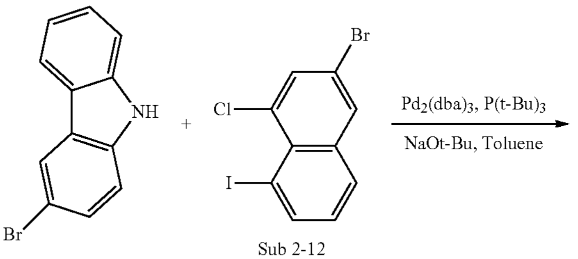

Sub 1-12

Sub 2-12

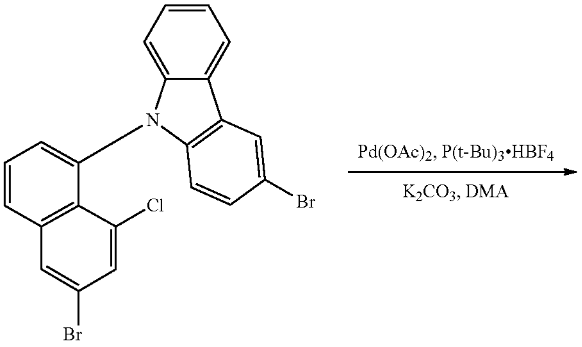

Sub 3-12

-continued

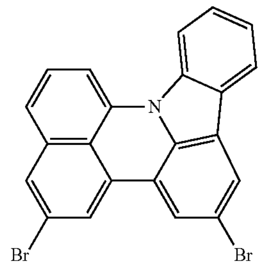

Sub A-15

(1) Synthesis of Sub 3-12

Sub 1-12 (100 g, 406.32 mmol), Sub 2-12 (149.29 g, 406.32 mmol), $Pd_2(dba)_3$ (18.60 g, 20.32 mmol), NaOt-Bu (117.15 g, 1,218.97 mmol), $P(t\text{-}Bu)_3$ (8.22 g, 40.63 mmol), and toluene (2,000 mL) were added, and a product in the amount of 136.14 g (yield: 69%) was obtained using the synthesis method of Sub 3-1 above.

(2) Synthesis of Sub A-15

Sub 3-12 (100 g, 205.93 mmol), $Pd(OAc)_2$ (2.31 g, 10.30 mmol), $P(t\text{-}Bu)_3 \cdot HBF_4$ (5.97 g, 20.59 mmol), $K_2CO_3$ (85.26 g, 617.79 mmol), and DMA (1,000 mL) were added, and a product in the amount of 58.27 g (yield: 63%) was obtained using the synthesis method of Sub A-1 above.

10. Synthesis Example of Sub A-18

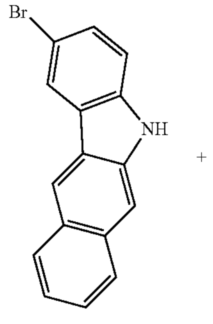

Sub 1-13

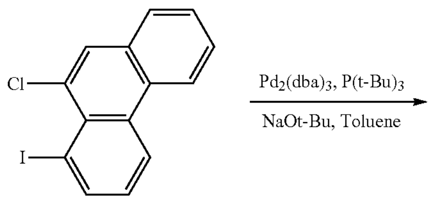

Sub 2-13

-continued

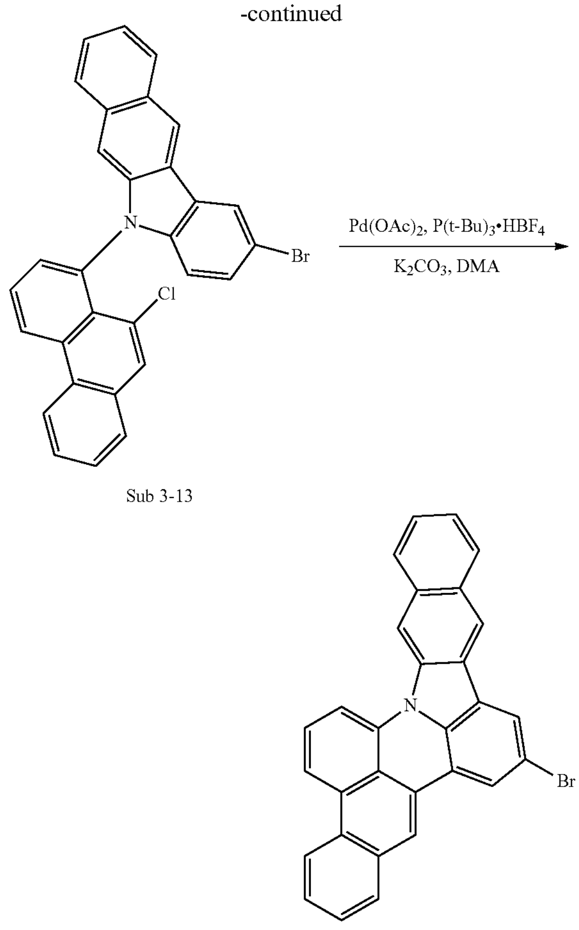

Sub 3-13

Sub A-18

(1) Synthesis of Sub 3-13

Sub 1-13 (100 g, 337.64 mmol), Sub 2-13 (114.32 g, 337.64 mmol), $Pd_2(dba)_3$ (15.46 g, 16.88 mmol), NaOt-Bu (97.35 g, 1012.93 mmol), $P(t\text{-}Bu)_3$ (6.83 g, 33.76 mmol), and toluene (1,700 mL) were added, and a product in the amount of 145.45 g (yield: 85%) was obtained using the synthesis method of Sub 3-1 above.

(2) Synthesis of Sub A-18

Sub 3-13 (100 g, 197.30 mmol), $Pd(OAc)_2$ (2.21 g, 9.87 mmol), $P(t\text{-}Bu)_3 \cdot HBF_4$ (5.72 g, 19.73 mmol), $K_2CO_3$ (81.68 g, 591.91 mmol), and DMA (1,000 mL) were added, and a product in the amount of 33.41 g (yield: 36%) was obtained using the synthesis method of Sub A-1 above.

11. Synthesis Example of Sub A-31

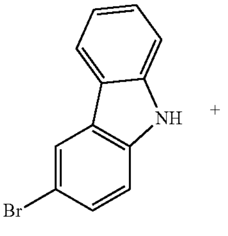

Sub 1-14

-continued

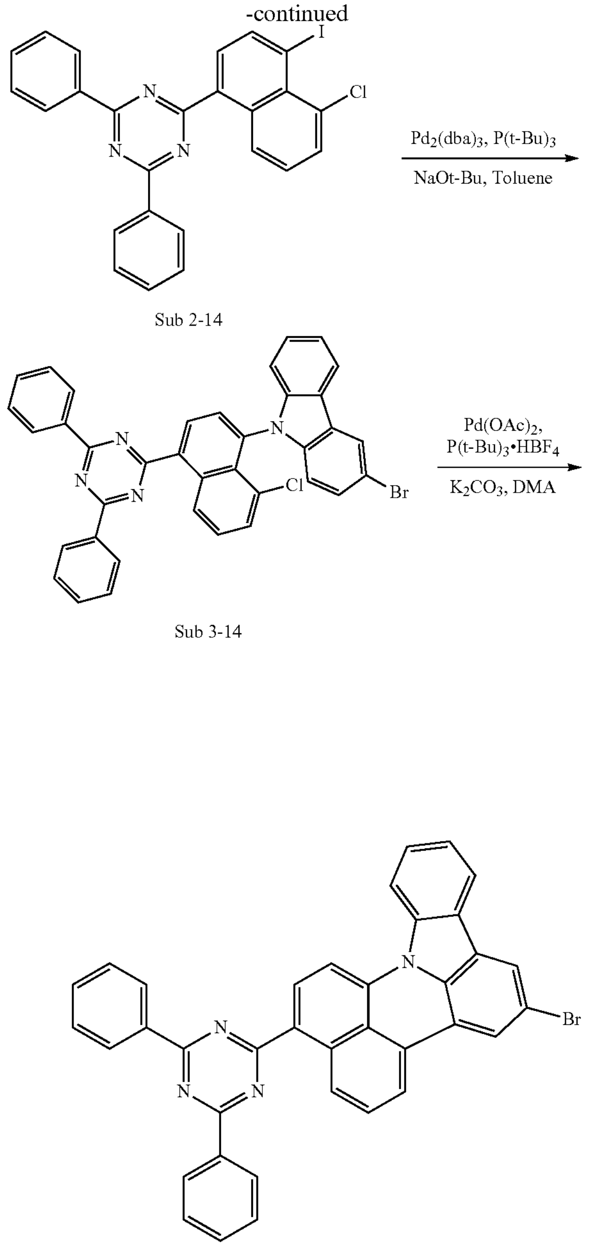

Sub 2-14

Sub 3-14

Sub A-31

(1) Synthesis of Sub 3-14

Sub 1-14 (100 g, 406.32 mmol), Sub 2-14 (211.19 g, 406.32 mmol), $Pd_2(dba)_3$ (18.60 g, 20.32 mmol), NaOt-Bu (117.14 g, 1218.97 mmol), $P(t\text{-}Bu)_3$ (8.22 g, 40.63 mmol), and toluene (2,000 mL) were added, and a product in the amount of 145.16 g (yield: 56%) was obtained using the synthesis method of Sub 3-1 above.

(2) Synthesis of Sub A-31

Sub 3-14 (100 g, 156.75 mmol), $Pd(OAc)_2$ (1.76 g, 7.84 mmol), $P(t\text{-}Bu)_3{\cdot}HBF_4$ (4.55 g, 15.67 mmol), $K_2CO_3$ (64.99 g, 470.24 mmol), and DMA (1,000 mL) were added, and a product in the amount of 38.66 g (yield: 41%) was obtained using the synthesis method of Sub A-1 above.

Meanwhile, the compounds belonging to Sub A may be those shown below, but are not limited thereto.

Sub A-1

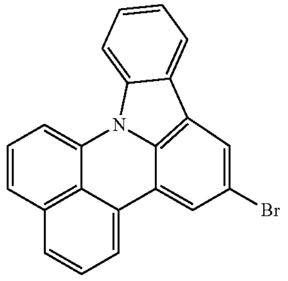

Sub A-2

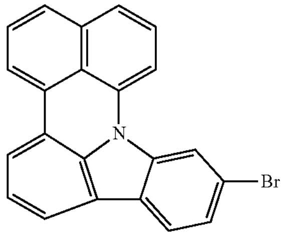

Sub A-3

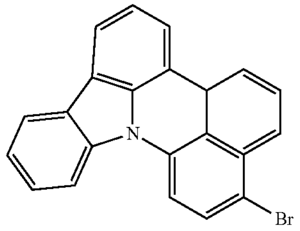

Sub A-4

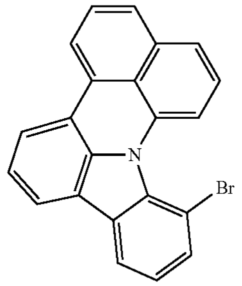

Sub A-5

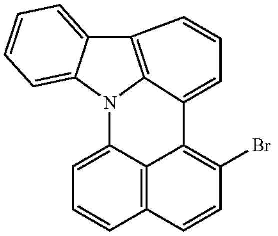

Sub A-6

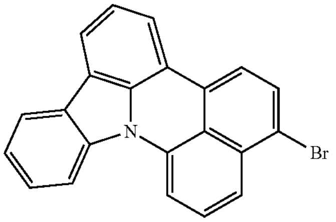

-continued
Sub A-7
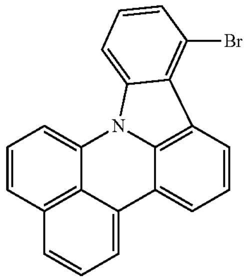
Sub A-8
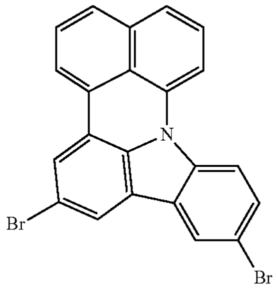
Sub A-9
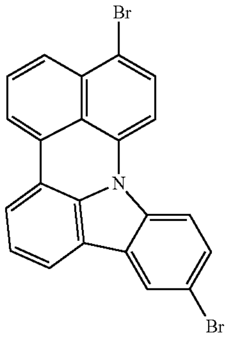
Sub A-10
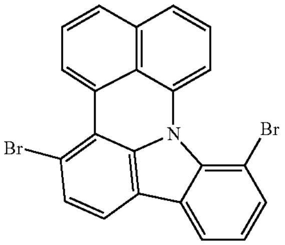
Sub A-11
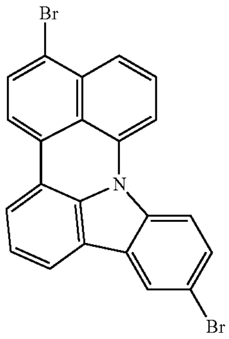
-continued
Sub A-12
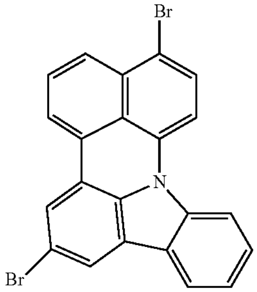
Sub A-13
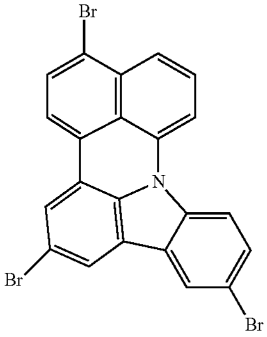
Sub A-14
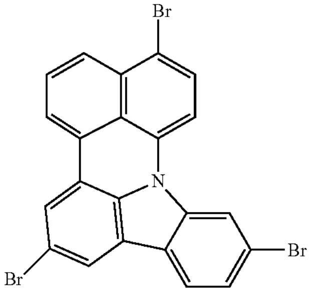
Sub A-15
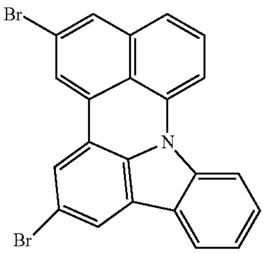
Sub A-16
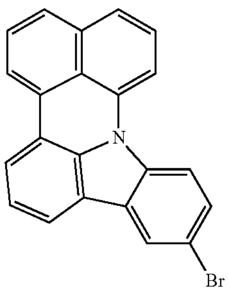

Sub A-17
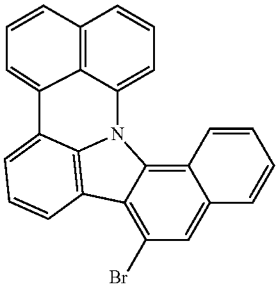
Sub A-18
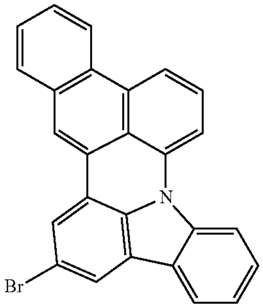
Sub A-19
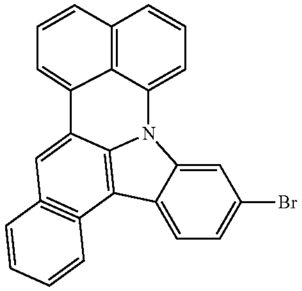
Sub A-20
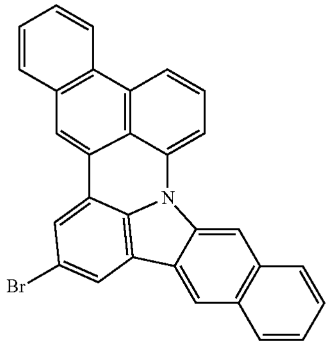
Sub A-21
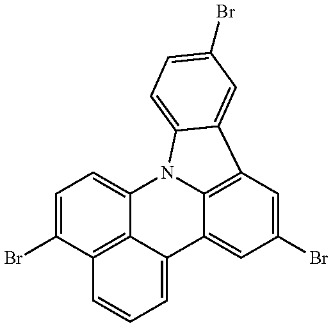
Sub A-22
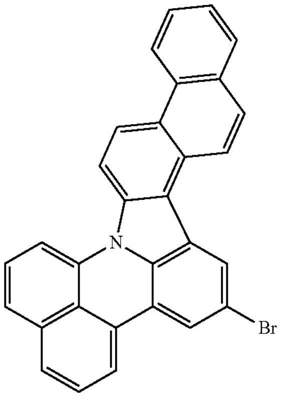
Sub A-23
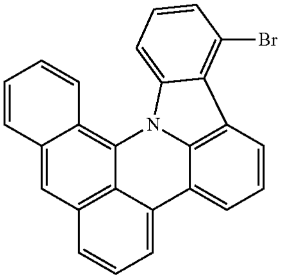
Sub A-24
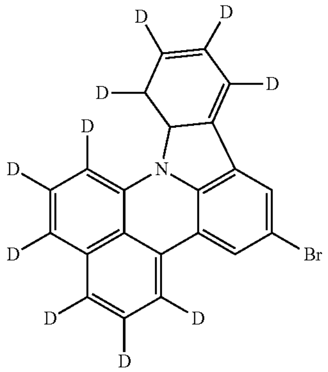
Sub A-25
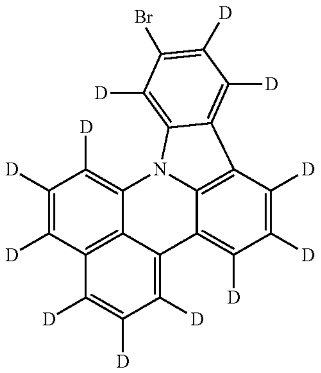

-continued
Sub A-26
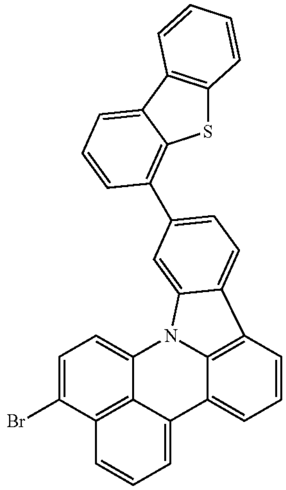
Sub A-27
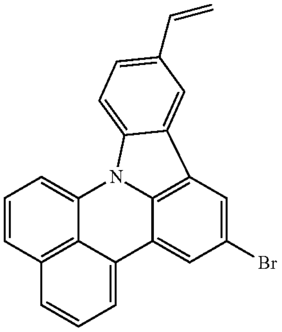
Sub A-28
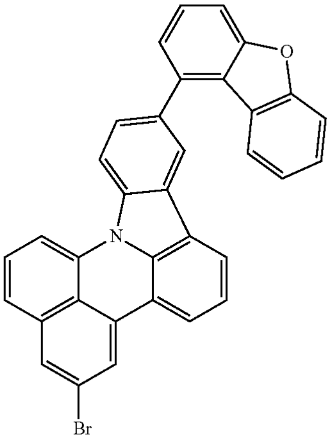
Sub A-29
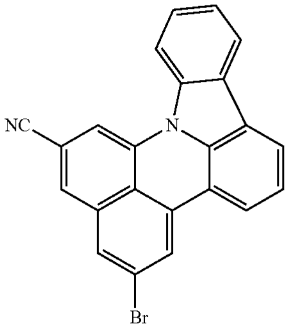
-continued
Sub A-30
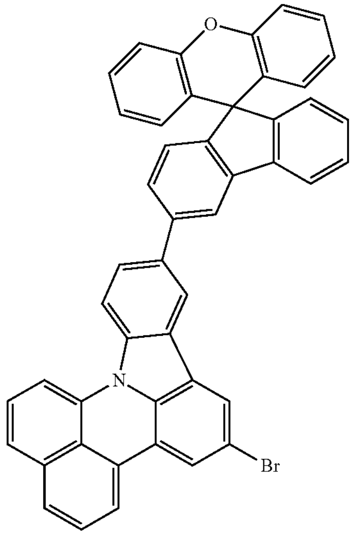
Sub A-31
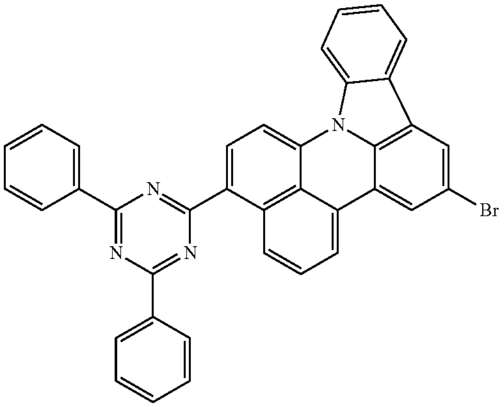
Sub A-32
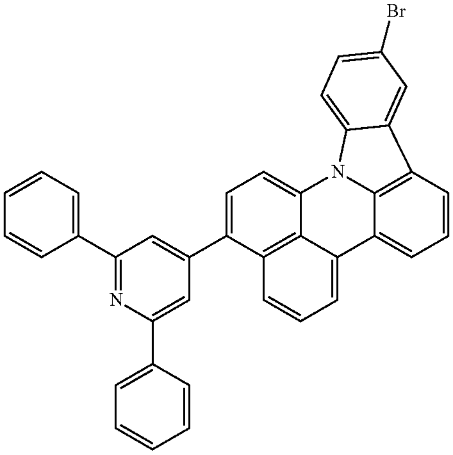

-continued
Sub A-33
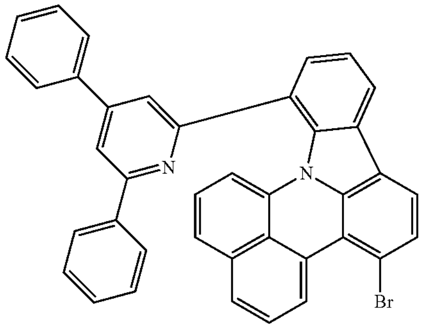
Sub A-34
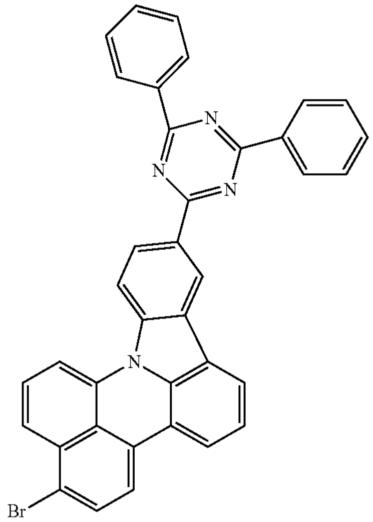
Sub A-35
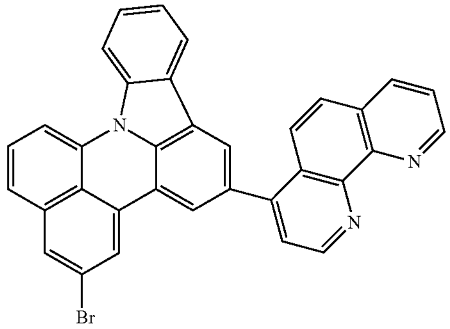
-continued
Sub A-36
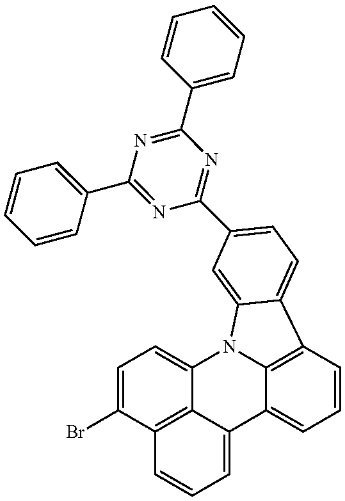
Sub A-37
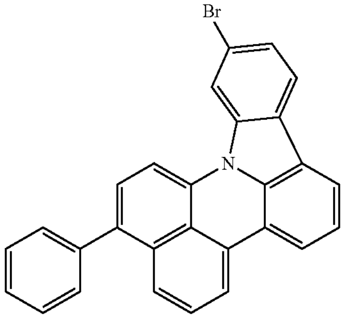
Sub A-38
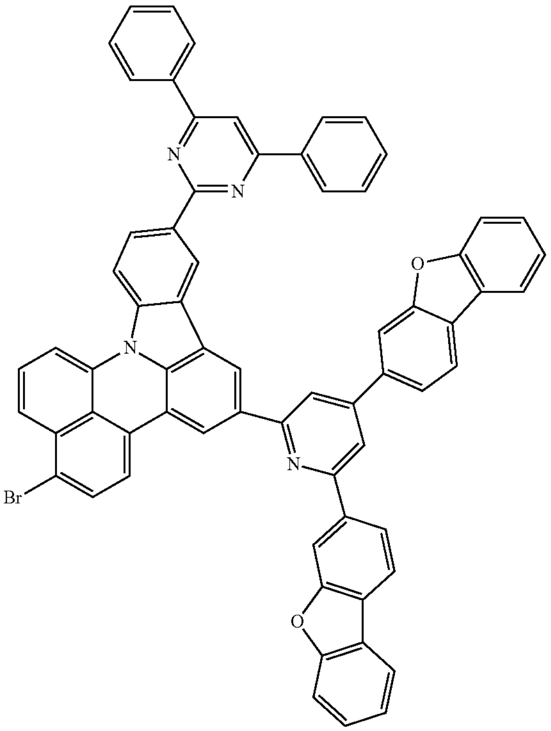

-continued
Sub A-39
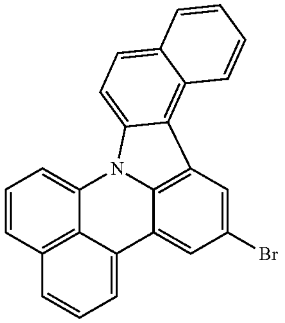
Sub A-40
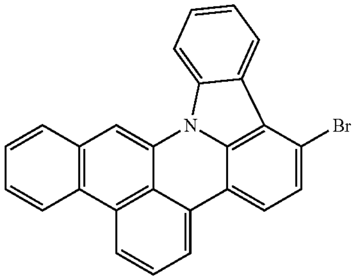
Sub A-41
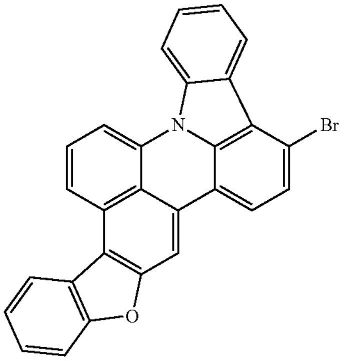
Sub A-42
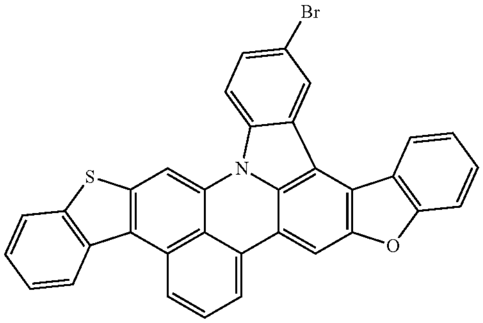
Sub A-43
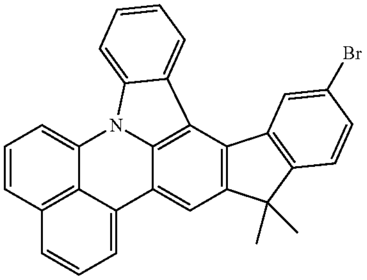
-continued
Sub A-44
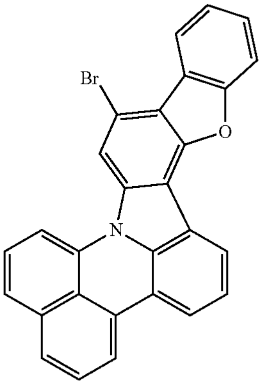
Sub A-45
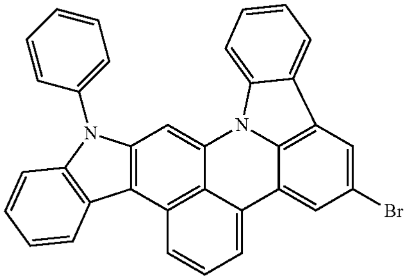
Sub A-46
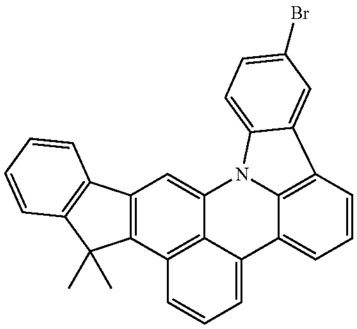
Sub A-47
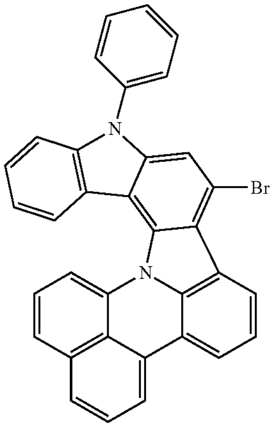

-continued
Sub A-48
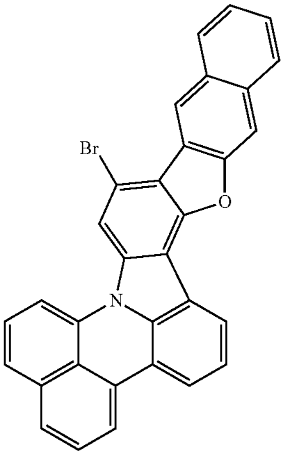
Sub A-49
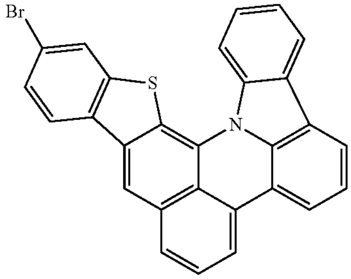
Sub A-50
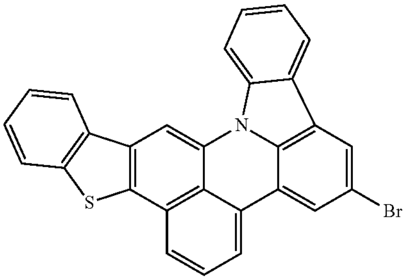
Sub A-51
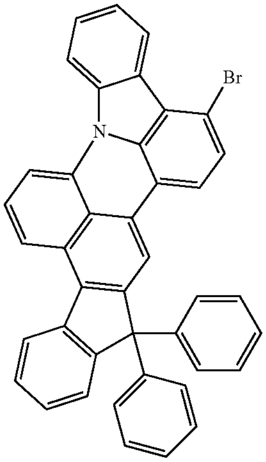
-continued
Sub A-52
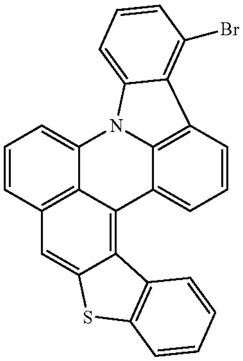
Sub A-53
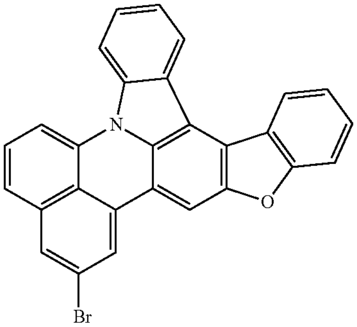
Sub A-54
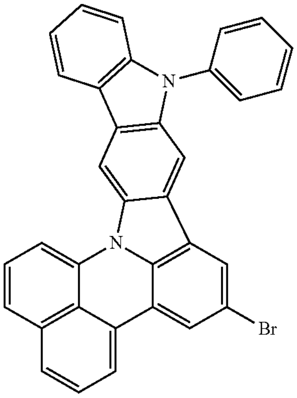
Table 1 below shows FD-MS values of compounds belonging to Sub A.
TABLE 1
| Compound | FD-MS |
|---|---|
| Sub A-1 | m/z = 369.02 ($C_{22}H_{12}BrN$ = 370.25) |
| Sub A-2 | m/z = 369.02 ($C_{22}H_{12}BrN$ = 370.25) |
| Sub A-3 | m/z = 369.02 ($C_{22}H_{12}BrN$ = 370.25) |
| Sub A-4 | m/z = 369.02 ($C_{22}H_{12}BrN$ = 370.25) |
| Sub A-5 | m/z = 369.02 ($C_{22}H_{12}BrN$ = 370.25) |
| Sub A-6 | m/z = 369.02 ($C_{22}H_{12}BrN$ = 370.25) |
| Sub A-7 | m/z = 369.02 ($C_{22}H_{12}BrN$ = 370.25) |
| Sub A-8 | m/z = 446.93 ($C_{22}H_{11}Br_2N$ = 449.15) |

TABLE 1-continued

| Compound | FD-MS |
| --- | --- |
| Sub A-9 | m/z = 446.93 ($C_{22}H_{11}Br_2N$ = 449.15) |
| Sub A-10 | m/z = 446.93 ($C_{22}H_{11}Br_2N$ = 449.15) |
| Sub A-11 | m/z = 446.93 ($C_{22}H_{11}Br_2N$ = 449.15) |
| Sub A-12 | m/z = 446.93 ($C_{22}H_{11}Br_2N$ = 449.15) |
| Sub A-13 | m/z = 524.84 ($C_{22}H_{10}Br_3N$ = 528.04) |
| Sub A-14 | m/z = 524.84 ($C_{22}H_{10}Br_3N$ = 528.04) |
| Sub A-15 | m/z = 446.93 ($C_{22}H_{11}Br_2N$ = 449.15) |
| Sub A-16 | m/z = 3 69. 02 ($C_{22}H_{12}BrN$ = 370.25) |
| Sub A-17 | m/z = 419.03 ($C_{26}H_{14}BrN$ = 420.31) |
| Sub A-18 | m/z = 419.03 ($C_{26}H_{14}BrN$ = 420.31) |
| Sub A-19 | m/z = 419.03 ($C_{26}H_{14}BrN$ = 420.31) |
| Sub A-20 | m/z = 469.05 ($C_{30}H_{16}BrN$ = 470.37) |
| Sub A-21 | m/z = 524.84 ($C_{22}H_{10}Br_3N$ = 528.04) |
| Sub A-22 | m/z = 469.05 ($C_{30}H_{16}BrN$ = 470.37) |
| Sub A-23 | m/z = 419.03 ($C_{26}H_{14}BrN$ = 420.31) |
| Sub A-24 | m/z = 381.09 ($C_{22}H_4D_{10}BrN$ = 382.33) |
| Sub A-25 | m/z = 381.09 ($C_{22}H_{12}BrN$ = 382.32) |
| Sub A-26 | m/z = 551.03 ($C_{34}H_{18}BrNS$ = 552.49) |
| Sub A-27 | m/z = 395.03 ($C_{24}H_{14}BrN$ = 396.29) |
| Sub A-28 | m/z = 535.06 ($C_{34}H_{18}BrNO$ = 536.43) |
| Sub A-29 | m/z = 394.01 ($C_{23}H_{11}BrN_2$ = 395.26) |
| Sub A-30 | m/z = 699.12 ($C_{47}H_{26}BrNO$ = 700.64) |
| Sub A-31 | m/z = 600.09 ($C_{37}H_{21}BrN_4$ = 601.51) |
| Sub A-32 | m/z = 598.1 ($C_{39}H_{23}BrN_2$ = 599.53) |
| Sub A-33 | m/z = 598.10 ($C_{39}H_{23}BrN_2$ = 599.53) |
| Sub A-34 | m/z = 600.09 ($C_{37}H_{21}BrN_4$ = 601.51) |
| Sub A-35 | m/z = 547.07 ($C_{34}H_{18}BrN_3$ = 548.44) |
| Sub A-36 | m/z = 600.09 ($C_{37}H_{21}BrN_4$ = 601.51) |
| Sub A-37 | m/z = 445.05 ($C_{28}H_{16}BrN$ = 446.35) |
| Sub A-38 | m/z = 1008.21 ($C_{67}H_{37}BrN_4O_2$ = 1009.96) |
| Sub A-39 | m/z = 4 19. 03 ($C_{26}H_{14}BrN$ = 420.31) |
| Sub A-40 | m/z = 419.03 ($C_{26}H_{14}BrN$ = 420.31) |
| Sub A-41 | m/z = 459.03 (C28H14BrNO = 460.33) |
| Sub A-42 | m/z = 565.01 (C34H16BrNOS = 566.47) |
| Sub A-43 | m/z = 485.08 (C31H20BrN = 486.41) |
| Sub A-44 | m/z = 459.03 (C28H14BrNO = 460.33) |
| Sub A-45 | m/z = 534.07 (C34H19BrN2 = 535.44) |
| Sub A-46 | m/z = 485.08 (C31H20BrN = 486.41) |
| Sub A-47 | m/z = 534.07 (C34H19BrN2 = 535.44) |
| Sub A-48 | m/z = 509.04 (C32H16BrNO = 510.39) |
| Sub A-49 | m/z = 475.00 (C28H14BrNS = 476.39) |
| Sub A-50 | m/z = 475.00 (C28H14BrNS = 476.39) |
| Sub A-51 | m/z = 609.11 (C41H24BrN = 610.55) |
| Sub A-52 | m/z = 475.00 (C28H14BrNS = 476.39) |
| Sub A-53 | m/z = 459.03 (C28H14BrNO = 460.33) |
| Sub A-54 | m/z = 534.07 (C34H19BrN2 = 535.44) |

II. Synthesis of Sub 4

Sub 4 of Reaction Scheme 1 may be synthesized by the reaction route of Reaction Scheme 3 below, but is not limited thereto. (Hal$^2$ is Br, I, or $C_1$)

<Reaction Scheme 3>

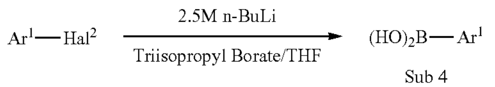

Sub 4

1. Synthesis Example of Sub 4-2

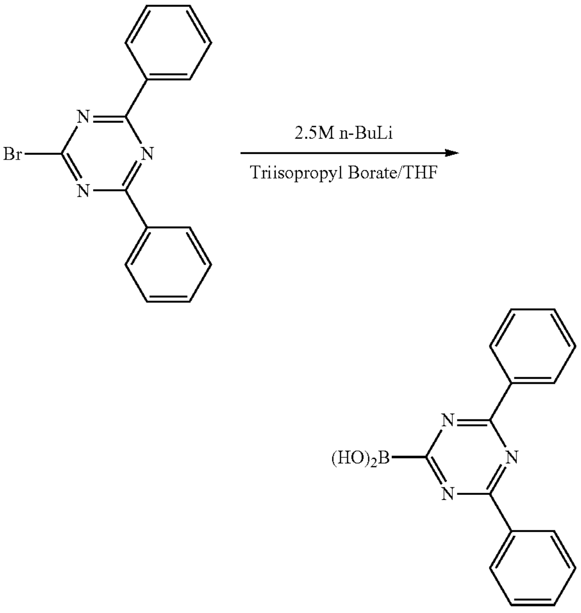

Sub 4-2

2.5M n-BuLi (162.52 mL, 406.32 mmol) and THF (1,600 mL) were added to 2-bromo-4,6-diphenyl-1,3,5-triazine (100 g, 320.33 mmol) and mixed at −78° C. for 1 hour, and triisopropyl borate (60.24 g, 320.33 mmol) was added thereto. Upon completion of the reaction, HCl was added thereto and the resultant was extracted with $CH_2Cl_2$ and water, the organic layer was dried over $MgSO_4$ and concentrated, and the resulting compound was subjected to silica gel column and recrystallization to obtain 69.23 g (yield: 78%) of a product.

2. Synthesis Example of Sub 4-25

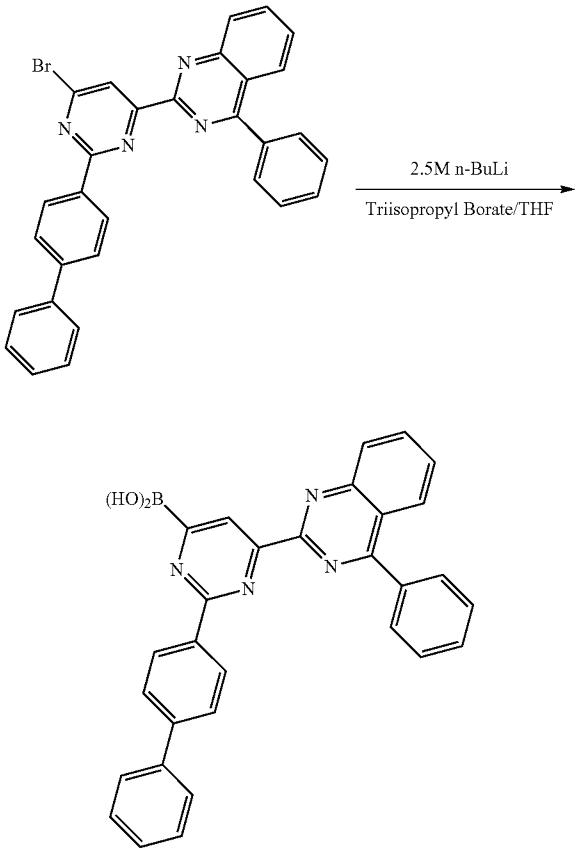

Sub 4-25

2-(2-([1,1'-biphenyl]-4-yl)-6-bromopyrimidin-4-yl)-4-phenylquinazoline (100 g, 194.02 mmol), 2.5M n-BuLi (77.60 ml, 194.02 mmol), triisopropyl borate (36.48 g, 194.02 mmol), and THF (1,000 mL) were added, and a product in the amount of 66.16 g (yield: 71%) was obtained using the synthesis method of Sub 4-2 above.

Meanwhile, the compounds belonging to Sub 4 may be those shown below, but are not limited thereto.

Sub 4-1

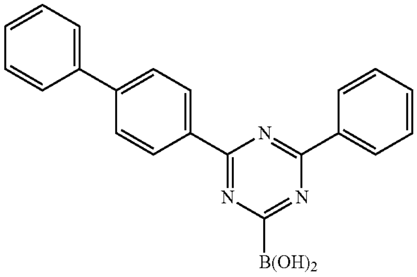

-continued

Sub 4-2

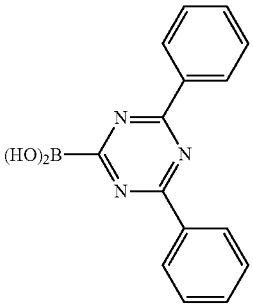

Sub 4-3

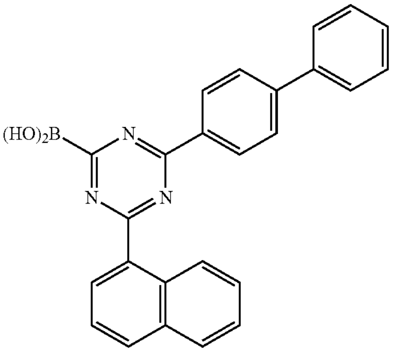

Sub 4-4

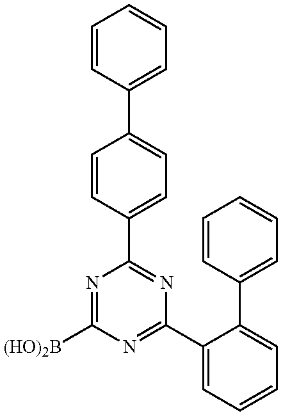

Sub 4-5

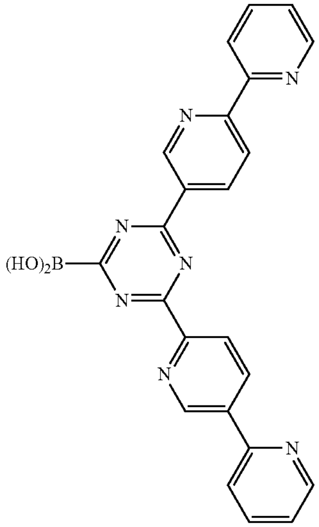

-continued
Sub 4-6
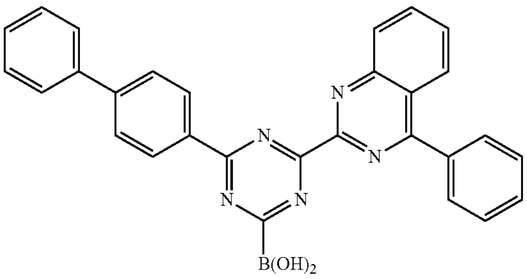
Sub 4-7
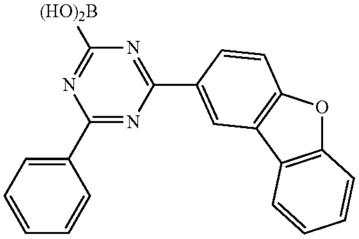
Sub 4-8
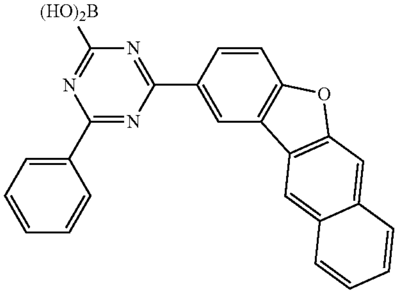
Sub 4-9
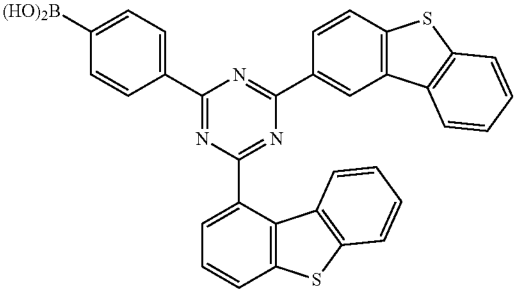
Sub 4-10
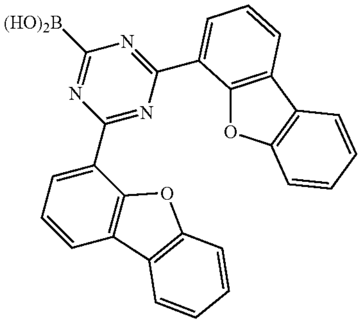
-continued
Sub 4-11
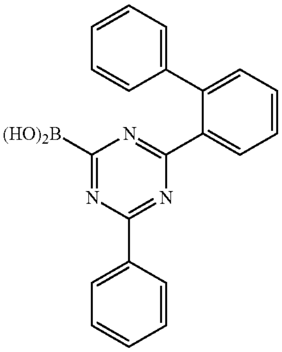
Sub 4-12
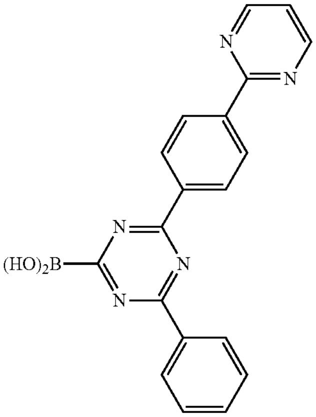
Sub 4-13
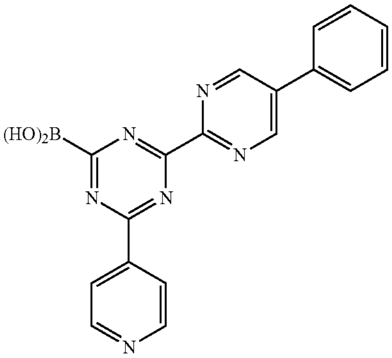
Sub 4-14
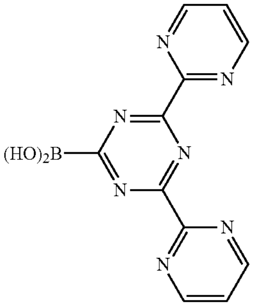

-continued
Sub 4-15
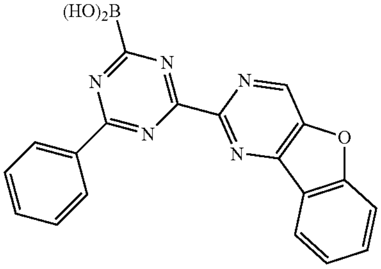
Sub 4-16
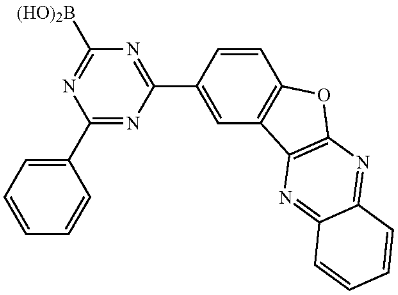
Sub 4-17
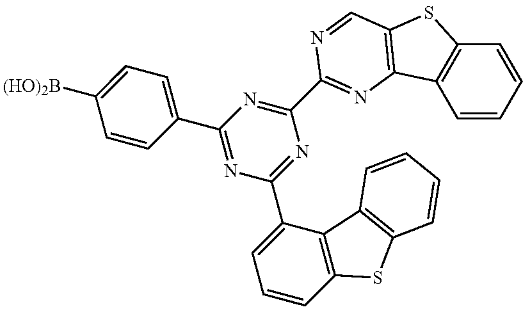
Sub 4-18
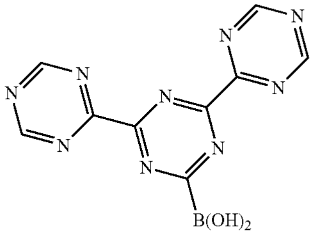
Sub 4-19
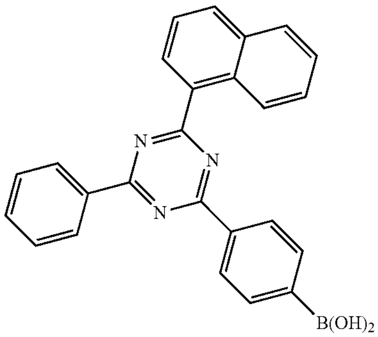
-continued
Sub 4-20
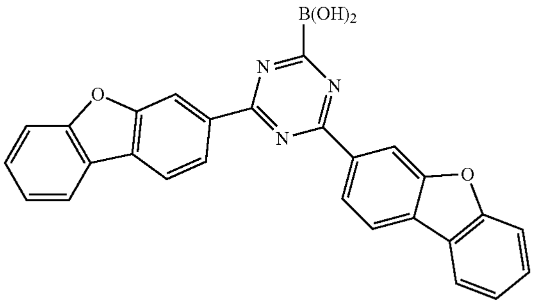
Sub 4-21
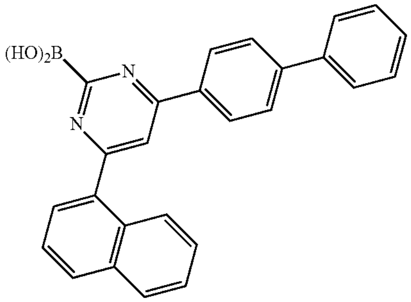
Sub 4-22
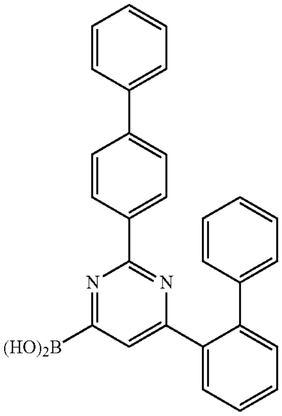
Sub 4-23
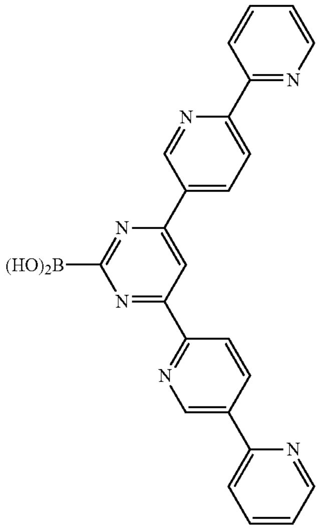

-continued
Sub 4-24
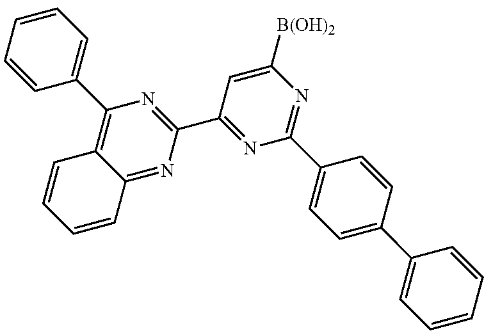
Sub 4-25
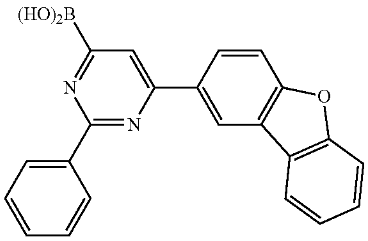
Sub 4-26
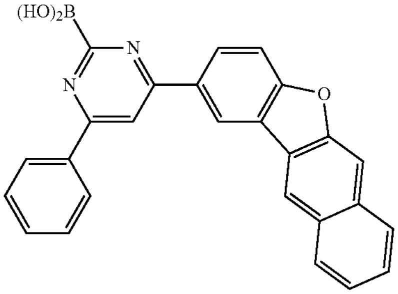
Sub 4-27
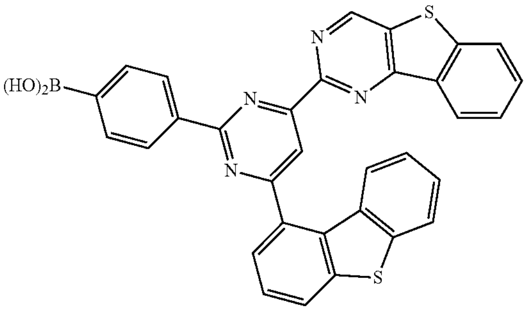
Sub 4-28
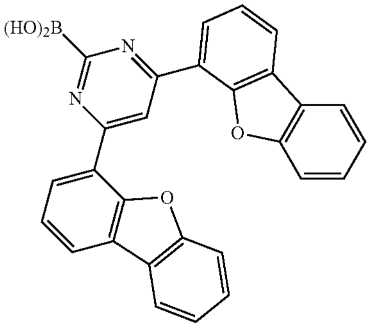
-continued
Sub 4-29
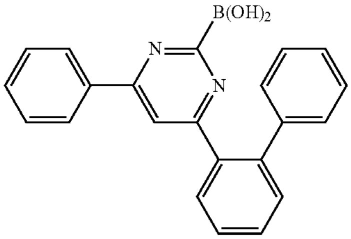
Sub 4-30
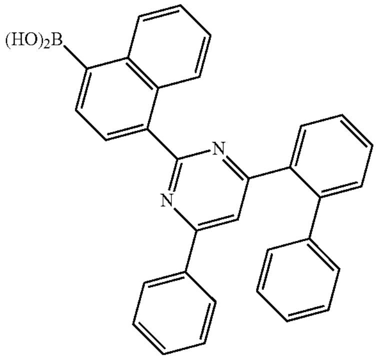
Sub 4-31
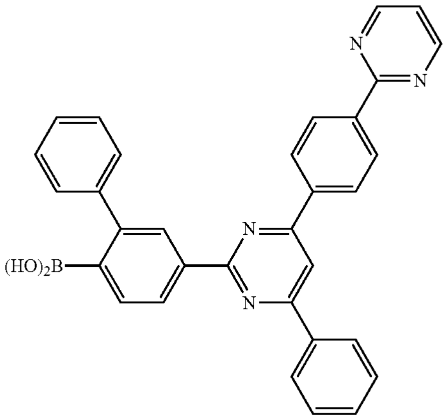
Sub 4-32
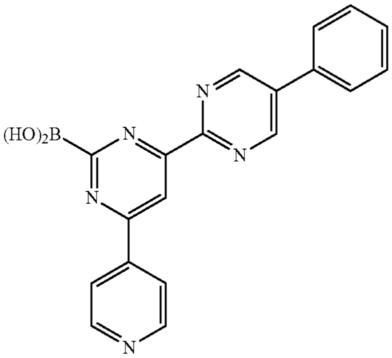

-continued
Sub 4-33
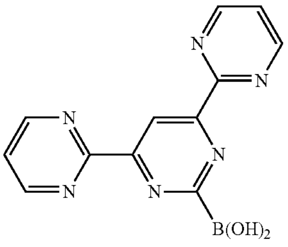
Sub 4-34
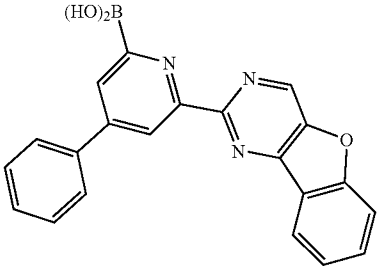
Sub 4-35
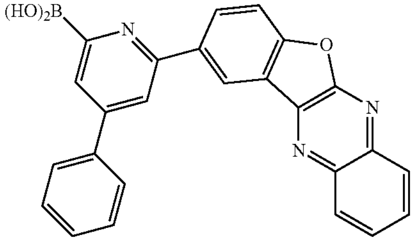
Sub 4-36
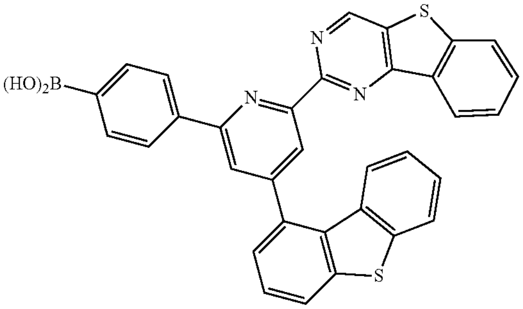
Sub 4-37
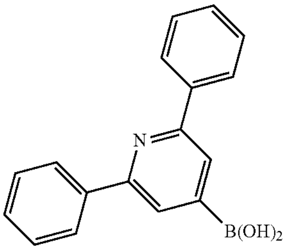
-continued
Sub 4-38
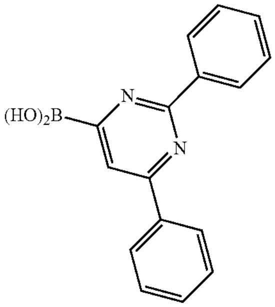
Sub 4-39
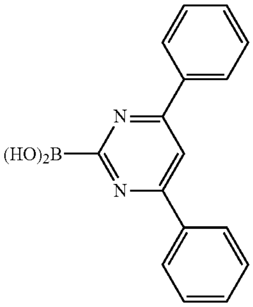
Sub 4-40
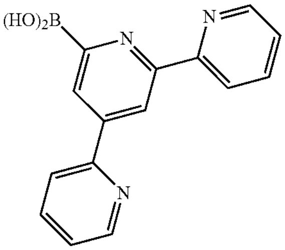
Sub 4-41
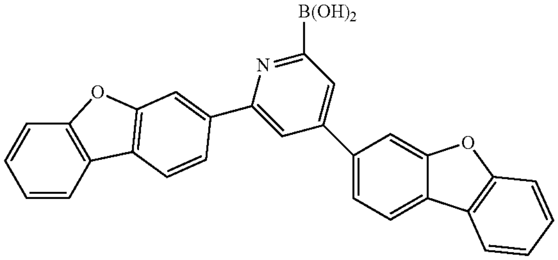
Sub 4-42
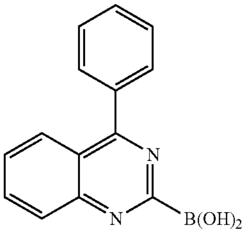

-continued
Sub 4-43
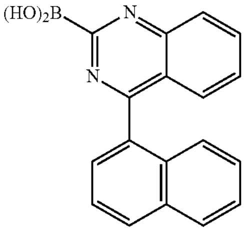
Sub 4-44
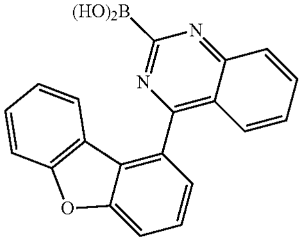
Sub 4-45
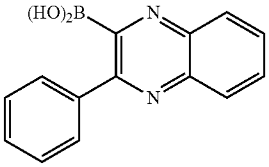
Sub 4-46
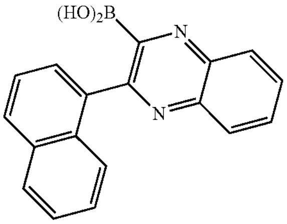
Sub 4-47
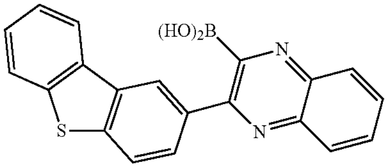
Sub 4-48
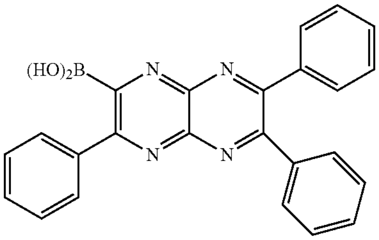
-continued
Sub 4-49
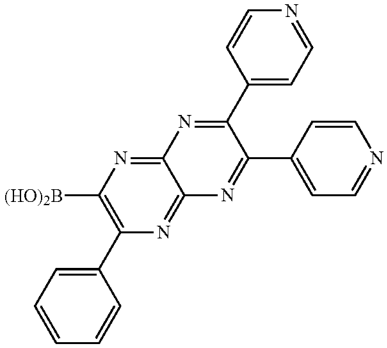
Sub 4-50
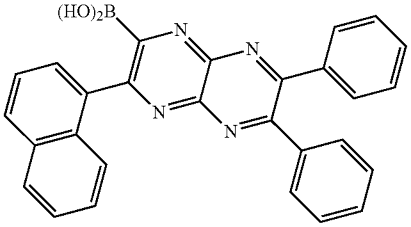
Sub 4-51
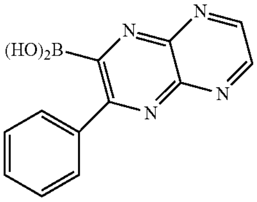
Sub 4-52
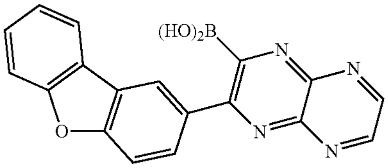
Sub 4-53
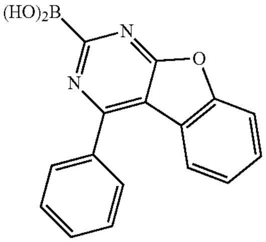
Sub 4-54
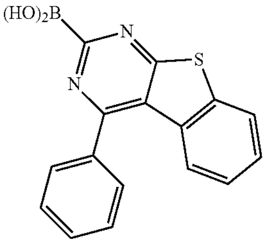
Sub 4-55
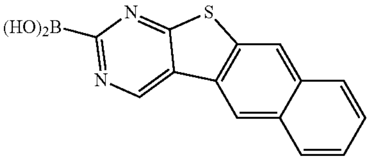

-continued
Sub 4-56
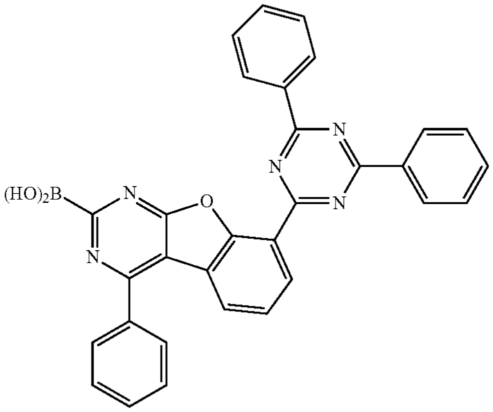
Sub 4-57
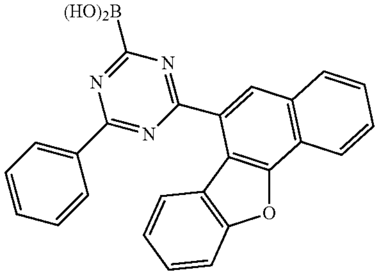
Sub 4-58
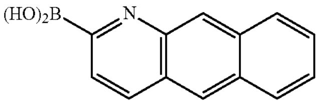
Sub 4-59
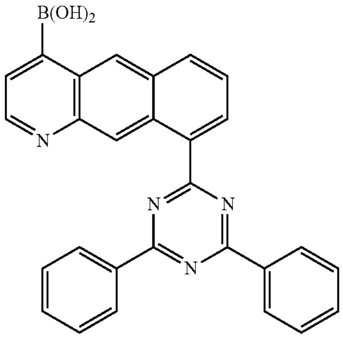
Sub 4-60
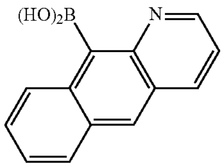
Sub 4-61
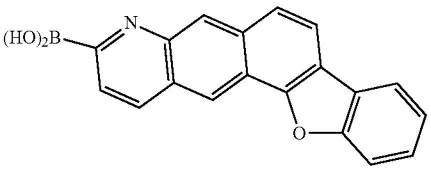
-continued
Sub 4-62
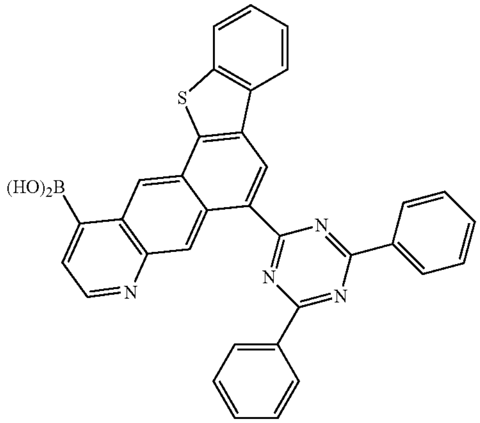
Sub 4-63
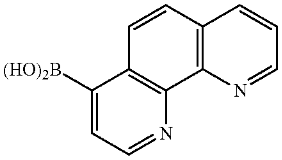
Sub 4-64
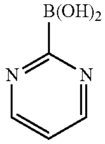
Sub 4-65
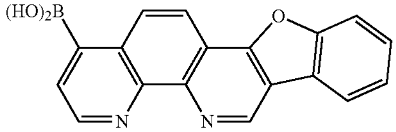
Sub 4-66
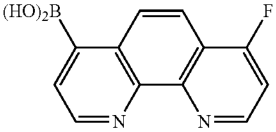
Sub 4-67
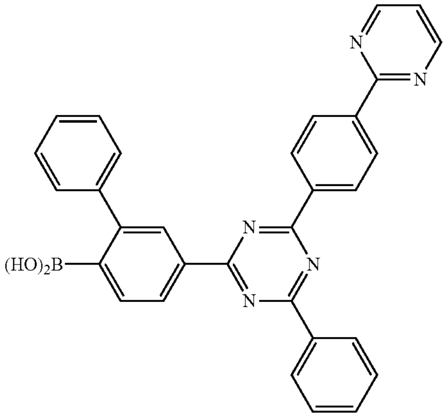

-continued
Sub 4-68
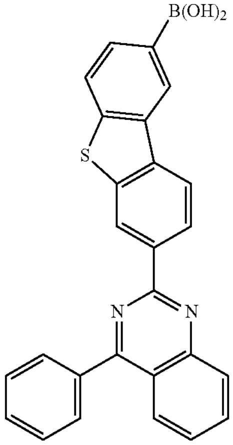
Sub 4-69
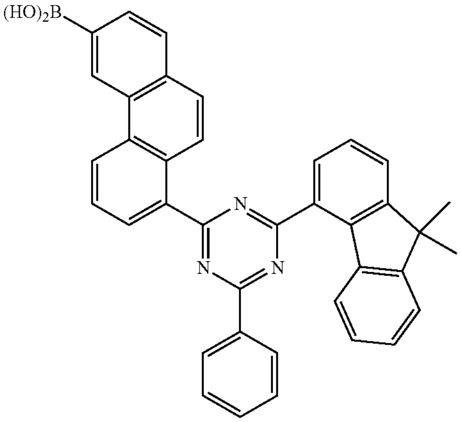
Sub 4-70
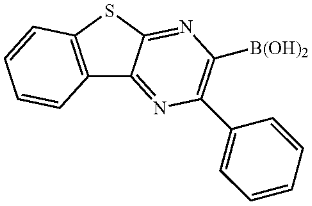
Sub 4-71
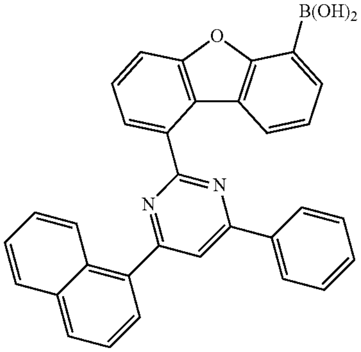
-continued
Sub 4-72
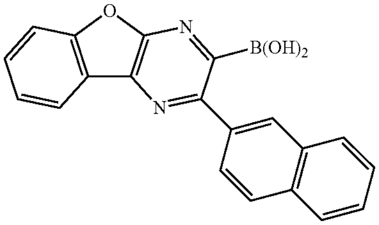
Sub 4-73
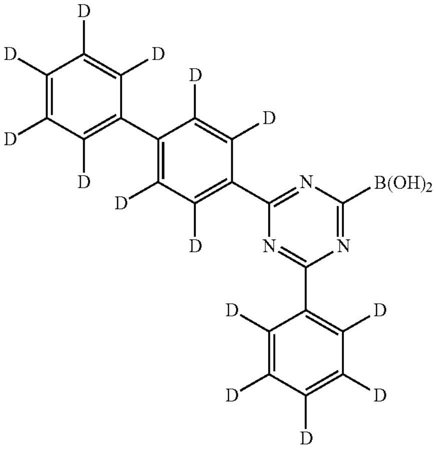
Sub 4-74
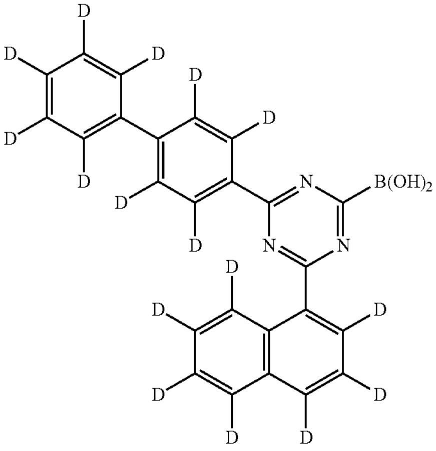
Sub 4-75
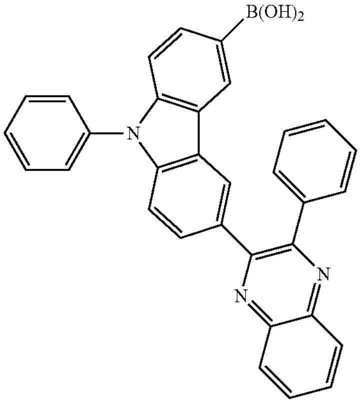

-continued
Sub 4-76
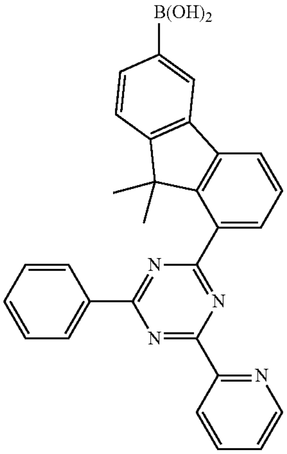
Sub 4-77
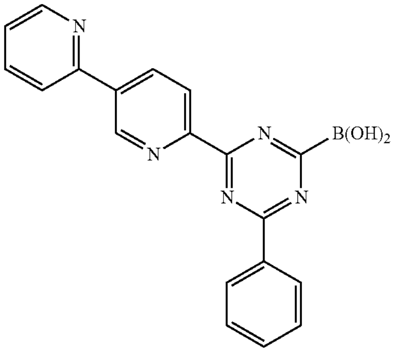
Sub 4-78
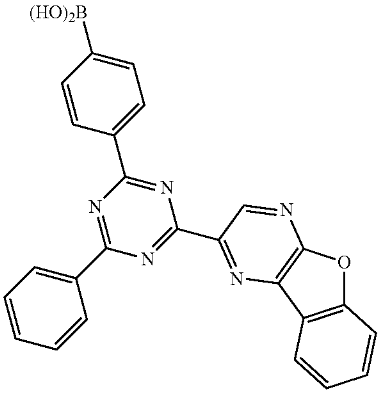
Sub 4-79
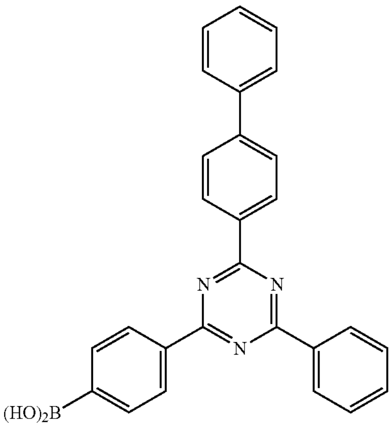
-continued
Sub 4-80
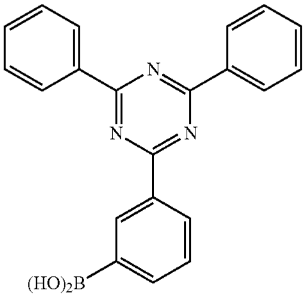
Sub 4-81
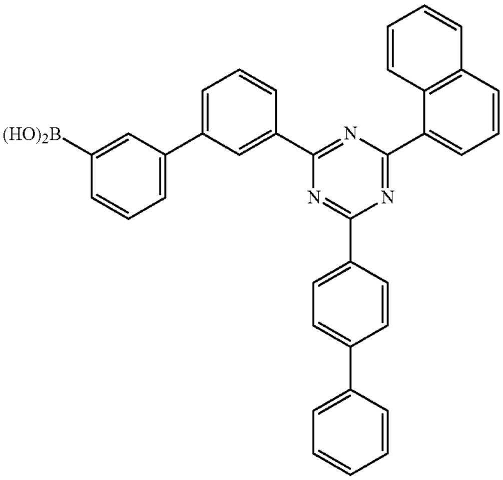
Sub 4-82
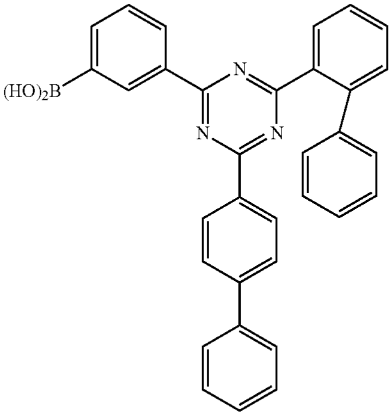
Sub 4-83
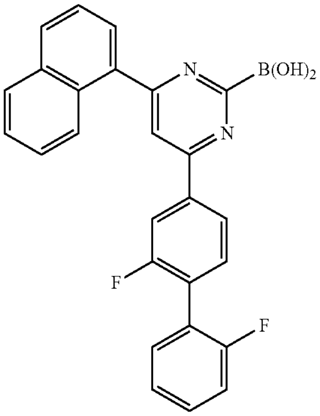

Sub 4-84
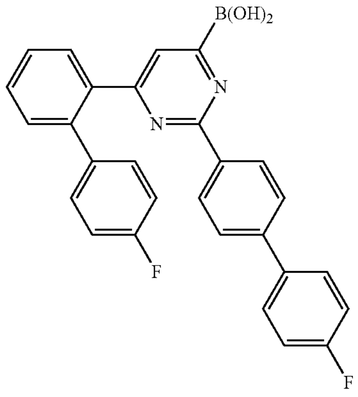
Sub 4-85
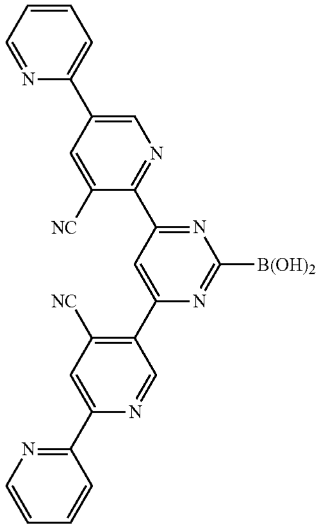
Sub 4-86
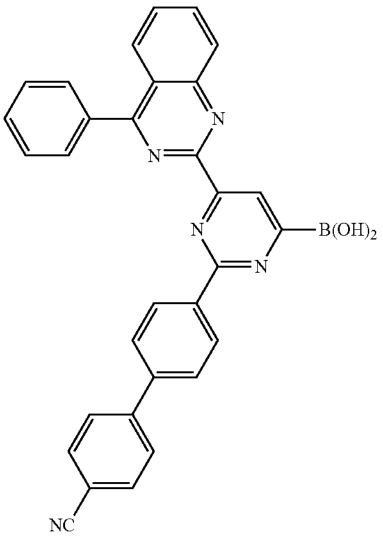
Sub 4-87
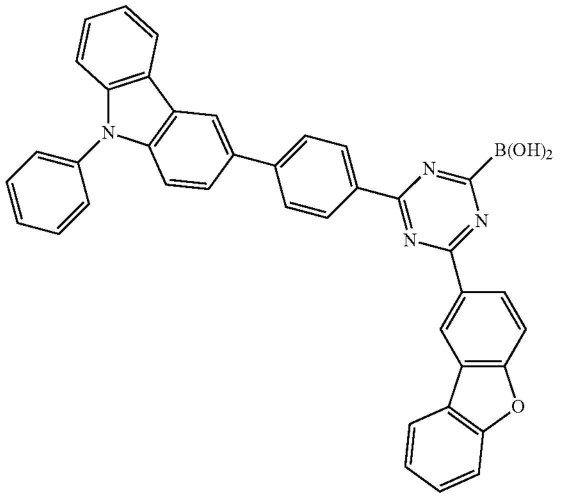
Sub 4-88
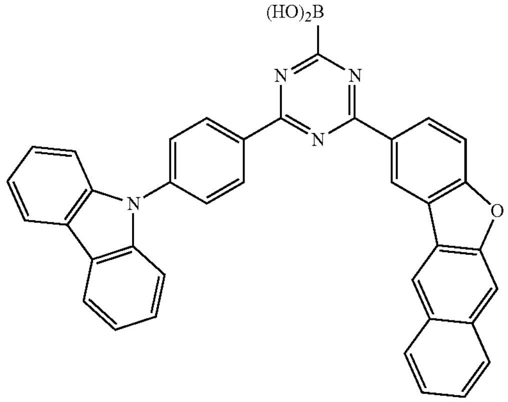
Sub 4-89
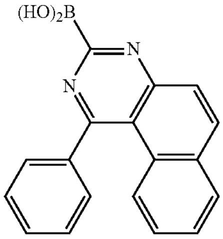
Sub 4-90
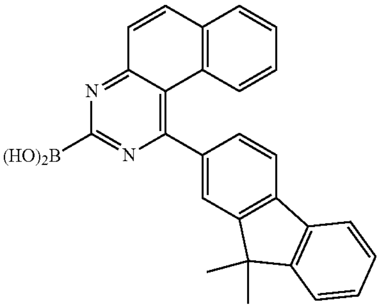

-continued

Sub 4-91

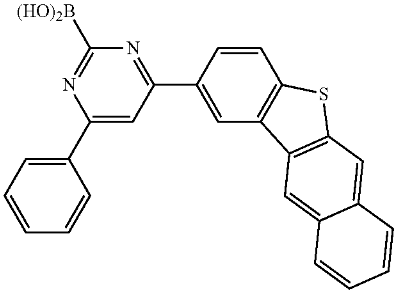

Sub 4-92

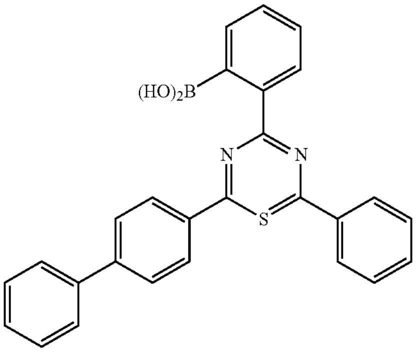

Sub 4-93

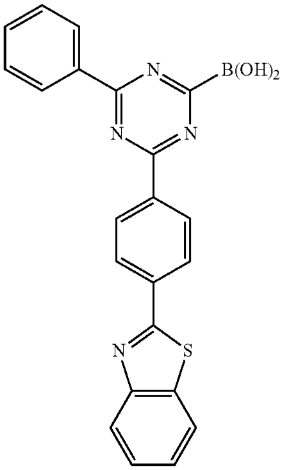

Sub 4-94

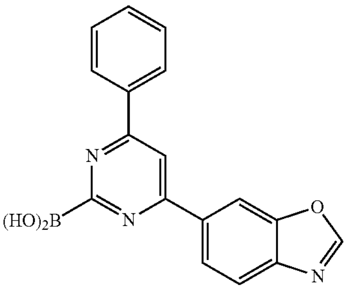

-continued

Sub 4-95

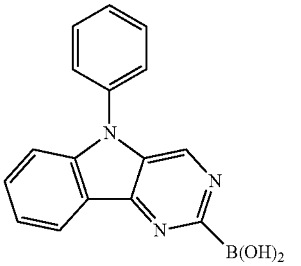

Sub 4-96

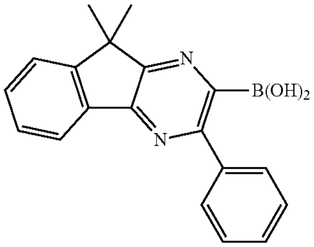

Table 2 below shows FD-MS values of compounds belonging to Sub 4.

TABLE 2

| Compound | FD-MS |
|---|---|
| Sub 4-1 | m/z = 353.13 ($C_{21}H_{16}BN_3O_2$ = 353.19) |
| Sub 4-2 | m/z = 277.10 ($C_{15}H_{12}BN_3O_2$ = 277.09) |
| Sub 4-3 | m/z = 403.15 ($C_{25}H_{18}BN_3O_2$ = 403.25) |
| Sub 4-4 | m/z = 429.16 ($C_{27}H_20BN_3O_2$ = 429.29) |
| Sub 4-5 | m/z = 433.15 ($C_{23}H_{16}BN_7O_2$ = 433.24) |
| Sub 4-6 | m/z = 481.17 ($C_{29}H_{20}BN_5O_2$ = 481.32) |
| Sub 4-7 | m/z = 367.11 ($C_{21}H_4BN_3O_3$ = 367.17) |
| Sub 4-8 | m/z = 417.13 ($C_{25}H_{16}BN_3O_3$ = 417.23) |
| Sub 4-9 | m/z = 565.11 ($C_{33}H_{20}N_3O_2S_2$ = 565.47) |
| Sub 4-10 | m/z = 457.12 ($C_{27}H_{16}BN_3O_4$ = 457.25) |
| Sub 4-11 | m/z = 353.13 ($C_{21}H_{16}BN_3O_2$ = 353.19) |
| Sub 4-12 | m/z = 355.12 ($C_{19}H_{14}BN_5O_2$ = 355.16) |
| Sub 4-13 | m/z = 356.12 ($C_{18}H_{13}BN_6O_2$ = 356.15) |
| Sub 4-14 | m/z = 281.08 ($C_{11}H_8BN_7O_2$ = 281.04) |
| Sub 4-15 | m/z = 369.10 ($C_{19}H_{12}BN_5O_3$ = 369.15) |
| Sub 4-16 | m/z = 419.12 ($C_{23}H_{14}BN_5O_3$-419.21) |
| Sub 4-17 | m/z = 567.10 ($C_{31}H_{18}BN_5O_2S_2$ = 567.45) |
| Sub 4-18 | m/z = 283.07 ($C_9H_6BN_9O_2$ = 283.02) |
| Sub 4-19 | m/z = 403.15 ($C_{25}H_{18}BN_3O_2$ = 403.25) |
| Sub 4-20 | m/z = 457.12 ($C_{27}H_{16}BN_3O_4$ = 457.25) |
| Sub 4-21 | m/z = 402.15 ($C_{26}H_{19}BN_2O_2$ = 402.26) |
| Sub 4-22 | m/z = 428.17 ($C_{28}H_{21}BN_2O_2$ = 428.30) |

TABLE 2-continued

| Compound | FD-MS |
|---|---|
| Sub 4-23 | m/z = 432.15 ($C_{24}H_{17}BN_6O_2$ = 432.25) |
| Sub 4-24 | m/z = 480.18 ($C_{30}H_{21}BN_4O_2$ = 480.33) |
| Sub 4-25 | m/z = 366.12 ($C_{22}H_{15}BN_2O_3$ = 366.18) |
| Sub 4-26 | m/z = 416.13 ($C_{26}H_{17}BN_2O3$ = 416.24) |
| Sub 4-27 | m/z = 566.10 ($C_{32}H_{19}BN_4O_2S_2$ = 566.46) |
| Sub 4-28 | m/z = 456.13 ($C_{28}H_{17}BN_2O_4$ = 456.26) |
| Sub 4-29 | m/z = 352.14 ($C_{22}H_{17}BN_2O_2$ = 352.20) |
| Sub 4-30 | m/z = 478.19 ($C_{32}H_{23}BN_2O_2$ = 478.36) |
| Sub 4-31 | m/z = 506.19 ($C_{32}H_{23}BN_4O_2$ = 506.37) |
| Sub 4-32 | m/z = 355.12 ($C_{19}H_{14}BN_5O_2$ = 355.16) |
| Sub 4-33 | m/z = 280.09 ($C_{12}H_9BN_6O_2$ = 280.05) |
| Sub 4-34 | m/z = 367.11 ($C_{21}H_{14}BN_3O_3$ = 367.17) |
| Sub 4-35 | m/z = 417.13 ($C_{25}H_{16}BN_3O_3$ = 417.23) |
| Sub 4-36 | m/z = 701.21 ($C_{50}H_{27}N_3O_2$ = 701.79) |
| Sub 4-37 | m/z = 275.11 ($C_{17}H_{14}BNO_2$ = 275.11) |
| Sub 4-38 | m/z = 276.11 ($C_{16}H_{13}BN_2O_2$ = 276.10) |
| Sub 4-39 | m/z = 276.11 ($C_{16}H_{13}BN_2O_2$ = 276.10) |
| Sub 4-40 | m/z = 277.10 ($C_{15}H_{12}BN_3O_2$ = 277.09) |
| Sub 4-41 | m/z = 455.13 ($C_{29}H_{38}BNO_4$ = 455.28) |
| Sub 4-42 | m/z = 250.09 ($C_{14}H_{11}BN_2O_2$ = 250.06) |
| Sub 4-43 | m/z = 300.11 ($C_{18}H_{13}BN_2O_2$ = 300.12) |
| Sub 4-44 | m/z = 340.10 ($C_{20}H_{13}BN_2O_3$ = 340.15) |
| Sub 4-45 | m/z = 250.09 ($C_{14}H_{11}BN_2O_2$ = 250.06) |
| Sub 4-46 | m/z = 300.11 ($C_{18}H_{13}BN_2O_2$ = 300.12) |
| Sub 4-47 | m/z = 356.08 ($C_{20}H_{13}BN_2O_2S$ = 356.21) |
| Sub 4-48 | m/z = 404.14 ($C_{24}H_{17}BN_4O_2$ = 404.24) |
| Sub 4-49 | m/z = 406.13 ($C_{22}H_{15}BN_6O_2$ = 406.21) |
| Sub 4-50 | m/z = 454.16 ($C_{28}H_{19}BN_4O_2$ = 454.30) |
| Sub 4-51 | m/z = 252.08 ($C_{12}H_9BN_4O_2$ = 252.04) |
| Sub 4-52 | m/z = 342.09 ($C_{18}H_{11}BN_4O_3$ = 342.12) |
| Sub 4-53 | m/z = 290.09 ($C_{16}H_{11}BN_2O_3$ = 290.09) |
| Sub 4-54 | m/z = 306.06 ($C_{16}H_{11}BN_2S$ = 306.15) |
| Sub 4-55 | m/z = 280.05 ($C_{14}H_9BN_2O_2S$ = 280. 11) |
| Sub 4-56 | m/z = 521.17 ($C_{31}H_{20}BN_5O_3$ = 521.34) |
| Sub 4-57 | m/z = 417.13 ($C_{25}H_{16}BN_3O_3$ = 417.23) |
| Sub 4-58 | m/z = 223.08 ($C_{13}H_{10}BNO_2$ = 223.04) |
| Sub 4-59 | m/z = 454.16 ($C_{28}H_{19}BN_4O_2$ = 454.30) |
| Sub 4-60 | m/z = 223.08 (C13H10BNO2 = 223.04) |
| Sub 4-61 | m/z = 313.09 (C19H12BNO3 = 313.12) |

TABLE 2-continued

| Compound | FD-MS |
|---|---|
| Sub 4-62 | m/z = 560.15 ($C_{34}H_{21}BN_4O_2S$ = 560.44) |
| Sub 4-63 | m/z = 224.08 ($C_{12}H_9BN_2O_2$ = 224.03) |
| Sub 4-64 | m/z = 124.04 ($C_4H_5BN_2O_2$ = 123.91) |
| Sub 4-65 | m/z = 314.09 ($C_{18}H_{11}BN_2O_3$ = 314.11) |
| Sub 4-66 | m/z = 242.07 ($C_{12}H_8BFN_2O_2$ = 242.02) |
| Sub 4-67 | m/z = 507.19 ($C_{31}H_{22}BN_5O_2$ = 507.36) |
| Sub 4-68 | m/z = 432.11 ($C_{26}H_{17}BN_2O_2S$ = 432.30) |
| Sub 4-69 | m/z = 569.23 ($C_{38}H_{28}BN_3O_2$ = 569.47) |
| Sub 4-70 | m/z = 369.10 ($C_{19}H_{12}BN_5O_3$ = 369.15) |
| Sub 4-71 | m/z = 419.12 ($C_{23}H_{14}BN_5O_3$ = 419.21) |
| Sub 4-72 | m/z = 567.10 ($C_{31}H_{18}BN_5O_2S_2$ = 567.45) |
| Sub 4-73 | m/z = 367.22 ($C_{21}H_2D_{14}BN_3O_2$ = 367.27) |
| Sub 4-74 | m/z = 419.25 ($C_{25}H_2D_{16}BN_3O_2$ = 419.35) |
| Sub 4-75 | m/z = 491.18 ($C_{32}H_{22}BN_3O_2$ = 491.36) |
| Sub 4-76 | m/z = 470.19 ($C_{29}H_{23}BN_4O_2$ = 470.34) |
| Sub 4-77 | m/z = 355.12 ($C_{19}H_{14}BN_5O_2$ = 355.1682) |
| Sub 4-78 | m/z = 445.13 ($C_{25}H_{16}BN_5O_3$ = 445.25) |
| Sub 4-79 | m/z = 429.16 ($C_{27}H_{20}BN_3O_2$ = 429.29) |
| Sub 4-80 | m/z = 353.13 ($C_{21}H_{16}BN_3O_2$ = 353.19) |
| Sub 4-81 | m/z = 555.21 ($C_{37}H_{26}BN_3O_2$ = 555.44) |
| Sub 4-82 | m/z = 505.20 ($C_{33}H_{24}BN_3O_2$ = 505.38) |
| Sub 4-83 | m/z = 438.14 ($C_{26}H_{17}BF_2N_2O_2$ = 438.24) |
| Sub 4-84 | m/z = 464.15 ($C_{28}H_{19}BF_2N_2O_2$ = 464.28) |
| Sub 4-85 | m/z = 482.14 ($C_{26}H_{15}BN_8O_2$ = 482.27) |
| Sub 4-86 | m/z = 505.17 ($C_{31}H_{20}BN_5O_2$ = 505.34) |
| Sub 4-87 | m/z = 608.20 ($C_{39}H_{25}BN_4O_3$ = 608.46) |
| Sub 4-88 | m/z = 582.19 ($C_{37}H_{23}BN_4O_3$ = 582.43) |
| Sub 4-89 | m/z = 300.11 ($C_{18}H_{13}BN_2O_2$ = 300.12) |
| Sub 4-90 | m/z = 416.17 ($C_{27}H_{21}BN_2O_2$ = 416.29) |
| Sub 4-91 | m/z = 432.11 ($C_{26}H_{17}BN_2O_2S$ = 432.30) |
| Sub 4-92 | m/z = 429.16 ($C_{27}H_{20}BN_3O_3$ = 429.29) |
| Sub 4-93 | m/z = 410.10 ($C_{22}H_{15}BN_4O_2S$ = 410.26) |
| Sub 4-94 | m/z = 317.10 ($C_{17}H_{12}BN_3O_3$ = 317.11) |
| Sub 4-95 | m/z = 289.10 ($C_{16}H_{12}BN_3O_2$ = 289.10) |
| Sub 4-96 | m/z = 316.14 ($C_{19}H_{17}BN_2O_2$ = 316.17) |

III. Synthesis of Sub 5

Sub 5 of Reaction Scheme 1 may be synthesized by the reaction route of Reaction Scheme 4 below, but is not limited thereto. (Hal is Br, I, or Cl)

<Reaction Scheme 4>

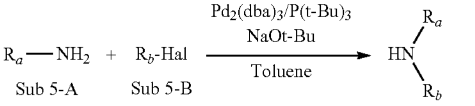

Sub 5-A Sub 5-B Sub 5

1. Synthesis Example of Sub 5-5

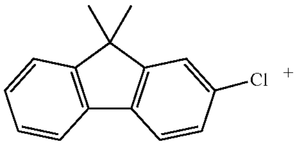

Sub 5-5a

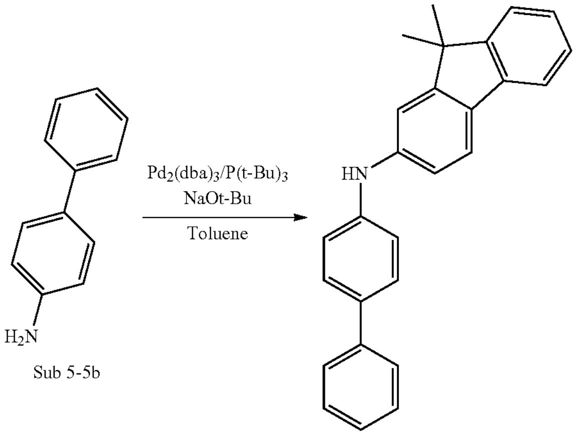

Sub 5-5b

Sub 5-5

After dissolving Sub 5-5a (50.0 g, 218.6 mmol) in toluene (1,093 mL) in a round bottom flask, Sub 5-5b (35.7 g, 218.6 mmol), $Pd_2(dba)_3$ (6.0 g, 6.6 mmol), $P(t\text{-}Bu)_3$ (2.7 g, 13.1 mmol), and NaOt-Bu (42.0 g, 437.2 mmol) were added thereto and allowed to react at 80° C. Upon completion of the reaction, the resultant was extracted with $CH_2Cl_2$ and water, the organic layer was dried over $MgSO_4$ and concentrated, and the resulting organic matter was subjected to silica gel column and recrystallization to obtain 58.2 g (yield: 73.6%) of a product.

2. Synthesis Example of Sub 5-10

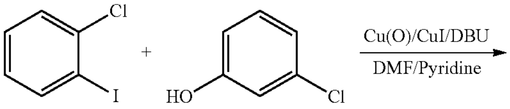

-continued

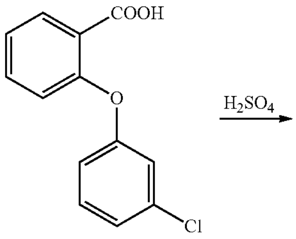

Sub 5-10a'

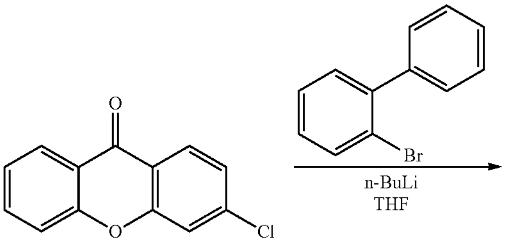

Sub 5-10a"

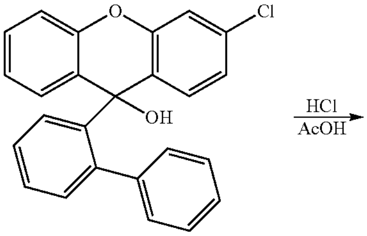

Sub 5-10aa

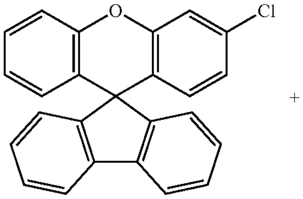

Sub 5-10a

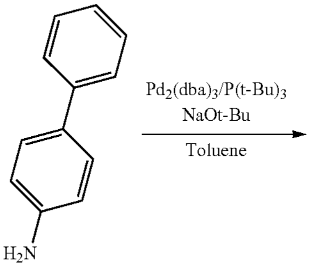

Sub 5-5b

-continued

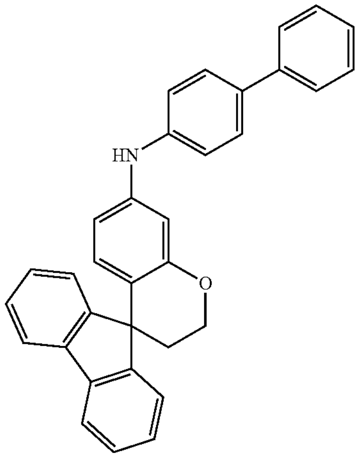

Sub 5-10

(1) Synthesis of Sub 5-10a'

2-iodobenzoic acid (30.0 g, 121.0 mmol), 3-chlorophenol (31.1 g, 241.9 mmol), 1,8-diazabicyclo[5.4.0]undec-7-ene (DBU) (55.2 g, 362.8 mmol), pyridine (1.9 mL), copper powder (1.0 g, 15.7 mmol), and CuI (1.0 g, 5.4 mmol) were added into in a round bottom flask, DMF (600 mL) was added thereto, and the mixture was refluxed for 3 hours. Upon completion of the reaction, the resultant was cooled to room temperature, and 3 M HCl was added until precipitation is completed. Thereafter, the precipitate was washed with water and dried to obtain 23.2 g (yield: 77.2%) of a product.

(2) Synthesis of Sub 5-10a"

Sub 5-10a' (23.2 g, 93.3 mmol) obtained in the above synthesis was added into a round-bottom flask, $H_2SO_4$ (700 mL) was added thereto, and the mixture was refluxed until all the starting materials were dissolved. When all the starting materials are dissolved, the resultant is cooled to room temperature, and precipitated by adding ice water.

(3) Synthesis of Sub 5-10aa 2-bromo-1,1'-biphenyl (15.0 g, 64.2 mmol) was dissolved in THF (107 mL) in a round-bottom flask under a nitrogen atmosphere and then cooled to −78° C. Then, n-BuLi (26 mL) was slowly titrated, and the mixture was stirred for 30 minutes. Subsequently, the Sub 5-10a" (14.8 g, 64.2 mmol) obtained in the above synthesis was dissolved in THF (107 mL), and the resultant was slowly titrated in the reacting round-bottom flask. The resultant was stirred for an additional 1 hour at −78° C., and the temperature was gradually raised to room temperature. Upon completion of the reaction, the resultant was extracted with ethyl acetate and water, the organic layer was dried over $MgSO_4$ and concentrated, and the resulting compound was subjected to silica gel column and recrystallization to obtain 20.1 g (yield: 81.2%) of a product.

(4) Synthesis of Sub 5-10a

Sub 5-10aa (20.1 g, 52.1 mmol) obtained in the synthesis, acetic acid (130 mL), and HCl (21 mL) were added into a round-bottom flask, and then stirred at 60° C. to 80° C. under a nitrogen atmosphere for 3 hours. Upon completion of the reaction, the resultant was extracted with $CH_2Cl_2$ and water, the organic layer was dried over $MgSO_4$ and concentrated, and the resulting organic matter was subjected to silica gel column and recrystallization to obtain 17.2 g (yield: 89.9%) of a product.

(5) Synthesis of Sub 5-10

Sub 5-10a (17.2 g, 46.9 mmol) obtained in the synthesis was added into toluene (234 mL), and Sub 5-5b (7.7 g, 46.9 mmol), $Pd_2(dba)_3$ (1.3 g, 1.4 mmol), $P(t\text{-}Bu)_3$ (0.6 g, 2.8 mmol), and NaOt-Bu (9.0 g, 93.8 mmol) were added thereto, and 18.2 g (yield: 77.6%) of a product was obtained in the same manner as in Sub 5-5.

Meanwhile, the compounds belonging to Sub 5 may be those shown below, but are not limited thereto.

Sub 5-1

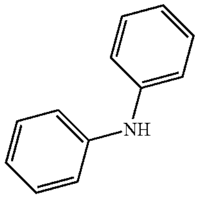

Sub 5-2

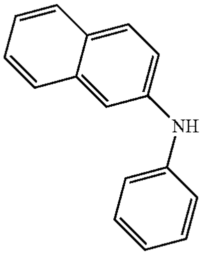

Sub 5-3

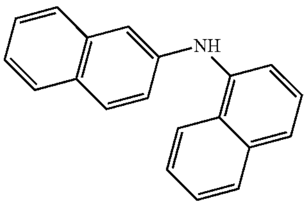

Sub 5-4

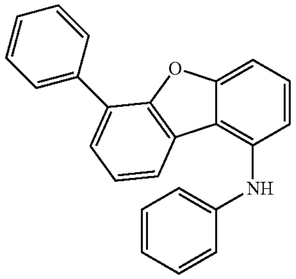

Sub 5-5

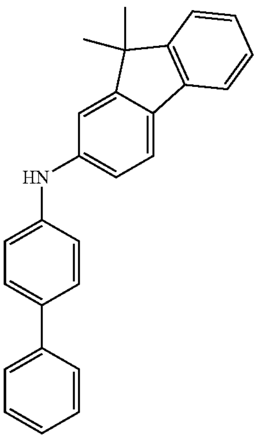

-continued
Sub 5-6
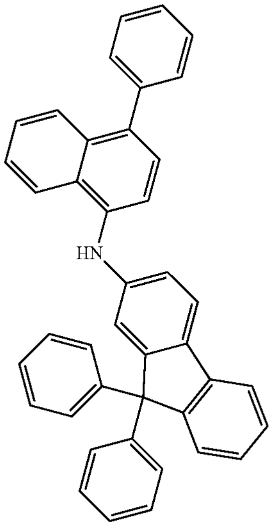
Sub 5-7
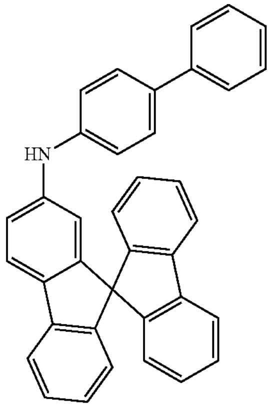
Sub 5-8
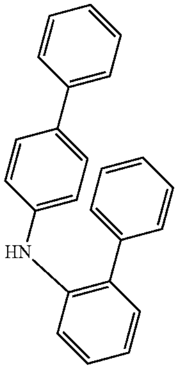
-continued
Sub 5-9
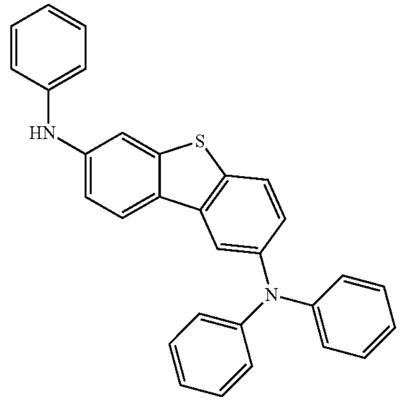
Sub 5-10
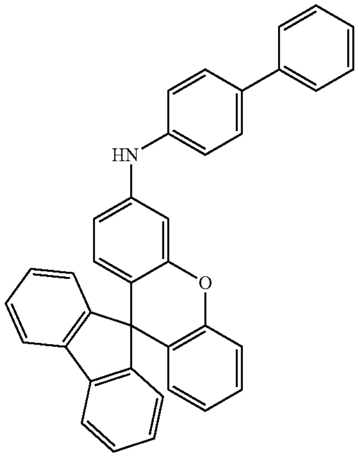
Sub 5-11
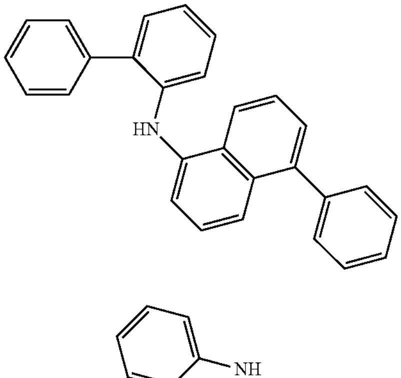
Sub 5-12
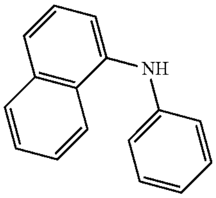

-continued
Sub 5-13
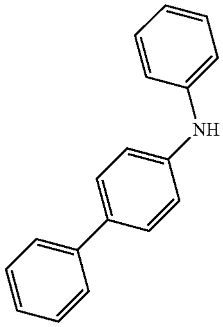
Sub 5-14
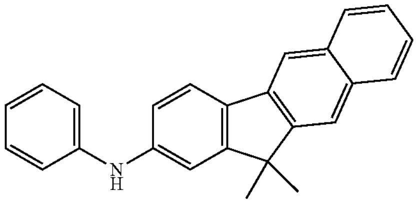
Sub 5-15
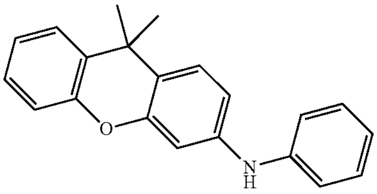
Sub 5-16
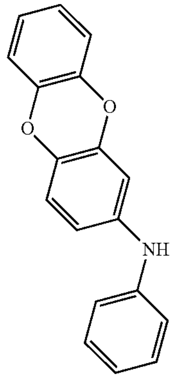
Sub 5-17
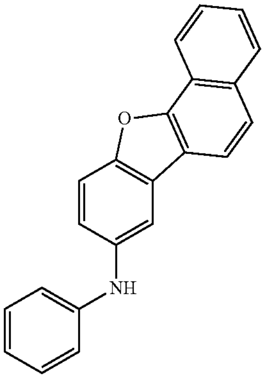
-continued
Sub 5-18
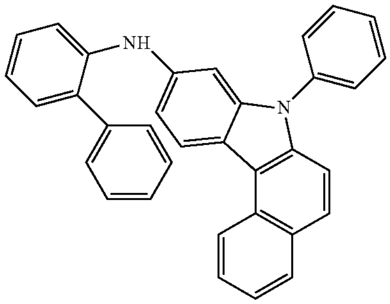
Sub 5-19
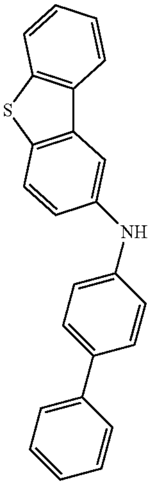
Sub 5-20
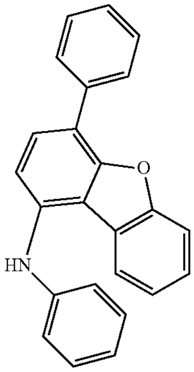
Sub 5-21
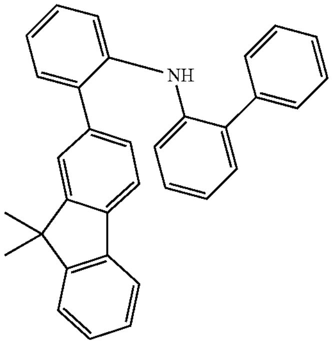

-continued
Sub 5-22
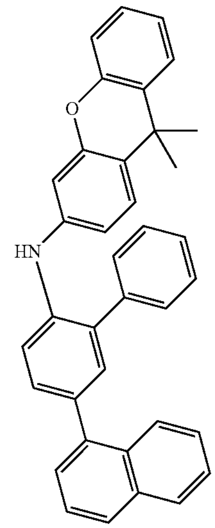
Sub 5-23
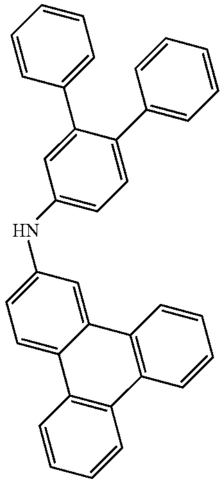
Sub 5-24
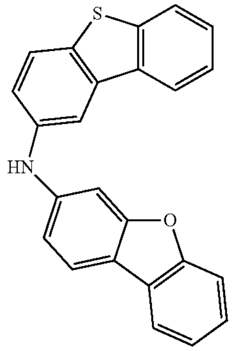
-continued
Sub 5-25
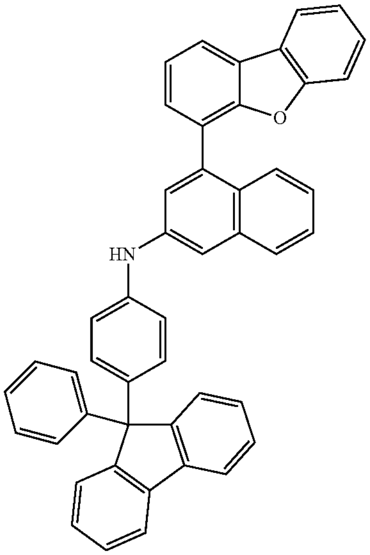
Sub 5-26
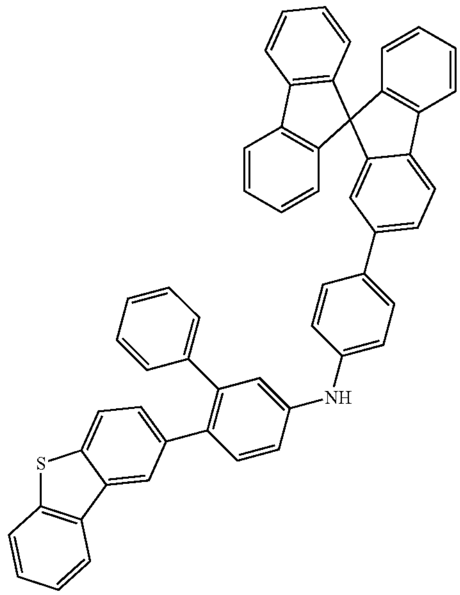
Sub 5-27
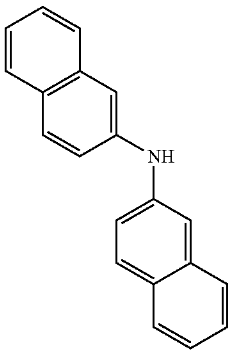

-continued
Sub 5-28
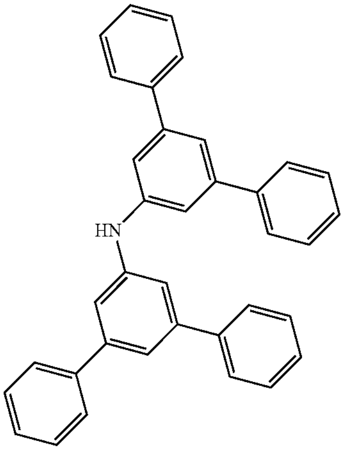
Sub 5-29
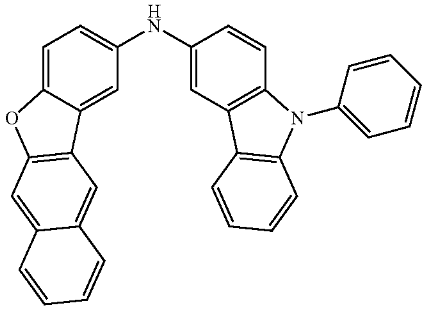
Sub 5-30
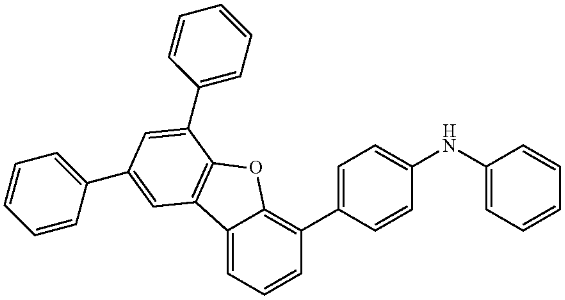
Sub 5-31
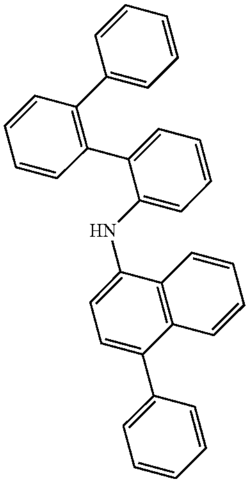
-continued
Sub 5-32
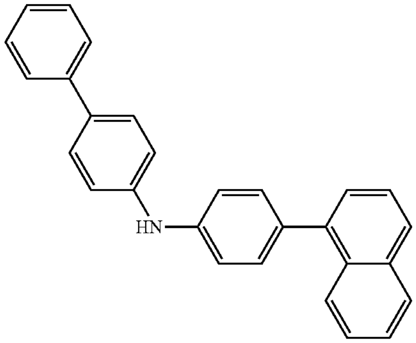
Sub 5-33
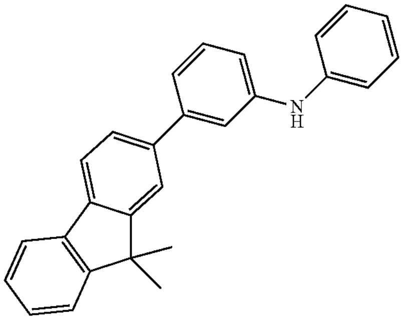
Sub 5-34
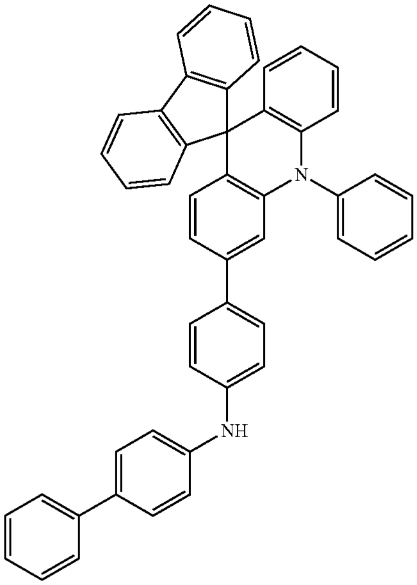

-continued
Sub 5-35
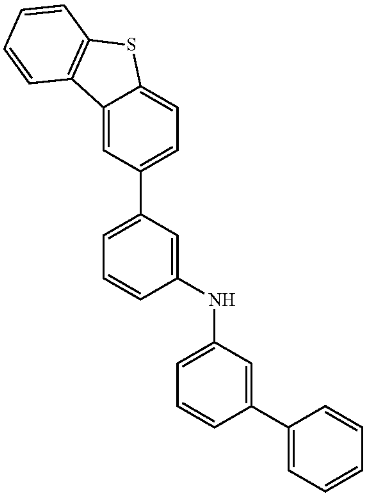
Sub 5-36
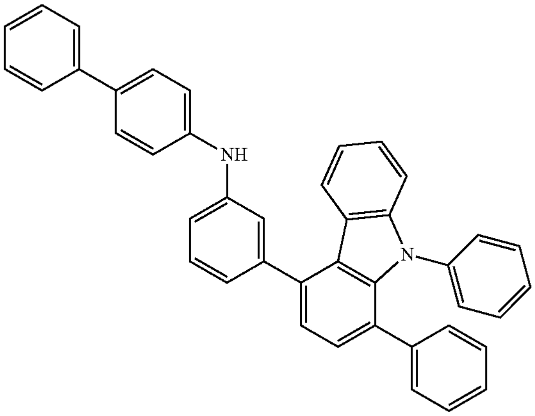
Sub 5-37
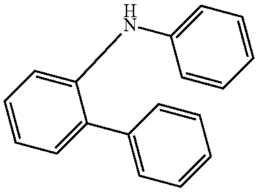
Sub 5-38
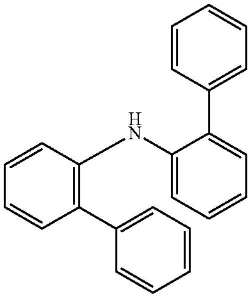
-continued
Sub 5-39
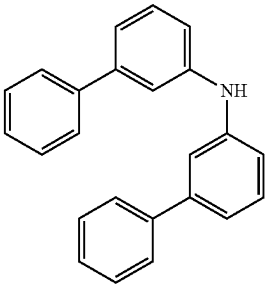
Sub 5-40
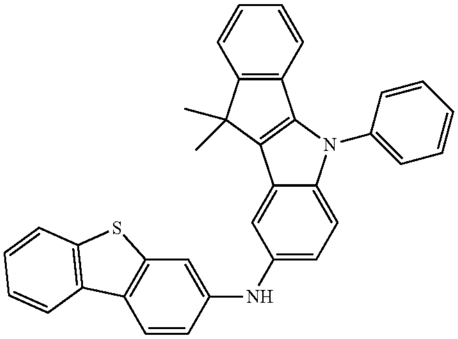
Sub 5-41
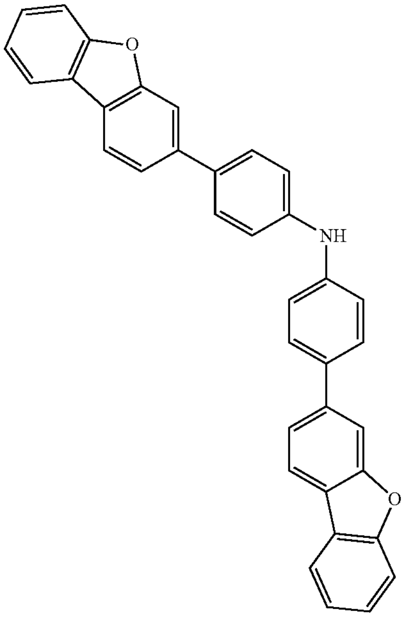
Sub 5-42
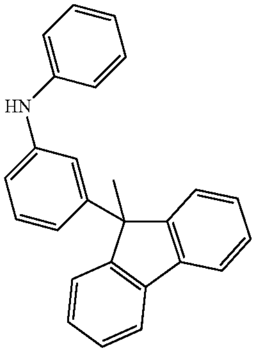

-continued
Sub 5-43
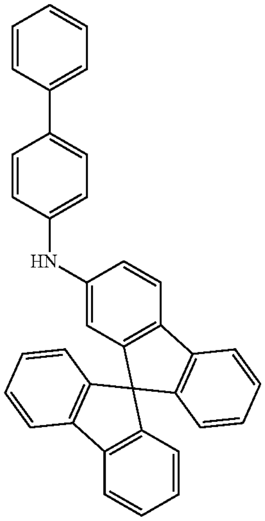
Sub 5-44
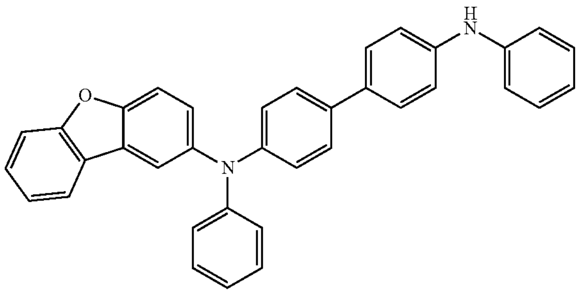
Sub 5-45
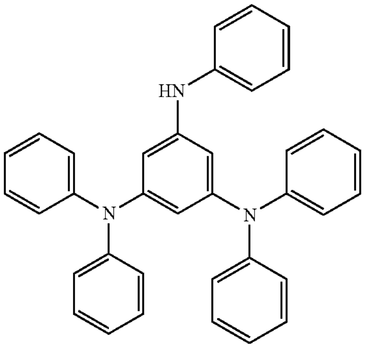
Sub 5-46
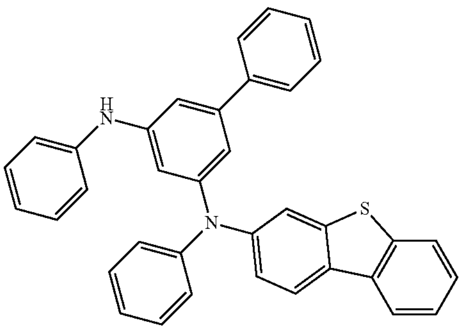
-continued
Sub 5-47
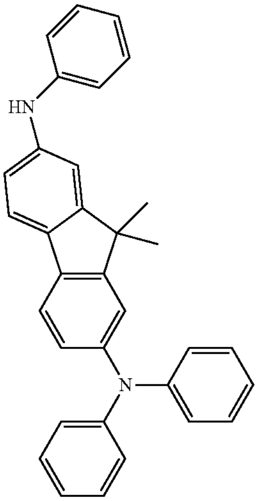
Sub 5-48
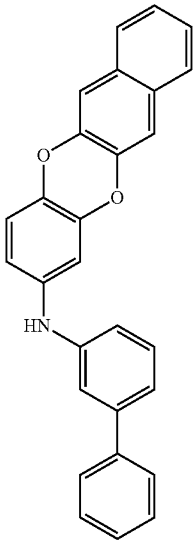
Sub 5-49
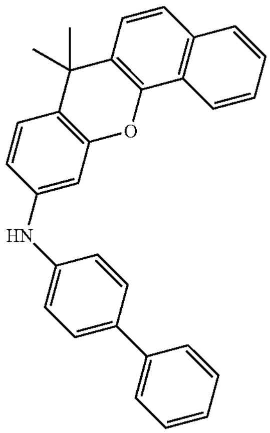

-continued
Sub 5-50
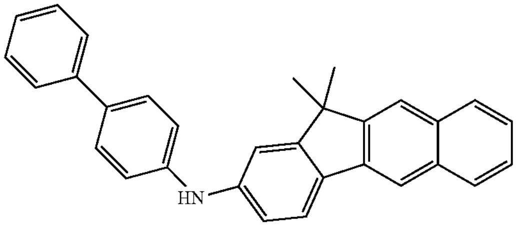
Sub 5-51
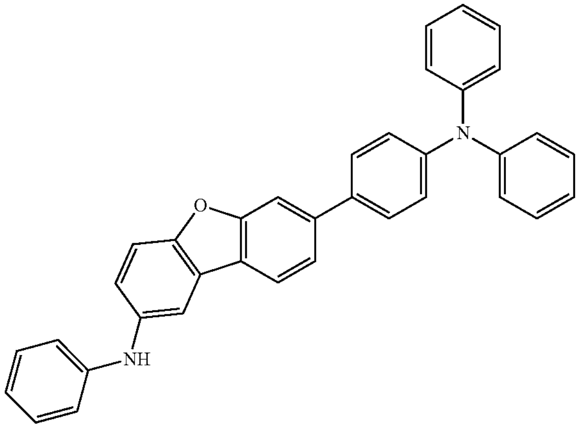
Sub 5-52
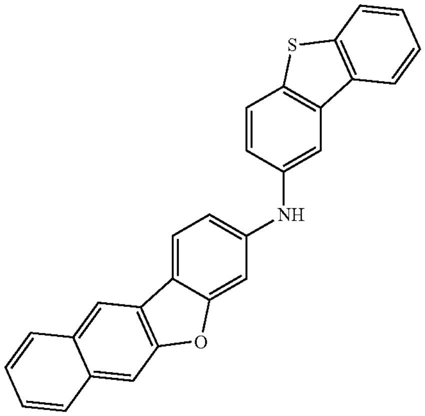
Sub 5-53
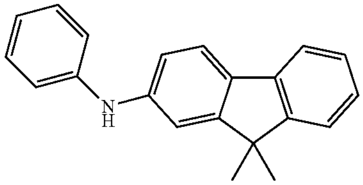
Sub 5-54
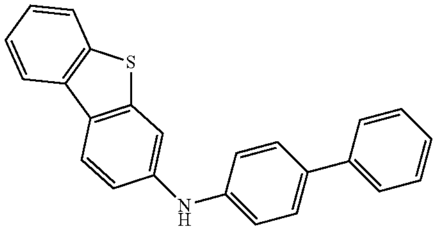
-continued
Sub 5-55
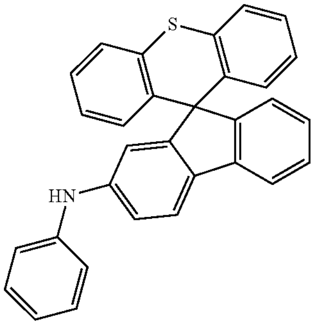
Sub 5-56
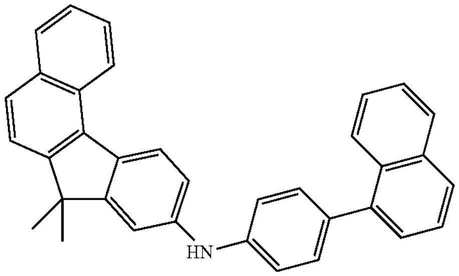
Sub 5-57
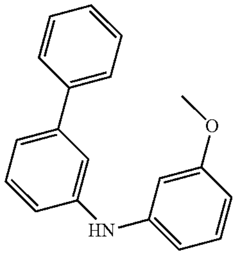
Sub 5-58
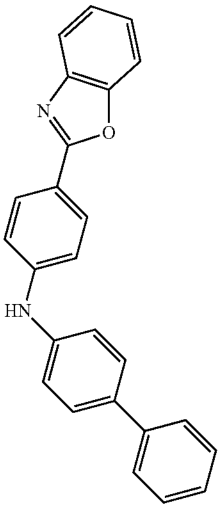

-continued

Sub 5-59

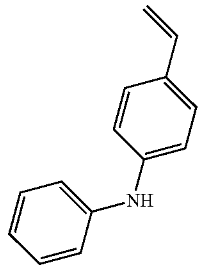

Sub 5-60

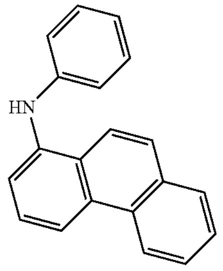

Sub 5-61

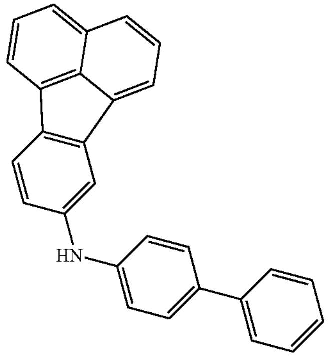

Sub 5-62

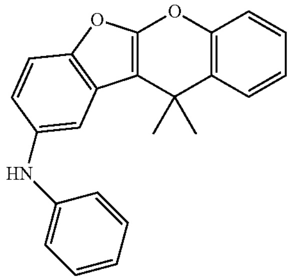

Table 3 below shows FD-MS values of compounds belonging to Sub 5.

TABLE 3

| Compound | FD-MS |
|---|---|
| Sub 5-1 | m/z = 169.09 ($C_{12}H_{11}N$ = 169.23) |
| Sub 5-2 | m/z = 219.10 ($C_{16}H_{13}N$ = 219.29) |
| Sub 5-3 | m/z = 269.12 ($C_{20}H_{15}N$ = 269.35) |
| Sub 5-4 | m/z = 335.13 ($C_{24}H_{17}NO$ = 335.41) |
| Sub 5-5 | m/z = 361.18 ($C_{27}H_{23}N$ = 361.49) |
| Sub 5-6 | m/z = 535.23 ($C_{41}H_{29}N$ = 535.69) |
| Sub 5-7 | m/z = 483.20 ($C_{37}H_{25}N$ = 483.61) |
| Sub 5-8 | m/z = 321.15 ($C_{24}H_{19}N$ = 321.42) |
| Sub 5-9 | m/z = 442.15 ($C_{30}H_{22}N_2S$ = 442.58) |
| Sub 5-10 | m/z = 499.19 ($C_{37}H_{25}NO$ = 499.61) |
| Sub 5-11 | m/z = 371.17 ($C_{28}H_{21}N$ = 371.48) |
| Sub 5-12 | m/z = 219.10 ($C_{16}H_{13}N$ = 219.29) |
| Sub 5-13 | m/z = 245.12 ($C_{18}H_{15}N$ = 245.33) |
| Sub 5-14 | m/z = 335.17 ($C_{25}H_{21}N$ = 335.45) |
| Sub 5-15 | m/z = 301.15 ($C_{21}H_{19}NO$ = 301.39) |
| Sub 5-16 | m/z = 275.09 ($C_{18}H_{13}NO_2$ = 275.31) |
| Sub 5-17 | m/z = 309.12 ($C_{22}H_{15}NO$ = 309.37) |
| Sub 5-18 | m/z = 460.19 ($C_{34}H_{24}N_2$ = 460.58) |
| Sub 5-19 | m/z = 351.11 ($C_{24}H_{17}NS$ = 351.47) |
| Sub 5-20 | m/z = 335.13 ($C_{24}H_{17}NO$ = 335.41) |
| Sub 5-21 | m/z = 437.21 ($C_{33}H_{27}N$ = 437.59) |
| Sub 5-22 | m/z = 503.22 ($C_{37}H_{29}NO$ = 503.65) |
| Sub 5-23 | m/z = 471.20 ($C_{36}H_{25}N$ = 471.60) |
| Sub 5-24 | m/z = 365.09 ($C_{24}H_{15}NOS$ = 365.45) |
| Sub 5-25 | m/z = 625.24 ($C_{47}H_{31}NO$ = 625.77) |
| Sub 5-26 | m/z = 741.25 ($C_{55}H_{35}NS$ = 741.95) |
| Sub 5-27 | m/z = 269.12 ($C_{20}H_{15}N$ = 269.35) |
| Sub 5-28 | m/z = 473.21 ($C_{36}H_{27}N$ = 473.62) |
| Sub 5-29 | m/z = 474.17 ($C_{34}H_{22}N_2O$ = 474.56) |
| Sub 5-30 | m/z = 487.19 ($C_{36}H_{25}NO$ = 487.60) |
| Sub 5-31 | m/z = 447.20 ($C_{34}H_{25}N$ = 447.58) |
| Sub 5-32 | m/z = 371.17 ($C_{28}H_{21}N$ = 371.48) |
| Sub 5-33 | m/z = 361.18 ($C_{27}H_{23}N$ = 361.49) |
| Sub 5-34 | m/z = 650.27 ($C_{49}H_{34}N_2$ = 650.83) |
| Sub 5-35 | m/z = 427.14 ($C_{30}H_{21}NS$ = 427.57) |
| Sub 5-36 | m/z = 562.24 ($C_{42}H_{30}N_2$ = 562.72) |
| Sub 5-37 | m/z = 245.12 ($C_{18}H_{15}N$ = 245.33) |
| Sub 5-38 | m/z = 321.15 ($C_{24}H_{19}N$ = 321.42) |
| Sub 5-39 | m/z = 321.15 ($C_{24}H_{19}N$ = 321.42) |
| Sub 5-40 | m/z = 506.18 ($C_{35}H_{26}N_2S$ = 506.67) |
| Sub 5-41 | m/z = 501.17 ($C_{36}H_{23}NO_2$ = 501.59) |
| Sub 5-42 | m/z = 347.17 ($C_{26}H_{21}N$ = 347.46) |
| Sub 5-43 | m/z = 483.20 ($C_{37}H_{25}N$ = 483.61) |
| Sub 5-44 | m/z = 502.20 ($C_{36}H_{26}N_2O$ = 502.62) |
| Sub 5-45 | m/z = 503.24 ($C_{36}H_{29}N_3$ = 503.65) |

TABLE 3-continued

| Compound | FD-MS |
|---|---|
| Sub 5-46 | m/z = 518.18 ($C_{36}H_{26}N_2S$ = 518.68) |
| Sub 5-47 | m/z = 452.23 ($C_{33}H_{28}N_2$ = 452.60) |
| Sub 5-48 | m/z = 401.14 ($C_{28}H_{19}NO_2$ = 401.47) |
| Sub 5-49 | m/z = 427.19 ($C_{33}H_{25}NO$ = 427.55) |
| Sub 5-50 | m/z = 411.20 ($C_{31}H_{25}N$ = 411.55) |
| Sub 5-51 | m/z = 502.20 ($C_{36}H_{26}N_2O$ = 502.62) |
| Sub 5-52 | m/z = 415.10 ($C_{28}H_{17}NOS$ = 415.51) |
| Sub 5-53 | m/z = 285.15 ($C_{21}H_{19}N$ = 285.39) |
| Sub 5-54 | m/z = 351.11 ($C_{24}H_{17}NS$ = 35 1.47) |
| Sub 5-55 | m/z = 439.14 ($C_{31}H_{21}NS$ = 439.58) |
| Sub 5-56 | m/z = 461.21 ($C_{35}H_{27}N$ = 461.61) |
| Sub 5-57 | m/z = 275.13 ($C_{19}H_{17}NO$ = 275.35) |
| Sub 5-58 | m/z = 362.14 ($C_{25}H_{18}N_2O$ = 362.43) |
| Sub 5-59 | m/z = 195.10 ($C_{14}H_{13}N$ = 195.27) |
| Sub 5-60 | m/z = 269.12 ($C_{20}H_{15}N$ = 269.35) |
| Sub 5-61 | m/z = 369.15 ($C_{28}H_{19}N$ = 369.47) |
| Sub 5-62 | m/z = 341.14 ($C_{23}H_{19}NO_2$ = 341.41) |

IV. Synthesis of Final Product

1. Synthesis Example of P-2

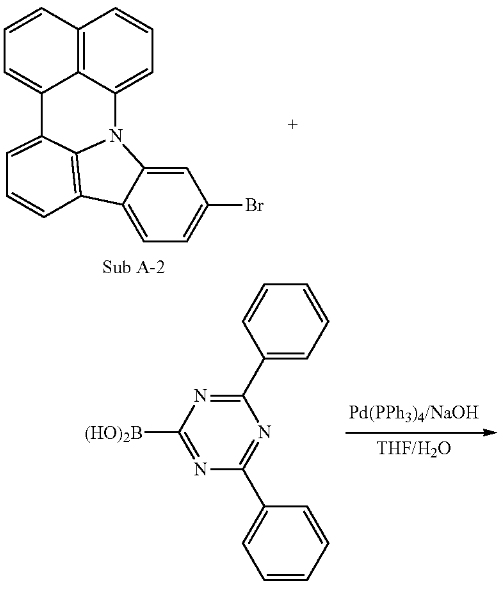

Sub A-2

Sub 4-2

-continued

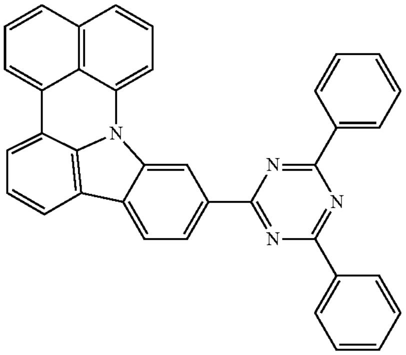

P-2

Sub 4-2 (22.45 g, 81.03 mmol), $Pd(PPh_3)_4$ (4.68 g, 4.05 mmol), NaOH (9.72 g, 243.08 mmol), THF (400 mL), and water (200 mL) were added to Sub A-2 (30 g, 81.03 mmol) and the mixture was stirred at 80° C. Upon completion of the reaction, the resultant was extracted with $CH_2Cl_2$ and water, the organic layer was dried over $MgSO_4$ and concentrated, and the resulting organic matter was subjected to silica gel column and recrystallization to obtain 38.96 g (yield: 92%) of a product.

2. Synthesis Example of P-3

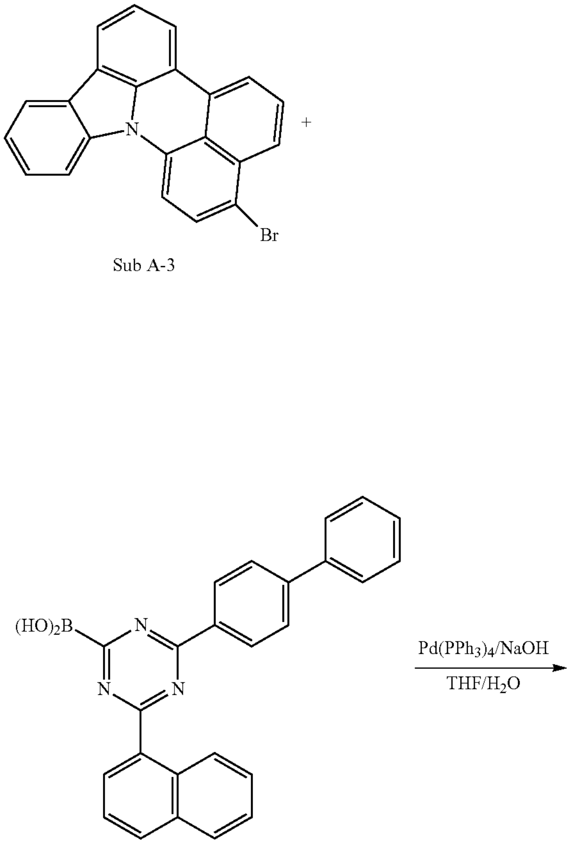

Sub A-3

Sub 4-3

-continued

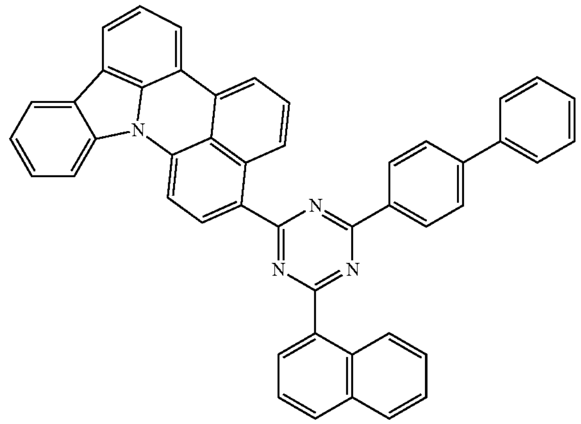

P-3

Sub 4-3 (32.67 g, 81.03 mmol), $Pd(PPh_3)_4$ (4.68 g, 4.05 mmol), NaOH (9.72 g, 243.08 mmol), THF (400 mL), and water (200 mL) were added to Sub A-3 (30 g, 81.03 mmol), and 38.37 g (yield: 73%) of a product was obtained using the P-2 synthesis method above.

3. Synthesis Example of P-22

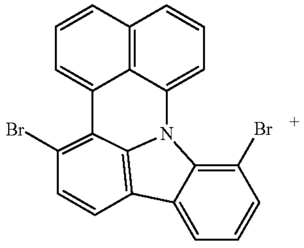

Sub A-10

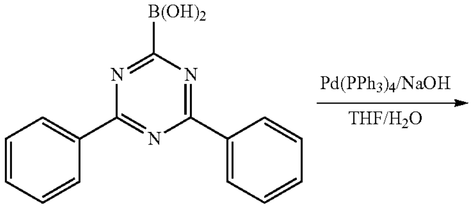

Sub 4-2

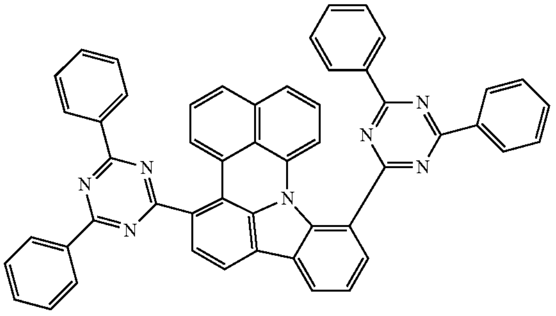

P-22

Sub 4-2 (30.34 g, 133.59 mmol), $Pd(PPh_3)_4$ (3.86 g, 3.34 mmol), NaOH (8.02 g, 200.38 mmol), THF (330 mL), and water (150 mL) were added to Sub A-10 (30 g, 66.79 mmol), and 46.32 g (yield: 92%) of a product was obtained using the P-2 synthesis method above.

4. Synthesis Example of P-32

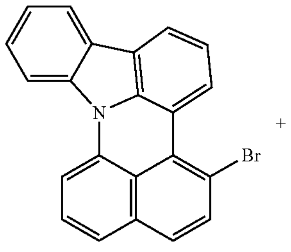

Sub A-5

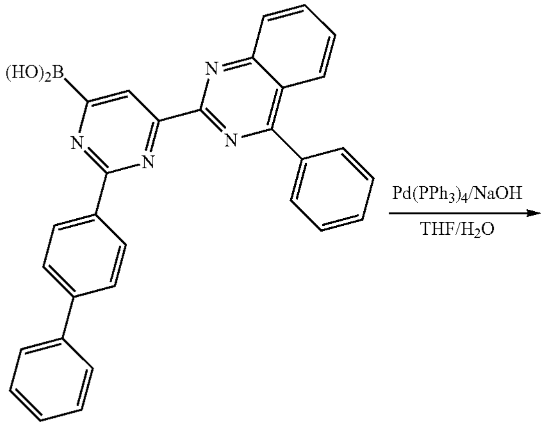

Sub 4-24

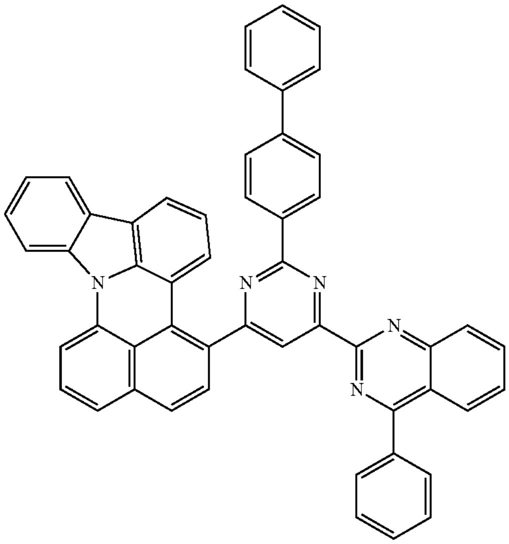

P-32

Sub 4-24 (38.92 g, 81.03 mmol), $Pd(PPh_3)_4$ (4.68 g, 4.05 mmol), NaOH (9.72 g, 243.08 mmol), THF (400 mL), and water (200 mL) were added to Sub A-5 (30 g, 81.03 mmol), and 35.88 g (yield: 61%), and 35.88 g (yield: 61%) of a product was obtained using the P-2 synthesis method above.

5. Synthesis Example of P-48

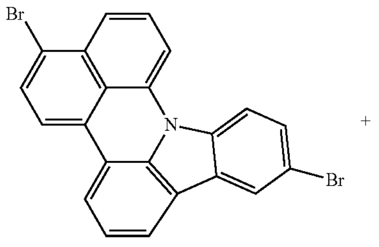

Sub A-11

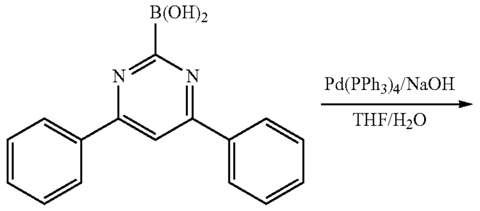

Sub 4-39

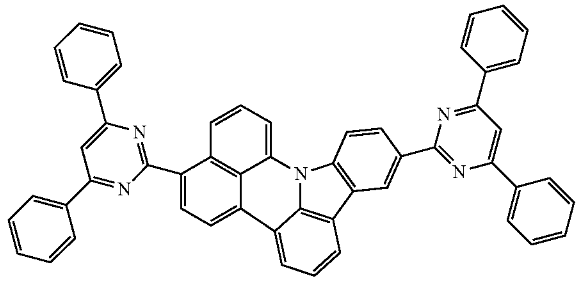

P-48

Sub 4-39 (36.88 g, 133.59 mmol), $Pd(PPh_3)_4$ (3.86 g, 3.34 mmol), NaOH (8.02 g, 200.38 mmol), THF (330 mL), and water (150 mL) were added to Sub A-11 (30 g, 66.79 mmol), and 35.88 g (yield: 61%) of a product was obtained using the P-2 synthesis method above.

6. Synthesis Example of P-50

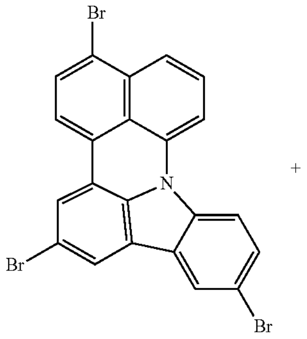

Sub A-13

-continued

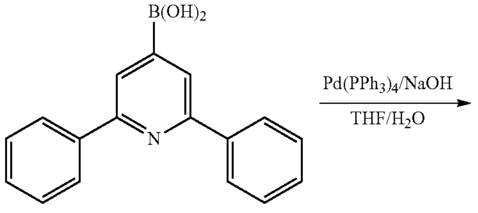

Sub 4-37

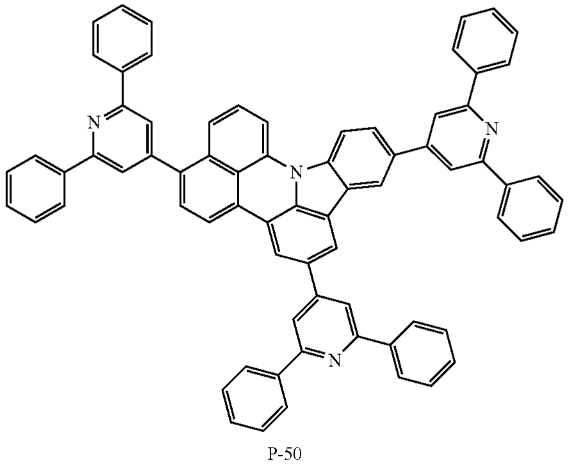

P-50

Sub 4-37 (46.89 g, 170.44 mmol), $Pd(PPh_3)_4$ (3.28 g, 2.84 mmol), NaOH (6.82 g, 170.44 mmol), THF (300 mL) and water (150 mL) were added to Sub A-13 (30 g, 56.81 mmol), and the mixture was stirred at 80° C. Upon completion of the reaction, the resultant was extracted with $CH_2Cl_2$ and water, the organic layer was dried over $MgSO_4$ and concentrated, and the resulting organic matter was subjected to silica gel column and recrystallization to obtain 48.40 g (yield: 87%) of a product.

7. Synthesis Example of P-90

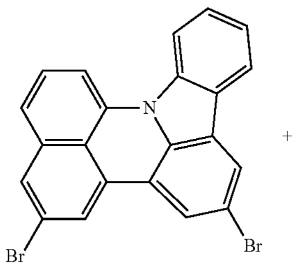

Sub A-15

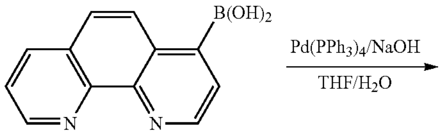

Sub 4-63

-continued

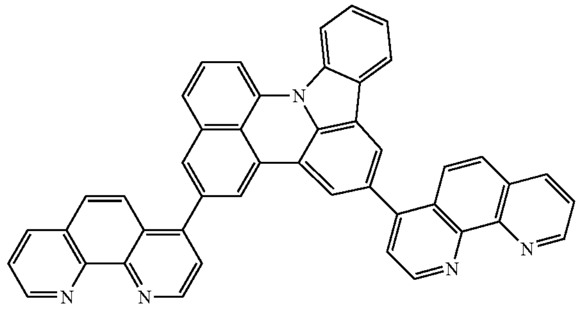

P-90

Sub 4-37 (46.89 g, 170.44 mmol), $Pd(PPh_3)_4$ (3.28 g, 2.84 mmol), NaOH (6.82 g, 170.44 mmol), THF (300 mL), and water (150 mL) were added to Sub A-13 (30 g, 56.81 mmol), and the mixture was stirred at 80° C. Upon completion of the reaction, the resultant was extracted with $CH_2Cl_2$ and water, the organic layer was dried over $MgSO_4$ and concentrated, and the resulting organic matter was subjected to silica gel column and recrystallization to obtain 48.40 g (yield: 87%) of a product.

8. Synthesis Example of P-96

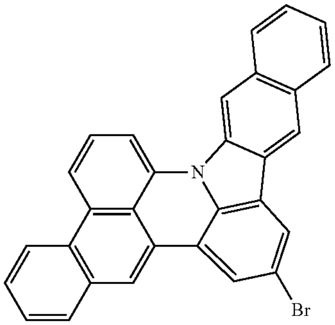

Sub A-18

+

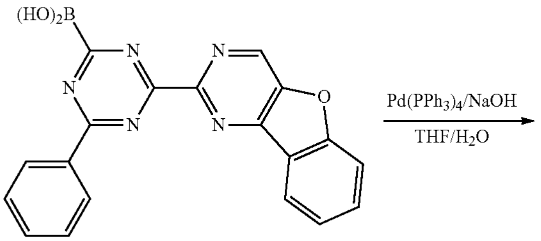

Sub 4-15

-continued

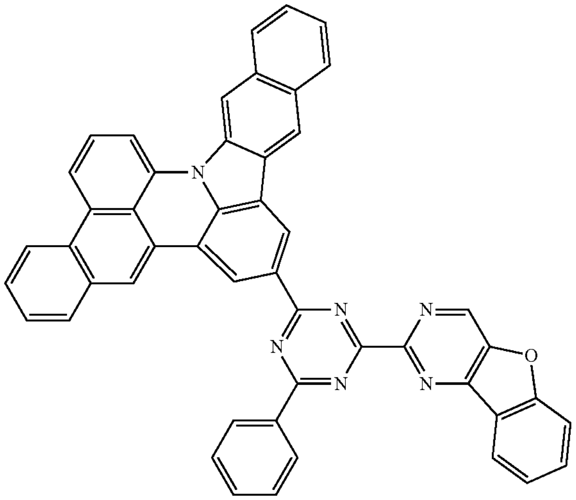

P-96

Sub 4-70 (23.54 g, 63.78 mmol), $Pd(PPh_3)_4$ (3.69 g, 3.19 mmol), NaOH (7.65 g, 191.34 mmol), THF (320 mL), and water (160 mL) were added to Sub A-18 (30 g, 63.78 mmol), and 21.43 g (yield: 47%) of a product was obtained using the P-2 synthesis method above.

9. Synthesis Example of P-137

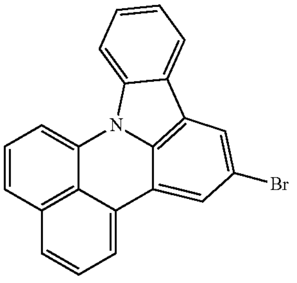

Sub A-2

+

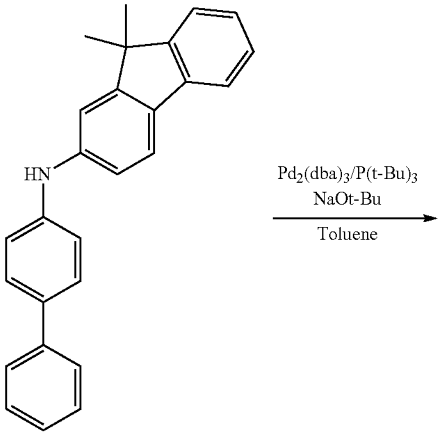

Sub 5-5

-continued

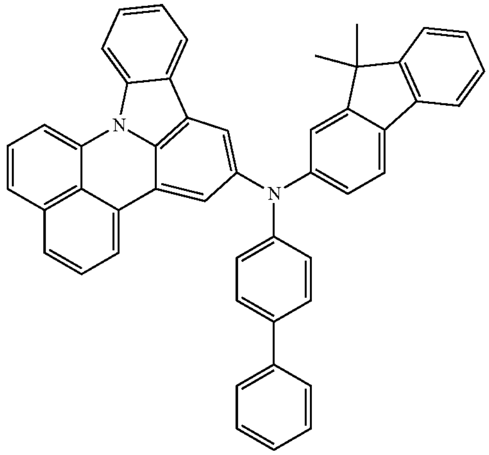

P-137

Sub A-2 (10.0 g, 27.0 mmol) was added into toluene (135 mL), and then Sub 5-5 (9.4 g, 27.0 mmol), $Pd_2(dba)_3$ (0.7 g, 0.8 mmol), $P(t\text{-}Bu)_3$ (0.3 g, 1.6 mmol), and NaOt-Bu (5.2 g, 54.0 mmol) were added thereto, and 13.1 g (yield: 74.6%) of a product was obtained using the same method as in Sub 5-5 above.

10. Synthesis Example of P-141

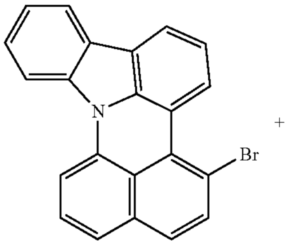

Sub A-5

+

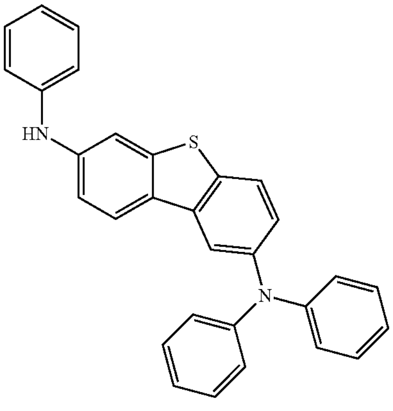

Sub 5-9

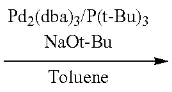

-continued

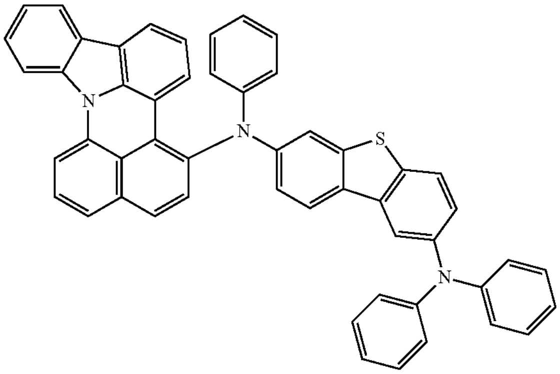

P-141

Sub A-5 (10.0 g, 27.0 mmol) was added into toluene (135 mL), and then Sub 5-9 (11.5 g, 27.0 mmol), $Pd_2(dba)_3$ (0.7 g, 0.8 mmol), $P(t\text{-}Bu)_3$ (0.3 g, 1.6 mmol), and NaOt-Bu (5.2 g, 54.0 mmol) were added thereto, and 15.4 g (yield: 78.1%) of a product was obtained using the same method as in Sub 5-5 above.

11. Synthesis Example of P-142

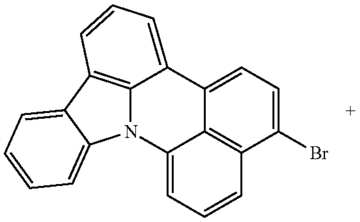

Sub A-6

+

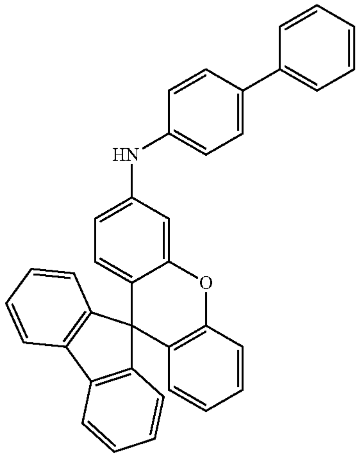

Sub 5-10

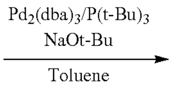

-continued

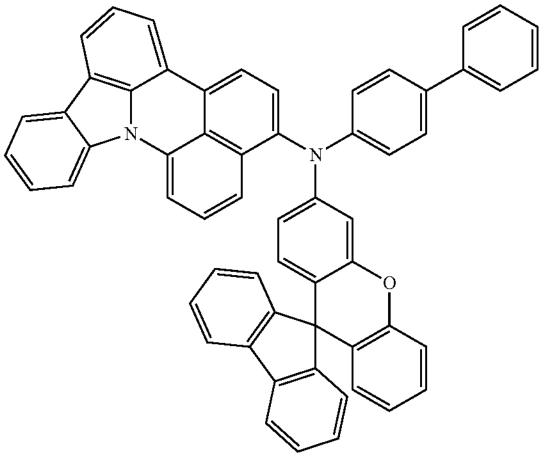

P-142

Sub A-6 (10.0 g, 27.0 mmol) was added into toluene (135 mL), and then Sub 5-10 (13.0 g, 27.0 mmol), $Pd_2(dba)_3$ (0.7 g, 0.8 mmol), $P(t-Bu)_3$ (0.3 g, 1.6 mmol), and NaOt-Bu (5.2 g, 54.0 mmol) were added thereto, and 15.5 g (yield: 72.9%) of a product was obtained using the same method as in Sub 5-5 above.

12. Synthesis Example of P-153

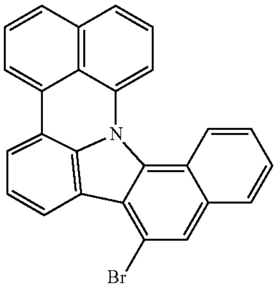

Sub A-17

+

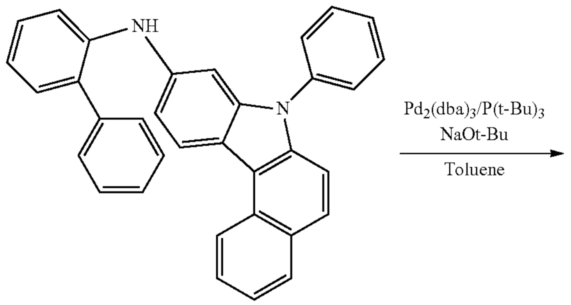

Sub 5-18

-continued

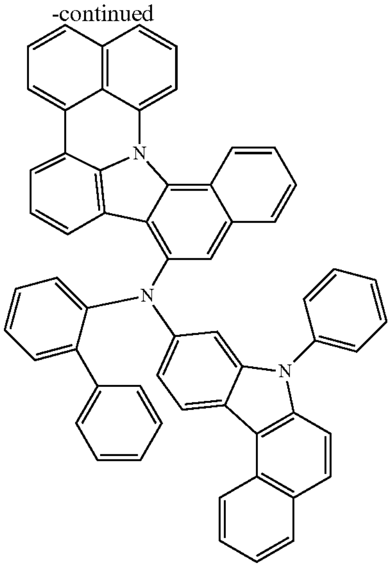

P-153

Sub A-17 (10.0 g, 23.8 mmol) was added into toluene (119 mL), and then Sub 5-18 (10.6 g, 23.8 mmol), $Pd_2(dba)_3$ (0.7 g, 0.7 mmol), $P(t-Bu)_3$ (0.3 g, 1.4 mmol), and NaOt-Bu (4.6 g, 47.6 mmol) were added thereto, and 14.4 g (yield: 75.7%) of a product was obtained using the same method as in Sub 5-5 above.

Meanwhile, the FD-MS values of the compounds P-1 to P-212 of the present disclosure prepared according to the synthesis examples as described above are shown in Table 4 below.

TABLE 4

| Compound | FD-MS |
|---|---|
| P-1 | m/z = 598.22($C_{43}H_{26}N_4$ = 598.71) |
| P-2 | m/z = 522.18($C_{37}H_{22}N_4$ = 522.6 1) |
| P-3 | m/z = 648.23($C_{47}H_{28}N_4$ = 648.77) |
| P-4 | m/z = 674.25($C_{49}H_{30}N_4$ = 674.8 1) |
| P-5 | m/z = 678.23($C_{45}H_{26}N_8$ = 678.76) |
| P-6 | m/z = 726.25($C_{51}H_{30}N_6$ = 726.84) |
| P-7 | m/z = 612.20($C_{43}H_{24}N_4O$ = 612.69) |
| P-8 | m/z = 662.21($C_{47}H_{26}N_4O$ = 662.75) |
| P-9 | m/z = 810.19($C_{55}H_{30}N_4S_2$ = 810.99) |
| P-10 | m/z = 702.21($C_{49}H_{26}N_4O_2$ = 702.77) |
| P-11 | m/z = 598.22($C_{43}H_{26}N_4$ = 598.71) |
| P-12 | m/z = 724.26($C_{53}H_{32}N_4$ = 724.87) |
| P-13 | m/z = 752.27($C_{53}H_{32}N_6$ = 752.88) |
| P-14 | m/z = 601.20($C_{40}H_{23}N_7$ = 601.67) |
| P-15 | m/z = 526.17($C_{33}H_{18}N_8$ = 526.56) |
| P-16 | m/z = 614.19($C_{41}H_{22}N_6O$ = 614.67) |
| P-17 | m/z = 664.20($C_{45}H_{24}N_6O$ = 664.73) |
| P-18 | m/z = 812.18($C_{53}H_{28}N_6S_2$ = 812.97) |
| P-19 | m/z = 753.26($C_{52}H_{31}N_7$ = 753.87) |
| P-20 | m/z = 753.26($C_{52}H_{31}N_7$ = 753.87) |
| P-21 | m/z = 765.21($C_{40}H_{19}N_{19}$ = 765.73) |
| P-22 | m/z = 753.26($C_{52}H_{31}N_7$ = 753.87) |
| P-23 | m/z = 753.26($C_{52}H_{31}N_7$ = 753.87) |
| P-24 | m/z = 879.31($C_{62}H_{37}N_7$ = 880.03) |
| P-25 | m/z = 984.34($C_{67}H_{40}N_{10}$ = 985.13) |
| P-26 | m/z = 1164.36($C_{79}H_{44}N_{10}O_2$ = 1165.29) |
| P-27 | m/z = 597.22($C_{44}H_{27}N_3$ = 597.72) |
| P-28 | m/z = 521.19($C_{38}H_{23}N_3$ = 521.62) |
| P-29 | m/z = 647.24($C_{48}H_{29}N_3$ = 647.78) |
| P-30 | m/z = 673.25($C_{50}H_{31}N_3$ = 673.82) |
| P-31 | m/z = 677.23($C_{46}H_{27}N_7$ = 677.77) |
| P-32 | m/z = 725.26($C_{52}H_{31}N_5$ = 725.86) |
| P-33 | m/z = 611.20($C_{44}H_{25}N_3O$ = 611.70) |
| P-34 | m/z = 677.19($C_{48}H_{27}N_3S$ = 677.83) |

TABLE 4-continued

| Compound | FD-MS |
|---|---|
| P-35 | m/z = 811.19($C_{54}H_{29}N_5S_2$ = 811.98) |
| P-36 | m/z = 701.21($C_{50}H_{27}N_3O_2$ = 701.79) |
| P-37 | m/z = 597.22($C_{44}H_{27}N_3$ = 597.72) |
| P-38 | m/z = 723.27($C_{54}H_{33}N_3$ = 723.88) |
| P-39 | m/z = 751.27($C_{54}H_{33}N_5$ = 751.89) |
| P-40 | m/z = 600.21($C_{41}H_{24}N_6$ = 600.69) |
| P-41 | m/z = 525.17($C_{34}H_{19}N_7$ = 525.58) |
| P-42 | m/z = 612.20($C_{43}H_{24}N_4O$ = 612.69) |
| P-43 | m/z = 662.21($C_{47}H_{26}N_4O$ = 662.75) |
| P-44 | m/z = 810.19($C_{55}H_{30}N_4S_2$ = 810.99) |
| P-45 | m/z = 753.26($C_{52}H_{31}N_7$ = 753.87) |
| P-46 | m/z = 750.28($C_{55}H_{34}N_4$ = 750.91) |
| P-47 | m/z = 751.27($C_{54}H_{33}N_5$ = 751.89) |
| P-48 | m/z = 751.27($C_{54}H_{33}N_5$ = 751.89) |
| P-49 | m/z = 929.33($C_{66}H_{39}N_7$ = 930.09) |
| P-50 | m/z = 978.37($C_{73}H_{46}N_4$ = 979.20) |
| P-51 | m/z = 1161.38($C_{82}H_{47}N_7O_2$ = 1162.33) |
| P-52 | m/z = 495.17($C_{36}H_{21}N_3$ = 495.59) |
| P-53 | m/z = 495.17($C_{36}H_{21}N_3$ = 495.59) |
| P-54 | m/z = 545.19($C_{40}H_{23}N_3$ = 545.65) |
| P-55 | m/z = 699.24($C_{50}H_{29}N_5$ = 699.82) |
| P-56 | m/z = 903.31($C_{64}H_{37}N_7$ = 904.05) |
| P-57 | m/z = 585.18($C_{42}H_{23}N_3O$ = 585.67) |
| P-58 | m/z = 495.17($C_{36}H_{21}N_3$ = 495.59) |
| P-59 | m/z = 495.17($C_{36}H_2N_3$ = 495.59) |
| P-60 | m/z = 545.19($C_{40}H_{23}N_3$ = 545.65) |
| P-61 | m/z = 699.24($C_{50}H_{29}N_5$ = 699.82) |
| P-62 | m/z = 930.32($C_{65}H_{38}N_8$ = 931.08) |
| P-63 | m/z = 601.16($C_{42}H_{23}N_3S$ = 601.73) |
| P-64 | m/z = 649.23($C_{46}H_{27}N_5$ = 649.76) |
| P-65 | m/z = 651.22($C_{44}H_{25}N_7$ = 651.73) |
| P-66 | m/z = 699.24($C_{50}H_{29}N_5$ = 699.82) |
| P-67 | m/z = 703.22($C_{46}H_{25}N_9$ = 703.77) |
| P-68 | m/z = 934.30($C_{61}H_{34}N_{12}$ = 935.03) |
| P-69 | m/z = 587.17($C_{40}H_{21}N_5O$ = 587.64) |
| P-70 | m/z = 535.17($C_{38}H_{21}N_3O$ = 535.61) |
| P-71 | m/z = 551.15($C_{38}H_{21}N_3S$ = 551.67) |
| P-72 | m/z = 756.21($C_{51}H_{28}N_6S$ = 756.89) |
| P-73 | m/z = 766.25($C_{53}H_{30}N_6O$ = 766.86) |
| P-74 | m/z = 779.23($C_{54}H_{29}N_5O_2$ = 779.86) |
| P-75 | m/z = 468.16($C_{35}H_{20}N_2$ = 468.56) |
| P-76 | m/z = 699.24($C_{50}H_{29}N_5$ = 699.82) |
| P-77 | m/z = 699.24($C_{50}H_{29}N_5$ = 699.82) |
| P-78 | m/z = 558.17($C_{41}H_{22}N_2O$ = 558.64) |
| P-79 | m/z = 805.23($C_{56}H_{31}N_5S$ = 805.96) |
| P-80 | m/z = 930.32($C_{65}H_{38}N_8$ = 931.08) |
| P-81 | m/z = 469.16($C_{34}H_{19}N_3$ = 469.55) |
| P-82 | m/z = 469.16($C_{34}H_{19}N_3$ = 469.55) |
| P-83 | m/z = 469.16($C_{34}H_{19}N_3$ = 469.55) |
| P-84 | m/z = 547.18($C_{38}H_{21}N_5$ = 547.62) |
| P-85 | m/z = 545.19($C_{40}H_{23}N_3O$ = 545.65) |
| P-86 | m/z = 700.24($C_{49}H_{28}N_6$ = 700.81) |
| P-87 | m/z = 469.16($C_{34}H_{19}N_3$ = 469.55) |
| P-88 | m/z = 651.18($C_{46}H_{25}N_3S$ = 651.79) |
| P-89 | m/z = 661.25($C_{49}H_{31}N_3$ = 661.81) |
| P-90 | m/z = 647.21($C_{46}H_{25}N_5$ = 647.74) |
| P-91 | m/z = 487.15($C_{34}H_{18}FN_3$ = 487.54) |
| P-92 | m/z = 598.22($C_{43}H_{26}N_4$ = 598.71) |
| P-93 | m/z = 802.28($C_{57}H_{34}N_6$ = 802.94) |
| P-94 | m/z = 651.22($C_{44}H_{25}N_7$ = 651.73) |
| P-95 | m/z = 576.18($C_{37}H_{20}N_8$ = 576.62) |
| P-96 | m/z = 714.22($C_{49}H_{26}N_6O$ = 714.79) |
| P-97 | m/z = 762.24($C_{55}H_{30}N_4O$ = 762.87) |
| P-98 | m/z = 764.23($C_{53}H_{28}N_6O$ = 764.85) |
| P-99 | m/z = 862.20($C_{57}H_{30}N_6S_2$ = 863.03) |
| P-100 | m/z = 626.39($C_{43}H_2D_{26}N_4$ = 626.88) |
| P-101 | m/z = 534.26($C_{37}H_{10}D_{12}N_4$ = 534.68) |
| P-102 | m/z = 664.33($C_{47}H_{12}D_{16}N_4$ = 664.87) |
| P-103 | m/z = 759.24($C_{46}H_{25}N_{13}$ = 759.80) |
| P-104 | m/z = 843.27($C_{58}H_{33}N_7O$ = 843.95) |
| P-105 | m/z = 831.29($C_{56}H_{33}N_9$ = 831.94) |
| P-106 | m/z = 921.30($C_{62}H_{35}N_9O$ = 922.02) |
| P-107 | m/z = 674.25($C_{49}H_{30}N_4$ = 674.81) |
| P-108 | m/z = 598.22($C_{43}H_{26}N_4$ = 598.71) |
| P-109 | m/z = 800.29($C_{59}H_{36}N_4$ = 800.97) |
| P-110 | m/z = 750.28($C_{55}H_{34}N_4$ = 750.91) |
| P-111 | m/z = 655.18($C_{44}H_{25}N_5S$ = 655.78) |
| P-112 | m/z = 709.23($C_{50}H_{29}F_2N_3$ = 709.80) |

TABLE 4-continued

| Compound | FD-MS |
|---|---|
| P-113 | m/z = 727.22($C_{48}H_{25}N_9$ = 727.79) |
| P-114 | m/z = 750.25($C_{53}H_{30}N_6$ = 750.87) |
| P-115 | m/z = 853.28($C_{61}H_{35}N_5O$ = 853.99) |
| P-116 | m/z = 827.27($C_{59}H_{33}N_5O$ = 827.95) |
| P-117 | m/z = 677.19($C_{48}H_{27}N_3S$ = 677.83) |
| P-118 | m/z = 814.31($C_{60}H_{38}N_4$ = 814.99) |
| P-119 | m/z = 551.15($C_{38}H_{21}N_3S$ = 551.67) |
| P-120 | m/z = 737.25($C_{54}H_{31}N_3O$ = 737.86) |
| P-121 | m/z = 585.18($C_{42}H_{23}N_3O$ = 585.67) |
| P-122 | m/z = 727.21($C_{52}H_{29}N_3S$ = 727.89) |
| P-123 | m/z = 495.17($C_{36}H_{21}N_3$ = 495.59) |
| P-124 | m/z = 687.23($C_{50}H_{29}N_3O$ = 687.8) |
| P-125 | m/z = 736.26($C_{54}H_{32}N_4$ = 736.88) |
| P-126 | m/z = 715.27($C_{51}H_{33}N_5$ = 715.86) |
| P-127 | m/z = 576.14($C_{39}H_{20}N_4S$ = 576.68) |
| P-128 | m/z = 902.30($C_{66}H_{38}N_4O$ = 903.06) |
| P-129 | m/z = 534.18($C_{38}H_{22}N_4$ = 534.62) |
| P-130 | m/z = 561.22($C_{41}H_{27}N_3$ = 561.69) |
| P-131 | m/z = 545.19($C_{40}H_{23}N_3$ = 545.65) |
| P-132 | m/z = 612.20($C_{43}H_{24}N_4O$ = 612.69) |
| P-133 | m/z = 458.18($C_{34}H_{22}N_2$ = 458.56) |
| P-134 | m/z = 508.19($C_{38}H_{24}N_2$ = 508.62) |
| P-135 | m/z = 558.21($C_{42}H_{26}N_2$ = 558.68) |
| P-136 | m/z = 624.22($C_{46}H_{28}N_2O$ = 624.74) |
| P-137 | m/z = 650.27($C_{49}H_{34}N_2$ = 650.83) |
| P-138 | m/z = 824.32($C_{63}H_{40}N_2$ = 825.03) |
| P-139 | m/z = 772.29($C_{59}H_{36}N_2$ = 772.95) |
| P-140 | m/z = 610.24($C_{46}H_{30}N_2$ = 610.76) |
| P-141 | m/z = 731.24($C_{52}H_{33}N_3S$ = 731.92) |
| P-142 | m/z = 788.28($C_{59}H_{36}N_2O$ = 788.95) |
| P-143 | m/z = 660.26($C_{50}N_{32}N_2$ = 660.82) |
| P-144 | m/z = 725.28($C_{54}H_{35}N_3$ = 725.90) |
| P-145 | m/z = 625.25($C_{46}H_{31}N_3$ = 625.78) |
| P-146 | m/z = 777.31($C_{58}H_{39}N_3$ = 777.97) |
| P-147 | m/z = 957.41($C_{72}H_{51}N_3$ = 958.22) |
| P-148 | m/z = 863.31($C_{61}H_{41}N_3O_3$ = 864.02) |
| P-149 | m/z = 792.33($C_{58}H_{40}N_4$ = 792.99) |
| P-150 | m/z = 792.33($C_{58}H_{40}N_4$ = 792.99) |
| P-151 | m/z = 765.28($C_{56}H_{35}N_{3O}$ = 765.92) |
| P-152 | m/z = 650.27($C_{49}H_{34}N_2$ = 650.83) |
| P-153 | m/z = 799.3($C_{60}H_{37}N_3$ = 799.98) |
| P-154 | m/z = 690.21($C_{50}H_{30}N_2S$ = 690.86) |
| P-155 | m/z = 674.24($C_{50}H_{30}N_2O$ = 674.80) |
| P-156 | m/z = 826.33($C_{63}H_{42}N_2$ = 827.04) |
| P-157 | m/z = 792.31($C_{59}H_{40}N_2O$ = 792.98) |
| P-158 | m/z = 860.32($C_{66}H_{40}N_2$ = 861.06) |
| P-159 | m/z = 704.19($C_{50}H_{28}N_2OS$ = 704.85) |
| P-160 | m/z = 926.41($C_{69}H_{34}D_{10}N_2O$ = 927.19) |
| P-161 | m/z = 1042.41($C_{77}H_{34}D_{12}N_2S$ = 1043.36) |
| P-162 | m/z = 740.23($C_{54}H_{32}N_2S$ = 740.92) |
| P-163 | m/z = 788.32($C_{60}H_{40}N_2$ = 788.99) |
| P-164 | m/z = 929.30($C_{68}H_{39}N_3O_2$ = 930.08) |
| P-165 | m/z = 801.28($C_{59}H_{35}N_{3O}$ = 801.95) |
| P-166 | m/z = 1066.39($C_{81}H_{50}N_2O$ = 1067.3) |
| P-167 | m/z = 689.26($C_{49}H_{31}N_5$ = 689.82) |
| P-168 | m/z = 889.35($C_{67}H_{43}N_3$ = 890.10) |
| P-169 | m/z = 650.27($C_{49}H_{34}N_2$ = 650.83) |
| P-170 | m/z = 939.36($C_{71}H_{45}N_3$ = 940.16) |
| P-171 | m/z = 716.23($C_{52}H_{32}N_2S$ = 716.90) |
| P-172 | m/z = 851.33($C_{64}H_{41}N_3$ = 852.05) |
| P-173 | m/z = 763.30($C_{57}H_{37}N_3$ = 763.94) |
| P-174 | m/z = 689.26($C_{49}H_{31}N_5$ = 689.82) |
| P-175 | m/z = 788.29($C_{58}H_{36}N_4$ = 788.95) |
| P-176 | m/z = 841.32($C_{61}H_{39}N_5$ = 842.02) |
| P-177 | m/z = 871.30($C_{63}H_{41}N_3S$ = 872.10) |
| P-178 | m/z = 1429.46($C_{103}H_{59}N_5O_4$ = 1430.64) |
| P-179 | m/z = 686.27($C_{52}H_{34}N_2$ = 686.86) |
| P-180 | m/z = 822.30($C_{63}H_{38}N_2$ = 823 .01) |
| P-181 | m/z = 791.29($C_{58}H_{37}N_3O$ = 791.95) |
| P-182 | m/z = 792.33($C_{58}H_{40}N_4$ = 792.99) |
| P-183 | m/z = 807.27($C_{58}H_{37}N_3S$ = 808.02) |
| P-184 | m/z = 741.31($C_{55}H_{39}N_3$ = 741.94) |
| P-185 | m/z = 690.23($C_{50}H_{30}N_2O_2$ = 690.80) |
| P-186 | m/z = 716.28($C_{53}H_{36}N_2O$ = 716.88) |
| P-187 | m/z = 700.29($C_{53}H_{36}N_2$ = 700.89) |
| P-188 | m/z = 791.29($C_{58}H_{37}N_3O$ = 791.95) |
| P-189 | m/z = 780.22($C_{56}H_{32}N_2OS$ = 780.95) |
| P-190 | m/z = 766.24($C_{56}H_{34}N_2S$ = 766.96) |

TABLE 4-continued

| Compound | FD-MS |
|---|---|
| P-191 | m/z = 640.20($C_{46}H_{28}N_2S$ = 640.80) |
| P-192 | m/z = 650.27($C_{49}H_{34}N_2$ = 650.83) |
| P-193 | m/z = 674.24($C_{50}H_{30}N_2O$ = 674.80) |
| P-194 | m/z = 699.27($C_{52}H_{33}N_3$ = 699.86) |
| P-195 | m/z = 650.27($C_{49}H_{34}N_2$ = 650.83) |
| P-196 | m/z = 716.23($C_{52}H_{32}N_2S$ = 716.90) |
| P-197 | m/z = 684.26($C_{52}H_{32}N_2$ = 684.84) |
| P-198 | m/z = 956.32($C_{71}H_{144}N_2S$ = 957.21) |
| P-199 | m/z = 730.21($C_{52}H_{30}N_2OS$ = 730 .89) |
| P-200 | m/z = 946.30($C_{69}H_{42}N_2OS$ = 947.17) |
| P-201 | m/z = 574.24($C_{43}H_{30}N_2$ = 5 74.73) |
| P-202 | m/z = 548.19($C_{40}H_{24}N_2O$ = 548.65) |
| P-203 | m/z = 739.30($C_{55}H_{37}N_3$ = 739.92) |
| P-204 | m/z = 680.28($C_{50}H_{36}N_2O$ = 680.85) |
| P-205 | m/z = 816.29($C_{59}H_{36}N_4O$ = 816.96) |
| P-206 | m/z = 750.27($C_{56}H_{34}N_2O$ = 750.90) |
| P-207 | m/z = 590.18($C_{42}H_{26}N_2S$ = 590.74) |
| P-208 | m/z = 664.20($C_{48}H_{28}N_2S$ = 664.83) |
| P-209 | m/z = 898.33($C_{69}H_{42}N_2$ = 899.11) |
| P-210 | m/z = 736.22($C_{51}H_{32}N_2O_2S$ = 736.89) |
| P-211 | m/z = 598.20($C_{44}H_{26}N_2O$ = 598.71) |
| P-212 | m/z = 699.27($C_{52}H_{33}N_3$ = 699.86) |

Evaluation of Manufacturing of Organic Electric Device (Example 1) Manufacture and Testing of Red Organic Light Emitting Device $N^1$-(naphthalen-2-yl)-$N^4$,$N^4$-bis(4-(naphthalen-2-yl(phenyl)amino)phenyl)-$N^1$-phenylbenzene-1,4-diamine (abbreviated as "2-TNATA") film was vacuum-deposited on top of an ITO layer (cathod) formed on a glass substrate and a hole injection layer with a thickness of 60 nm was formed.

N,N'-Bis(1-naphthalenyl)-N,N'-bis-phenyl-(1,1'-biphenyl)-4,4'-diamine (hereinafter abbreviated as "NPB"), as a hole transport compound, was vacuum-deposited on top of the hole injection layer, and a hole transport layer with a thickness of 60 nm was formed.

The compound P-2 represented by Formula 1 was used as a host on the hole transport layer, and as a dopant, a light emitting layer with a thickness of 30 nm was deposited by doping bis-(1-phenylisoquinolyl) iridium (III) acetylacetonate (hereinafter abbreviated as "$(piq)_2Ir(acac)$") at a weight of 95:5.

(1,1'-biphenyl-4-olato)bis(2-methyl-8-quinolinolato)aluminum (hereinafter abbreviated as "BAlq") was vacuum-deposited to a thickness of 10 nm on top of the light emitting layer to form a hole blocking layer.

Tris-(8-hydroxyquinoline)aluminum (hereinafter abbreviated as "Alq3") was deposited on the hole blocking layer to a thickness of 40 nm to form an electron transport layer.

Thereafter, as an electron injection layer, LiF (which is an alkali metal halide) was deposited to a thickness of 0.2 nm, and then A1 was deposited to a thickness of 150 nm and used as a anode to manufacture an organic electroluminescent device.

Examples 2 to 20

An organic electroluminescent device was manufactured in the same manner as in Example 1, except that the compound of the present disclosure described in Table 5 below was used instead of Compound P-2 of the present disclosure in Example 1.

Comparative Example 1

An organic electroluminescent device was manufactured in the same manner as in Example 1, except that Comparative Compound 1 below was used instead of Compound P-2 of the present disclosure in Example 1.

<Comparative Compound 1>

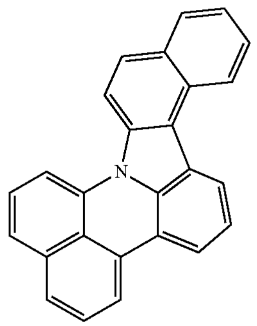 [SMILES: c1ccc2c(c1)ccc1c2c2cccc3c4cccc5cccc(c54)n1c32]

The electroluminescence (EL) characteristics were measured with the PR-650 of Photo Research Inc., by applying a forward bias DC voltage to the organic electroluminescent devices manufactured according to Examples 1 to 20 and Comparative Example 1, and the T95 lifetime was measured using a lifetime measuring device manufactured by McScience at 2,500 $cd/m^2$ standard luminance. Table 5 below shows the evaluation results of the manufactured devices.

TABLE 5

| | Compound | Voltage (V) | Current Density ($mA/cm^2$) | Luminance ($cd/m^2$) | Efficiency (cd/A) | Lifetime T (95) | CIE x | CIE y |
|---|---|---|---|---|---|---|---|---|
| Comparative Example 1 | Comparative Compound 1 | 7.2 | 33.8 | 2500.0 | 7.4 | 61.8 | 0.63 | 0.33 |
| Example 1 | P-2 | 5.4 | 11.5 | 2500.0 | 21.8 | 123.3 | 0.65 | 0.32 |
| Example 2 | P-6 | 5.5 | 11.6 | 2500.0 | 21.6 | 117.9 | 0.65 | 0.30 |
| Example 3 | P-7 | 5.5 | 10.6 | 2500.0 | 23.6 | 121.4 | 0.61 | 0.33 |
| Example 4 | P-9 | 5.5 | 11.4 | 2500.0 | 21.9 | 121.3 | 0.63 | 0.33 |
| Example 5 | P-23 | 5.8 | 16.1 | 2500.0 | 15.6 | 124.3 | 0.64 | 0.31 |
| Example 6 | P-27 | 5.8 | 10.6 | 2500.0 | 23.6 | 117.5 | 0.64 | 0.31 |
| Example 7 | P-34 | 5.8 | 15.9 | 2500.0 | 15.7 | 122.4 | 0.62 | 0.34 |
| Example 8 | P-50 | 5.5 | 11.4 | 2500.0 | 21.9 | 115.8 | 0.61 | 0.31 |
| Example 9 | P-54 | 5.6 | 12.7 | 2500.0 | 19.7 | 129.8 | 0.61 | 0.35 |
| Example 10 | P-63 | 5.8 | 11.4 | 2500.0 | 21.9 | 125.7 | 0.61 | 0.35 |
| Example 11 | P-64 | 5.7 | 11.6 | 2500.0 | 21.5 | 117.2 | 0.61 | 0.34 |
| Example 12 | P-70 | 5.6 | 14.5 | 2500.0 | 17.2 | 116.3 | 0.65 | 0.34 |
| Example 13 | P-81 | 5.7 | 14.6 | 2500.0 | 17.1 | 115.6 | 0.61 | 0.30 |

TABLE 5-continued

| | Compound | Voltage (V) | Current Density (mA/cm²) | Luminance (cd/m²) | Efficiency (cd/A) | Lifetime T (95) | CIE x | CIE y |
|---|---|---|---|---|---|---|---|---|
| Example 14 | P-89 | 5.7 | 11.5 | 2500.0 | 21.8 | 117.5 | 0.62 | 0.32 |
| Example 15 | P-92 | 5.7 | 16.0 | 2500.0 | 15.6 | 126.0 | 0.64 | 0.34 |
| Example 16 | P-97 | 5.7 | 17.5 | 2500.0 | 14.3 | 118.1 | 0.64 | 0.33 |
| Example 17 | P-108 | 5.7 | 14.2 | 2500.0 | 17.6 | 127.3 | 0.62 | 0.34 |
| Example 18 | P-117 | 5.5 | 16.8 | 2500.0 | 14.9 | 129.1 | 0.61 | 0.30 |
| Example 19 | P-119 | 5.7 | 15.5 | 2500.0 | 16.1 | 126.7 | 0.63 | 0.32 |
| Example 20 | P-131 | 5.7 | 13.6 | 2500.0 | 18.4 | 124.6 | 0.62 | 0.32 |

As can be seen from the results of Table 5, when a red organic light emitting device was manufactured using the material for an organic electroluminescent device of the present disclosure as a phosphorescent host material, not only it was possible to lower the driving voltage of the organic light emitting device, but also the efficiency and lifetime of the organic light emitting device were significantly improved, compared to the case of using Comparative Compound 1.

More specifically, although Comparative compound 1 and the compound of the present disclosure have similar cores, it was confirmed that the devices of Examples 1 to 20 manufactured with the compounds of the present disclosure, to which specific substituents with excellent electron transport properties were bound, showed remarkably excellent results in terms of driving voltage, efficiency, and lifetime. This can be explained that even though the core is similar, that the energy bandgap changes by the binding of a specific substituent and causes high electron mobility.

Referring to Table 6 below, it can be seen that the compound of the present disclosure has a narrower energy bandgap than Comparative Compound 1. As a result, it is determined that the dopant having a very narrow energy bandgap compared to the host and the compound of the present disclosure have the most appropriate energy level difference, and that light emission is better achieved inside the light emitting layer by increasing the charge balance.

TABLE 6

| | Comparative Compound 1 | P-2 |
|---|---|---|
| Structure | 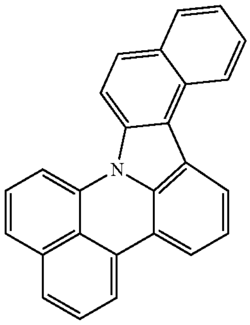 [SMILES: c1ccc2c(c1)ccc1c2c2cccc3c4cccc5cccc(c54)n1c32] | 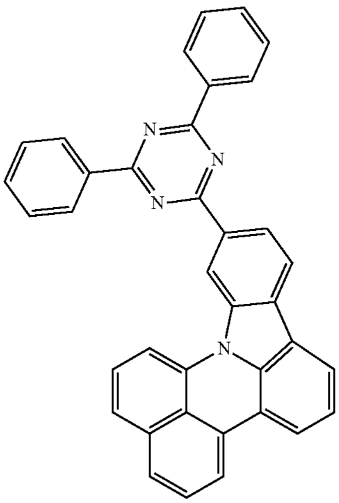 [SMILES: c1ccc(-c2nc(-c3ccccc3)nc(-c3ccc4c5cccc6c7cccc8cccc(c87)n(c4c3)c65)n2)cc1] |
| G. HOMO (eV) | −4.808 | −4.857 |
| G. LUMO (eV) | −1.732 | −2.017 |
| Band gap (eV) | −3.076 | −2.840 |

(Example 21) Red Organic Electroluminescent Device (a Hole Transport Layer)

First, $N^1$-(naphthalen-2-yl)-$N^4$,$N^4$-bis(4-(naphthalen-2-yl(phenyl)amino)phenyl)-N'-phenylbenzene-1,4-diamine (abbreviated as "2-TNATA") film was vacuum-deposited on top of an ITO layer (cathod) formed on a glass substrate and a hole injection layer with a thickness of 60 nm was first formed.

On top of the hole injection layer, the compound P-136 of the disclosure represented by Formula 1 was vacuum-deposited to a thickness of 60 nm to form a hole transport layer.

On top of the hole transport layer, a light emitting layer with a thickness of 30 nm was deposited by doping a dopant such that the weight ratio was 95:5, by using [4,4'-N,N'-dicarbazole-biphenyl] (hereinafter abbreviated as "CBP") as a host while using bis-(1-phenylisoquinolyl) iridium (III) acetylacetonate (hereinafter abbreviated as "$(piq)_2Ir(acac)$") as a dopant.

On top of the light emitting layer, (1,1'-biphenyl-4-olato) bis(2-methyl-8-quinolinolato)aluminum (hereinafter abbreviated as "BAlq") was vacuum-deposited to a thickness of 10 nm to form a hole blocking layer.

On top of the hole blocking layer, Tris-(8-hydroxyquinoline)aluminum (hereinafter abbreviated as "Alq3") was deposited on the hole blocking layer to a thickness of 40 nm to form an electron transport layer.

Thereafter, an electron injection layer was formed by depositing LiF to a thickness of 0.2 nm on top of the electron transport layer, and a anode was formed by depositing A1 to a thickness of 150 nm on top of the electron injection layer.

Examples 22 to 35

An organic electroluminescent device was manufactured in the same manner as in Example 21, except that the compound of the present disclosure listed in Table 7 below was used as the material for the hole transport layer, instead of compound P-136 of the present disclosure.

Comparative Example 2

An organic electroluminescent device was manufactured in the same manner as in Example 21, except that N,N'-bis (1-naphthalenyl)-N,N'-bis-phenyl-(1,1'-biphenyl)-4,4'-diamine (hereinafter abbreviated as "NPB") was used instead of compound P-136 of the present disclosure as the material for the hole transport layer.

The electroluminescence (EL) characteristics were measured with the PR-650 of Photo Research Inc., by applying a forward bias DC voltage to the organic electroluminescent devices manufactured according to Example 21 to 35 and Comparative Example 2, and as a result of the measurement, the T95 lifetime was measured using a lifetime measuring device manufactured by McScience at 2,500 cd/m$^2$ standard luminance. Table 7 below shows the manufactured devices and evaluation thereof.

T1) have suitable properties as a material for the hole transport layer, and thus, it acts as a major factor in improving device performances during device deposition (i.e., charge balance between holes and electrons, hole mobility, and electron mobility), resulting in improvement in driving voltage, efficiency, and lifetime.

In addition, in the evaluation results of the device manufacture, although the device characteristics in which the compounds of the present disclosure are applied only to a light emitting layer and a hole transport layer have been described, the compound of the present disclosure may be applied to one or more layers of the light emitting layer, the hole transport layer, and the auxiliary light emitting layer.

As can be seen from the results of Table 7, when a red organic light emitting device was manufactured using the material for an organic light emitting device of the present disclosure as a material for the hole transport layer, the driving voltage was lowered, and the luminous efficiency and lifetime were significantly improved, compared to when NPB was used.

This can be explained that the energy levels of the compounds of the present disclosure (e.g., HOMO, LUMO, T1) have suitable properties as a material for the hole transport layer, and thus, it acts as a major factor in improving device performances during device deposition (i.e., charge balance between holes and electrons, hole mobility, and electron mobility), resulting in improvement in driving voltage, efficiency, and lifetime.

In addition, in the evaluation results of the device manufacture, although the device characteristics in which the compounds of the present disclosure are applied only to a light emitting layer and a hole transport layer have been described, the compound of the present disclosure may be applied to one or more layers of the light emitting layer, the hole transport layer, and the auxiliary light emitting layer.

TABLE 7

| | Compound | Voltage (V) | Current Density (mA/cm$^2$) | Luminance (cd/m$^2$) | Efficiency (cd/A) | Lifetime T (95) | CIE x | CIE y |
|---|---|---|---|---|---|---|---|---|
| Comparative Example 2 | NPB | 6.8 | 35.2 | 2500.0 | 7.1 | 61.6 | 0.64 | 0.34 |
| Example 21 | P-136 | 5.3 | 13.4 | 2500.0 | 18.7 | 114.7 | 0.63 | 0.32 |
| Example 22 | P-137 | 5.3 | 13.0 | 2500.0 | 19.2 | 120.7 | 0.63 | 0.32 |
| Example 23 | P-141 | 5.2 | 12.2 | 2500.0 | 20.5 | 117.4 | 0.62 | 0.31 |
| Example 24 | P-142 | 5.3 | 11.6 | 2500.0 | 21.5 | 115.8 | 0.63 | 0.30 |
| Example 25 | P-152 | 5.3 | 14.0 | 2500.0 | 17.8 | 110.9 | 0.62 | 0.31 |
| Example 26 | P-153 | 5.3 | 13.4 | 2500.0 | 18.6 | 119.2 | 0.62 | 0.32 |
| Example 27 | P-159 | 5.3 | 14.0 | 2500.0 | 17.9 | 111.6 | 0.63 | 0.32 |
| Example 28 | P-169 | 5.4 | 12.3 | 2500.0 | 20.4 | 112.1 | 0.62 | 0.32 |
| Example 29 | P-180 | 5.3 | 11.9 | 2500.0 | 21.0 | 116.0 | 0.63 | 0.31 |
| Example 30 | P-181 | 5.2 | 13.0 | 2500.0 | 19.3 | 115.5 | 0.63 | 0.31 |
| Example 31 | P-184 | 5.2 | 13.3 | 2500.0 | 18.8 | 118.0 | 0.63 | 0.32 |
| Example 32 | P-187 | 5.3 | 12.6 | 2500.0 | 19.9 | 119.6 | 0.63 | 0.32 |
| Example 33 | P-189 | 5.4 | 12.0 | 2500.0 | 20.8 | 113.8 | 0.62 | 0.32 |
| Example 34 | P-196 | 5.3 | 13.8 | 2500.0 | 18.1 | 118.9 | 0.63 | 0.31 |
| Example 35 | P-203 | 5.3 | 12.1 | 2500.0 | 20.7 | 114.0 | 0.62 | 0.31 |

As can be seen from the results of Table 7, when a red organic light emitting device was manufactured using the material for an organic light emitting device of the present disclosure as a material for the hole transport layer material, the driving voltage was lowered, and the luminous efficiency and lifetime were significantly improved, compared to when NPB was used.

This can be explained that the energy levels of the compounds of the present disclosure (e.g., HOMO, LUMO, Code Explanation

100, 200, 300: organic electric device 110: first electrode
120: hole injection layer 130: hole transport layer
140: light emitting layer 150: electron transport layer
160: electron injection layer 170: second electrode
180: capping layer 210: buffer layer
220: auxiliary light emitting layer 320: first hole injection layer

330: first hole transport layer 340: first light emitting layer

350: first electron transport layer 360: first charge generation layer

361: second electron transport layer 420: second hole injection layer

430: second hole transport layer 440: second light emitting layer

450: second electron transport layer CGL: charge generation layer

ST1: first stack ST2: second stack

INDUSTRIAL APPLICABILITY

The present disclosure relates to a compound for an organic electric device, an organic electric device using the same, and an electronic device thereof.

What is claimed is:

1. A compound represented by Formula 1:

<Formula 1>

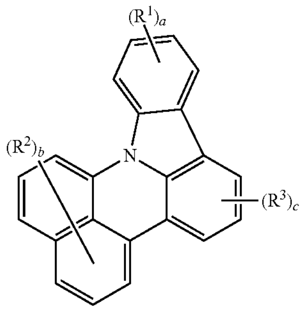

wherein:

1) $R^1$ to $R^3$ are each independently selected from the group consisting of hydrogen; deuterium; a halogen; an amino group; a cyano group; a nitro group; a $C_{6-60}$ aryl group; a fluorenyl group; a $C_{2-60}$ heterocyclic group comprising at least one heteroatom among O, N, S, Si, and P; a fused ring group between a $C_{3-60}$ aliphatic ring and a $C_{6-60}$ aromatic ring; a $C_{1-50}$ alkyl group; a $C_{2-20}$ alkenyl group; a $C_{2-20}$ alkynyl group; a $C_{1-30}$ alkoxyl group; a $C_{6-30}$ aryloxy group; Formula 1-1; Formula 1-2; and Formula 1-3, or adjacent groups thereof can bind to one another to form a ring, wherein at least one of $R^1$ to $R^3$ is any one of Formula 1-1 to Formula 1-3:

<Formula 1-1>

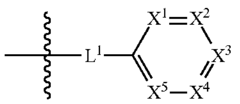

<Formula 1-2>

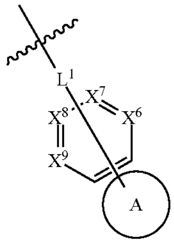

-continued

<Formula 1-3>

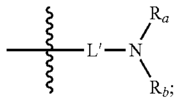

2) L' is selected from the group consisting of a single bond; a $C_{6-60}$ arylene group; a fluorenylene group; a fused ring group between a $C_{3-60}$ aliphatic ring and a $C_{6-60}$ aromatic ring; a $C_{2-60}$ heterocyclic group comprising at least one heteroatom among O, N, S, Si, and P; and a combination thereof; and 3) $R_a$ and $R_b$ are each independently selected from the group consisting of a $C_{6-60}$ aryl group; a fluorenyl group; a $C_{3-60}$ aliphatic ring group; a $C_{2-60}$ heterocyclic group comprising at least one heteroatom among O, N, S, Si, and P; and a combination thereof;

4) A is an integer of 0 to 4; b is an integer of 0 to 6; c is an integer of 0 to 3; and a+b+c is greater than or equal to 1;

5) When a, b, and care 2 or greater, a plurality of $R^1$ to $R^3$ are the same as or different from one another, and a plurality of $R^1$, or a plurality of $R^2$, or a plurality of $R^3$ may bind to one another to form a ring;

6) $X^1$ to $X^9$ are each independently N or $C(R_c)$;

7) at least one of $X^1$ to $X^5$ and at least one of $X^6$ to $X^9$ are N;

8) $L^1$ is selected from the group consisting of a single bond; a $C_{6-60}$ arylene group; a fluorenylene group; a fused ring group between a $C_{3-60}$ aliphatic ring and a $C_{6-60}$ aromatic ring; a $C_{2-60}$ heterocyclic group comprising at least one heteroatom among O, N, S, Si, and P; and a combination thereof;

9) $R^c$ is selected from the group consisting of hydrogen; deuterium; a halogen; an amino group; a cyano group; a nitro group; a $C_{6-60}$ aryl group; a fluorenyl group; a $C_{2-60}$ heterocyclic group comprising at least one heteroatom among O, N, S, Si, and P; a fused ring group between a $C_{3-60}$ aliphatic ring and a $C_{6-60}$ aromatic ring; a $C_{1-50}$ alkyl group; a $C_{2-20}$ alkenyl group; a $C_{2-20}$ alkynyl group; a $C_{1-30}$ alkoxyl group; a $C_{6-30}$ aryloxy group; and —L'—$N(R_c)(R_d)$;

10) the definitions of $R_c$ and $R_d$ are the same as those of $R_a$ and $R_b$ above;

11) the ring A of Formula 1-2 is selected from the group consisting of Formula A-1 to Formula A-16:

<Formula A-1>

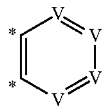

<Formula A-2>

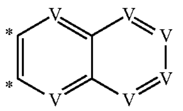

<Formula A-3>

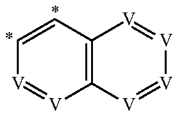

-continued

<Formula A-4>

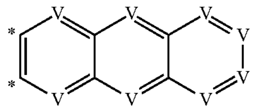

<Formula A-5>

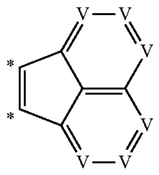

<Formula A-6>

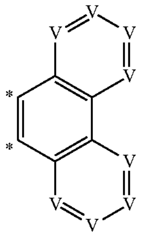

<Formula A-7>

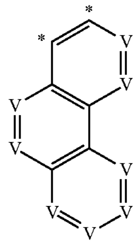

<Formula A-8>

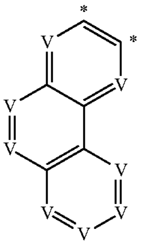

<Formula A-9>

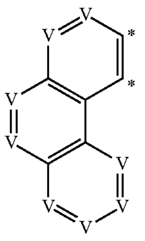

<Formula A-10>

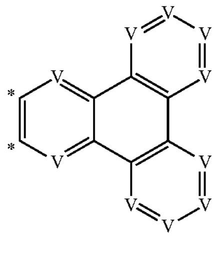

-continued

<Formula A-11>

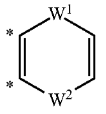

<Formula A-12>

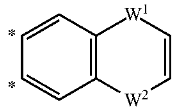

<Formula A-13>

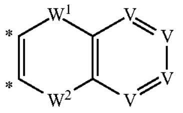

<Formula A-14>

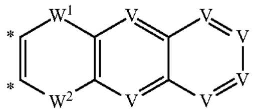

<Formula A-15>

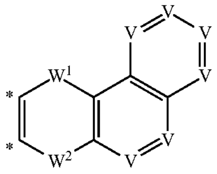

<Formula A-16>

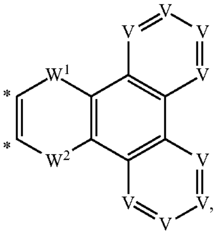

wherein:

11-1) * is a site to be bound to a ring comprising $X^6$ to $X^9$;

11-2) V is N or $C(R^e)$;

11-3) $W^1$ and $W^2$ are each independently a single bond, —N—$L^3$-$Ar^3$, S, O, or CR'R", with the proviso that $W^1$ and $W^2$ are not a single bond at the same time;

11-4) $L^3$ is the same as the definition of $L^1$ in Formula 1;

11-5) $Ar^3$ is selected from the group consisting of a $C_{6-60}$ aryl group; a fluorenyl group; a fused ring group between a $C_{3-60}$ aliphatic ring and a $C_{6-60}$ aromatic ring; a $C_{2-60}$ heterocyclic group comprising at least one heteroatom among O, N, S, Si, and P; and a combination thereof; and 11-6) $R^e$, R', and R" are each selected from the group consisting of hydrogen; deuterium; a halogen; an amino group; a cyano group; a nitro group; a $C_{6-60}$ aryl group; a fluorenyl group; a $C_{2-60}$ heterocyclic group comprising at least one heteroatom among O, N, S, Si, and P; a fused ring group between a $C_{3-60}$ aliphatic ring and a $C_{6-60}$ aromatic ring; a $C_{1-50}$ alkyl group; a $C_{2-20}$ alkenyl group; a $C_{2-20}$ alkynyl group; a $C_{1-30}$ alkoxyl group; a $C_{6-30}$ aryloxy group; or —L'—$N(R_c)(R_d)$; or these groups can bind to one another to form a ring; or R' and R" can bind to one another to form a spiro ring; and 12) The rings formed by $R^1$ to $R^3$, $L^1$, L', $L^3$, $Ar^3$, $R_a$ to $R_d$, $R^c$, $R^e$, R', R", and adjacent groups thereof can be each further substituted with one or more substituents selected from the group consisting of deuterium; a halogen; a silane group substituted or unsubstituted with a $C_{1-20}$ alkyl group or a $C_{6-20}$ aryl group; a siloxane group; a boron group; a germanium group; a cyano group; an amino group; a nitro group; a $C_{1-20}$ alkylthio group; a $C_{1-20}$ alkoxy group; a $C_{6-20}$ arylalkoxy group; a $C_{1-20}$ alkyl group; a $C_{2-20}$ alkenyl group; a $C_{2-20}$ alkynyl group; a $C_{6-20}$ aryl group; a $C_{6-20}$ aryl group substituted with a deuterium; a fluorenyl group; a $C_{2-20}$ heterocyclic group comprising at least one heteroatom among O, N, S, Si, and P; a $C_{3-20}$ aliphatic ring group; a $C_{7-20}$ arylalkyl group; a $C_{8-20}$ arylalkenyl group; and a combination thereof; or adjacent groups thereof can form a ring with one another.

2. The compound of claim 1, wherein the compound of Formula 1-1 or Formula 1-2 is represented by one of Formula B-1 to Formula B-12:

B-1

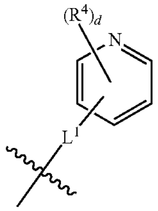

B-2

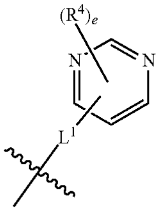

B-3

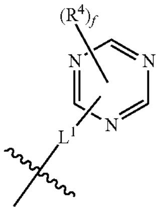

B-4

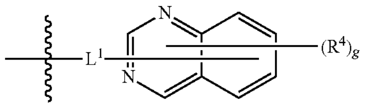

B-5

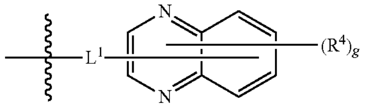

B-6

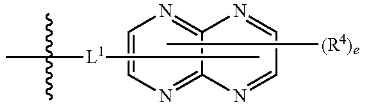

B-7

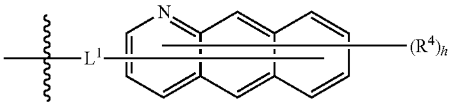

-continued

B-8

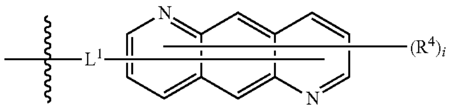

B-9

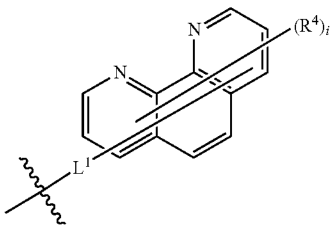

B-10

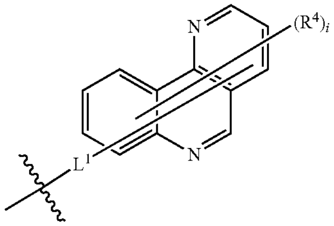

B-11

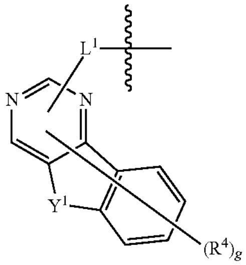

B-12

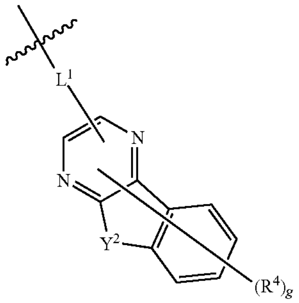

wherein:

1) $R^4$ is the same as the definition of $R^1$ of Formula 1 of claim 1;

2) $Y^1$ and $Y^2$ are each independently —N—$L^3$—$Ar^3$, S, O, or CR'R";

3) d is an integer of 0 to 4; e is an integer of 0 to 3; f is an integer of 0 to 2; g is an integer of 0 to 5; h is an integer of 0 to 8; and i is an integer of 0 to 7; and 4) $L^1$, $L^3$, $Ar^3$, R', and R" are the same as defined in Formula 1 of claim 1.

3. The compound of claim 1, wherein the compound of Formula 1 is represented by one of Formula P-1 to Formula P-212:

P-1
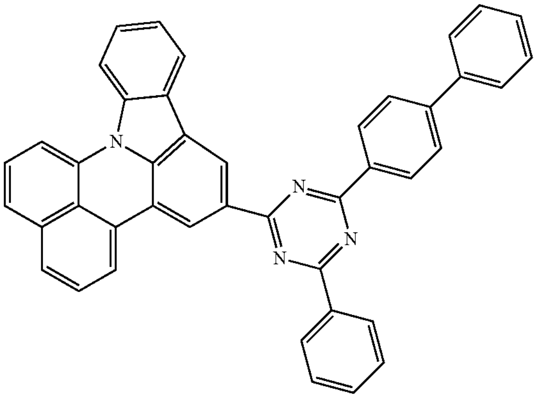
P-2
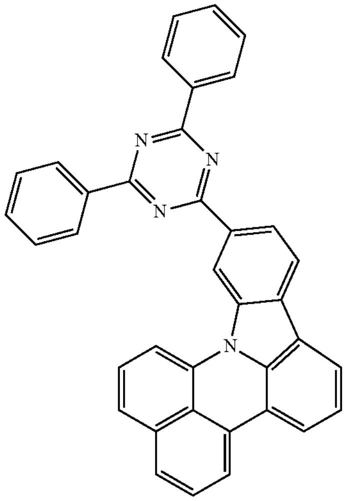
P-3
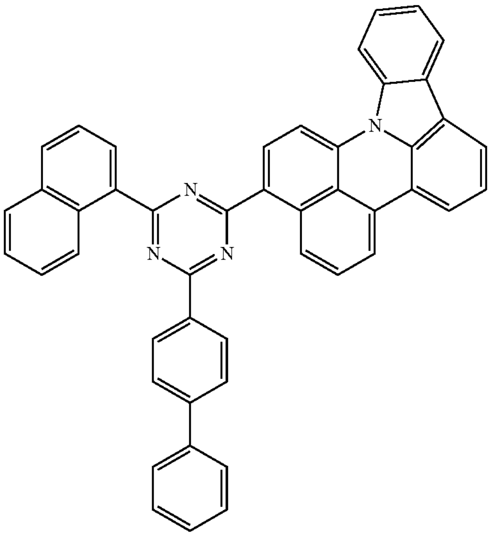
P-4
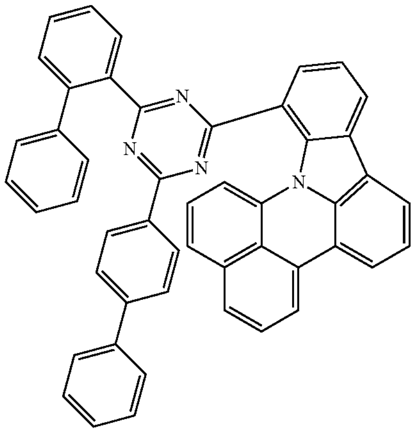
P-5
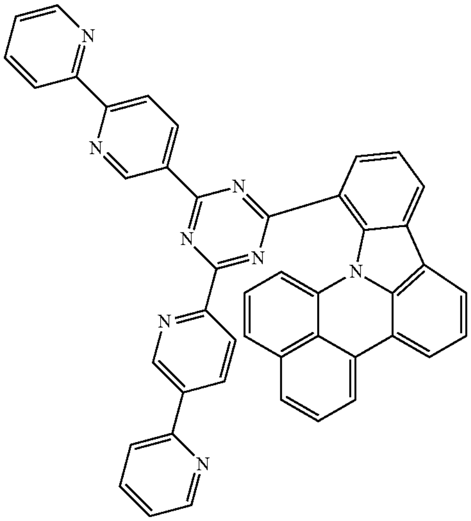
P-6
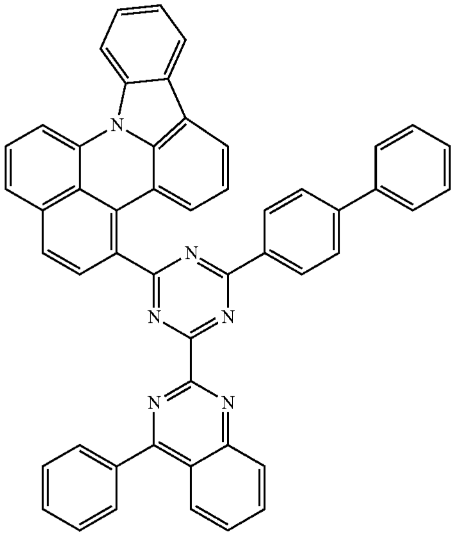

-continued
P-7
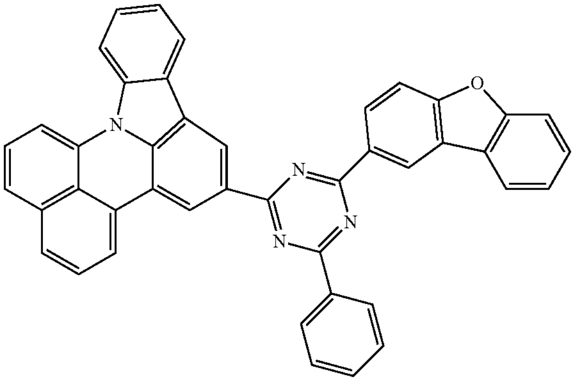
P-8
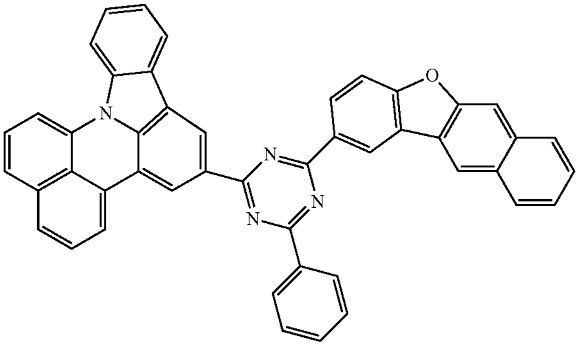
P-9
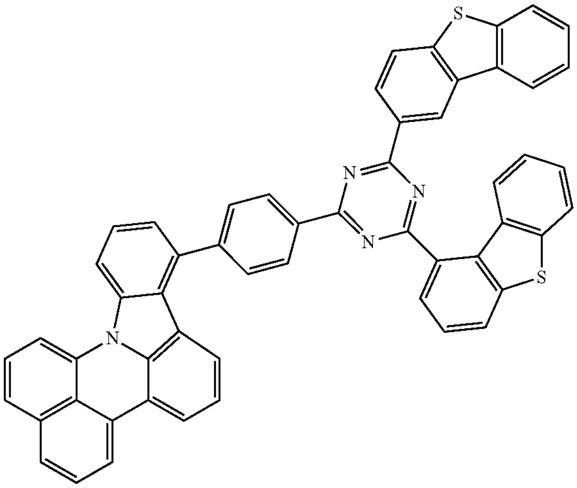
P-10
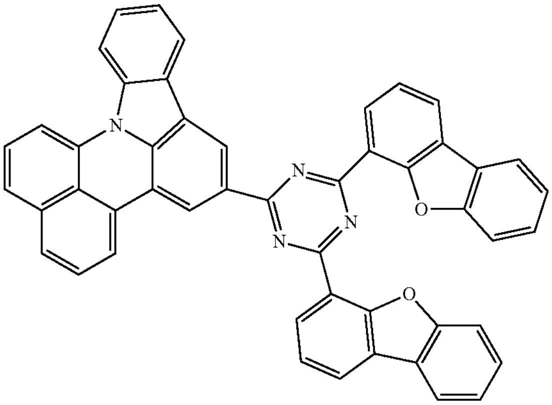
P-11
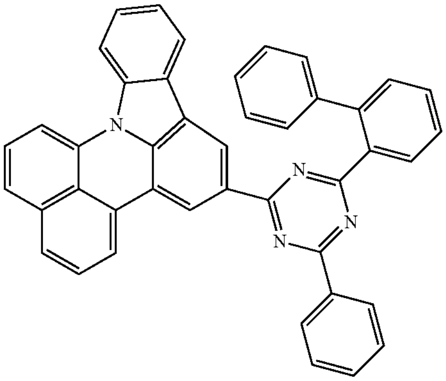
P-12
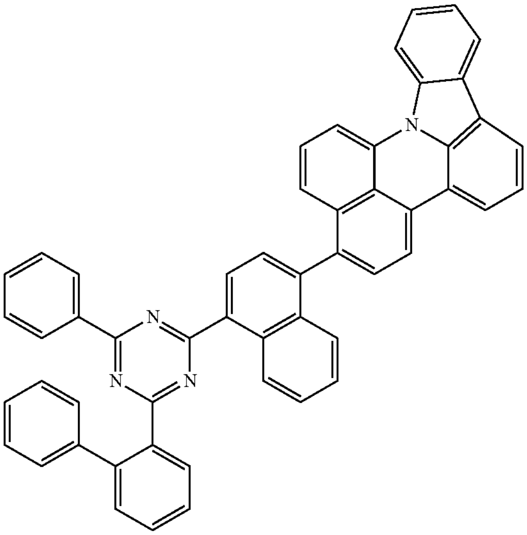

-continued
P-13
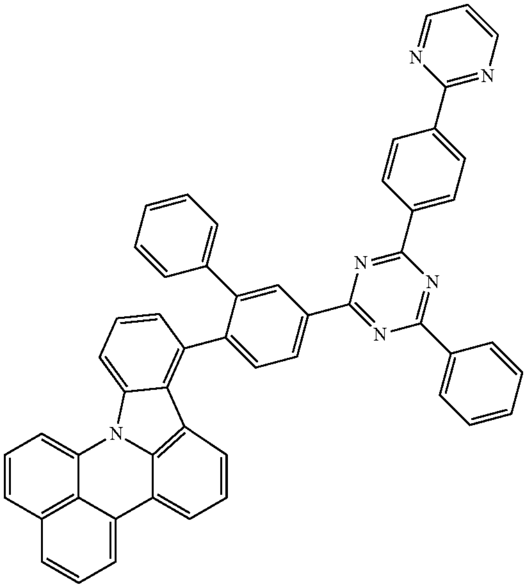
P-14
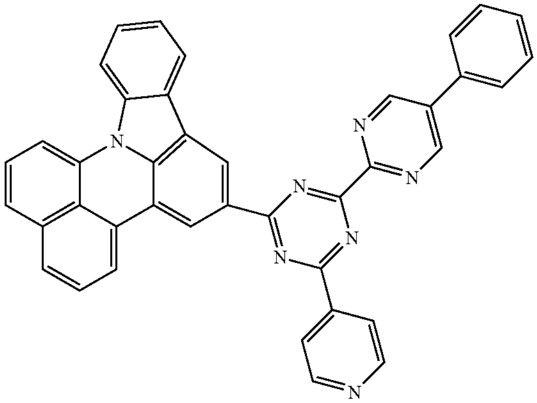
P-15
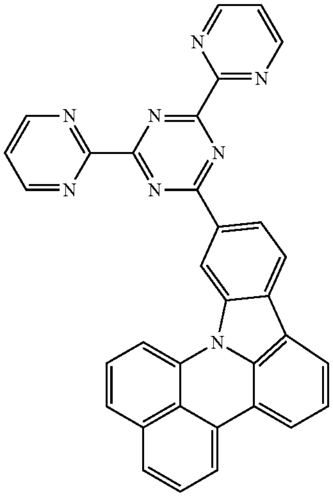
P-16
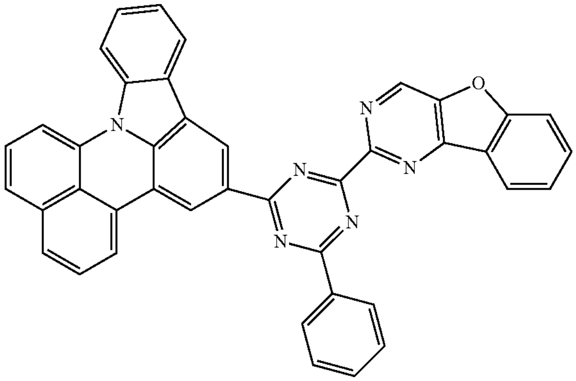
P-17
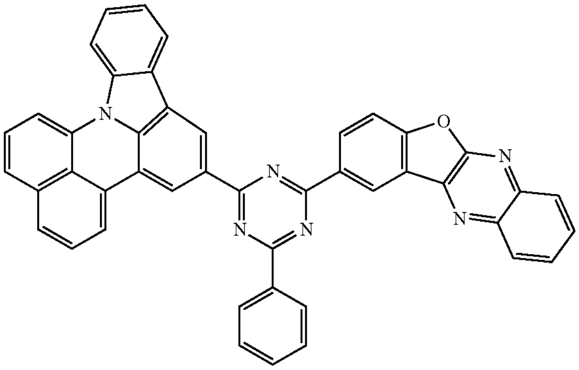
P-18
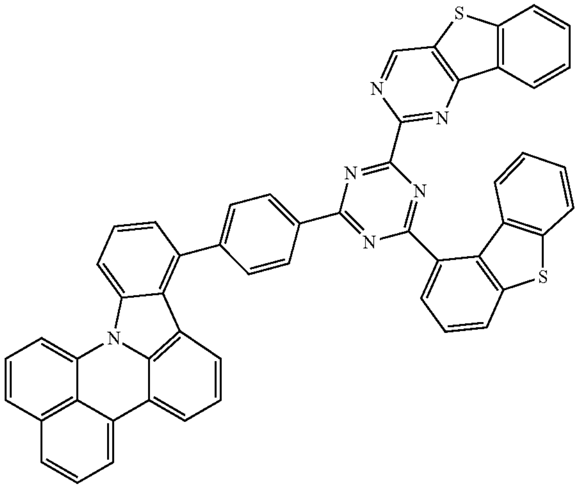

-continued
P-19
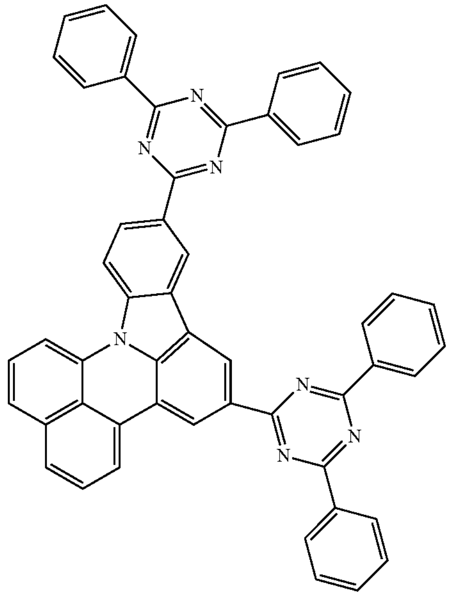
P-20
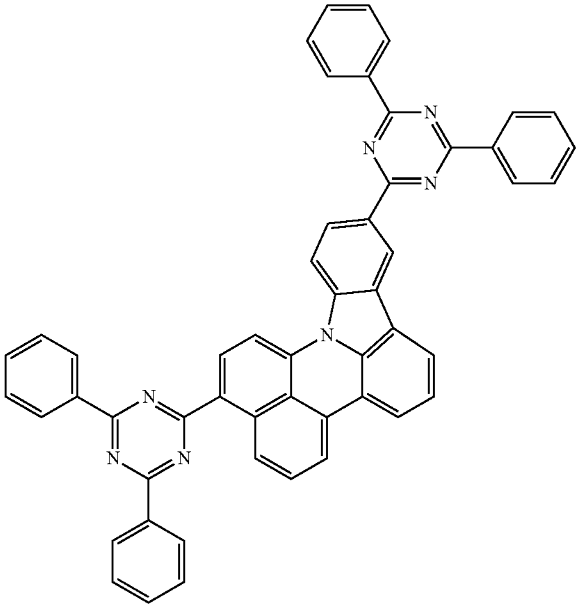
P-21
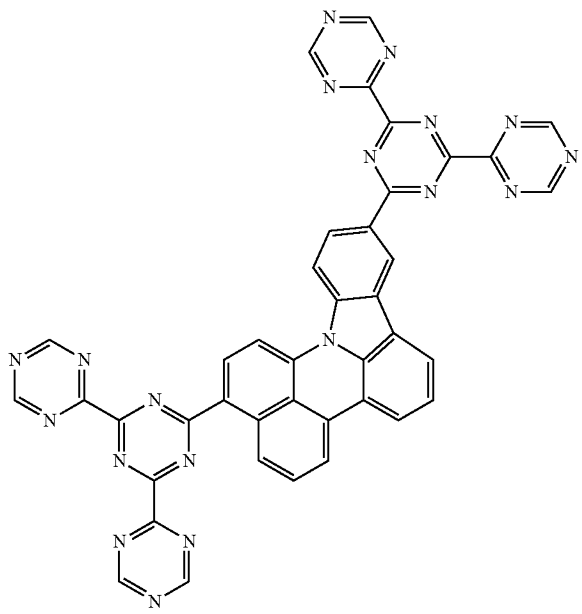
P-22
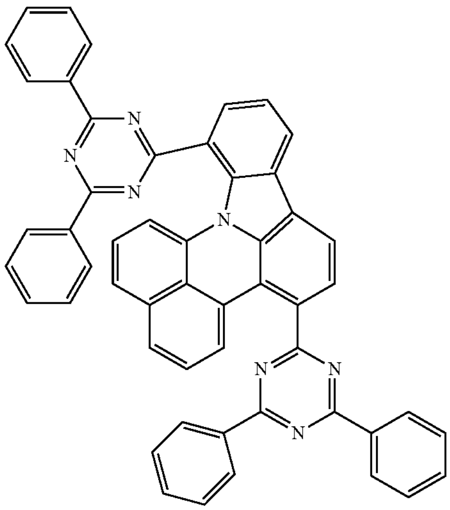

-continued
P-23
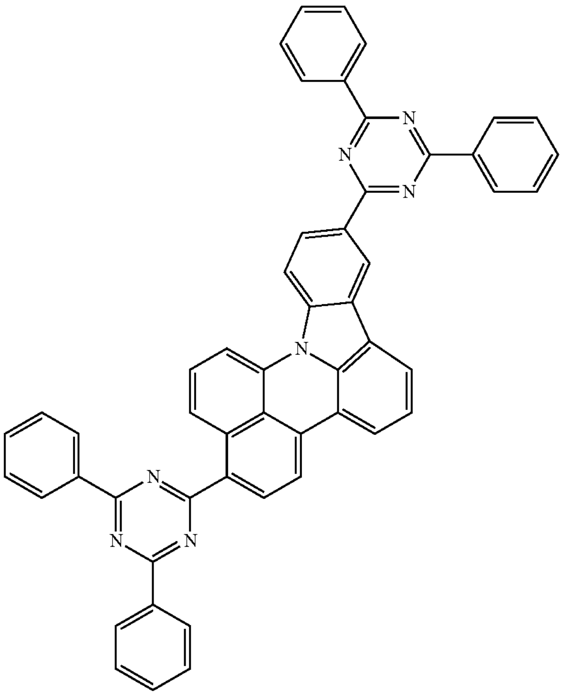
P-24
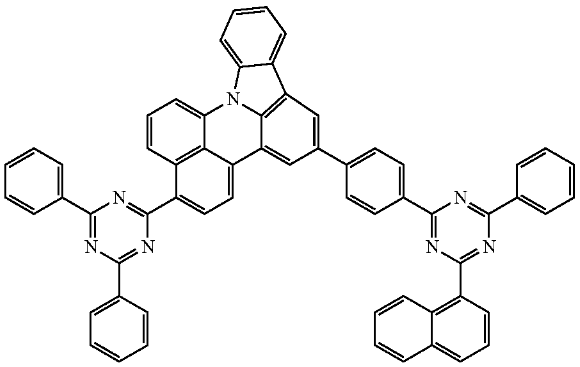
P-25
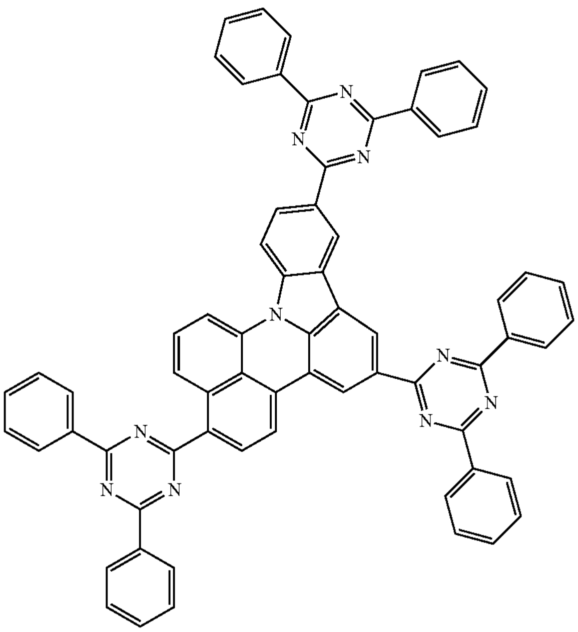
P-26
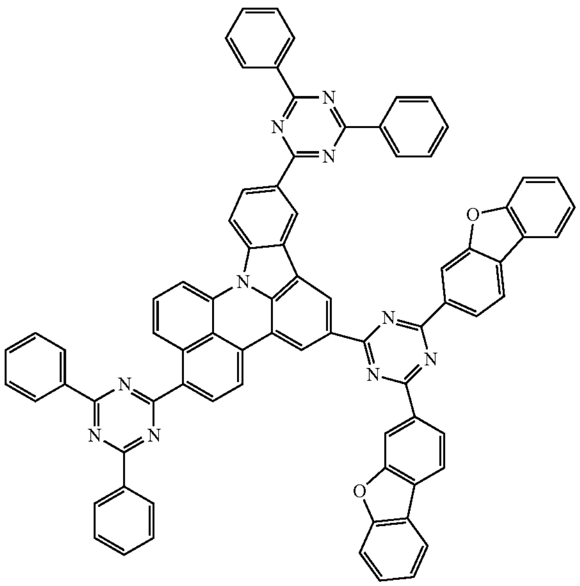

-continued
P-27
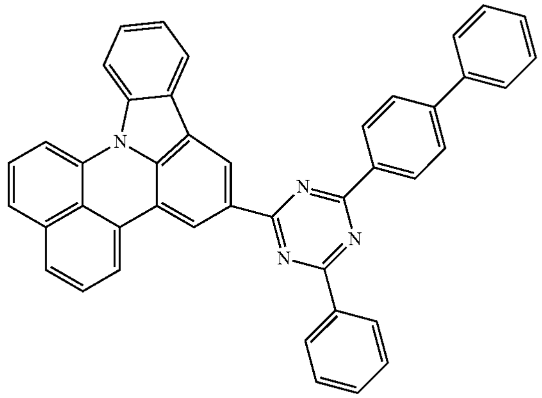
P-28
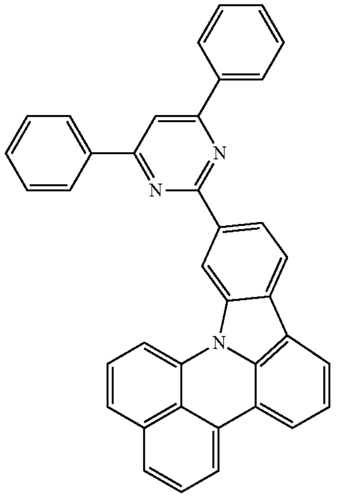
P-29
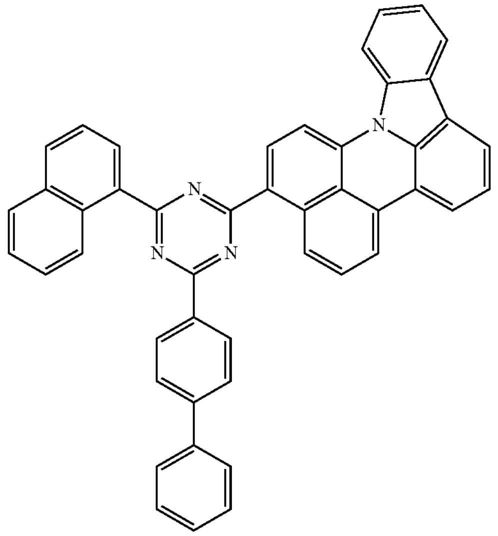
P-30
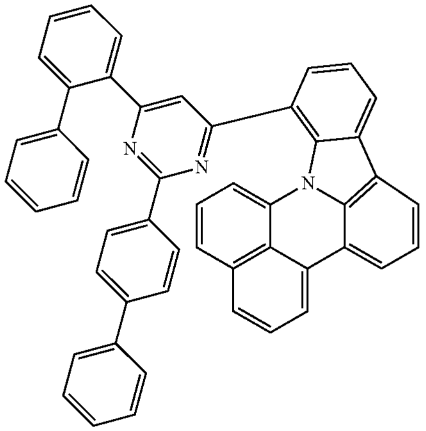
P-31
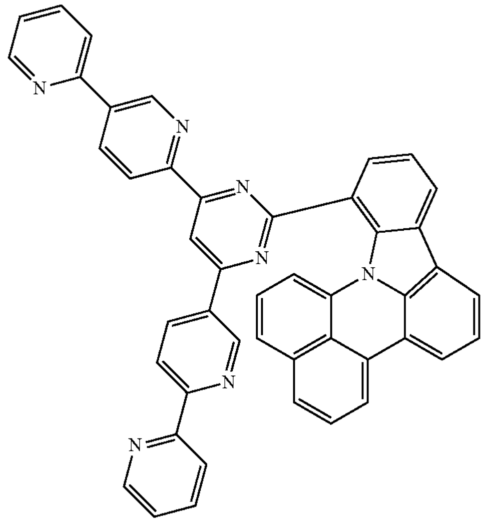
P-32
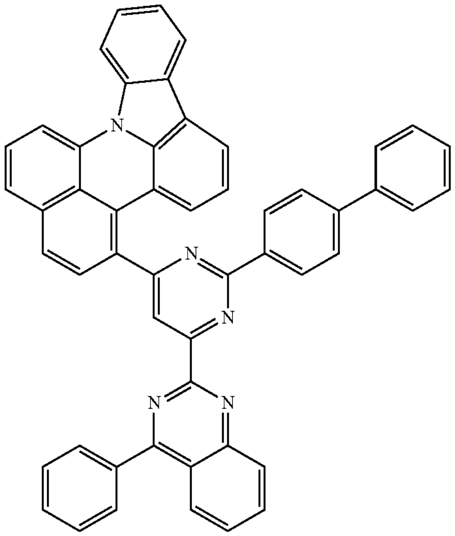

-continued
P-33
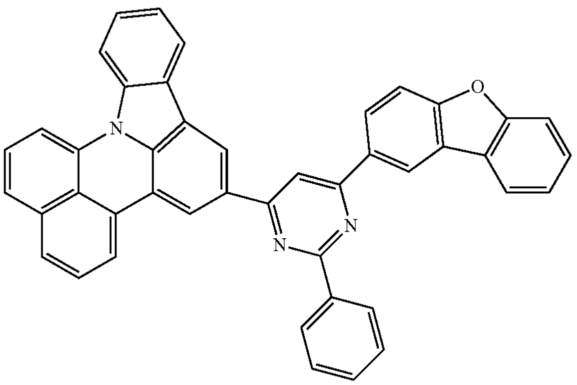
P-34
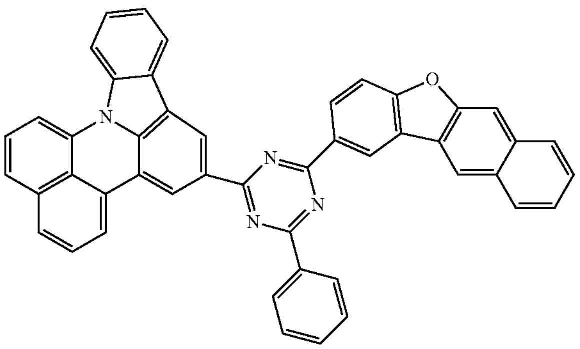
P-35
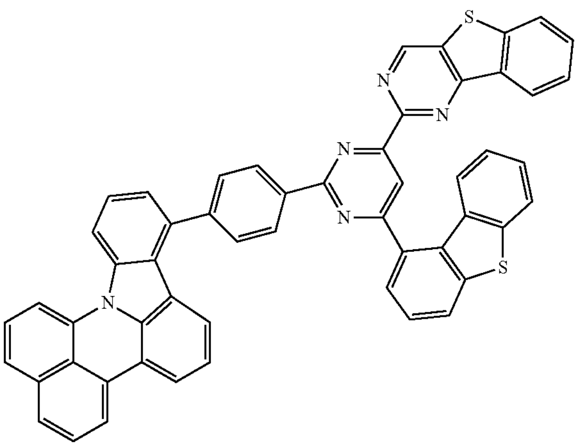
P-36
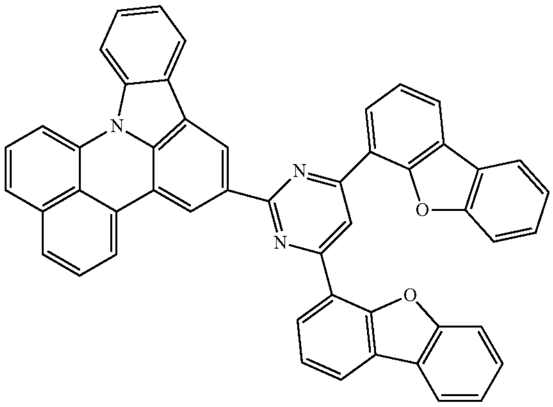
P-37
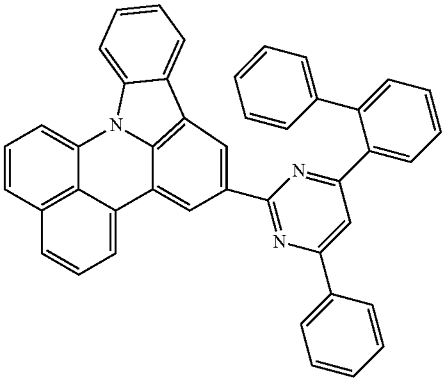
P-38
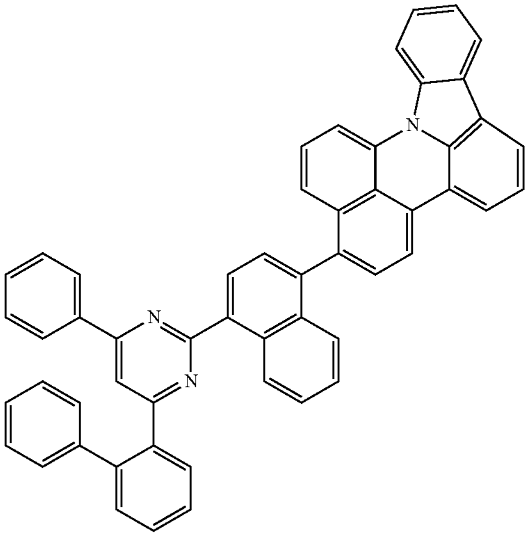

-continued
P-39
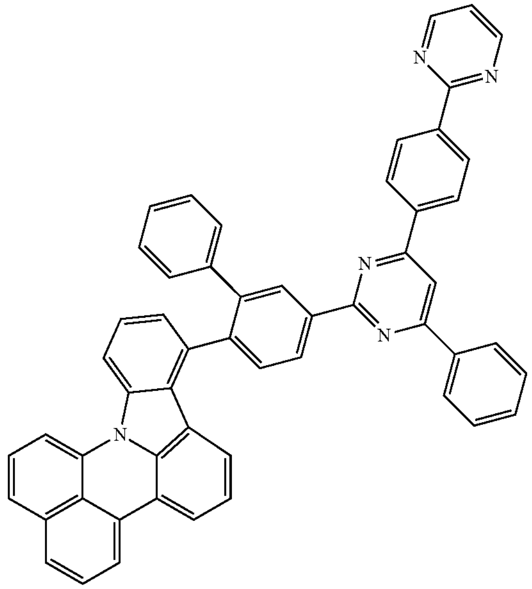
P-40
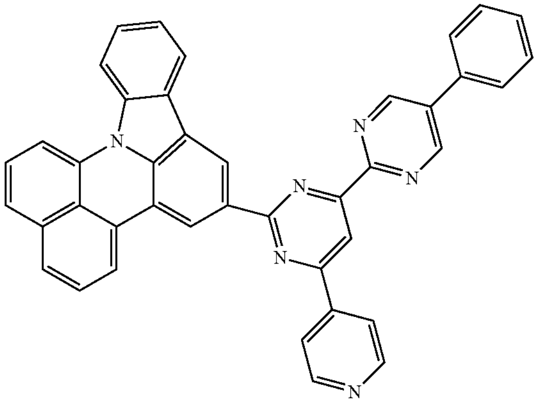
P-41
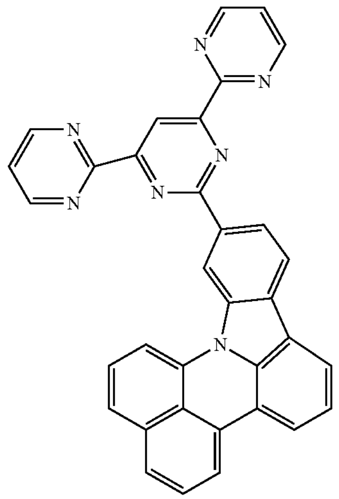
P-42
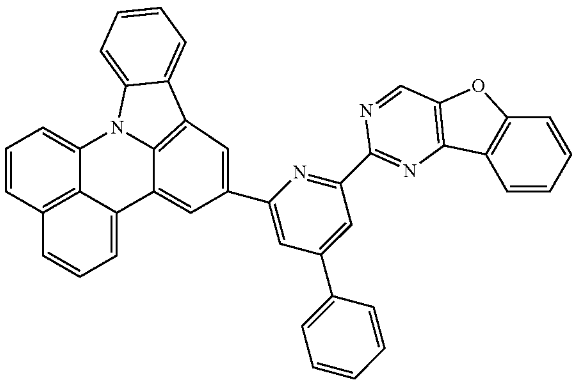
P-43
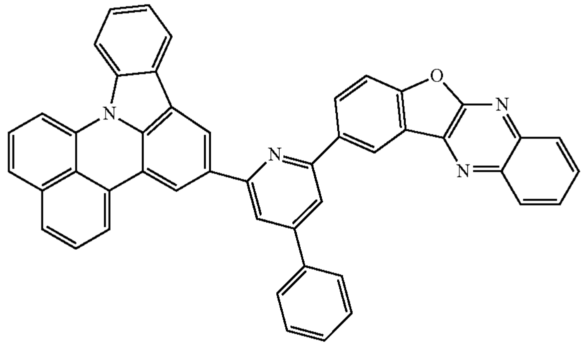
P-44
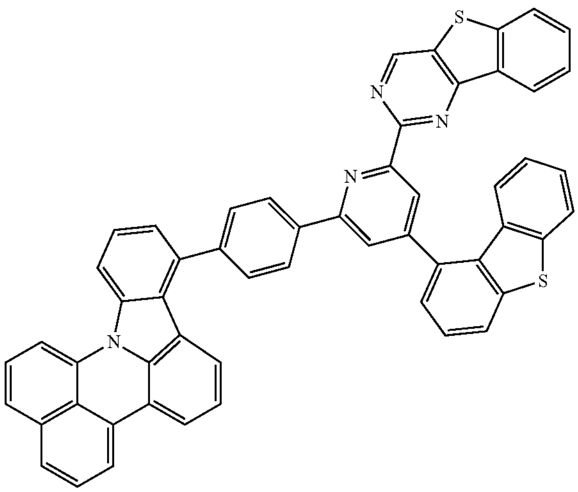

-continued
P-45
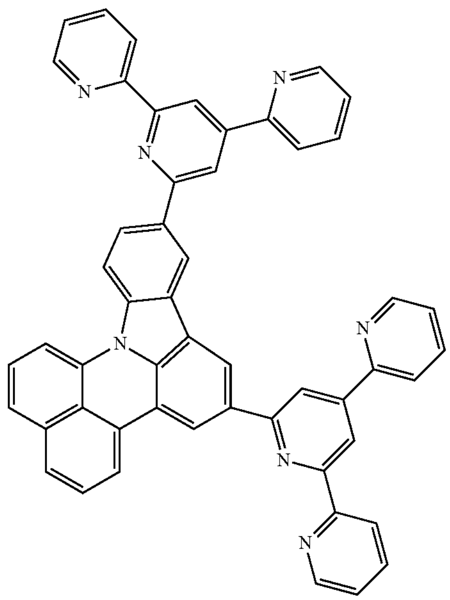
P-46
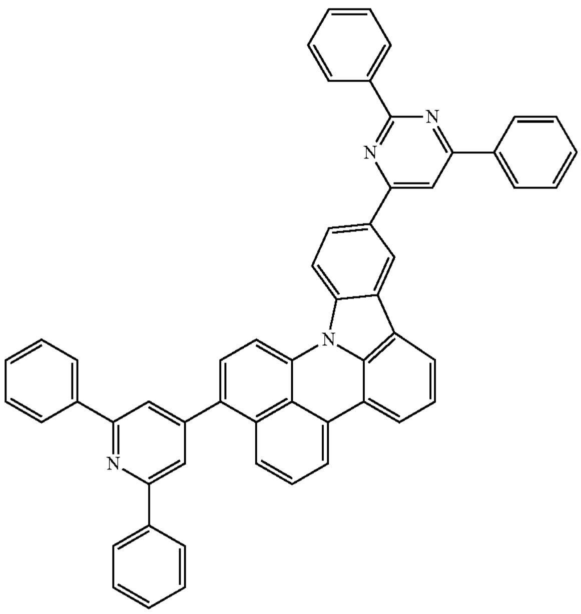
P-47
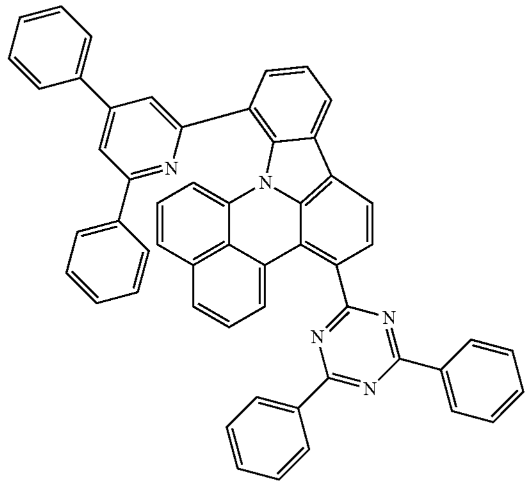
P-48
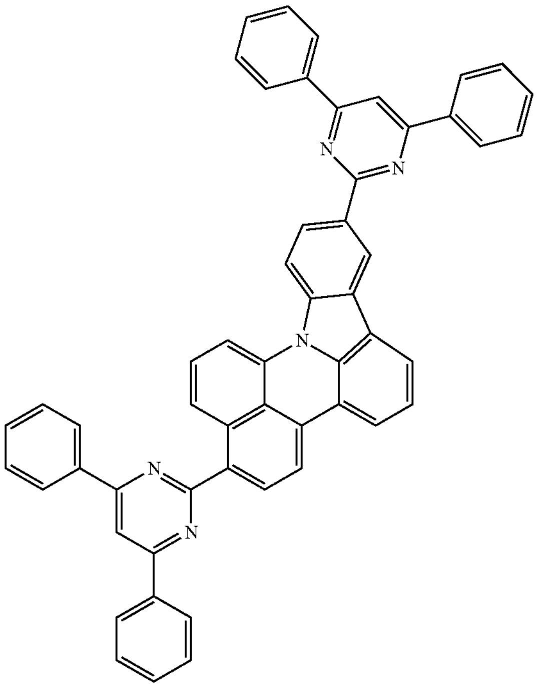

-continued
P-49
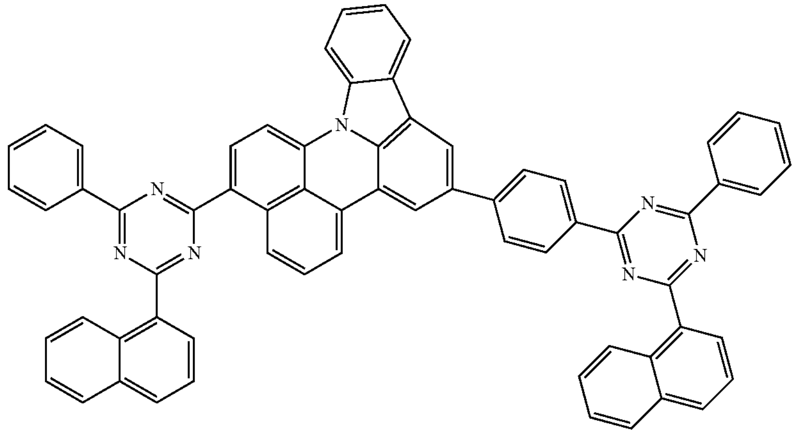
P-50
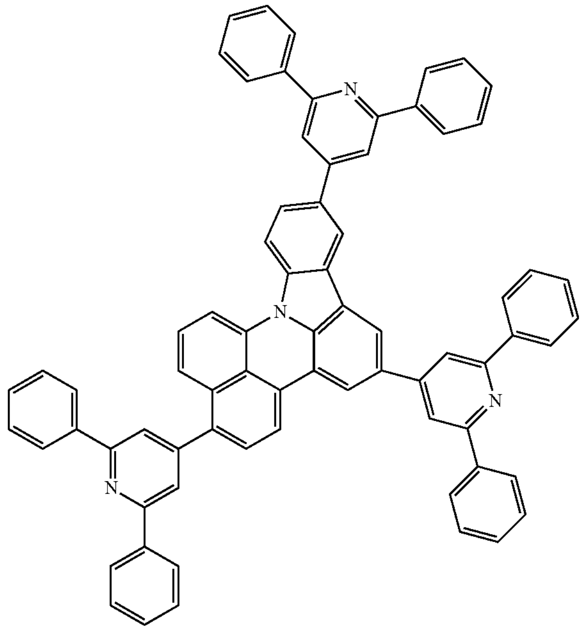
P-51
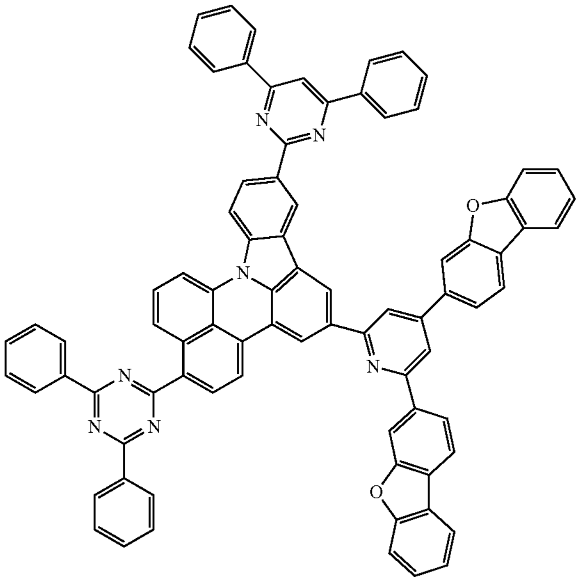
P-52
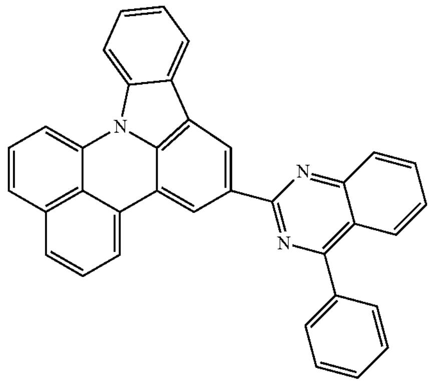
P-53
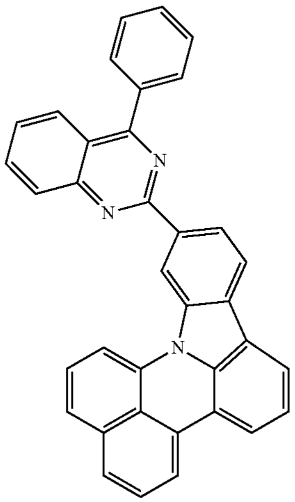

-continued
P-54
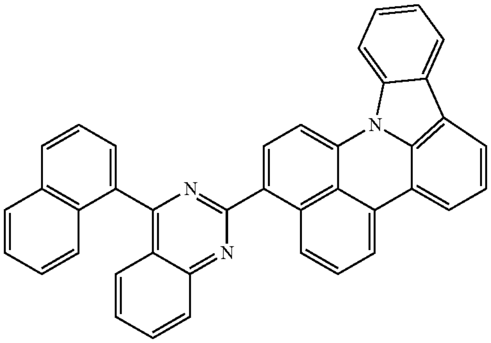
P-55
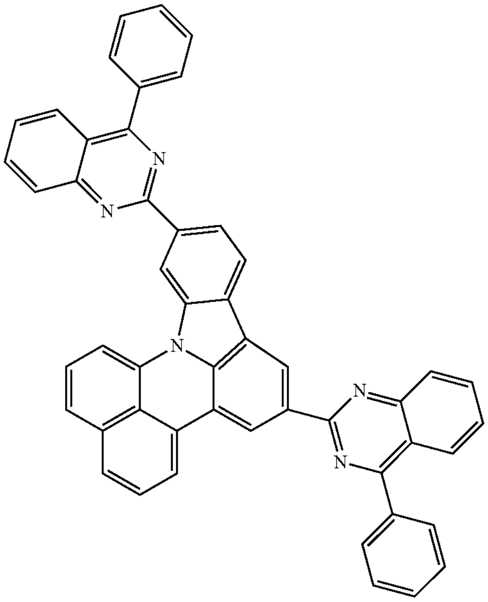
P-56
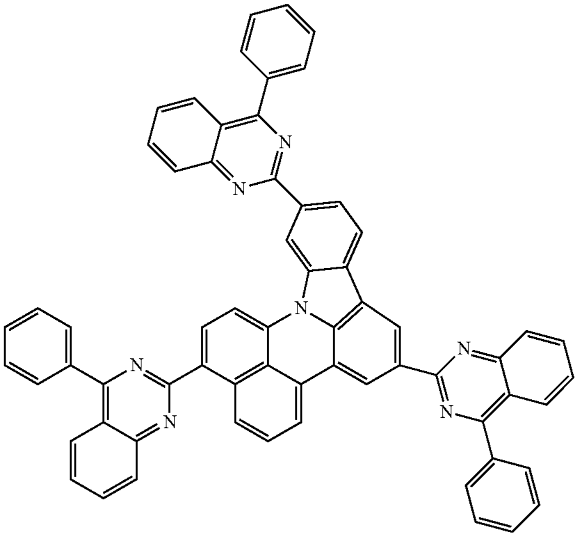
P-57
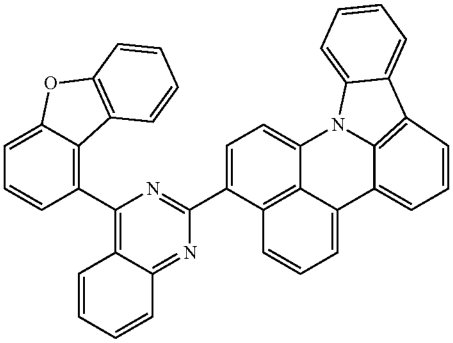
P-58
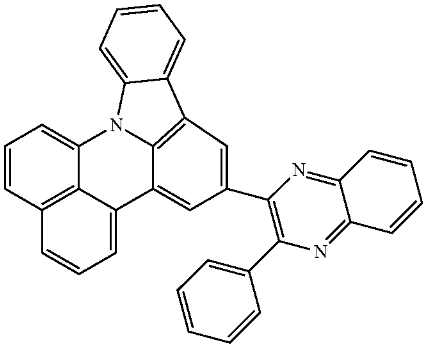
P-59
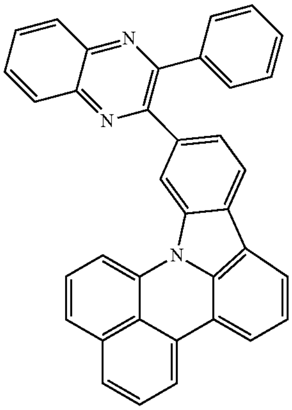

-continued
P-60
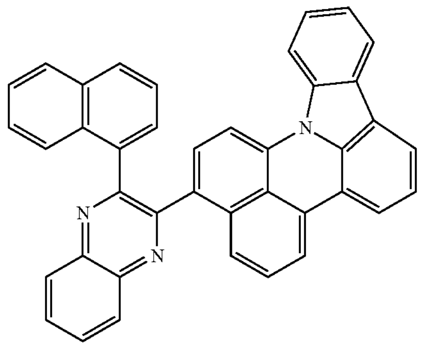
P-61
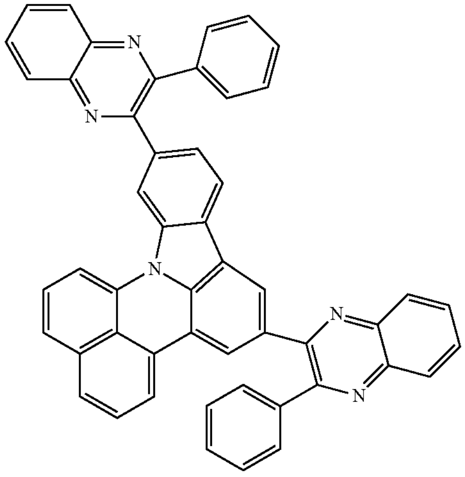
P-62
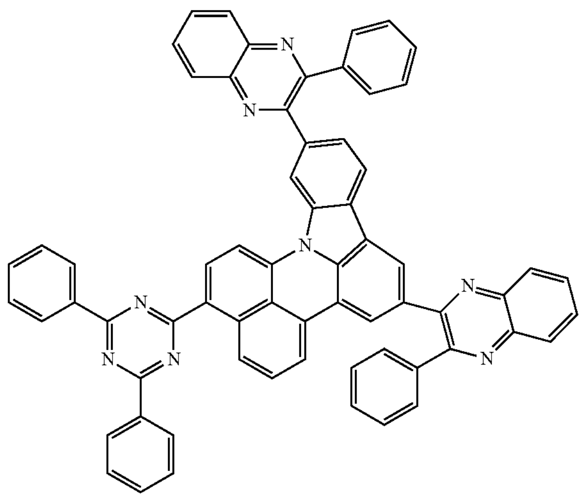
P-63
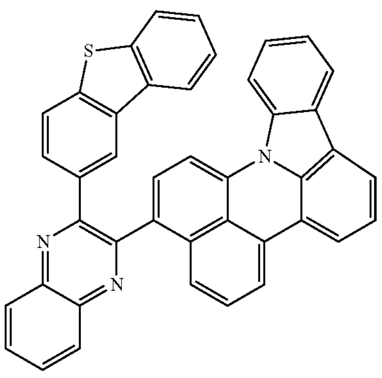
P-64
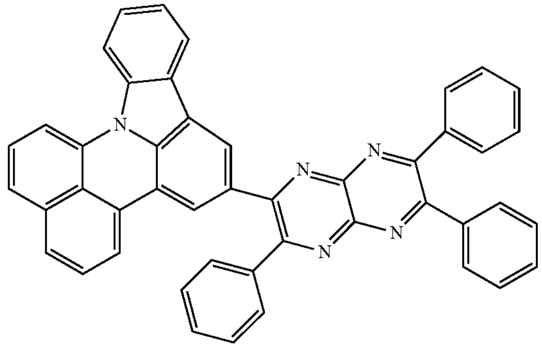
P-65
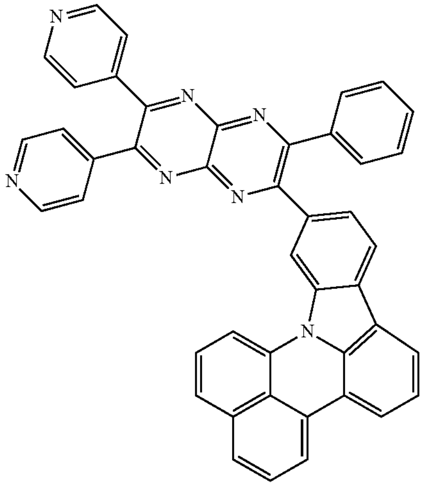

-continued
P-66
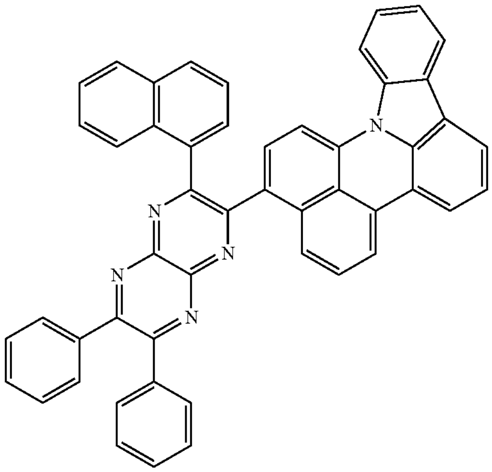
P-67
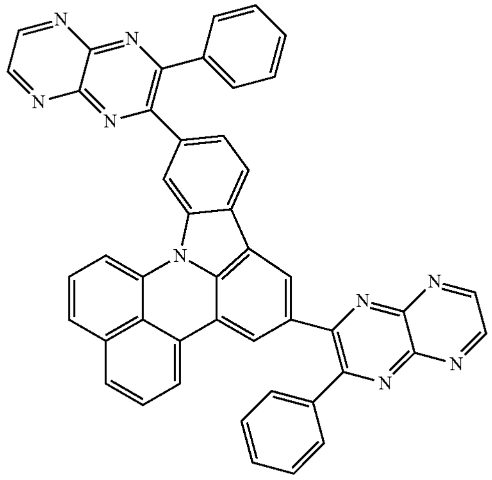
P-68
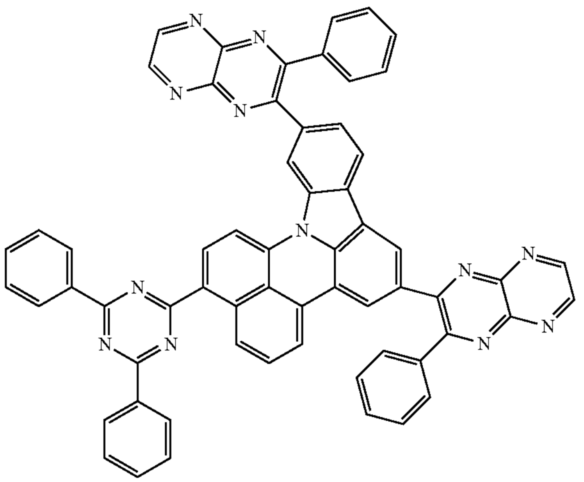
P-69
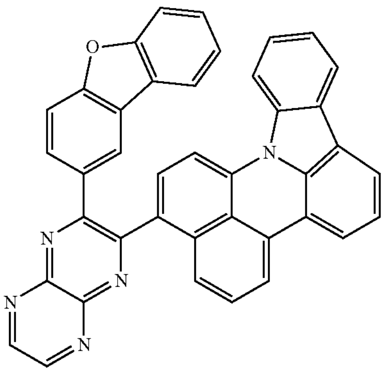
P-70
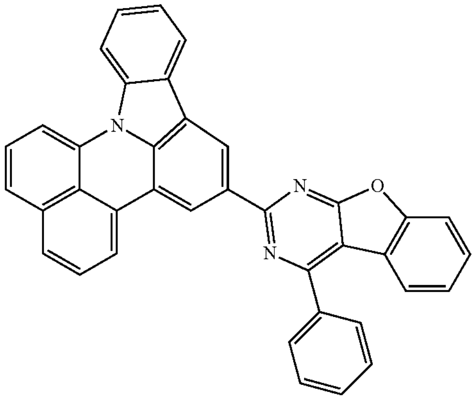
P-71
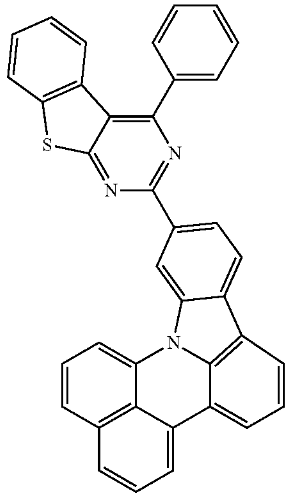

-continued
P-72
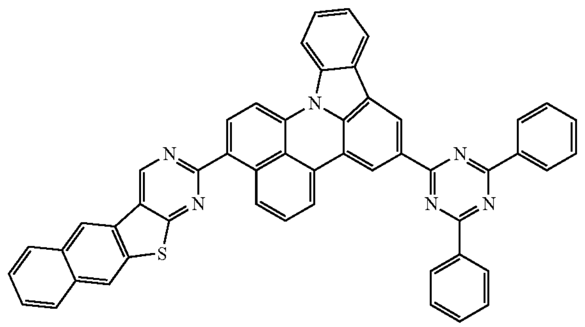
P-73
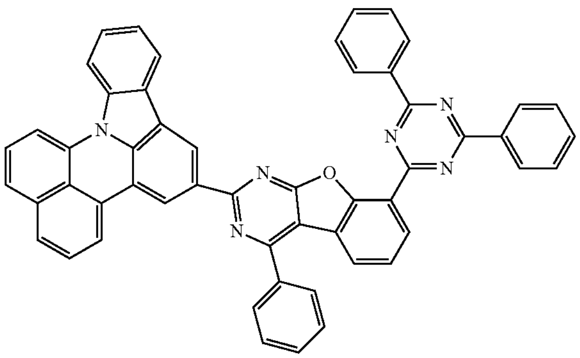
P-74
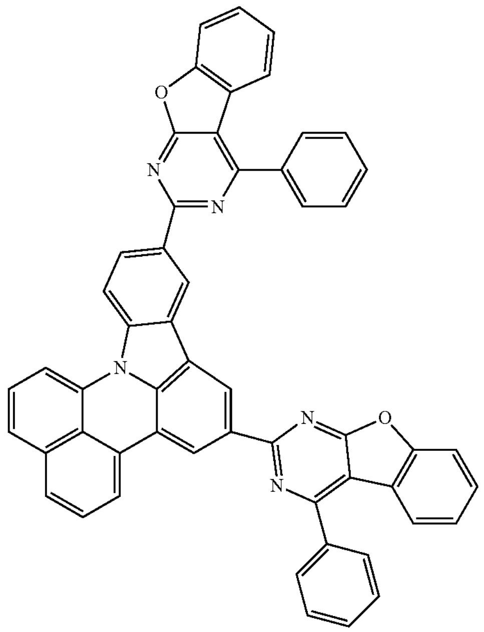
P-75
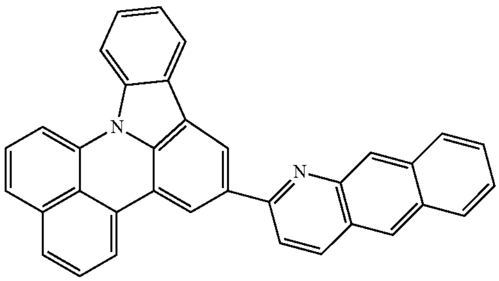
P-76
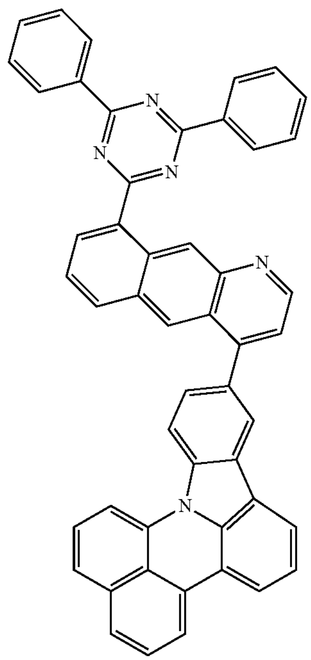
P-77
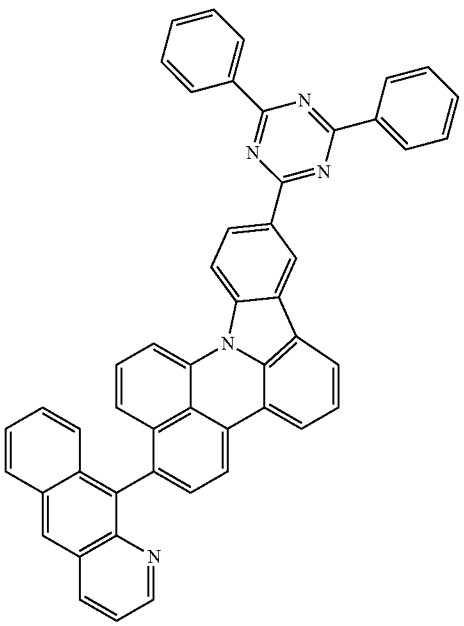

-continued
P-78
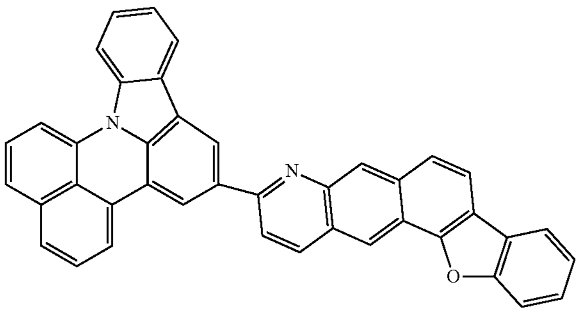
P-79
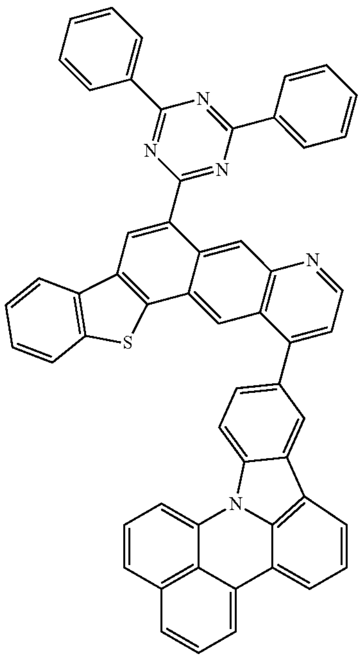
P-80
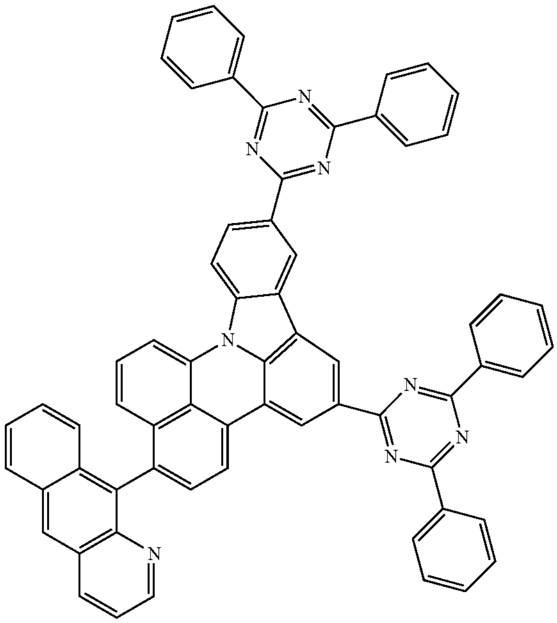
P-81
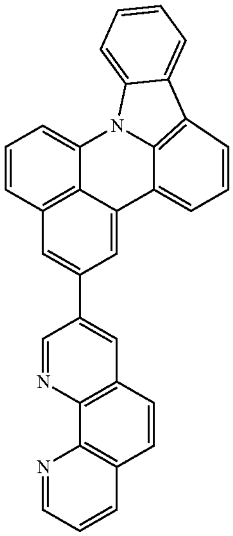

-continued
P-82
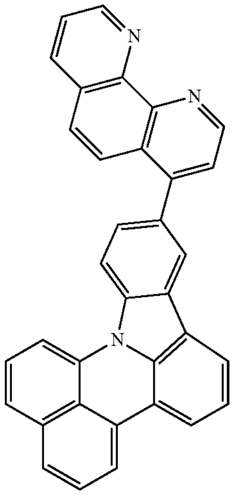
P-83
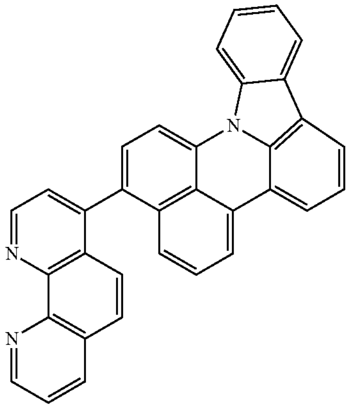
P-84
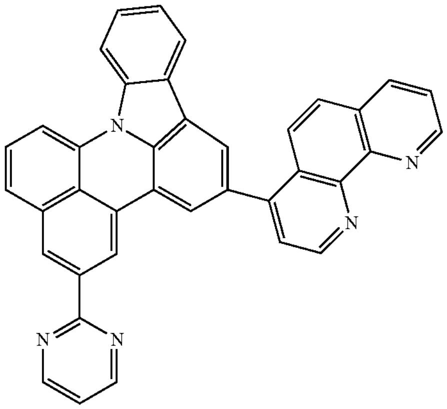
P-85
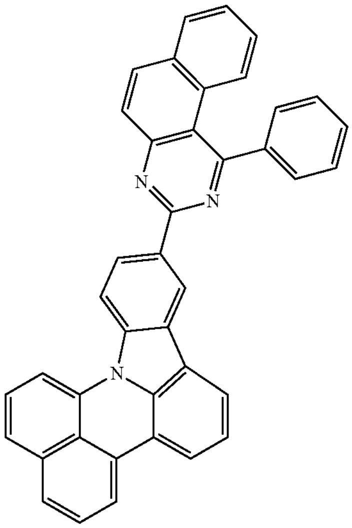
P-86
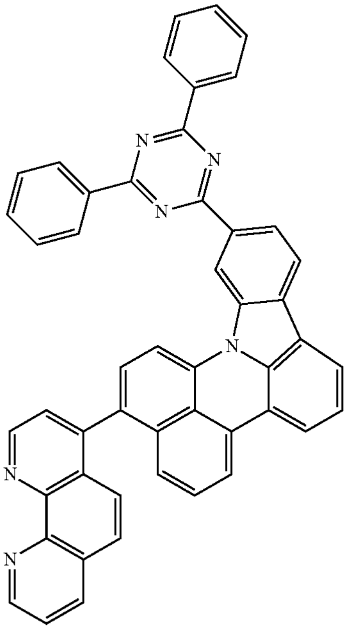
P-87
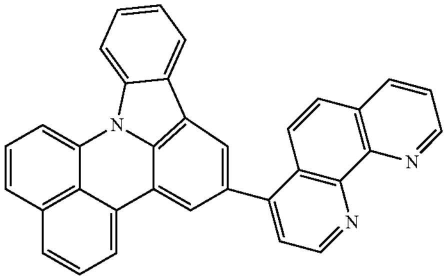

-continued
P-88
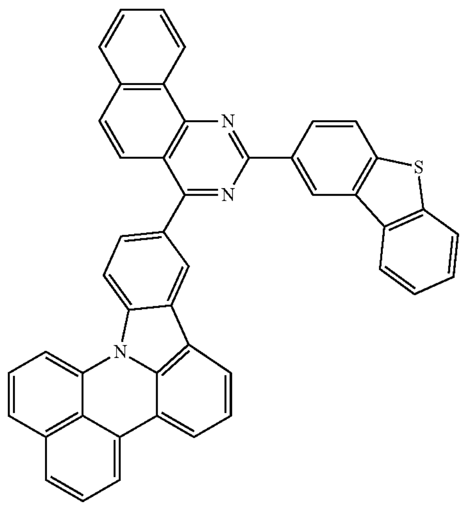
P-89
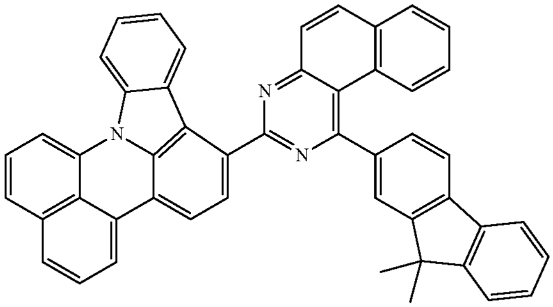
P-90
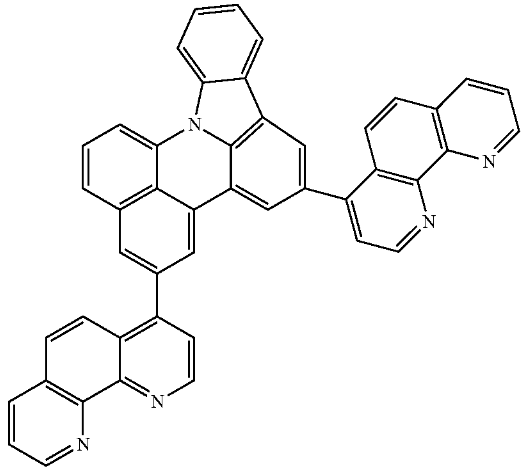
P-91
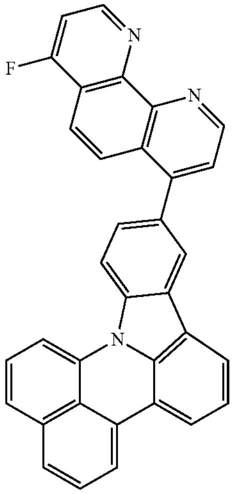
P-92
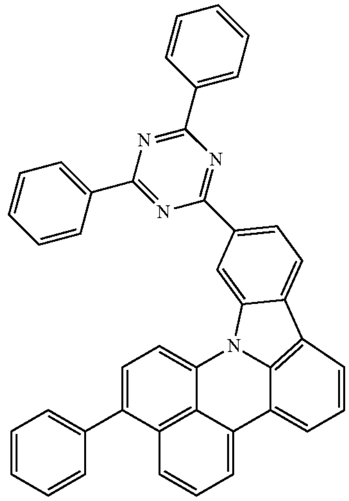
P-93
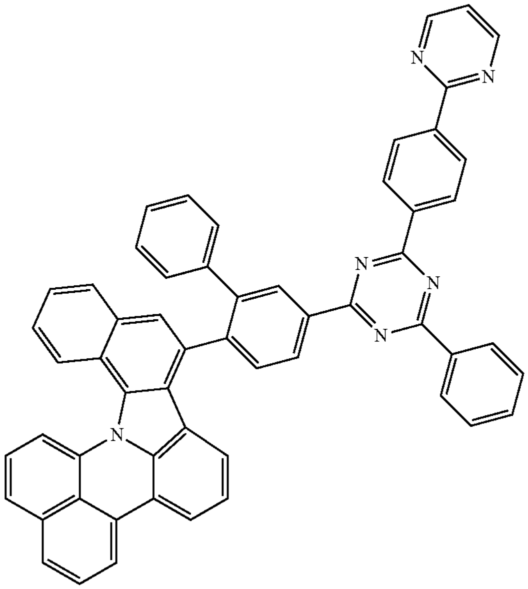

-continued
P-94
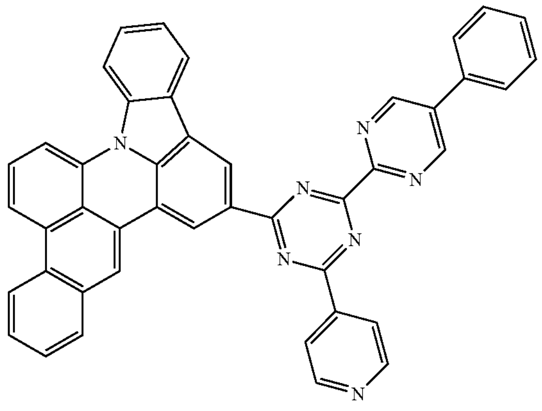
P-95
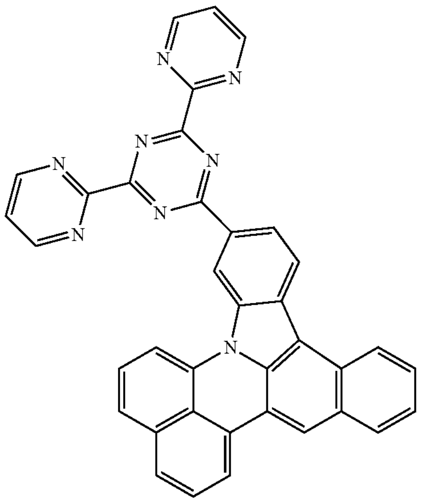
P-96
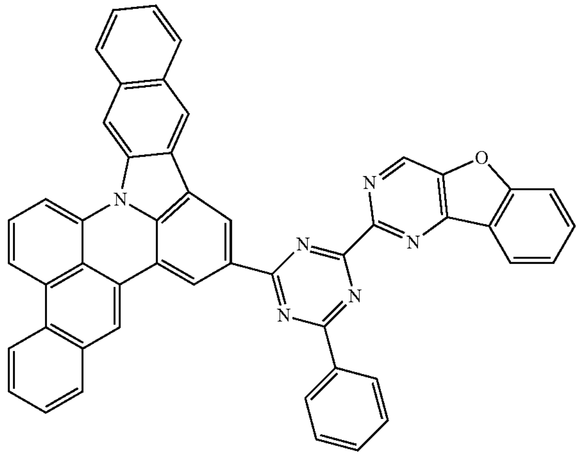
P-97
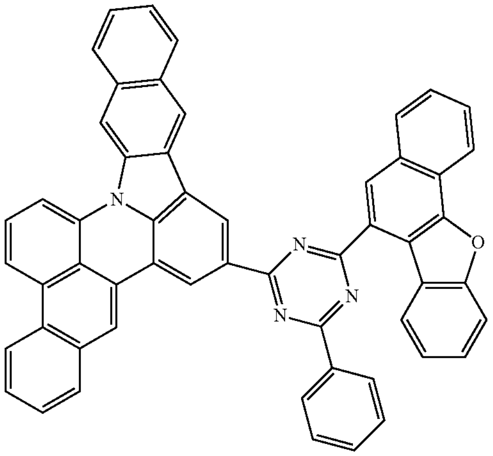
P-98
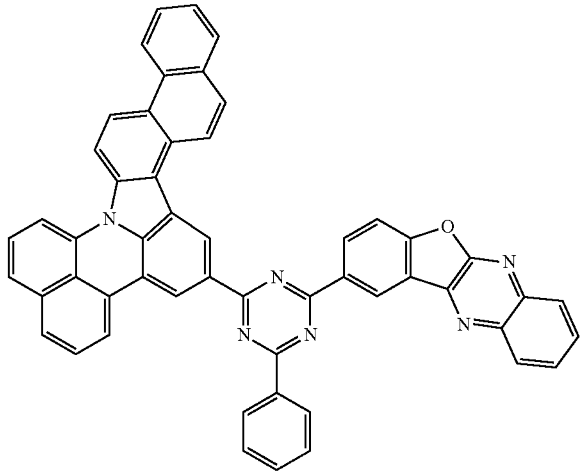
P-99
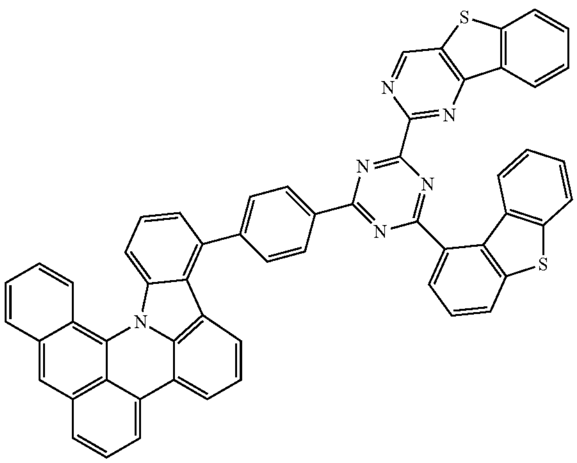

-continued
P-100
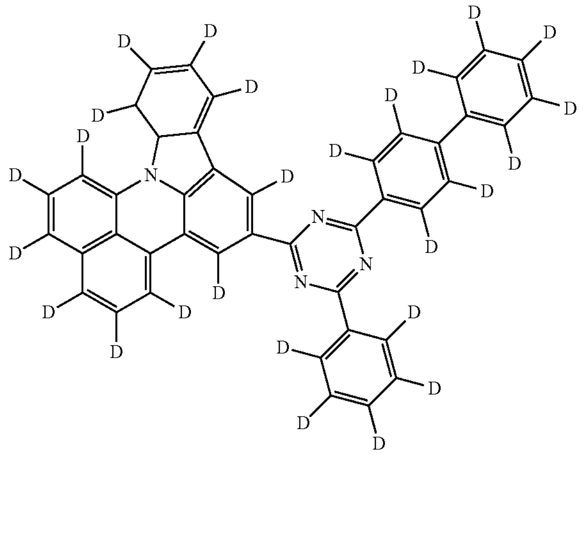
P-101
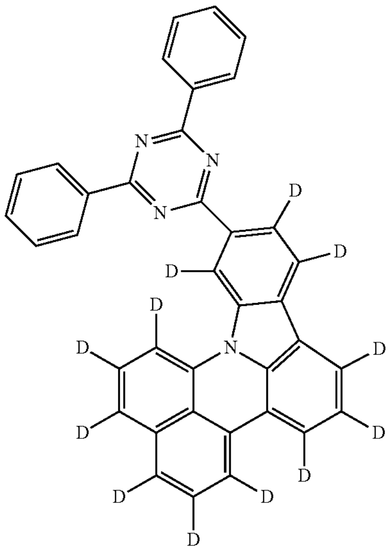
P-102
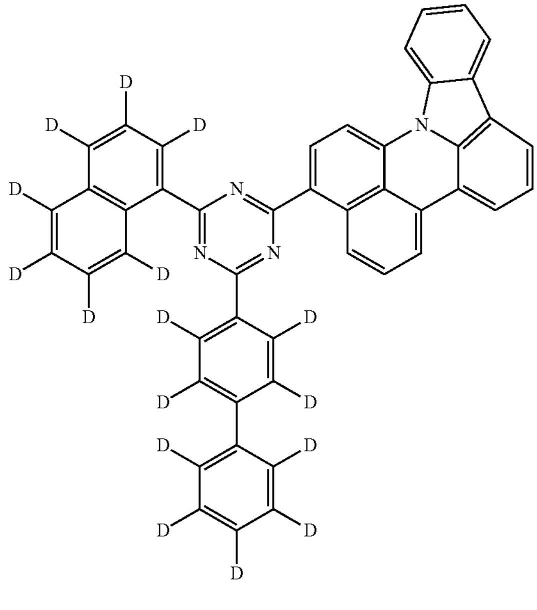
P-103
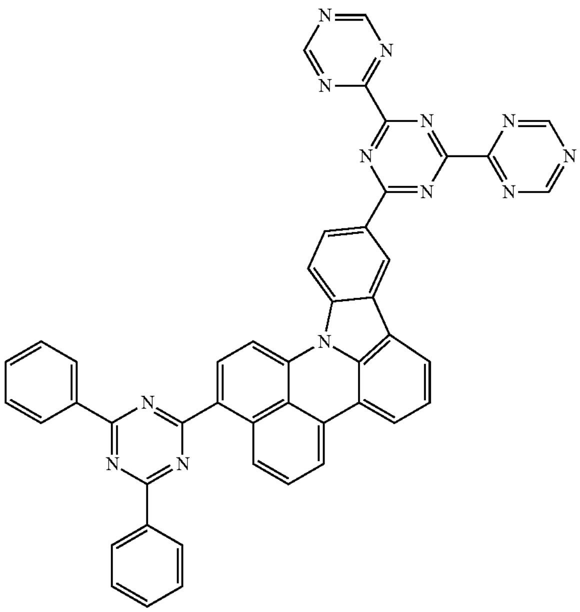

-continued
P-104
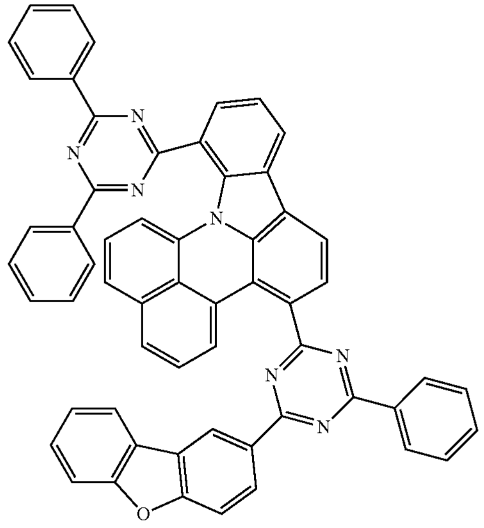
P-105
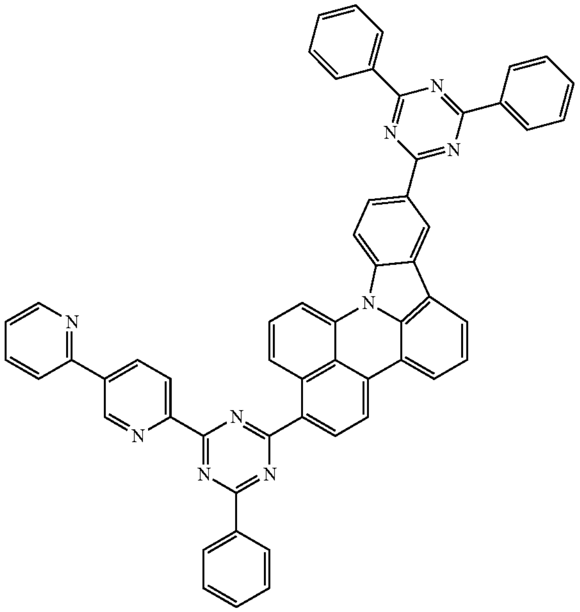
P-106
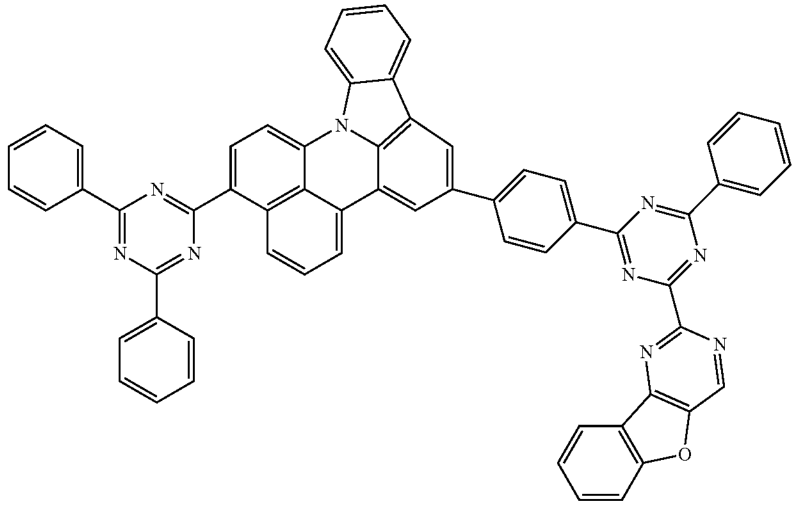
P-107
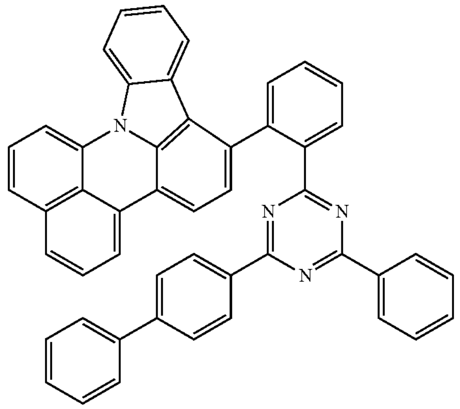
P-108
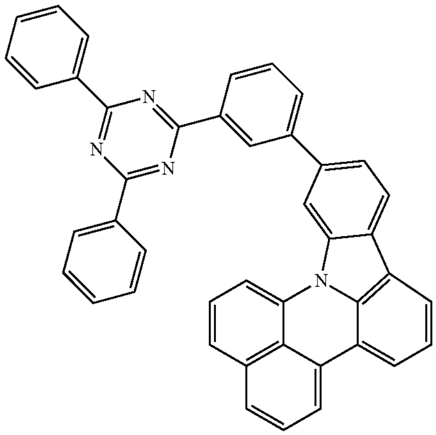

-continued
P-109
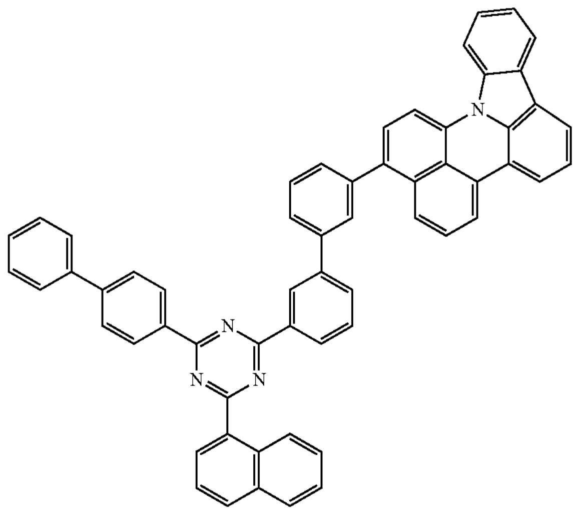
P-110
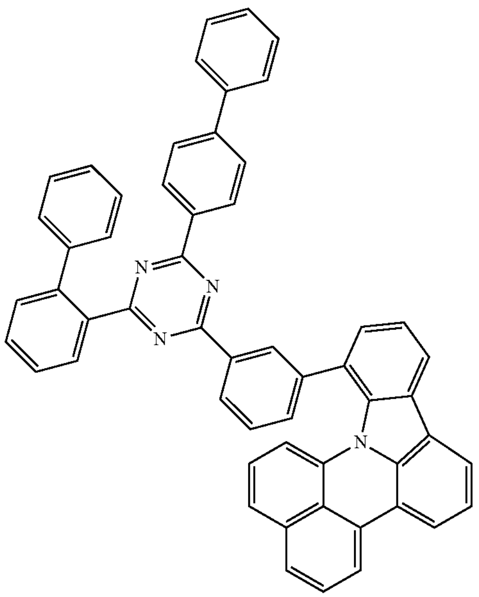
P-111
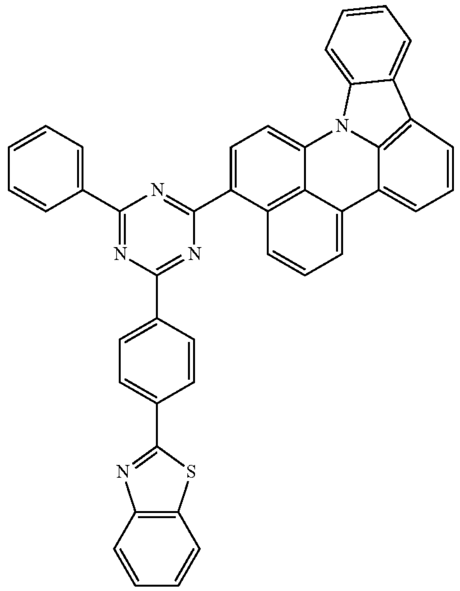
P-112
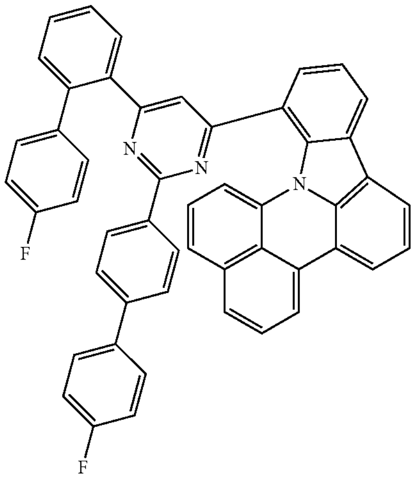

-continued
P-113
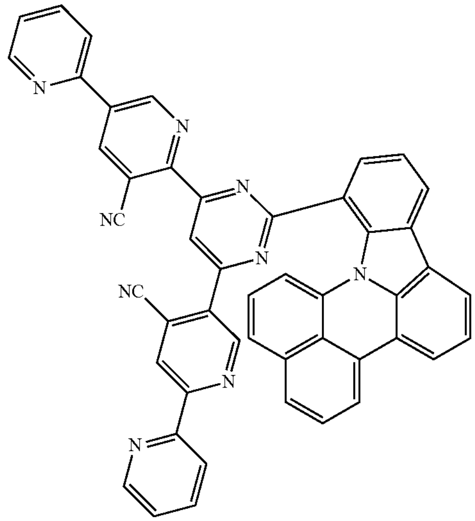
P-114
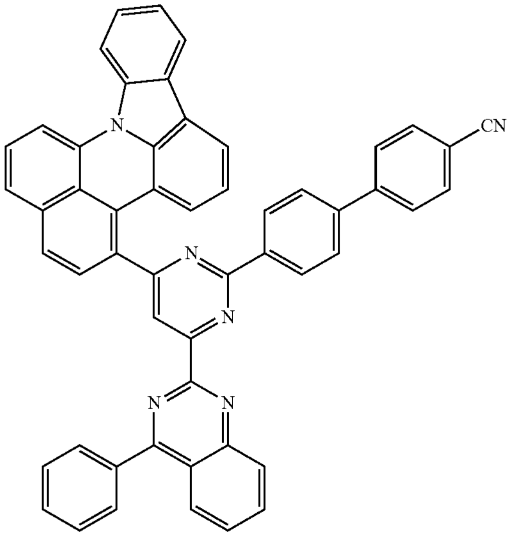
P-115
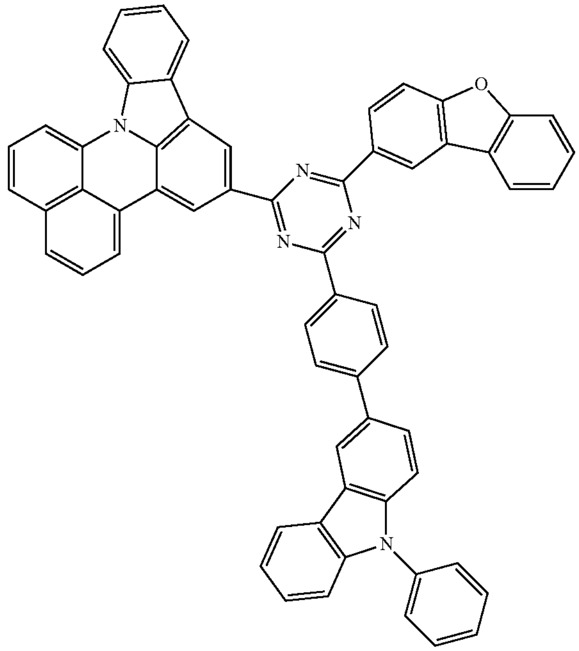
P-116
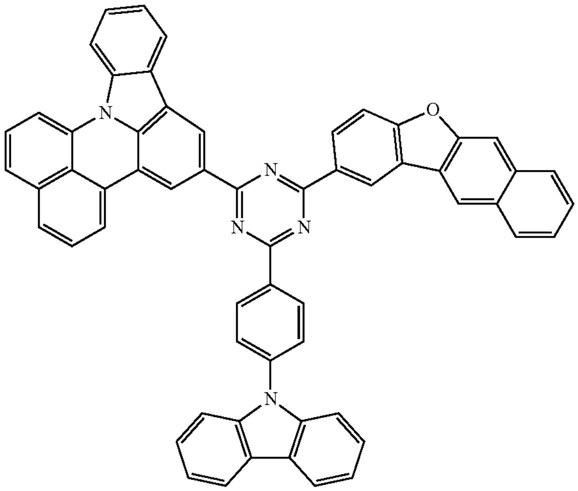

-continued
P-117
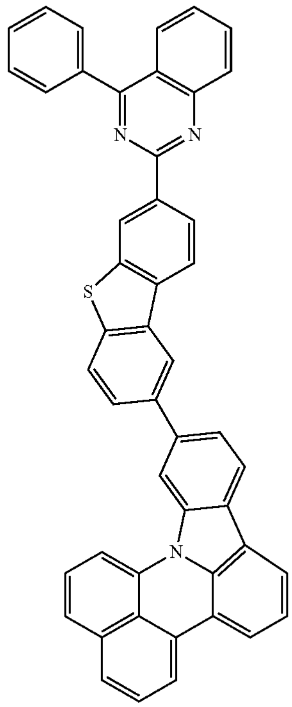
P-118
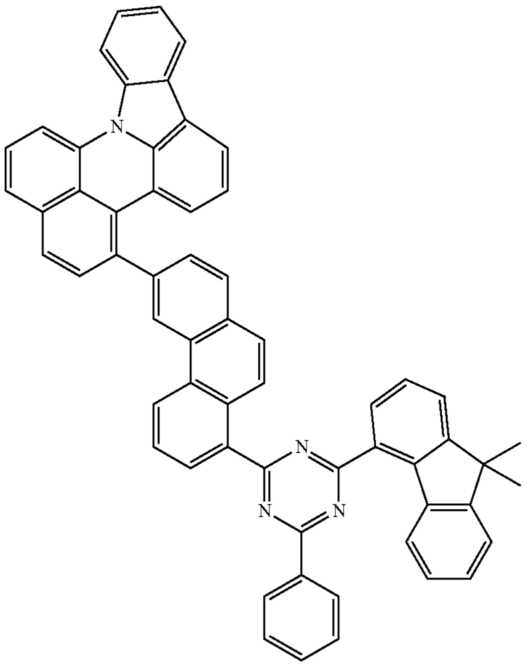
P-119
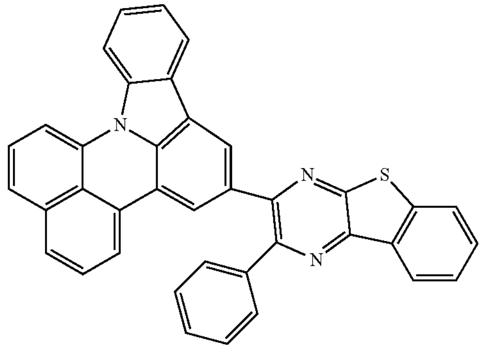
P-120
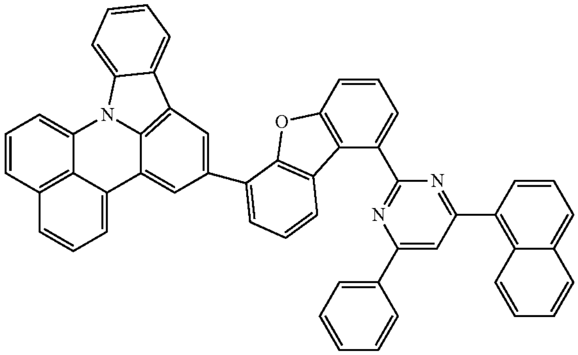

-continued
P-121
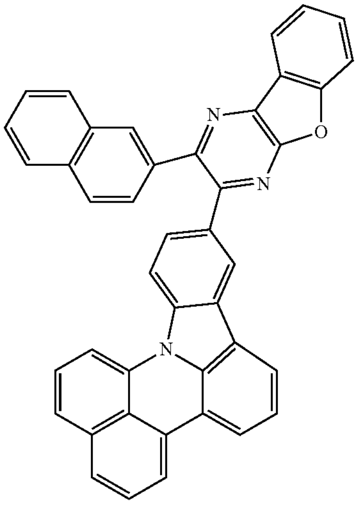
P-122
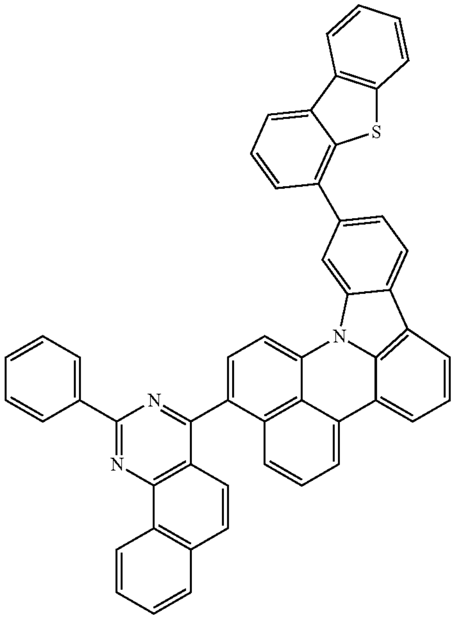
P-123
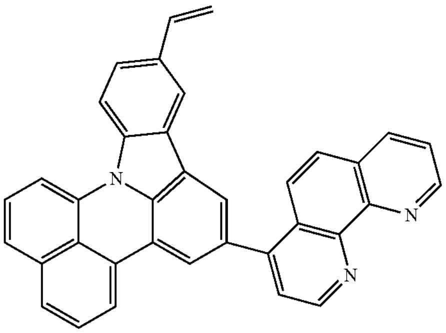
P-124
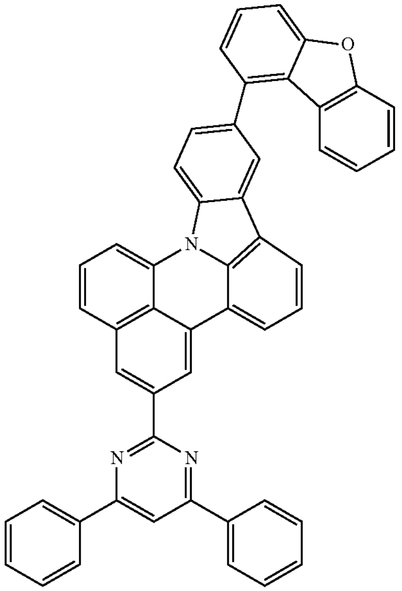

-continued
P-125
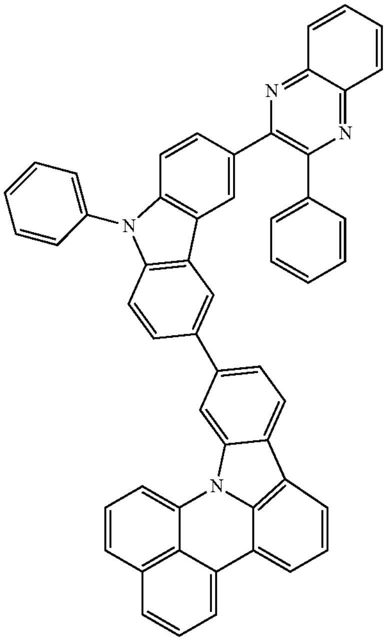
P-126
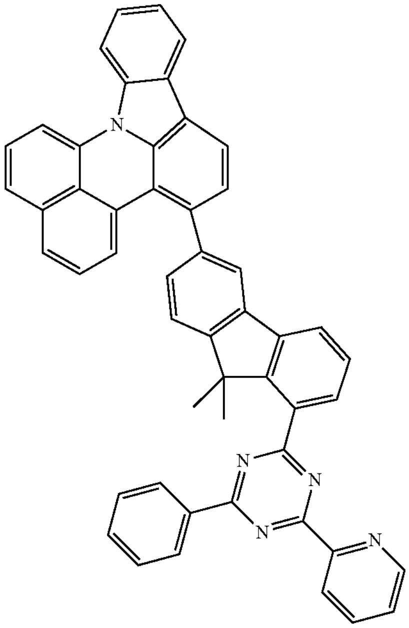
P-127
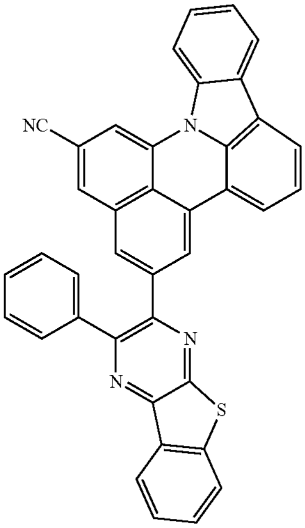
P-128
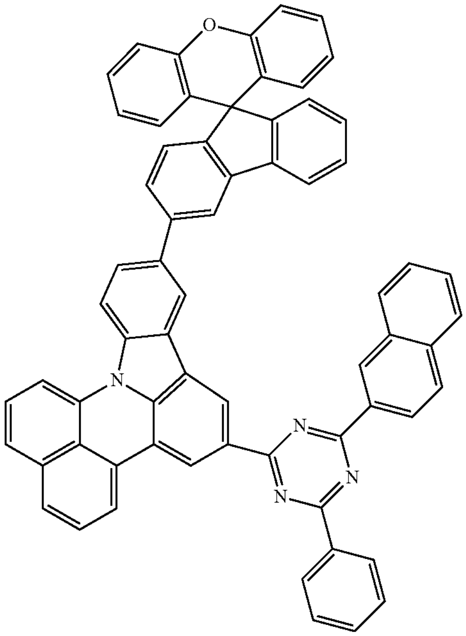

-continued
P-129
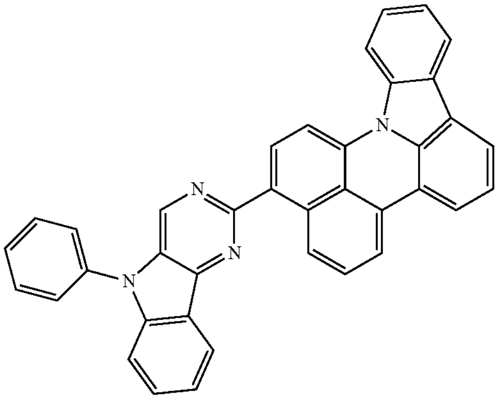
P-130
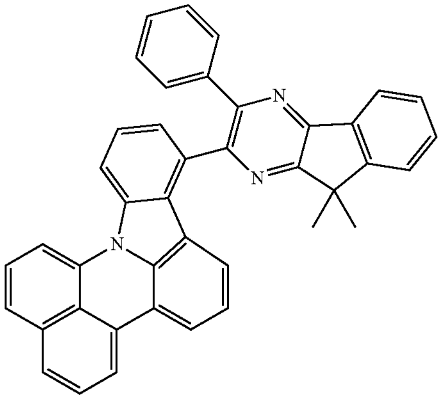
P-131
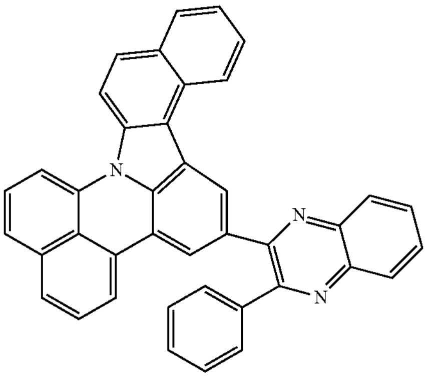
P-132
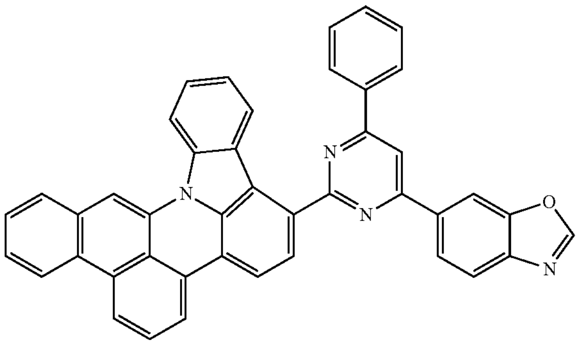
P-133
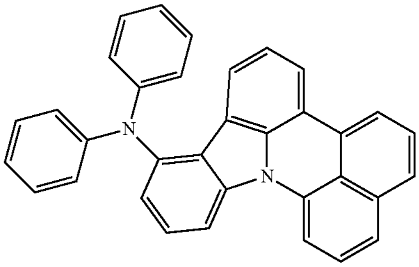
P-134
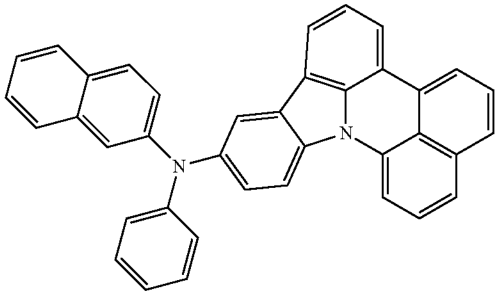
P-135
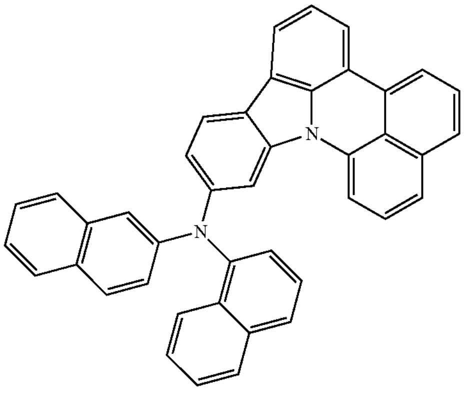
P-136
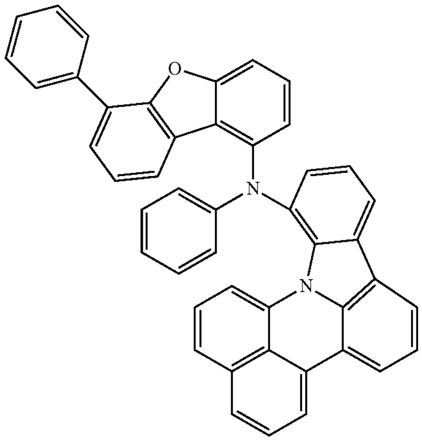

-continued
P-137
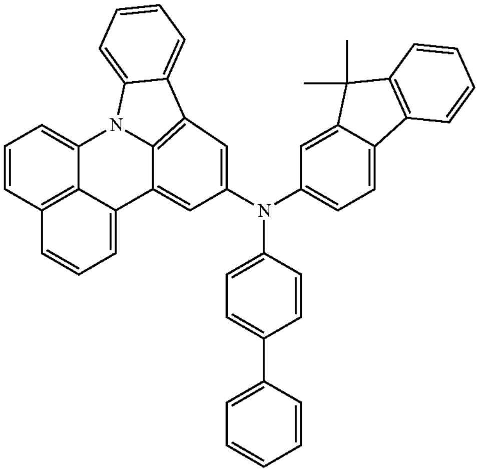
P-138
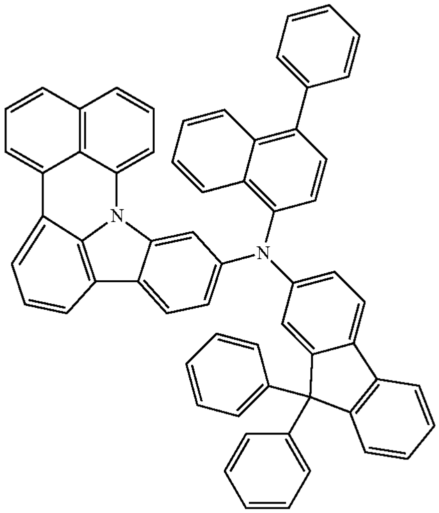
P-139
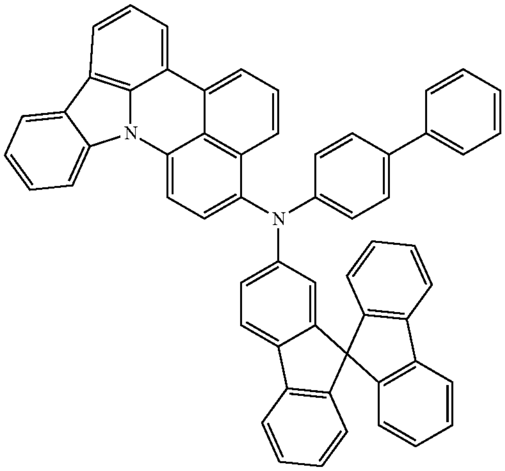
P-140
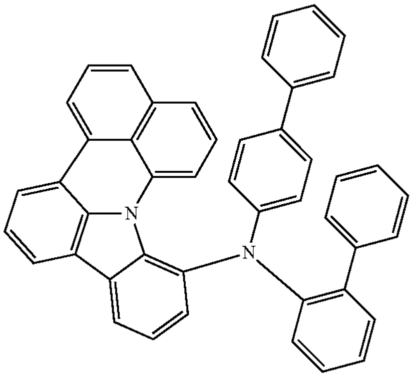
P-141
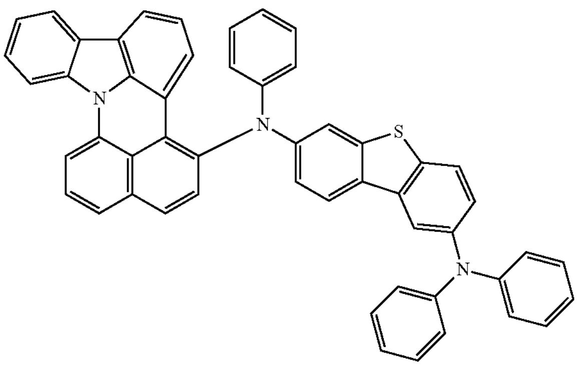
P-142
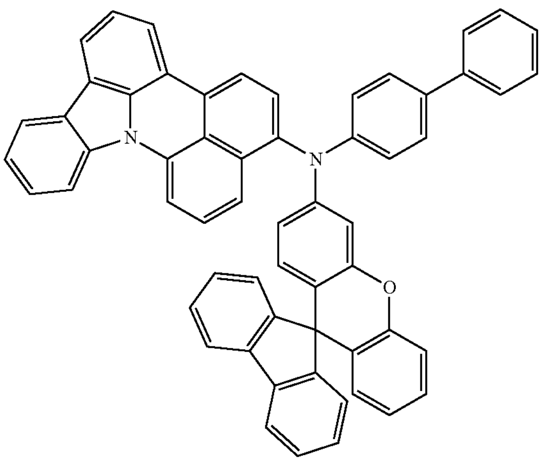

-continued
P-143
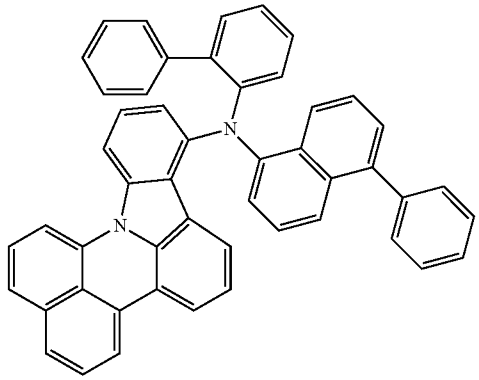
P-144
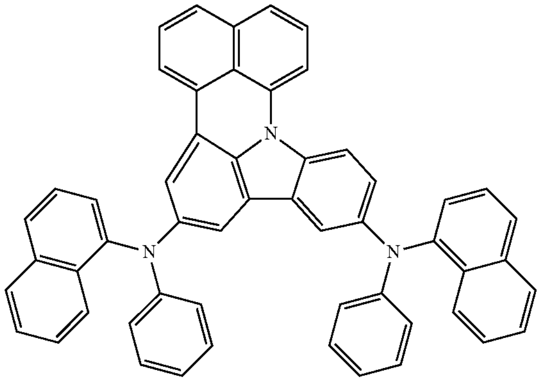
P-145
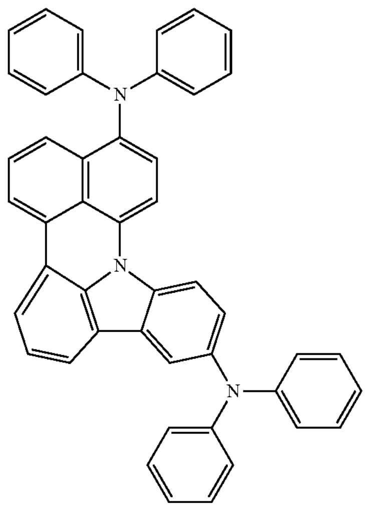
P-146
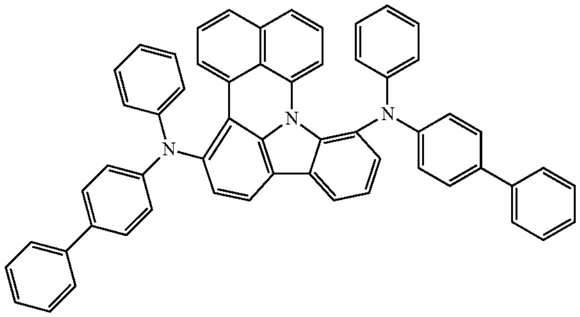
P-147
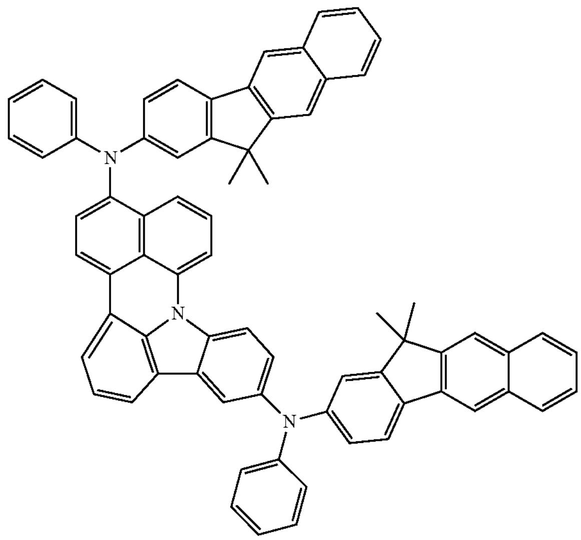
P-148
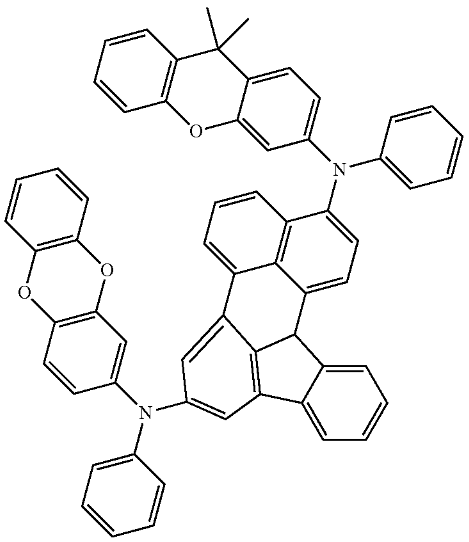

-continued
P-149
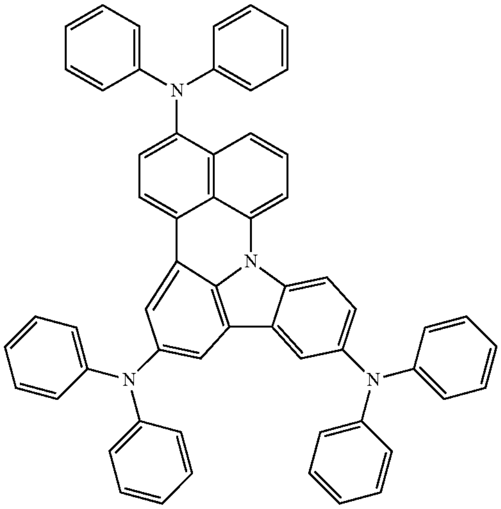
P-150
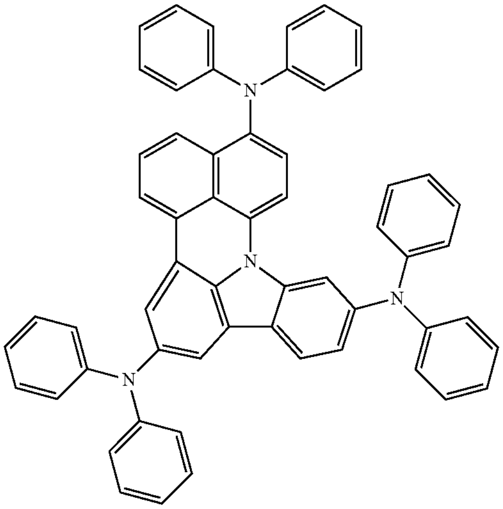
P-151
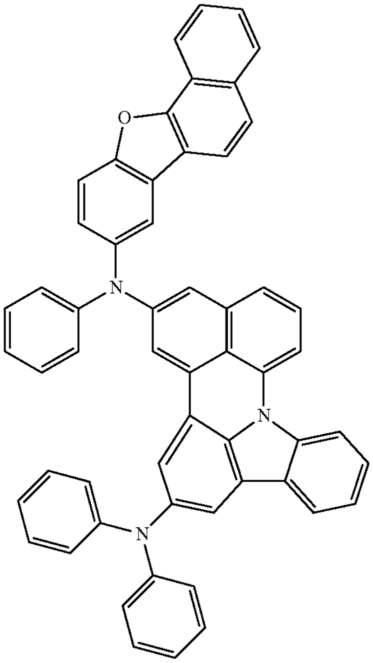
P-152
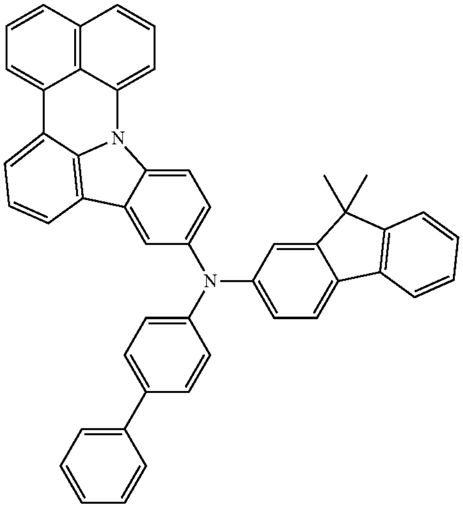

-continued
P-153
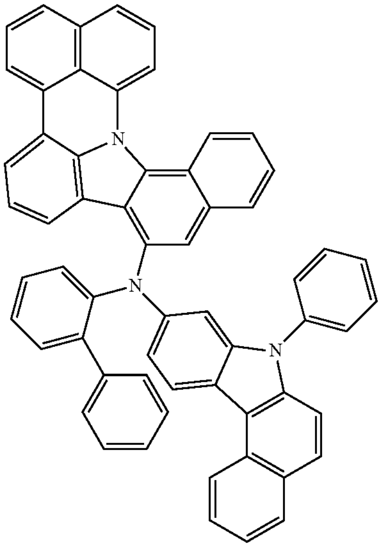
P-154
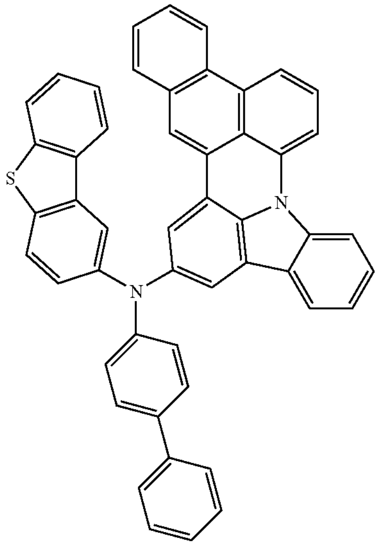
P-155
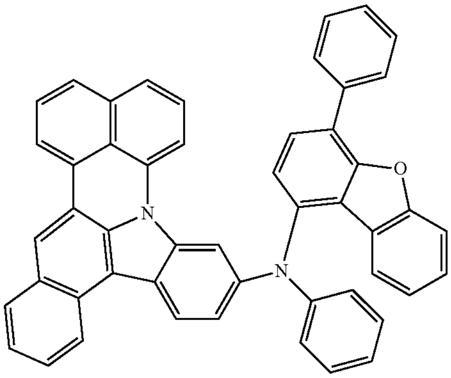
P-156
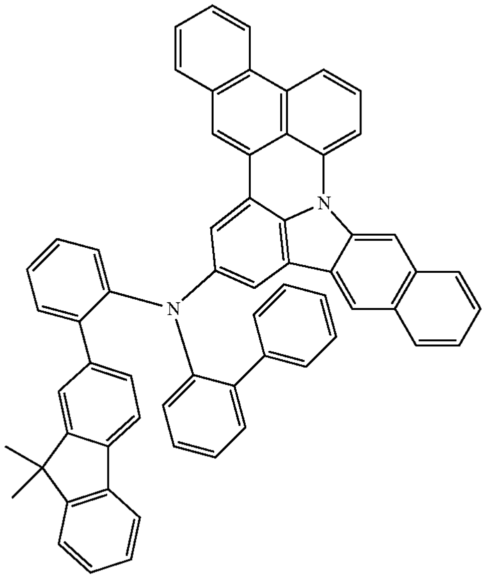

-continued
P-157
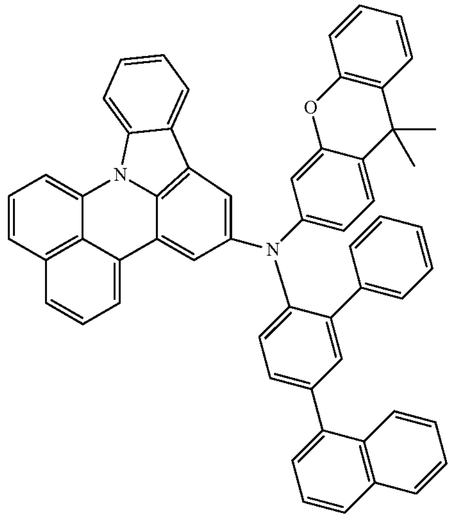
P-158
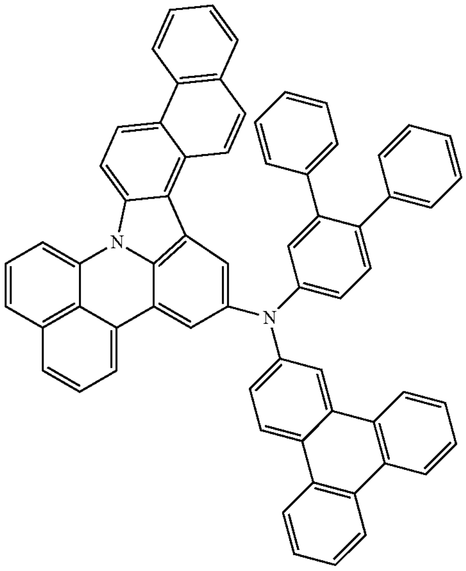
P-159
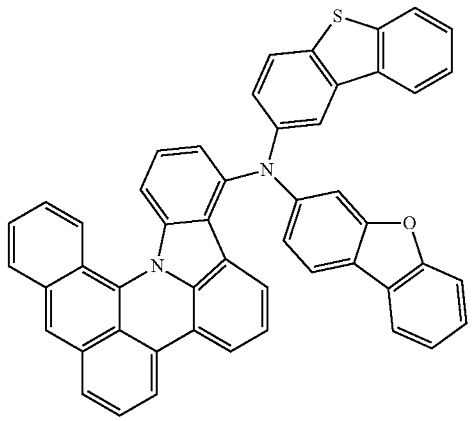
P-160
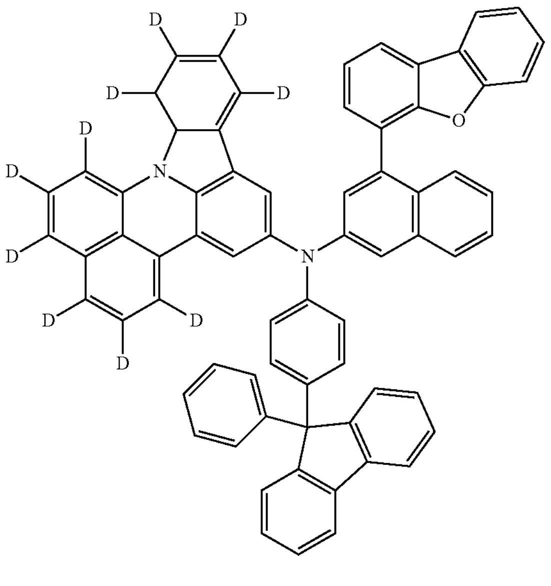

-continued
P-161
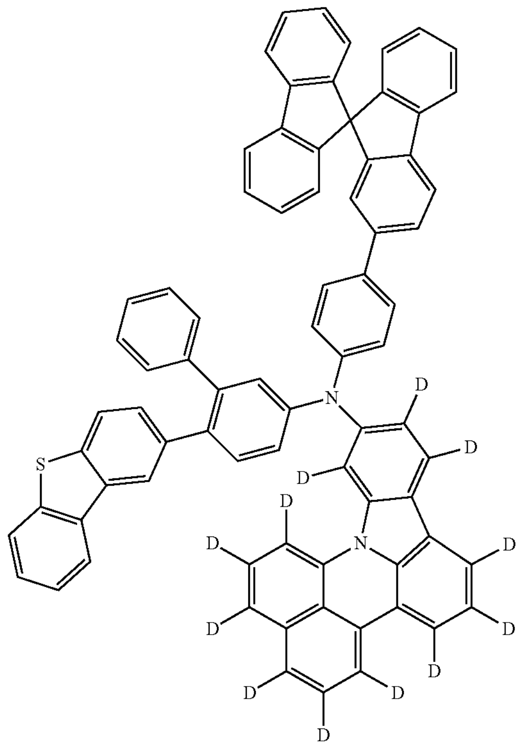
P-162
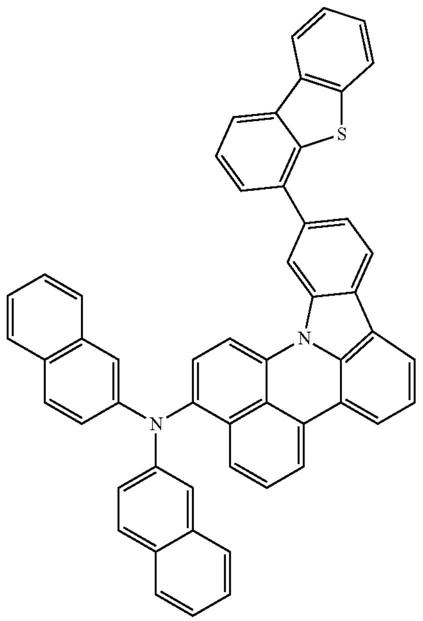
P-163
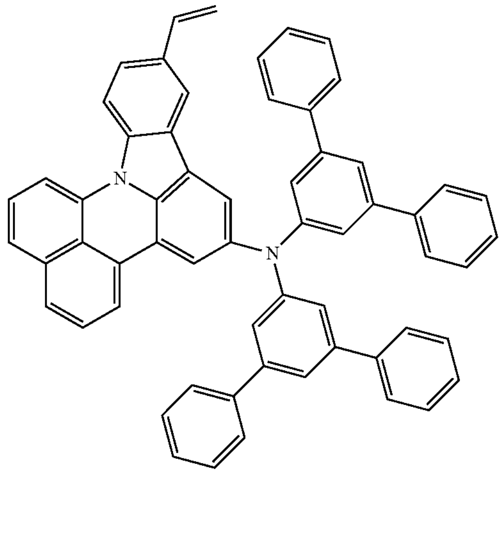
P-164
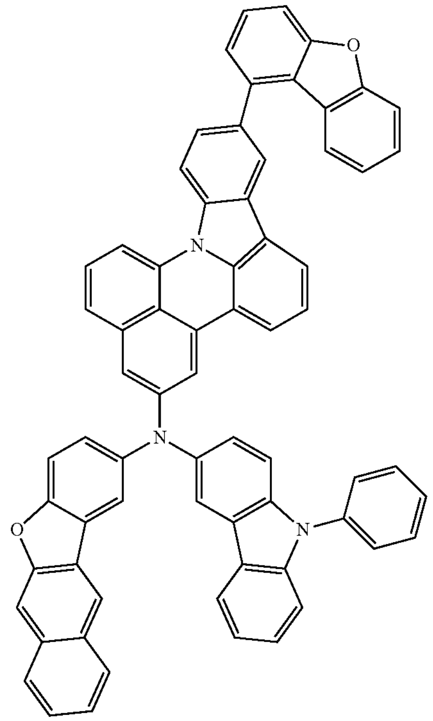

-continued
P-165
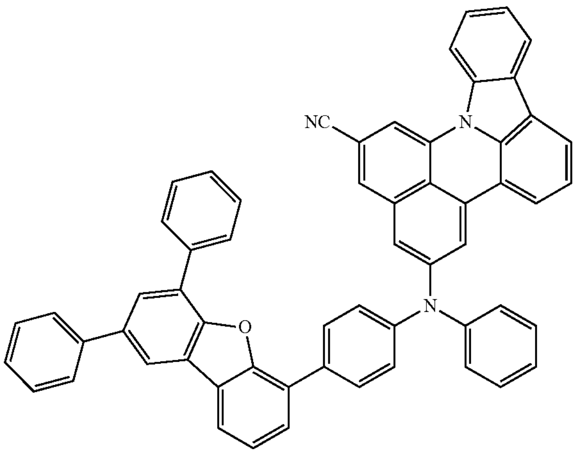
P-166
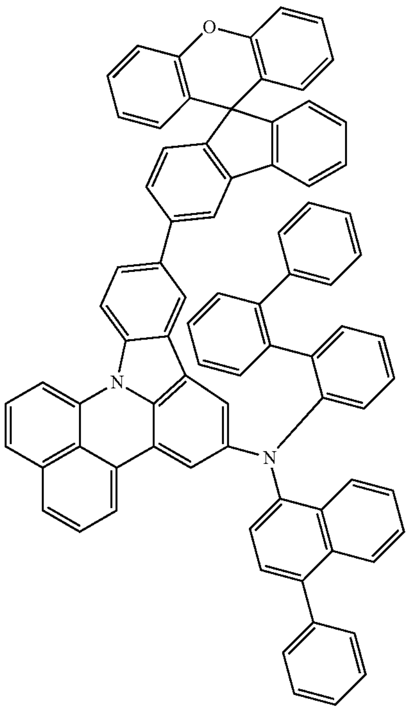
P-167
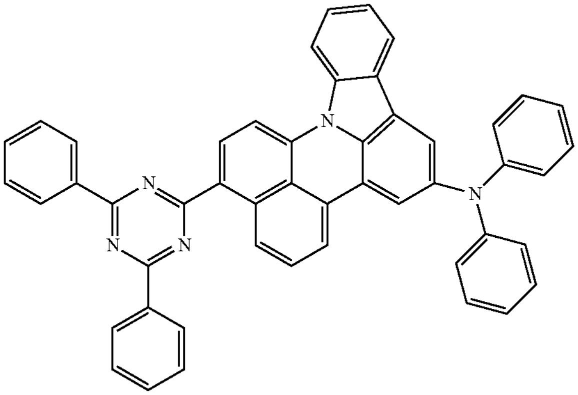
P-168
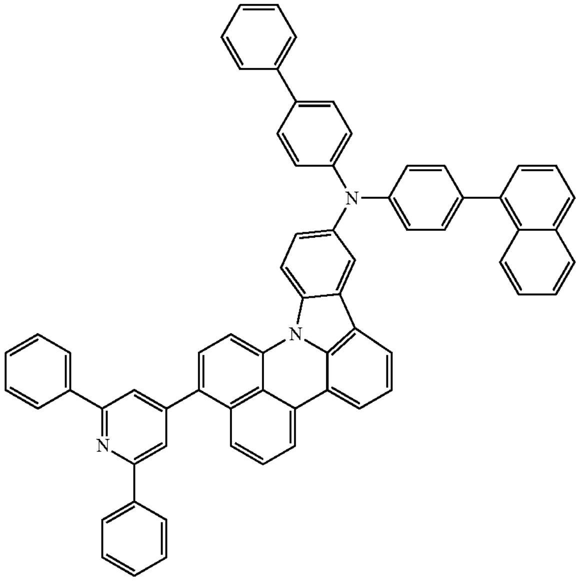

-continued
P-169
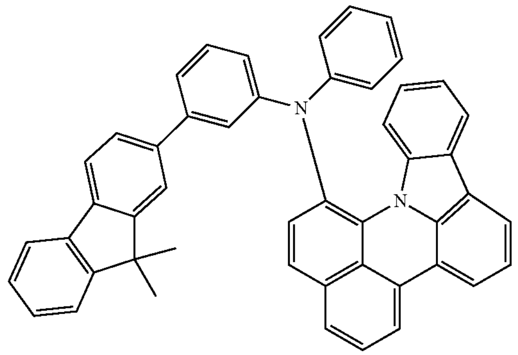
P-170
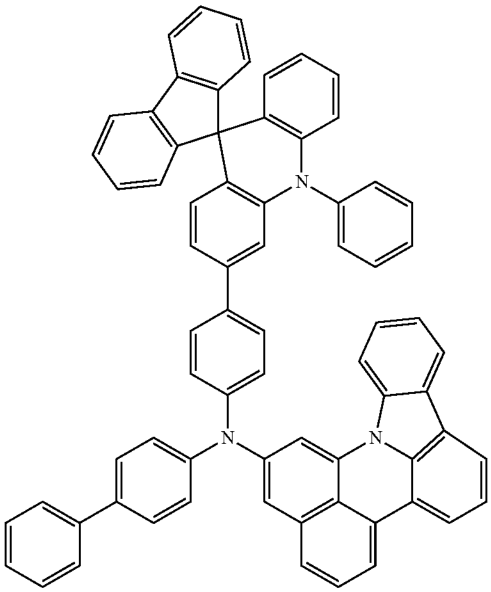
P-171
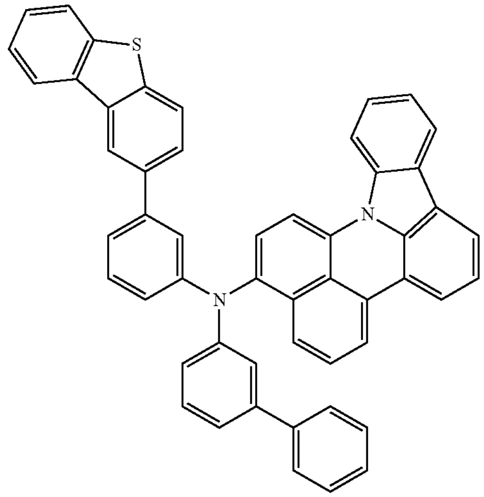
P-172
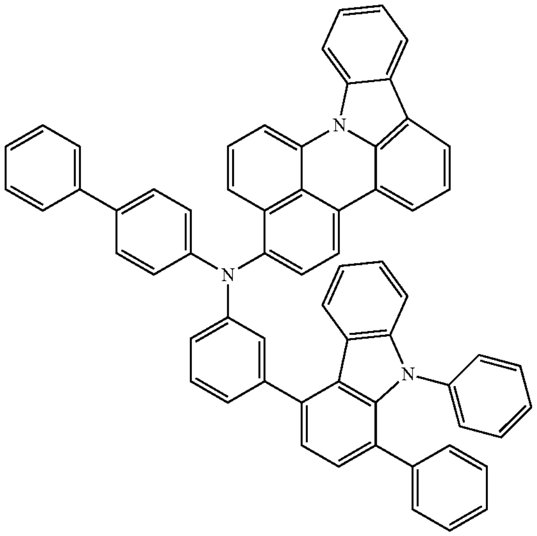

-continued
P-173
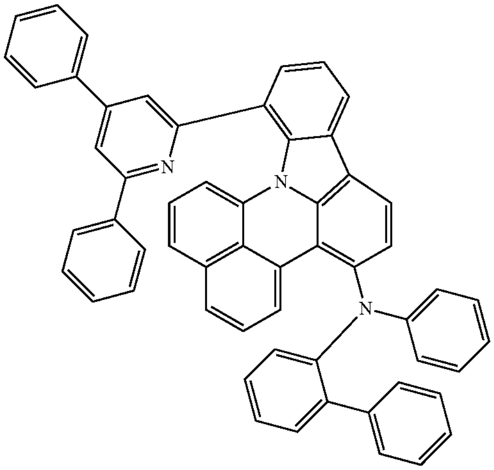
P-174
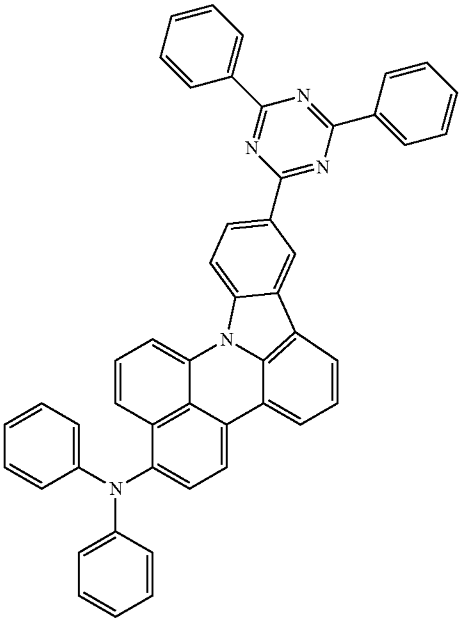
P-175
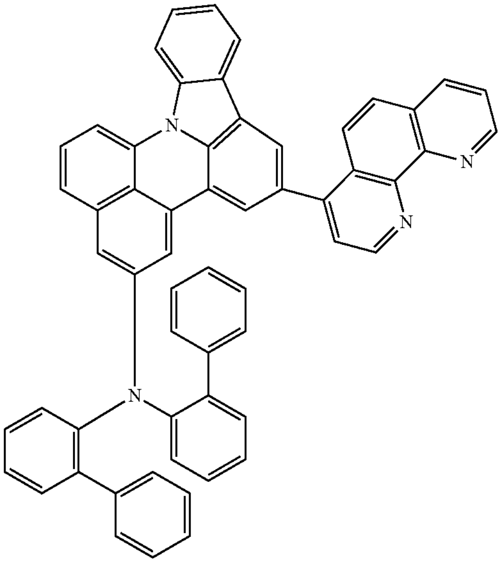
P-176
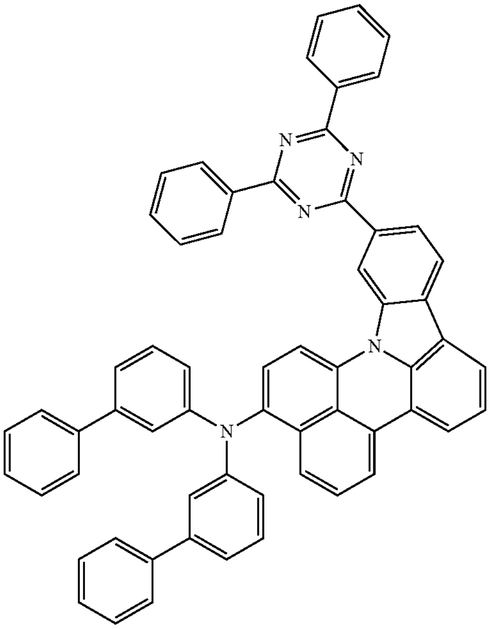

-continued
P-177
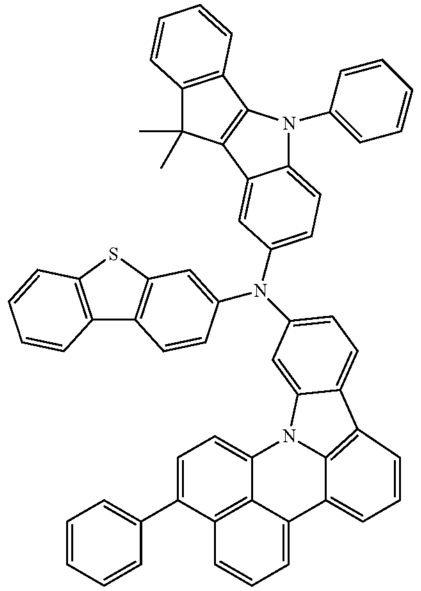
P-178
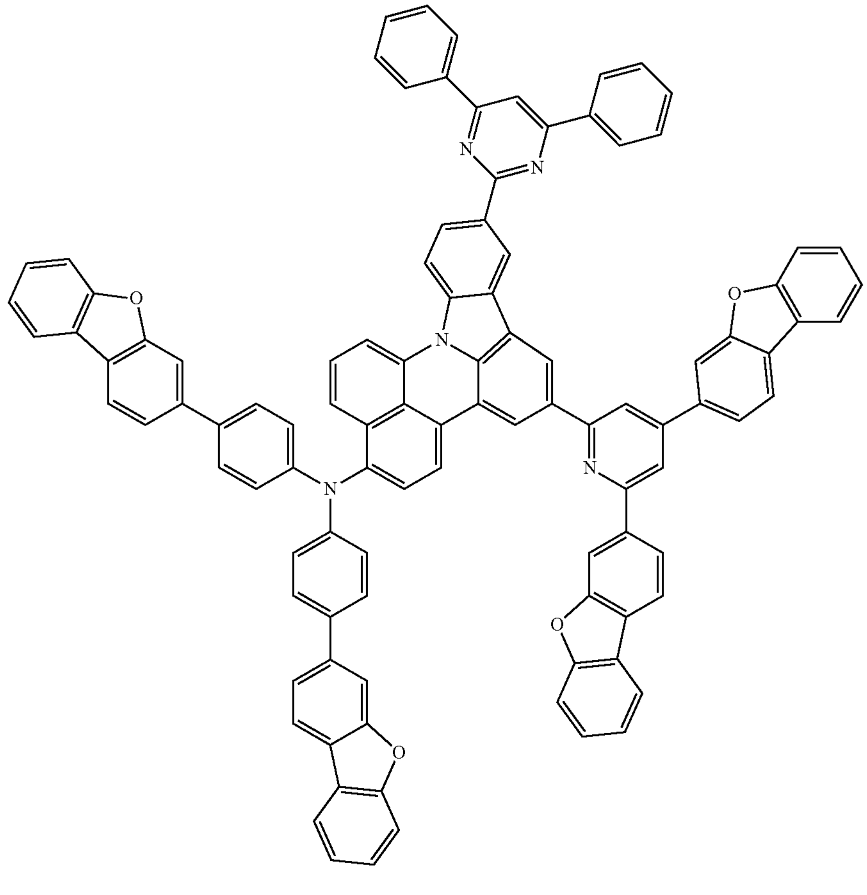

-continued
P-179
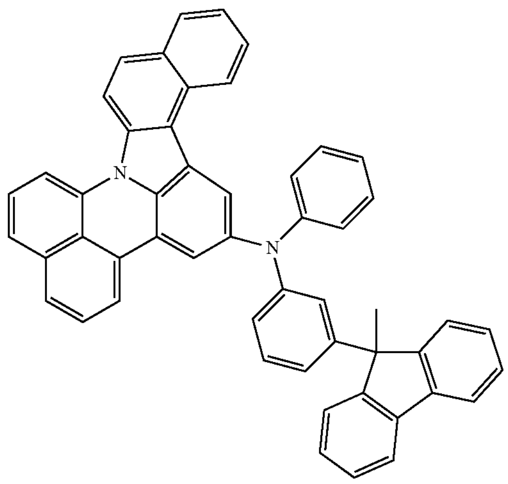
P-180
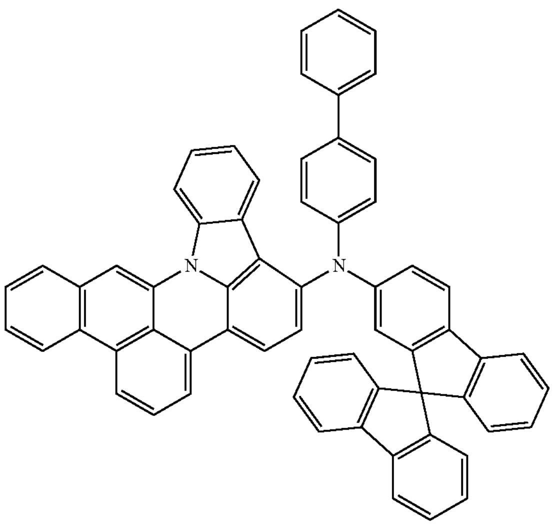
P-181
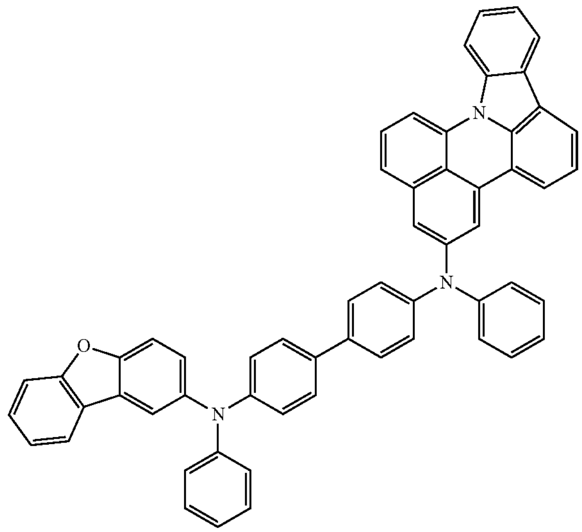
P-182
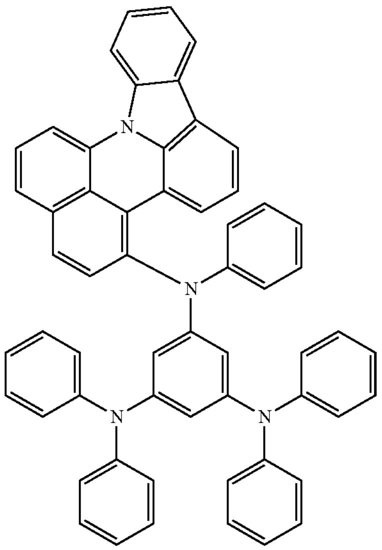

-continued
P-183
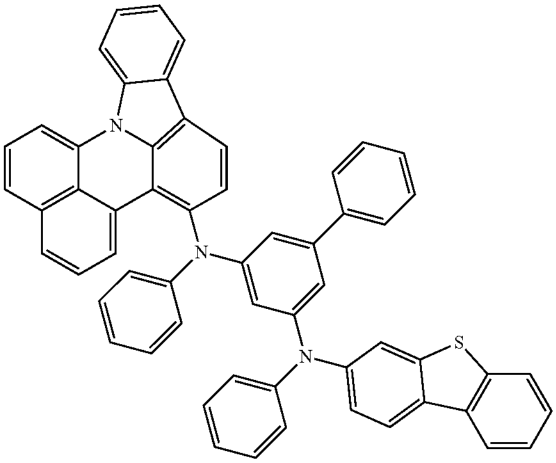
P-184
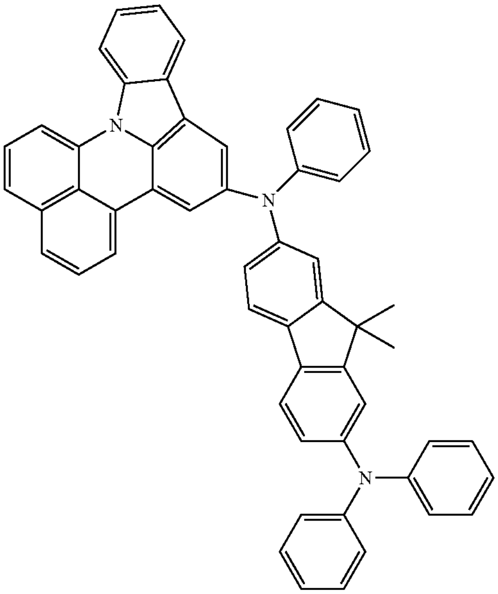
P-185
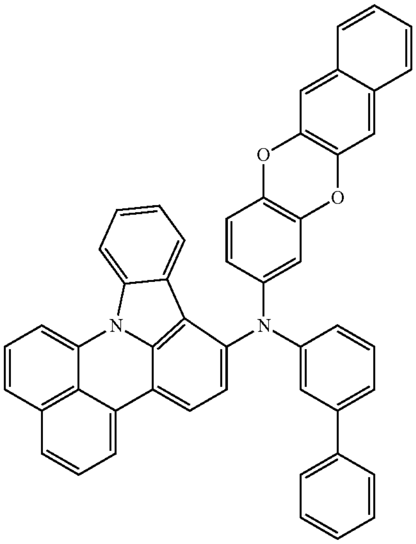
P-186
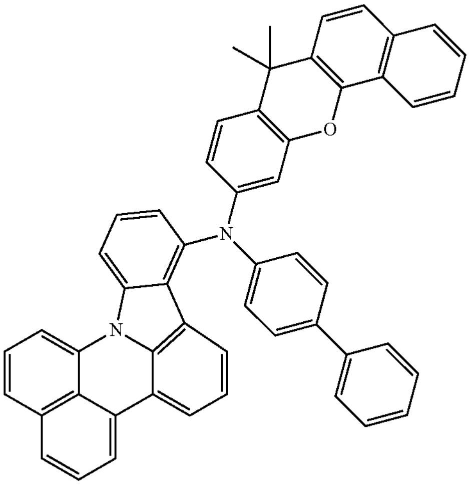

-continued
P-187
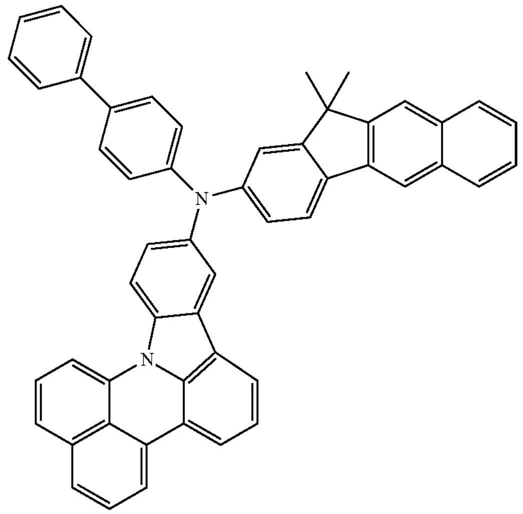
P-188
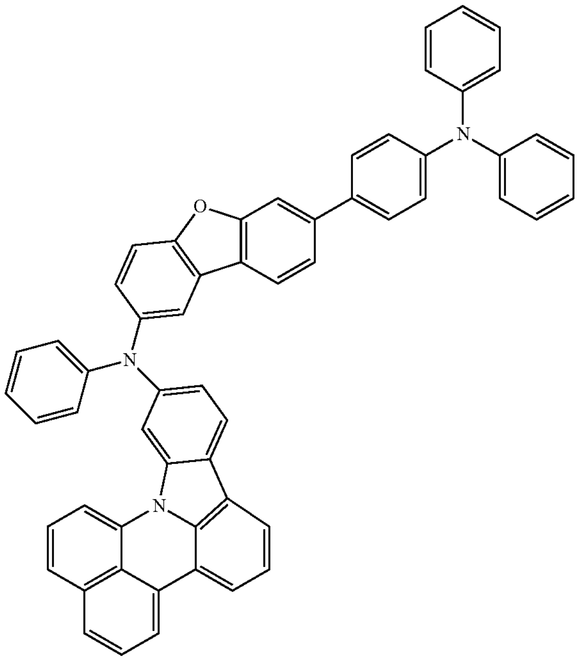
P-189
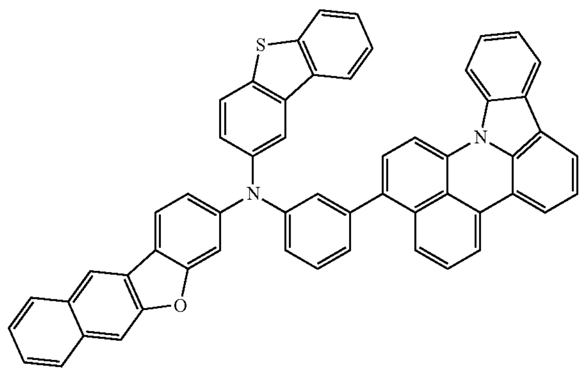
P-190
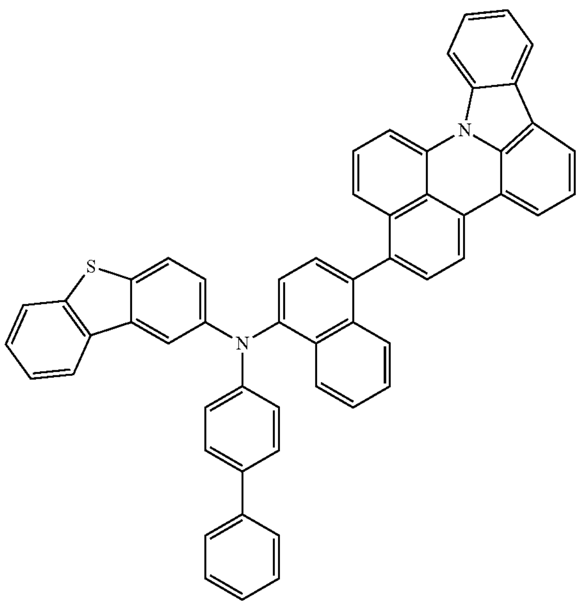

-continued
P-191
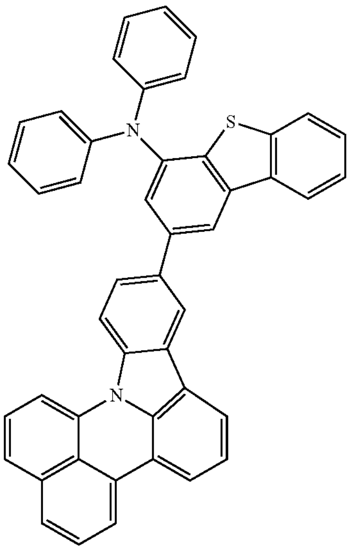
P-192
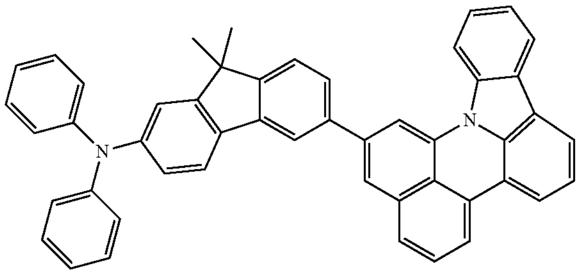
P-193
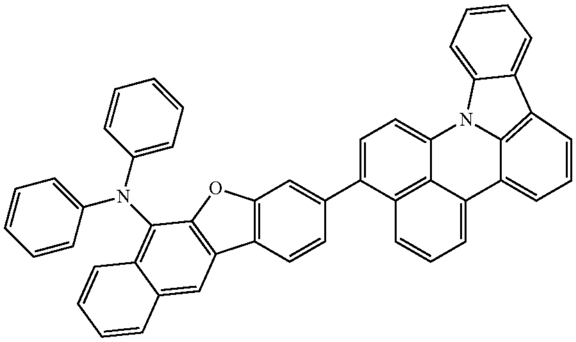
P-194
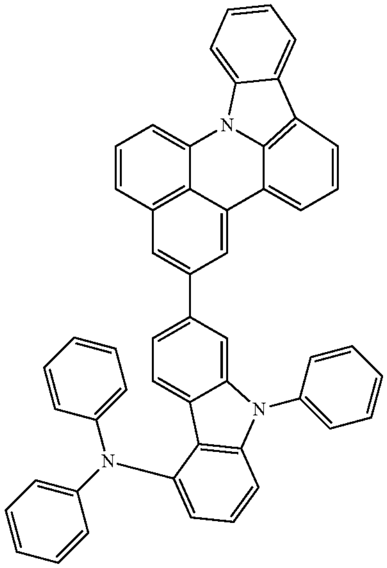
P-195
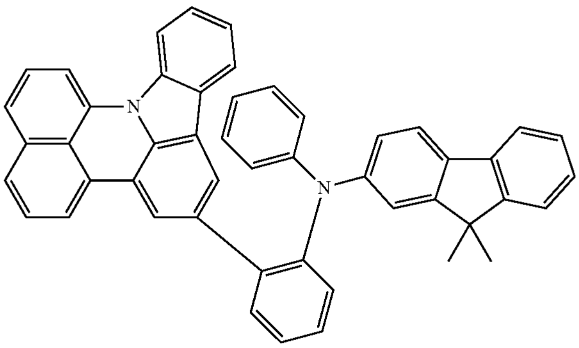
P-196
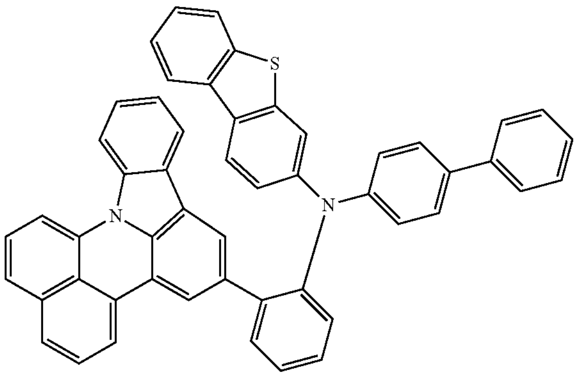

-continued
P-197
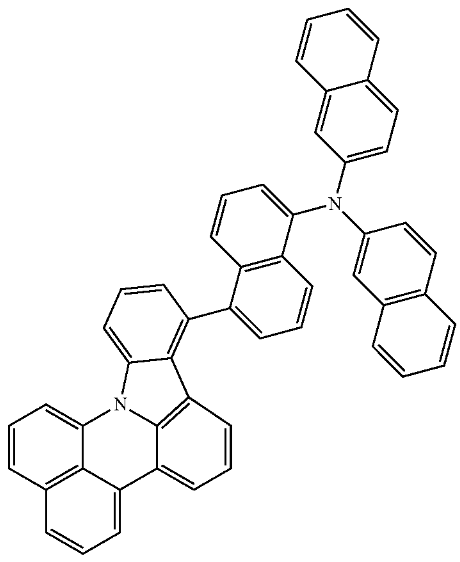
P-198
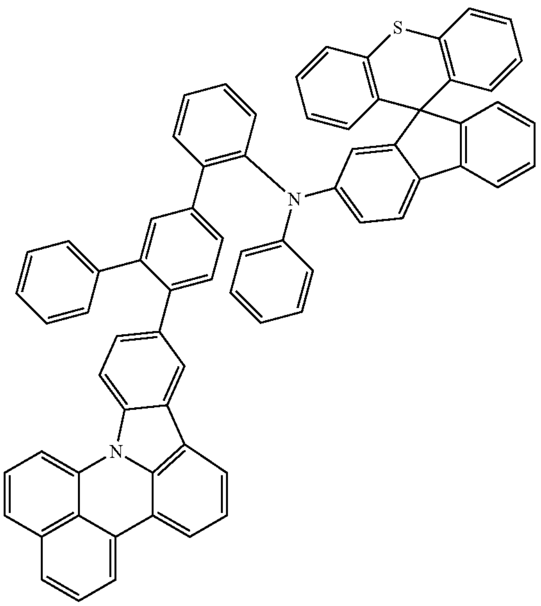
P-199
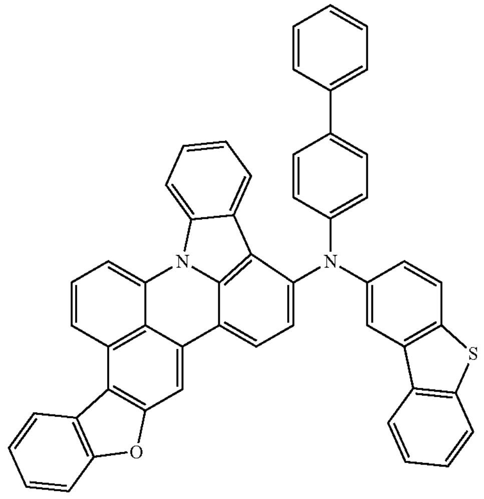
P-200
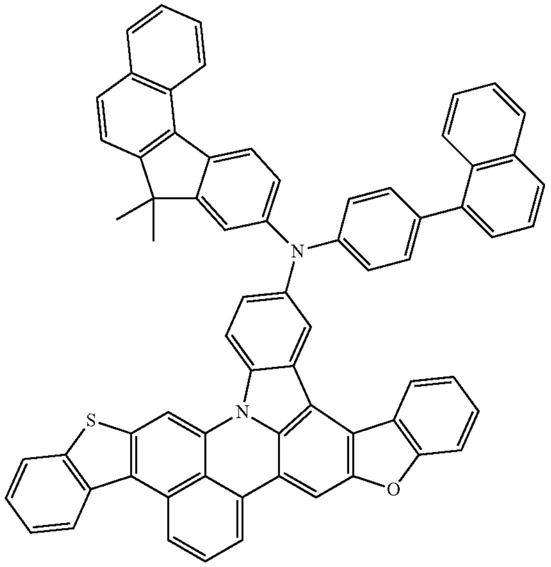
P-201
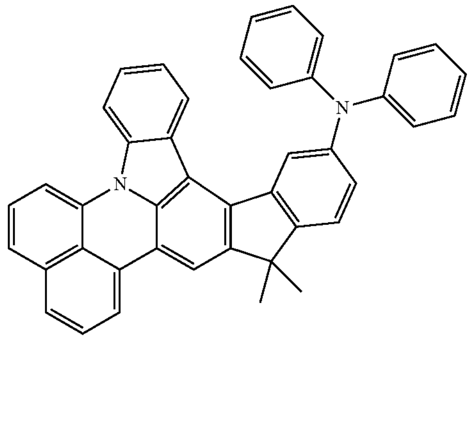
P-202
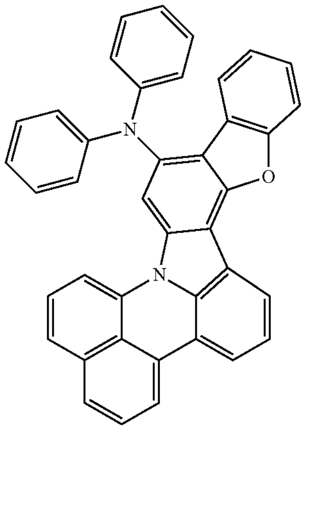

-continued
P-203
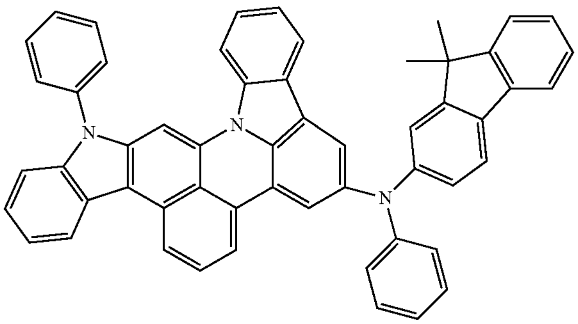
P-204
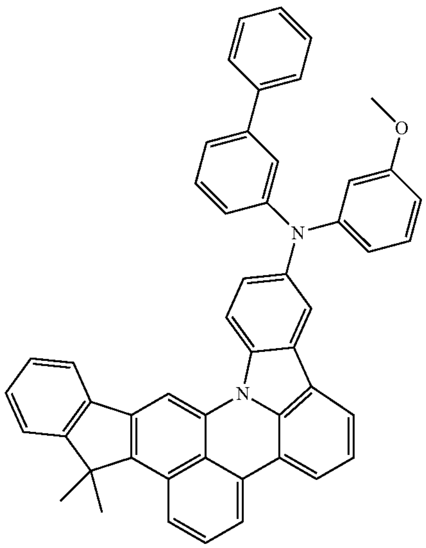
P-205
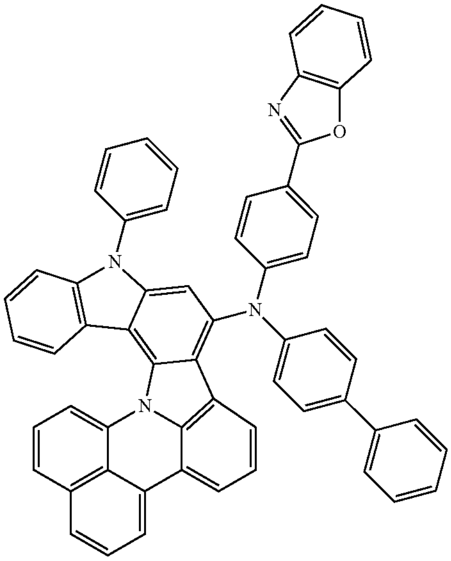
P-206
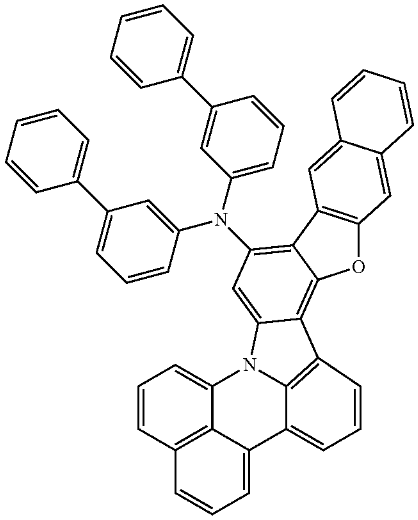
P-207
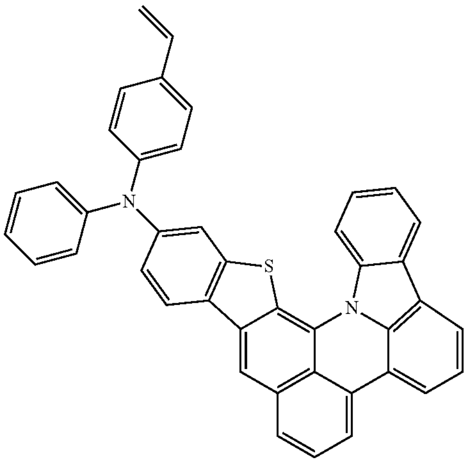
P-208
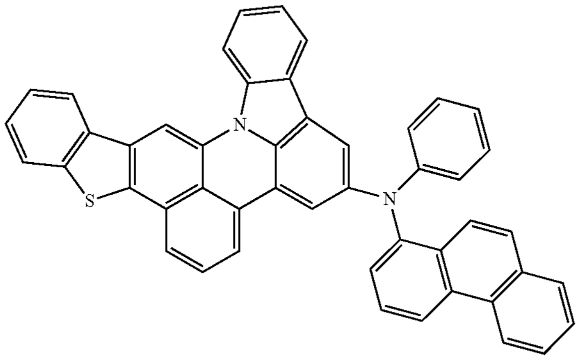

-continued

P-209

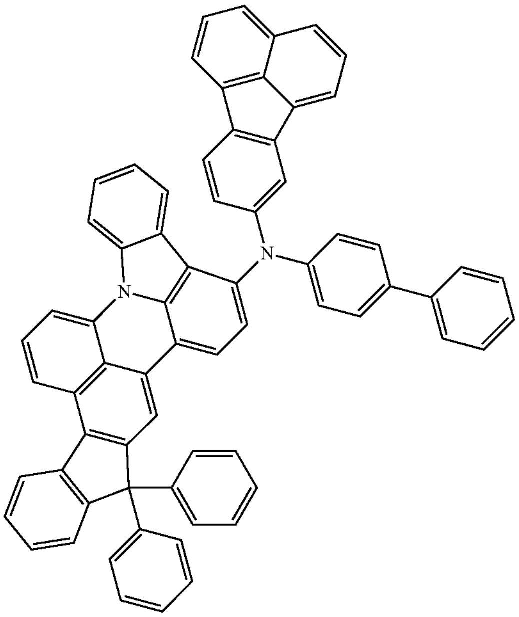

P-210

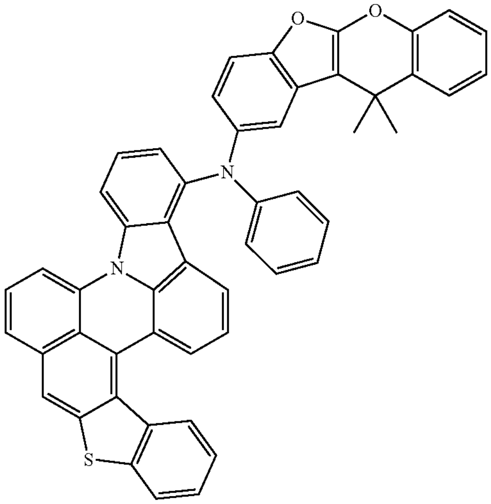

P-211

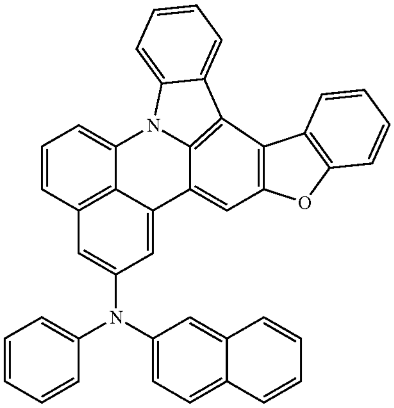

P-212

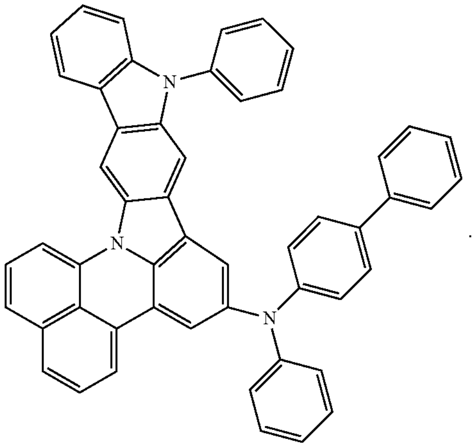

4. An organic electric element comprising a first electrode; a second electrode; and an organic material layer formed between the first electrode and the second electrode, wherein the organic material layer comprises one or more of the compounds represented by Formula 1 of claim 1.

5. An organic electric element comprising a first electrode; a second electrode; an organic material layer formed between the first electrode and the second electrode; and a capping layer, wherein the capping layer is formed on one surface of the first or the second electrode that is not in contact with the organic material layer; and the organic material layer or capping layer comprises one of more of the compounds represented by Formula 1 of claim 1.

6. The organic electric element of claim 4, wherein the organic material layer comprises at least one layer selected from the group consisting of a hole injection layer, a hole transport layer, an auxiliary light emitting layer, a light emitting layer, an auxiliary electron transport layer, an electron transport layer, and an electron injection layer.

7. The organic electric element of claim 6, wherein the organic material layer comprises at least one layer of the hole transport layer, the light emitting layer, and the auxiliary light emitting layer.

8. The organic electric element of claim 4, wherein the organic material layer comprises two or more stacks, each stack comprising a hole transport layer, a light emitting layer, and an electron transport layer sequentially formed between the two electrodes.

9. The organic electric element of claim 8, wherein the organic material layer further comprises a charge generation layer formed between the two or more stacks.

10. An electronic device, which comprises a display device comprising the organic electric element of claim 4; and a control unit that drives the display device.

11. The electronic device of claim 10, wherein the organic electric device is selected from the group consisting of an organic electroluminescent device, an organic solar cell, an organic photoconductor, an organic transistor, a single color lighting device, and a quantum dot display device.

12. The organic electric element of claim 5, wherein the organic material layer comprises at least one layer selected from the group consisting of a hole injection layer, a hole transport layer, an auxiliary light emitting layer, a light emitting layer, an auxiliary electron transport layer, an electron transport layer, and an electron injection layer.

13. The organic electric element of claim 12, wherein the organic material layer comprises at least one layer of the hole transport layer, the light emitting layer, and the auxiliary light emitting layer.

14. The organic electric element of claim 5, wherein the organic material layer comprises two or more stacks, each stack comprising a hole transport layer, a light emitting layer, and an electron transport layer sequentially formed between the two electrodes.

15. The organic electric element of claim 14, wherein the organic material layer further comprises a charge generation layer formed between the two or more stacks.

16. An electronic device comprising a display device comprising the organic electric element of claim 5, and a control unit driving the display device.

17. The electronic device of claim 10, wherein the organic electric device is selected from the group consisting of an organic electroluminescent device, an organic solar cell, an organic photoconductor, an organic transistor, a single color lighting device, and a quantum dot display device.

* * * * *